(12) United States Patent
Iannotti et al.

(10) Patent No.: US 9,414,927 B2
(45) Date of Patent: Aug. 16, 2016

(54) SHOULDER ARTHROPLASTY

(71) Applicants: Joseph Iannotti, Strongsville, OH (US);
Gerald Williams, Villanova, PA (US);
Dinesh Koka, Orlando, FL (US);
Michael Chad Hollis, Collierville, TN (US)

(72) Inventors: Joseph Iannotti, Strongsville, OH (US);
Gerald Williams, Villanova, PA (US);
Dinesh Koka, Orlando, FL (US);
Michael Chad Hollis, Collierville, TN (US)

(73) Assignees: IMDS LLC, Providence, UT (US);
Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/708,799

(22) Filed: Dec. 7, 2012

(65) Prior Publication Data

US 2013/0150975 A1    Jun. 13, 2013

Related U.S. Application Data

(63) Continuation-in-part of application No. 13/367,165, filed on Feb. 6, 2012, now Pat. No. 8,920,508, which is a continuation-in-part of application No. 13/360,459, filed on Jan. 27, 2012.

(Continued)

(51) Int. Cl.
*A61F 2/40* (2006.01)
*A61F 2/46* (2006.01)
(Continued)

(52) U.S. Cl.
CPC ........... *A61F 2/4081* (2013.01); *A61F 2/30734* (2013.01); *A61F 2/30749* (2013.01);
(Continued)

(58) Field of Classification Search
CPC .............. A61B 17/17; A61B 17/1717; A61B 17/1721; A61B 17/1739; A61B 17/1742; A61B 17/1746; A61B 17/175; A61B 2017/1778; A61F 2/46; A61F 2/4603; A61F 2/4607; A61F 2/4609; A61F 2/461; A61F 2/4612; A61F 2/40; A61F 2/4081; A61F 2/30734; A61F 2002/4625; A61F 2002/4628; A61F 2002/4629; A61F 2002/4631; A61F 2002/4085; A61F 2002/30316; A61F 2002/30329; A61F 2002/30331; A61F 2002/30354; A61F 2002/30357; A61F 2002/30362; A61F 2002/30364; A61F 2002/30405; A61F 2002/30433; A61F 2002/30654; A61F 2002/30655; A61F 2002/30658; A61F 2002/3066; A61F 2002/30736; A61F 2002/30878
USPC ..................... 606/86 R, 87, 96–99, 102, 104; 623/19.11–19.14, 22.12
See application file for complete search history.

(56) References Cited

U.S. PATENT DOCUMENTS 1,105,105 A    7/1914    Sherman
2,580,821 A    1/1952    Nicola
(Continued)

FOREIGN PATENT DOCUMENTS

DE    3630276    3/1988
DE    10 2006 04155 A1    11/2007
(Continued)

OTHER PUBLICATIONS

Fucentese, Sandro; Total shoulder Arthroplasty with an Uncemented Soft-Metal-Backed Glenoid Component, Journal of shoulder elbow Surgery (2010) 19, 624-631.
(Continued)

*Primary Examiner* — Kevin T Truong
*Assistant Examiner* — Tracy Kamikawa
(74) *Attorney, Agent, or Firm* — Brinks Gilson & Lione; Craig Buschmann

(57) ABSTRACT

A joint prosthesis system, specifically a shoulder prosthesis, for shoulder replacement, revision and repair. The implants provide fixation into the best bone available to a surgeon. The implants are used in a superior-inferior and anterior-posterior construct forming a type of cross or X-shape. The implants allow for interchangeability of the articulating component as well as rotational orientation. The systems will allow for augments to accommodate bone loss. The implants may allow for additional security using screws or anchors inserted into the scapula.

18 Claims, 110 Drawing Sheets

Related U.S. Application Data

(60) Provisional application No. 61/568,530, filed on Dec. 8, 2011, provisional application No. 61/604,391, filed on Feb. 28, 2012, provisional application No. 61/615,560, filed on Mar. 26, 2012, provisional application No. 61/701,484, filed on Sep. 14, 2012.

(51) Int. Cl.
  *A61F 2/30* (2006.01)
  *A61F 2/28* (2006.01)
  *A61B 17/86* (2006.01)

(52) U.S. Cl.
  CPC ............. *A61F2/4003* (2013.01); *A61F 2/4059* (2013.01); *A61F 2/4637* (2013.01); *A61B 17/86* (2013.01); *A61F 2/4014* (2013.01); *A61F 2002/2835* (2013.01); *A61F 2002/305* (2013.01); *A61F 2002/3054* (2013.01); *A61F 2002/3085* (2013.01); *A61F 2002/30331* (2013.01); *A61F 2002/30332* (2013.01); *A61F 2002/30367* (2013.01); *A61F 2002/30387* (2013.01); *A61F 2002/30428* (2013.01); *A61F 2002/30492* (2013.01); *A61F 2002/30495* (2013.01); *A61F 2002/30507* (2013.01); *A61F 2002/30604* (2013.01); *A61F 2002/30663* (2013.01); *A61F 2002/30736* (2013.01); *A61F 2002/30774* (2013.01); *A61F 2002/30878* (2013.01); *A61F 2002/30884* (2013.01); *A61F 2002/30934* (2013.01); *A61F 2002/30975* (2013.01); *A61F 2002/4085* (2013.01); *A61F 2002/4641* (2013.01)

(56) References Cited

U.S. PATENT DOCUMENTS

| | | |
|---|---|---|
| 2,780,223 A | 2/1957 | Haggland |
| 3,593,709 A | 7/1971 | Halloran |
| 4,364,382 A | 12/1982 | Mennen |
| 4,429,690 A | 2/1984 | Angelino-Pievani |
| 5,047,058 A | 9/1991 | Roberts |
| 5,387,241 A | 2/1995 | Hayes |
| 5,487,741 A | 1/1996 | Maruyama et al. |
| 5,702,447 A | 12/1997 | Walch |
| 5,755,800 A | 5/1998 | O'Neil |
| 5,766,255 A | 6/1998 | Slamin |
| 5,984,969 A | 11/1999 | Matthews |
| 6,005,018 A | 12/1999 | Cicierega |
| 6,093,188 A | 7/2000 | Murray |
| 6,200,321 B1 | 3/2001 | Orbay et al. |
| 6,228,119 B1 | 5/2001 | Ondrla |
| 6,273,892 B1 | 8/2001 | Orbay et al. |
| 6,364,881 B1 | 4/2002 | Apgar et al. |
| 6,406,495 B1 | 6/2002 | Schoch |
| 6,514,287 B2 | 2/2003 | Ondrla |
| 6,699,289 B2 | 3/2004 | Iannotti |
| 6,953,478 B2 | 10/2005 | Bouttens |
| 7,169,184 B2 | 1/2007 | Dalla Pria |
| 7,204,854 B2 | 4/2007 | Guederian |
| 7,235,106 B2 | 6/2007 | Daniels et al. |
| 7,329,284 B2 | 2/2008 | Maroney |
| 7,445,638 B2 | 11/2008 | Beguin et al. |
| 7,604,665 B2 | 10/2009 | Iannotti |
| 7,608,109 B2 | 10/2009 | Dalla Pria |
| 7,611,539 B2 | 11/2009 | Bouttens |
| 7,753,959 B2 | 7/2010 | Berelsman |
| 7,892,287 B2 | 2/2011 | Deffenbaugh |
| 7,896,886 B2 | 3/2011 | Orbay et al. |
| 7,922,769 B2 | 4/2011 | Deffenbaugh |
| 8,007,538 B2 | 8/2011 | Gunther |
| 8,048,165 B2 | 11/2011 | Isch |
| 2004/0162619 A1 | 8/2004 | Baylock |
| 2005/0049709 A1 | 3/2005 | Tornier |
| 2005/0060039 A1 | 3/2005 | Cyprien |
| 2005/0192578 A1 | 9/2005 | Horst |
| 2005/0261775 A1 | 11/2005 | Baum |
| 2005/0278030 A1 | 12/2005 | Tornier |
| 2006/0074430 A1* | 4/2006 | Deffenbaugh et al. ......... 606/87 |
| 2006/0200248 A1 | 9/2006 | Beguin |
| 2006/0235407 A1 | 10/2006 | Wang et al. |
| 2006/0276905 A1 | 12/2006 | Calamel |
| 2007/0021838 A1 | 1/2007 | Dugas |
| 2007/0038302 A1 | 2/2007 | Shultz |
| 2007/0055380 A1 | 3/2007 | Berelsman |
| 2007/0142917 A1 | 6/2007 | Roche |
| 2007/0156246 A1 | 7/2007 | Meswania |
| 2007/0179624 A1 | 8/2007 | Stone |
| 2007/0225817 A1 | 9/2007 | Reubelt |
| 2007/0244563 A1 | 10/2007 | Roche |
| 2007/0260321 A1 | 11/2007 | Stchur |
| 2007/0270885 A1 | 11/2007 | Partin |
| 2008/0015589 A1 | 1/2008 | Hack |
| 2008/0109000 A1 | 5/2008 | Maroney |
| 2008/0208348 A1 | 8/2008 | Fitz |
| 2008/0243191 A1 | 10/2008 | Tipirneni et al. |
| 2009/0149961 A1 | 6/2009 | Dallmann |
| 2009/0164021 A1 | 6/2009 | Dallmann |
| 2009/0192621 A1 | 7/2009 | Winslow |
| 2009/0281630 A1 | 11/2009 | Delince |
| 2009/0292364 A1 | 11/2009 | Linares |
| 2010/0069966 A1 | 3/2010 | Castaneda et al. |
| 2010/0070044 A1 | 3/2010 | Maroney |
| 2010/0114326 A1 | 5/2010 | Winslow |
| 2010/0125336 A1 | 5/2010 | Johnson |
| 2010/0129138 A1* | 5/2010 | Lariviere ......................... 403/22 |
| 2010/0161065 A1 | 6/2010 | Williams, Jr. |
| 2010/0161066 A1 | 6/2010 | Iannotti |
| 2010/0217328 A1 | 8/2010 | Terrill et al. |
| 2010/0217399 A1 | 8/2010 | Groh |
| 2010/0222886 A1 | 9/2010 | Wiley |
| 2010/0228352 A1 | 9/2010 | Robert |
| 2010/0274359 A1 | 10/2010 | Brunnarius |
| 2011/0106266 A1 | 5/2011 | Schwyzer |
| 2011/0112651 A1 | 5/2011 | Baylock |
| 2011/0137424 A1 | 6/2011 | Lappin |
| 2011/0144758 A1 | 6/2011 | Deffenbaugh |
| 2011/0152946 A1 | 6/2011 | Frigg et al. |
| 2013/0090695 A1 | 4/2013 | Bernstein et al. |

FOREIGN PATENT DOCUMENTS

| | | |
|---|---|---|
| EP | 0339530 | 11/1989 |
| EP | 1488764 A1 | 12/2004 |
| EP | 1607067 A1 | 12/2005 |
| EP | 1782764 A2 | 5/2007 |
| EP | WO2007134691 | 11/2007 |
| EP | 1656910 | 9/2008 |
| EP | 1980221 | 10/2008 |
| FR | 2855743 A1 | 12/2004 |
| WO | WO9309733 | 5/1993 |
| WO | WO2008040408 | 4/2008 |
| WO | WO 2009/092830 A1 | 7/2009 |
| WO | WO 2009/100310 A1 | 8/2009 |

OTHER PUBLICATIONS

Jones, Geary C.; In-Vitro Evaluation of ta Polyurethane Compliant LA, Proc. IMechE vol. 224 Part H: J. Engineering in Medicine (2010) pp. 551-563.

Kasten, P.; Mid-Term Survivorship Analysis of a shoulder Replacement with a Keeled Glenoid and a Modern Cementing Technique, Journal of Bone and Joint Surgery (BR) Mar. (2010) vol. 92-B, No. 387-392.

Sharma, Gulshan B.; Effect of Glenoid Prosthesis Design on Glenoid Bone Remodeling: Adaptive Finite Element based Simulation. Journal of Biomechanics 43(2010) 1653-1659.

Throckmorton, Thomas W.; Pegged Versus Keeled Glenoid Components in Total Shoulder Arthroplasty, Journal of Shoulder and Elbow Surgery (2010) 19, 726-733.

(56) References Cited

OTHER PUBLICATIONS

International Preliminary Report on Patentability and Written Opinion for International Application No. PCT/US2012/024035, dated Jun. 10, 2014 (6 pages).
International Preliminary Report on Patentability and Written Opinion for International Application No. PCT/US2012/068605, dated Jun. 10, 2014 (6 pages).
International Search Report for International Application No. PCT/US2012/024035, dated Aug. 7, 2012 (2 pages).
International Search Report for International Application No. PCT/US2012/068605, dated Mar. 20, 2013 (3 pages).
Patent Examination Report No. 1 for Australian Application No. 2012321093, dated Feb. 26, 2014 (3 pages).
Patent Examination Report No. 2 for Australian Application No. 2012321093, dated Apr. 11, 2015 (3 pages).
Acumed Surgical Technique Brochure MHS00_01_A_11_2008.
Medartis Hand Webpage Oct. 6, 2011.
Medartis Hand 1.2/1.5 Product Page (Webpage) Oct. 7, 2011.
Osteomed M3-X Extremity Fixation System Webpage Oct. 7, 2011.
SBI Product Brochure Universal hand System MKT 30320 Rev. A Feb. 2006.
Stryker Product Brochure Stryker hand Plating System May 2011.
Synthes Product Brochure Modular Mini Fragment LCP System. 17545-E (2007).

* cited by examiner

SHOULDER ARTHROPLASTY

CROSS REFERENCE TO RELATED APPLICATIONS

This application claims the benefit of:

U.S. application Ser. No. 61/604,391, filed Feb. 28, 2012, entitled GLENOID AUGMENT PREPARATION INSTRUMENT;

U.S. application Ser. No. 61/615,560, filed Mar. 26, 2012, entitled SHOULDER GLENOID MODULAR ATTACHMENT; and U.S. application Ser. No. 61/701,484, filed Sep. 14, 2012, entitled SHOULDER ARTHROPLASTY.

This application is also a continuation-in-part of U.S. application Ser. No. 13/367,165, filed Feb. 6, 2012, entitled GLENOID VAULT FIXATION.

U.S. application Ser. No. 13/367,165 claims the benefit of:

U.S. application Ser. No. 61/568,530, filed Dec. 8, 2011, entitled GLENOID VAULT FIXATION; and is also a continuation-in-part of:

U.S. application Ser. No. 13/360,459, filed Jan. 27, 2012, entitled GLENOID VAULT FIXATION, which is pending.

U.S. application Ser. No. 13/360,459 claims the benefit of:

U.S. application Ser. No. 61/568,530, filed Dec. 8, 2011, entitled GLENOID VAULT FIXATION.

The above documents are incorporated herein by reference in their entirety.

BACKGROUND

The present disclosure relates to shoulder repair and revision surgery. More accurately, the present disclosure relates to a shoulder prosthetic and more precisely to a glenoid or glenosphere vault system for repairing or revising a shoulder. It is contemplated that this system is applicable to shoulder and reverse shoulder repair. It is contemplated that the systems and methods set forth herein, or any adaptations, may be useful outside of and beyond shoulder repair and humerus repair.

One attribute of shoulder repair surgery is the limit of anatomical bone the patient has to provide for adequate repair and even more so with shoulder revision. The shoulder naturally only provides a limited amount of bone for the shoulder joint to function. When shoulder repair is needed it is often performed with large anchor devices embedded in what bone is available to allow for proper security of an articulating surface or glenosphere to attach to the anchor. These devices require a large removal of bone. Further revision surgery requires even greater bone loss as original anchors are removed and replaced with new anchors. There is a need to have a smaller footprint anchor without limiting the fixation of the articulating components. There is also a need to have the ability for revision shoulder repair without removal of the original anchors, solely replacing the articulating components.

BRIEF DESCRIPTION OF THE DRAWINGS

Various embodiments of the present system will now be discussed with reference to the appended drawings. It is appreciated that these drawings depict only typical examples of the present system and are therefore not to be considered limiting of the scope of the invention, as set forth in the appended claims.

FIG. 112 is a bottom perspective view of a guide platform;

FIG. 113 is a top view of the guide platform of FIG. 112;

FIG. 114 is a bottom perspective view of another guide platform;

FIG. 115 is a top view of the guide platform of FIG. 114;

FIG. 116 is a top view of another guide platform;

FIG. 117 is a side view of a guide platform engaging an SI broach/trial; and

FIG. 118 is a side view of the guide platform of FIG. 117 operatively assembled with the SI broach/trial and a bone removal instrument.

DETAILED DESCRIPTION

The present disclosure provides systems, apparatus, and methods for shoulder replacement, repair and revision. The systems and methods described herein may improve shoulder prosthetics for use in shoulder arthroplasty and revision surgeries and provide stronger attachment of prosthetics to bone.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, standard shoulder anatomical terms are employed with their ordinary and customary meanings.

Figure 1A:
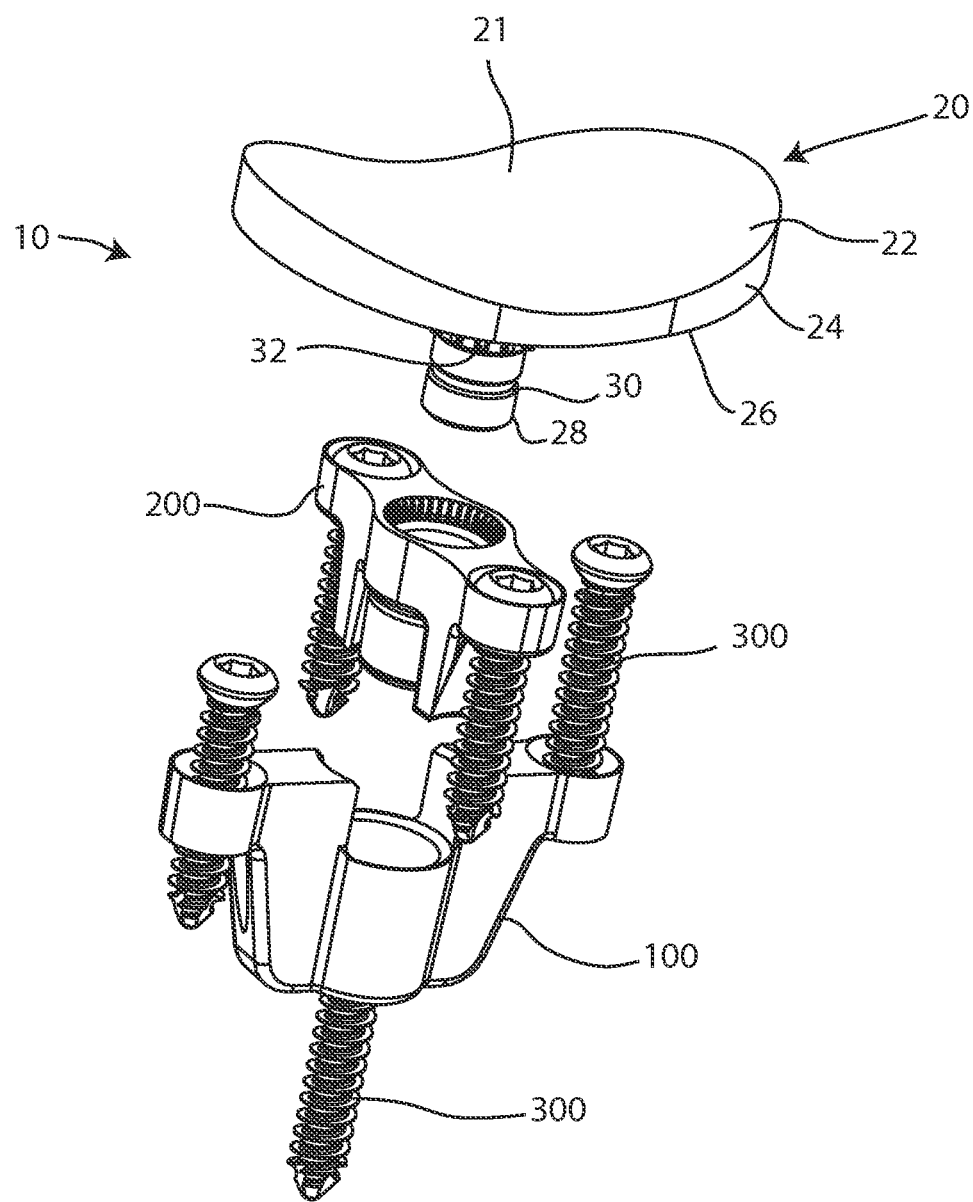
FIG. 1A is an exploded perspective view of a glenoid vault system with a superior-inferior (SI) component, an anterior-posterior (AP) component, an articulating component and screws.

Referring to FIG. 1A, a perspective view illustrates a glenoid vault system 10 that may be implanted into a shoulder. The glenoid vault system 10 includes an articulating component 20, which may also be referred to as a glenoid, anchoring components which include a superior-inferior (SI) or vertical component 100, an anterior-posterior (AP) or horizontal component 200 and anchors 300 which may be screws. The system 10 creates interaction the different components with the articulating component 20 engaging the AP component 200 and the AP component engaging the SI component 100. The screws 300 may pass through different portions of the AP component 200 and the SI component 100. The SI component 100 may have similar or identical features to SI components 5020 and 7102 described below. The AP component may share similar or identical features to AP component 7101 described below.

The articulating component 20 may include a body 21, an articulating surface 22 and a bone-facing surface 26. Articulating component 20 may include similar characteristics with glenoid component 7100 described below.

The body 21 may be shaped to mirror an anatomical shoulder. The articulating surface 22, which may also be referred to as a first surface, may be smooth or rough on a micro- or macroscopic level. The articulating surface 22 may be semi-spherical or concave, and may be peripherally surrounded by a wall 24, which may also be referred to as a side portion. The wall 24 may extend between the articulating surface 22 and the bone-facing surface 26, where the bone-facing surface 26 is opposite to the articulating surface 22. When inserted, the bone-facing surface 26 may rest against the shoulder bone.

Figure 1B:
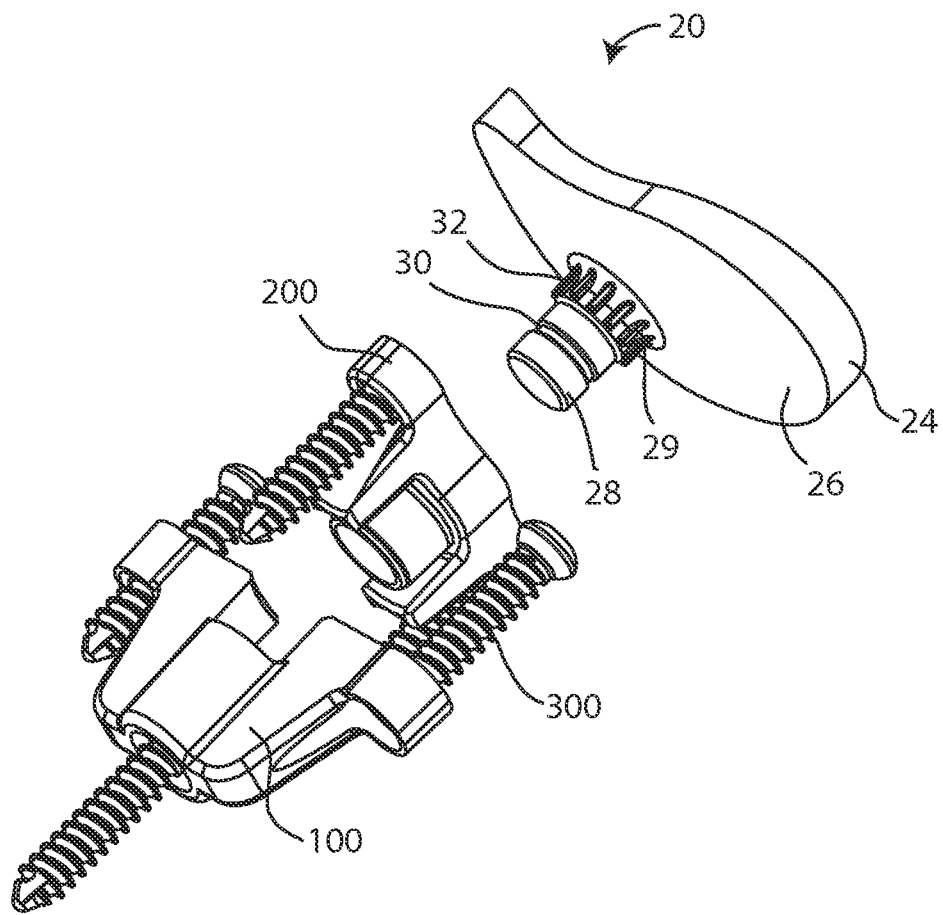
FIG. 1B is an exploded bottom perspective view of a glenoid vault system with a superior-inferior (SI) component, an anterior-posterior (AP) component, an articulating component and screws.

Referring to FIG. 1B, the bone-facing surface 26, which may also be referred to as a second surface, may include a post 28 extending outward from the bone-facing surface 26. The post 28 may be integral to the bone-facing surface 26, or may be separately formed from the body 21. The post 28 may extend substantially perpendicular to the articulating surface, and may be oriented such that it extends from a substantially central location of the bone-facing surface.

The post 28 may be substantially cylindrical and include a proximal shoulder portion 29, which may contact the bone-facing surface 26. The shoulder portion may include a plurality of notches 32, which may also be referred to as keels, teeth, blades, or leafs that extend along the length of the shoulder portion 29, and may be situated around the entire circumference of the post 28.

The post 28 may also include a circumferential groove or channel 30, which may also be referred to as a ring shaped cutout. The circumferential groove 30 may be located distal to the shoulder portion 29, and may extend continuously around the entire circumference of the post 28.

Figure 2:
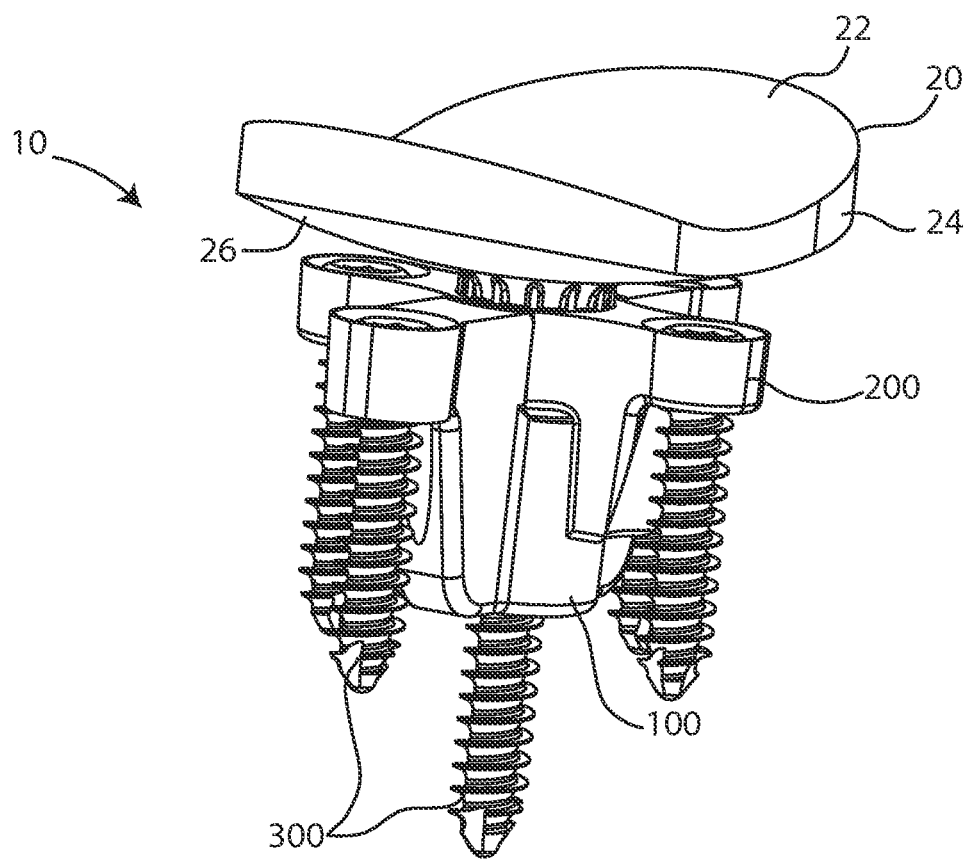
FIG. 2 is an assembled perspective view of the glenoid vault system of FIG. 1.
Figure 3:
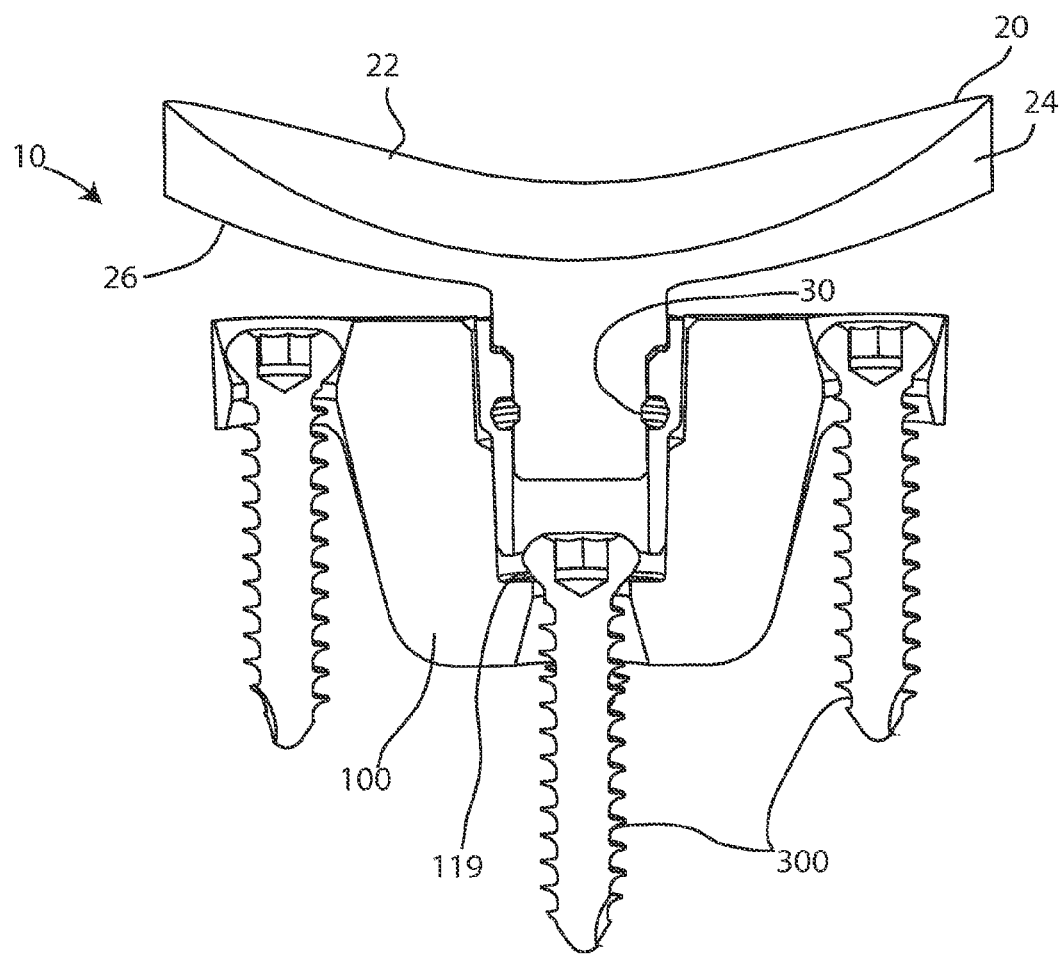
FIG. 3 is a cross sectional side view of the glenoid vault system of FIG. 1.
Figure 4:
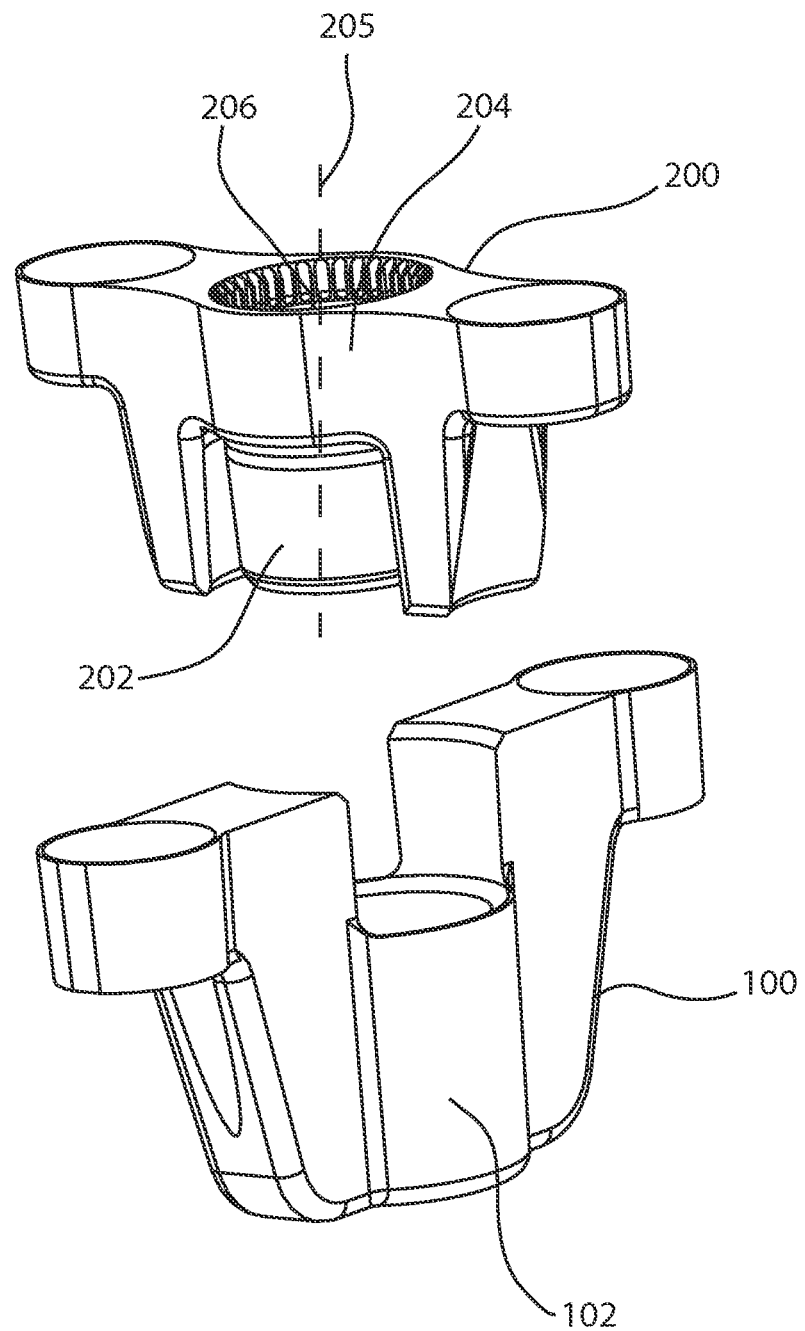
FIG. 4 is an exploded perspective view of the SI and AP components of FIG. 1.
Figure 5:
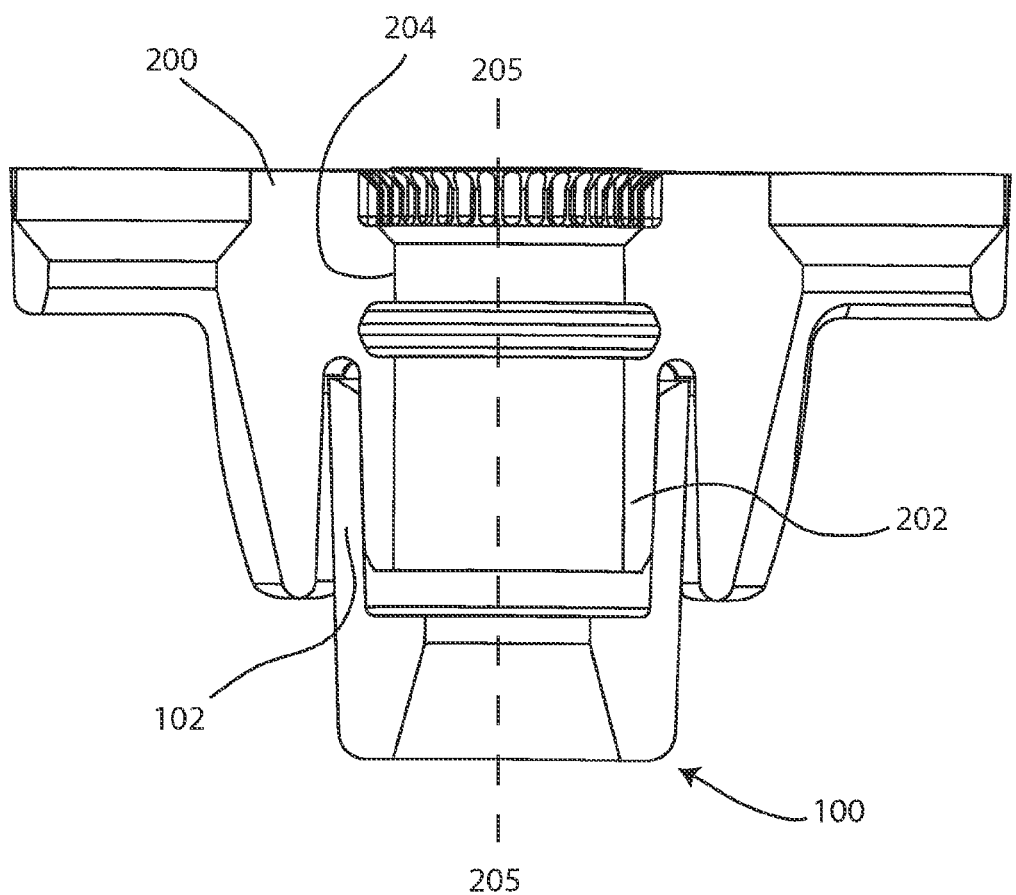
FIG. 5 is a cross-sectional side view of the assembled SI and AP components of FIG. 1.
Figure 6:
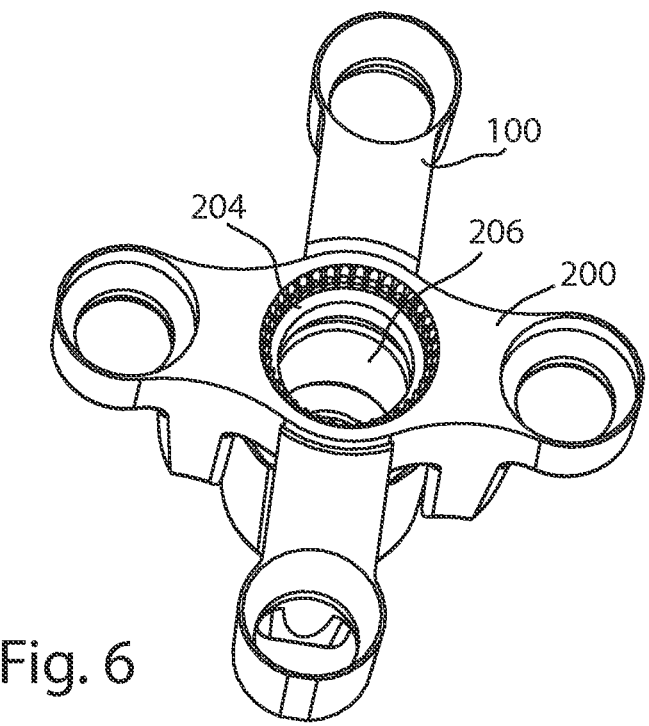
FIG. 6 is a perspective top view of the SI and AP components of FIG. 1.
Figure 7:
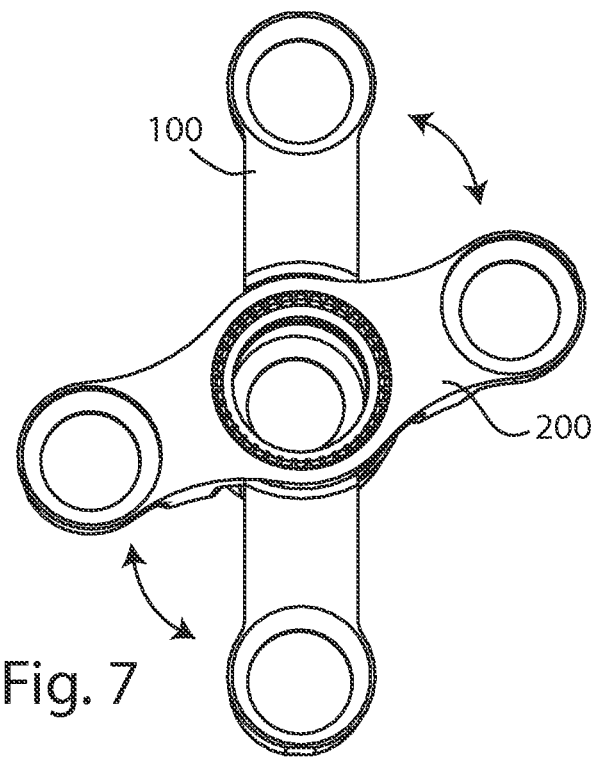
FIG. 7 is a top view of the SI and AP components of FIG. 1 with the AP component rotated to show it is rotatable about the center of the SI component.

Referring to FIGS. 2 and 3, the glenoid vault system 10 assembles with the SI component 100 being embedded in the bone (not shown). The AP component 200 may rotate about a portion of the SI component with at least a portion of the AP component 200 within the SI component 100 before the AP component 200 is secured to the bone.

The articulating component 20 may be lockably attached to the AP component 200 by inserting the post 28 into a portion of the AP component 200, and may be secured to the AP component 200 via a complementary fit of the circumferential groove 30 with a complementary feature on the AP component 200. The articulating component 20 may otherwise be secured to the AP component 200 by another locking means, such as a Morse taper (not shown).

The system is described in further detail herein.

Referring to FIGS. 4-7, the SI component 100 and AP component 200 interact through a body 102, which may be a central ring, of the SI component 100 and a tubular boss 202 of the AP component 200. The tubular boss 202 may also be referred to as a protruded portion. The body 102 may be a ring and the ring may be central to the SI component 100; however, the geometric component may be offset from the center as well and may be any shape including cylindrical or other polygonal shape. The tubular boss 202 extends distally from a cylindrical wall 204 defining a hole 206, wherein the hole may be a centralized or a central hole. The tubular boss 202 may slidably engage the central ring 102 allowing the AP component 200 to rotate about the central ring 102 of the SI component 100. The AP component 200 may be secured to the SI component 100 through a Morse taper. The SI and AP components 100, 200 form a cruciate when they are engaged. A cruciate means a cross shape or X shape.

Figure 8:
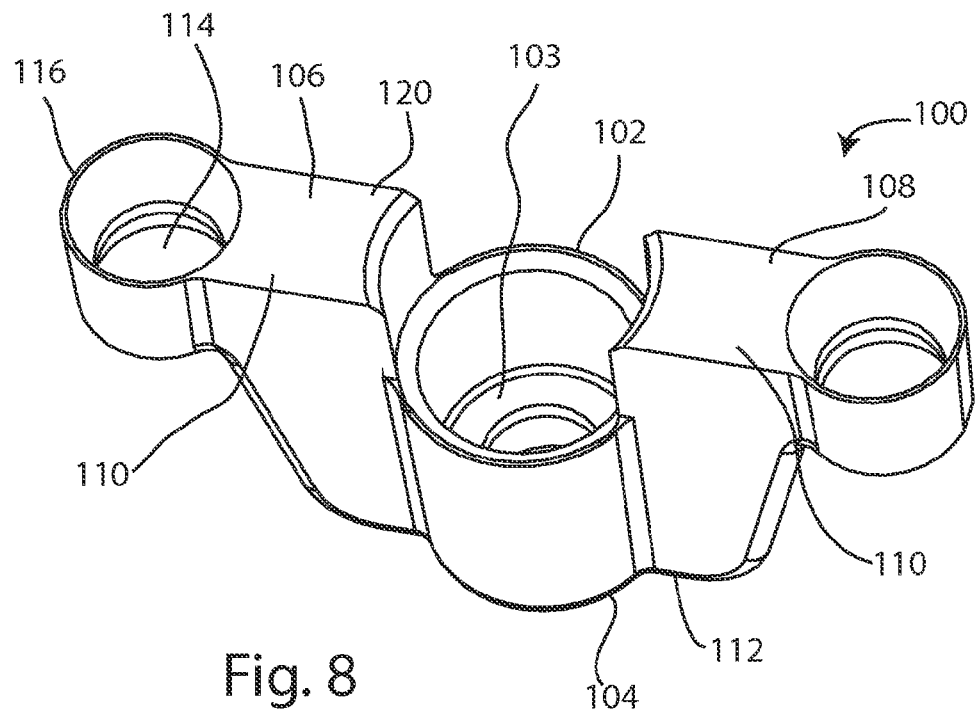
FIG. 8 is a perspective view of the SI component of FIG. 1.

Referring to FIG. 8, the SI component 100 may include a bore 103, which may be a central bore, extending at least partially through the body or central ring 102 in a longitudinal direction and may extend entirely through the central ring 102. The SI component includes a distal end 104 and may include two arms 106, 108 extending from the central ring 102. The arms 106,108 may be integral to the body 102, or may be separately formed. The arms 106, 108 include a proximal end 110 and a distal end 112 that is the same distal end 112, 104 of the SI component 100. Portions of the arms 106, 108 extend proximally from the central ring 102 giving the SI component 100 a V or U-shaped configuration for the SI component 100. The extension of the arms 106 proximally may be substantially parallel and substantially the same length, wherein the arms are coplanar; however the arms may differ in length slightly as well which may give the SI component 100 a J-shape, wherein the arms are not coplanar. The extension of the arms 106, 108 may be collinear and the arms 106, 108 may prove to be mirror images if a cross section is taken of the SI component 100. The portion of the arms 106, 108 toward the central ring 102 may cylindrically curve around the central ring 102 with the same degree of curvature as the central ring 102. The body of the SI component 100 may be longer than it is wide from a top view providing a narrow footprint when the SI component sits within the bone with the arms 106, 108 narrower than the central ring 102.

Figure 9:
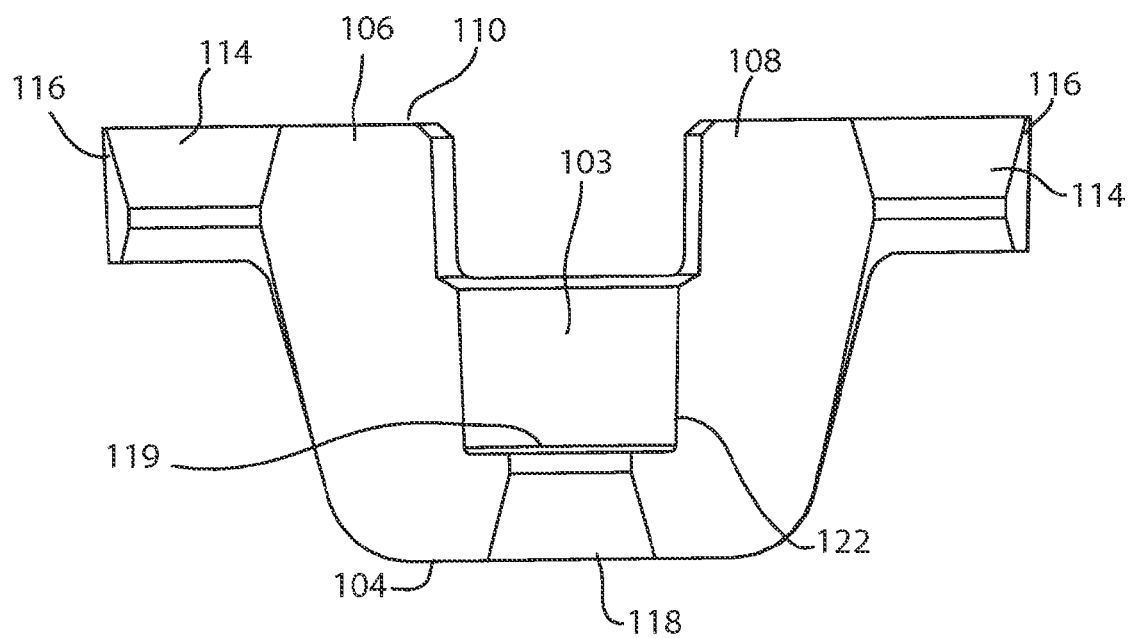
FIG. 9 is a cross-sectional side view of the SI component of FIG. 1.

The arm 106 may include an opening or bore 114 defined by a wall 116, which may be an arm ring, which may be cylindrical in shape, at the end of the arm 106. Bores 114 may also be referred to as lateral passages. The arm ring 116 may protrude from the arm 106 in substantially the same direction as the arm 106 extending from the central ring 102. The opening 114 may extend entirely through the arm ring 116 substantially parallel with the central bore 103. The opening 114 is substantially circular in cross section and configured to receive a screw 300. The opening 114 may include recesses, conical in shape, to guide the screw 300 into place in the SI component 100 as well as seat the screw 300 in its proper place. The opening 114 may be a double conical shape with the narrowest point seated toward the middle of the opening 114, the shape expanding outward toward either end of opening 114, as best seen in FIG. 9. The opening 114 may slidably or threadably receive the screws 300. The recesses in the openings 114 may allow for the heads of the screws 300 to sit flush with a proximal surface 120 at the proximal end 110 of the arms 106, 108 of the SI component 100. The arm 108 may include similar or identical features as arm 106, but extending in the opposite direction from the central ring 102.

The SI component 100 may be made from numerous different materials that include, but should not be limited to, titanium and alloys, cobalt-chrome and alloys, stainless steel, ceramic, tantalum, PEEK, PEAK, hydroxyapatite and biocompatible materials.

Referring to FIG. 9, the central ring 102 includes a larger cylindrical receiver 122 for receiving the tubular boss 202 of the AP component 200. The central ring 102 also includes a central opening 118 distal the cylindrical receiver 122. The central opening 118 may be conical in shape with the wider portion of the central opening toward the distal end 104. The proximal portion of the central opening 118 may include a seat 119, shaped to receive the head of a screw. One screw 300 may pass through the central bore 103, and the head of the screw may be captured on the seat 119, engaging the SI component 100 and locking it to the bone. The screw 300 may threadably or slidably engage the central bore 103.

A bone, wherein the bone may be a scapula, may be properly prepared by placing a guidewire on the bone. The bone is then reamed and a primary hole is drilled, the primary hole is drilled at size to allow the central ring 102 of the SI component 100 to fit within the primary hole. Secondary holes or pilot are drilled, sized, and shaped to accept other portions of the SI component. A cutting or punch instrument may be used to connect or bridge the primary and secondary holes. The bone is then broached for the near net shape of the SI component 100. An SI broach may be used as a trial implant. With the broach in the bone, or vault of the bone, the AP holes may be drilled to fit the exact size of the AP component 200. The same steps for the preparation of the SI component 100 are mimicked for the AP component 200 while the SI trial is in the bone, or vault of the bone. After proper size, shape and orientation are determined, the AP and SI trials are removed and replaced with the actual SI and AP components 100, 200, that can be secured to the bone using proper screws 300 or other anchors. The screws 300 may through the central bore 103 and the head of the screw 300 engages the SI component 100 through the conical shaped opening, securing the SI component to the bone. Additional screws may pass through the openings 114 for greater security of the SI component 100 to the bone. The AP component 200 may be further secured as well with screws that pass through holes 214 of the AP component 200

Figure 10:
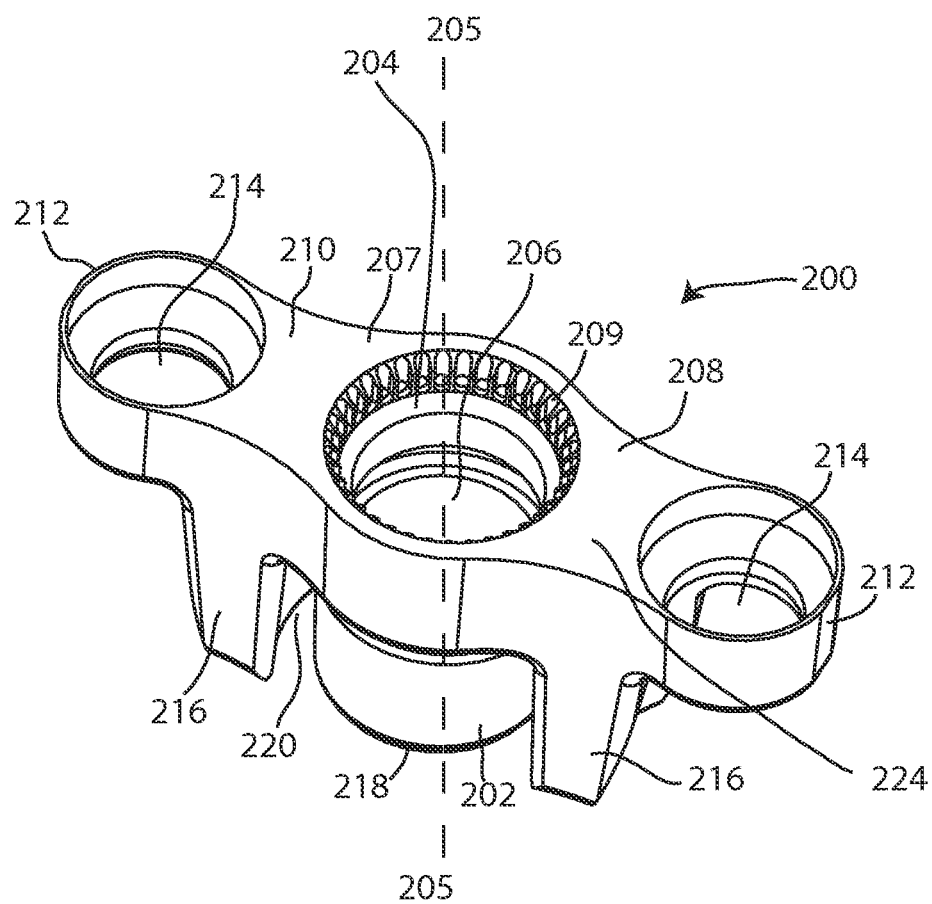
FIG. 10 is a perspective view of the AP component of FIG. 1.
Figure 11:
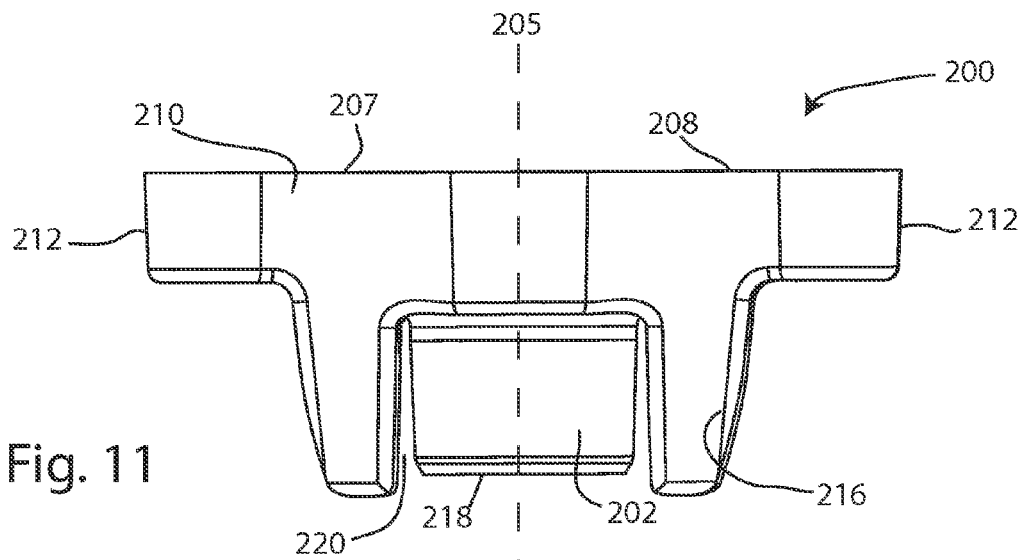
FIG. 11 is a side view of the AP component of FIG. 1.

Referring to FIGS. 10 and 11, the AP component 200 may include the central cylindrical wall 204 defining the central hole 206 extending entirely through the AP component with the central hole 206 passing into the tubular boss 202. The central hole 206 and tubular boss 202 may include a central axis 205 that extends through the center of the hole 206. The tubular boss 202 may be an extension of the central hole 206. The tubular boss 202 may be circumferentially smaller than the cylindrical wall 204 defining the central hole 206.

Figure 12:
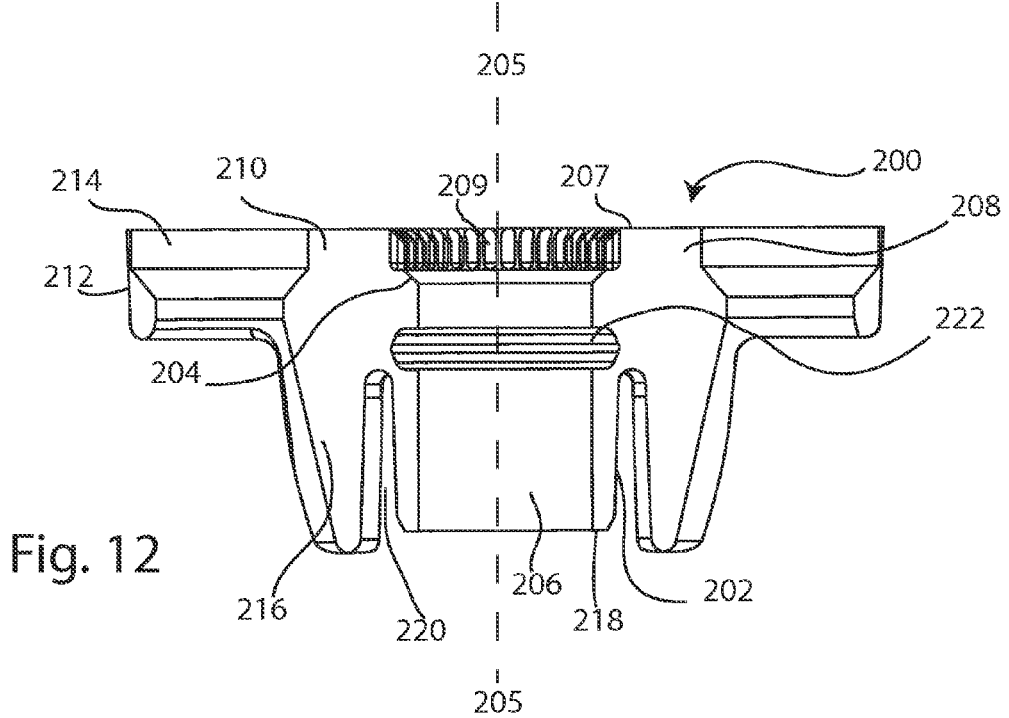
FIG. 12 is a cross-sectional side view of the AP component of FIG. 1.

The central hole 206, which may also be referred to as a first aperture, may be shaped to receive the post 28 of the articulating component 20. A proximal portion 207 of the central hole 206 may include a plurality of vertical grooves or channels 209 that are complimentary to the notches 32 on the shoulder portion 29 of the post 28. The grooves 209 may allow for rotational orientation of the articulating component 20 and may be cross-sectionally rounded or squared. Further, the central hole 206 may include a circumferential engagement ring 222, as illustrated in FIG. 12, that is distal to the plurality of grooves or channels 209, and proximal to the tubular boss 202. The engagement ring may have a complementary shape to the circumferential groove 30 on the post, and may protrude out from the central wall 204, extend toward the center of the central hole 206, or it may be a cut out within the central wall 204, extending away from the center of the central hole 206.

An alternate embodiment of an anti-rotation/rotational orientation feature which may take the place of the notches or grooves 209 may include splines (not shown) extending from a proximal surface 224 of either the AP or SI component 100, 200. The splines may engage crescent bosses (not shown) that extend from the bone facing surface 26 of the articulating component 20. The crescent bosses may include multiple holes for receiving the splines.

First and second AP arms 208, 210 extend away from the central hole at or toward the proximal end 206 of the AP component 200. The AP arms 208, 210 may be collinear with the first AP arm 208 extending in an opposite direction as the second AP arm 210. Each of the AP arms 208, 210 may be the same length; however, the AP arms 208, 210 may differ in length as well depending on the patient anatomy and what bone is available to secure the AP component 200 to. Similar to the SI component arms 106, 108 the AP arms 208, 210 each have arm walls 212, which may be AP arm rings. The AP arm rings 212 may protrude from the arms 208, 210 in substantially the same direction as the arms 208, 210 extending from the cylindrical wall 204. The AP arm rings 212 include holes 214 extending entirely through the AP arm rings. The holes 214 may also be referred to as AP lateral passages. The holes 214 may be substantially cylindrical in shape, to allow for passage of the screws 300 to aid in securing the AP component 200 to the bone.

One or more keels 216 may extend distally from the AP arms toward a distal end 218 of the tubular boss 202. The keels 216 may be used for bone purchase. The keels 216 may extend beyond the distal end 218 of the tubular boss. keels 216 may cylindrically curve around the tubular boss 202 with the same degree of curvature as the tubular boss 202. The keels 216 may extend substantially parallel to one another creating a slot 220 between each one of the keels 216 and the tubular boss 202. The slot 220 receives the central ring 102 of the SI component 100. The keels 216 may provide rotational stops when the keels engage the arms 106, 108 of the SI component 100 preventing any further rotations of the AP component 200. The body of the AP component 200 may be longer than it is wide providing a narrow footprint when the AP component 200 engages the SI component 100 and resides in the bone.

To engage the articulating component 20 with the AP component 200, the post 28 on the bone-facing surface 26 of the articulating component 20 may be at least partially inserted into the central hole 206 of the AP component 200, until the circumferential groove 30 on the post engages with the engagement ring 222 in the central hole 206. Once the post 28 has been inserted into the central hole 206, the complementary fit of the engagement ring 222 with the circumferential groove 30 serves to reversibly lock axial movement of the articulating component 20 with respect to the AP component 200. The interaction of the engagement ring 222 with the circumferential groove 30 may be a snap fit or a seal or another locking mechanism. Further, the plurality of grooves 209 on the central hole 206 may capture the proximal notches, which may restrict axial rotation about the central axis 205 of the central hole 206.

The holes 214 in the arms 208, 210 may taper or recess from the proximal end 207 toward a distal end providing guidance for the screws and engagement with the screw heads. The holes 214 may threadably or slidably receive the screws 300 and the recesses or tapers may allow the screw head to sit flush with a proximal surface 224 at the proximal end 207 of the AP component 200.

The AP component 200 may be made from numerous different materials, which include, but should not be limited to, titanium and alloys, cobalt-chrome and alloys, stainless steel, ceramic, tantalum, hydroxyapatite and biocompatible materials.

One method of implanting the system 10 includes preparing the bone as previously described and implanting the SI component 100 into the bone with appropriate screws 300. The AP component 200 may properly engage the SI component 100 with the tubular boss 202 slidably engaging the central ring 102, wherein a central axis of the tubular boss 205 may be axially aligned with a central axis of the central ring 102. The AP component 200 is carefully placed at a proper angle, which may be predetermined, within the best available bone to provide greater security. Screws 300 may pass through the holes 214 to secure the AP component 200 to the bone. The articulating component 20 may engage the AP component 200 after it the AP component 200 is properly placed and positioned within the SI component 100 and the bone. The order in which the components engage one another is not restrictive and separate order may be established such as engaging the SI and AP component 100, 200 prior to implanting into the bone.

Figure 13A:
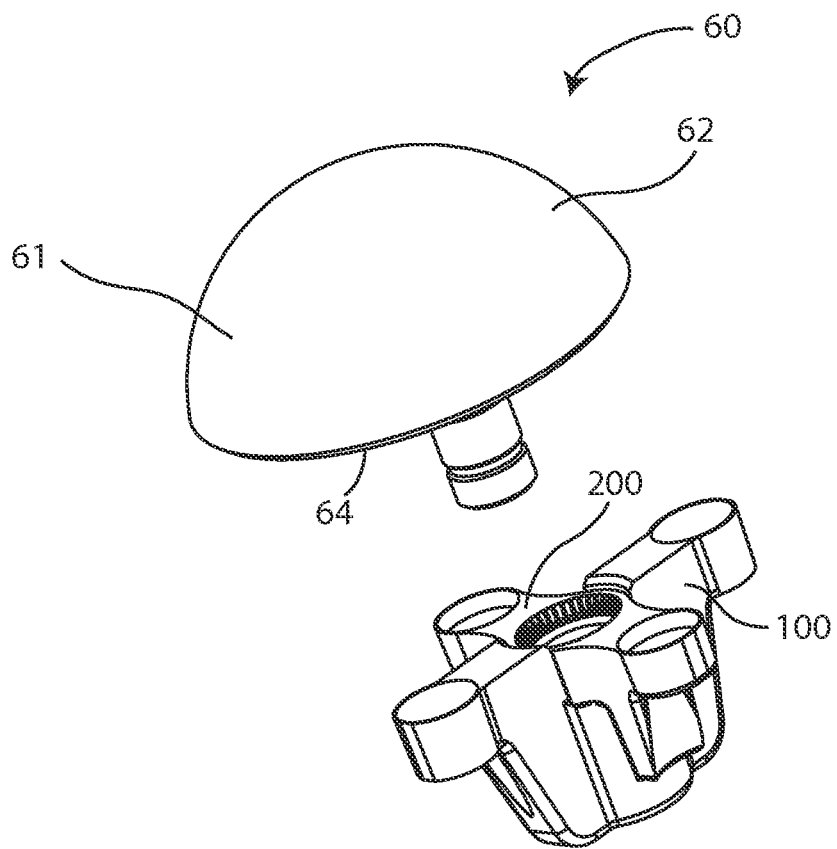
FIG. 13A is a partially exploded perspective view of the SI and AP components of FIG. 1 and a glenosphere.
Figure 13B:
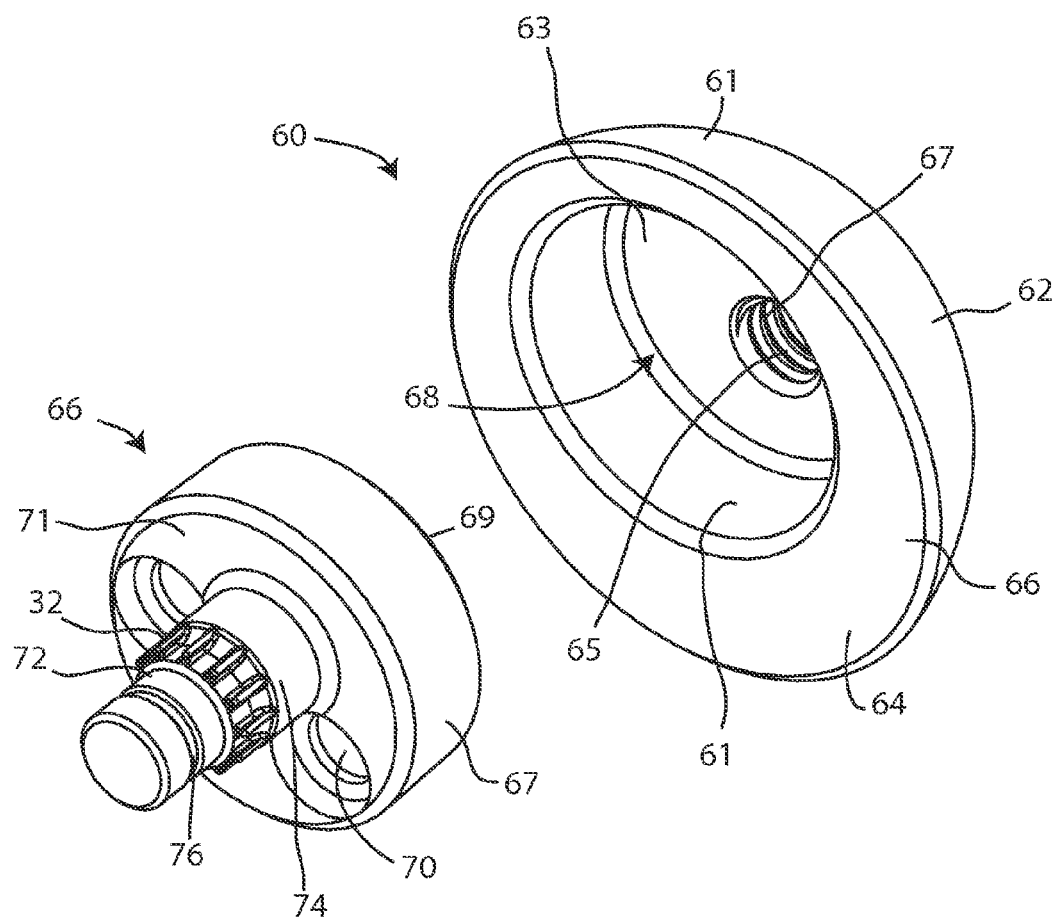
FIG. 13B is a bottom partially exploded perspective view of a glenosphere and a metaglene.

Referring to FIGS. 13A-13B, a glenosphere 60 may replace or be used instead of an articulating component 20. The glenosphere 60 may be used for a reverse shoulder arthroplasty but may engage the AP component 200 in the same manner as the articulating component 20 Referring to FIG. 13A, a glenosphere 60 is shown in relation to an AP-SI complex, wherein a post extending from a distal portion of the glenosphere is shaped to be received in the central hole 206 of the AP component.

The glenosphere 60 may include a body 61, an articulating surface 62 and a distal surface, bone-facing surface 64. The articulating surface 62 may be substantially semi-spherical or domed shape and may be smooth or rough on a micro- or macro scale. The articulating surface may also include an aperture 65 at or near the apex of the dome 62. The radius of curvature of the domed articulating surface 62 may vary to accommodate various patient anatomies.

Referring to FIG. 13B, the bone facing surface 64 is substantially circular, and intersects the dome-shaped articulating surface at all points along its circumference. The bone facing surface 64 may also include a substantially circular recessed portion 68 or dome cutout, which may be offset from the center of the bone facing surface 64. The recessed portion 68 may otherwise be oval or polygonally shaped. The recessed portion 68 may be shaped to receive a metaglene component 66. The recessed portion 68 may be defined by a circumferential wall 61 and include a ceiling surface 63. The aperture 65 may extend entirely from the articulating surface 62 to intersect the ceiling surface 63 of the recessed portion.

Figure 13C:
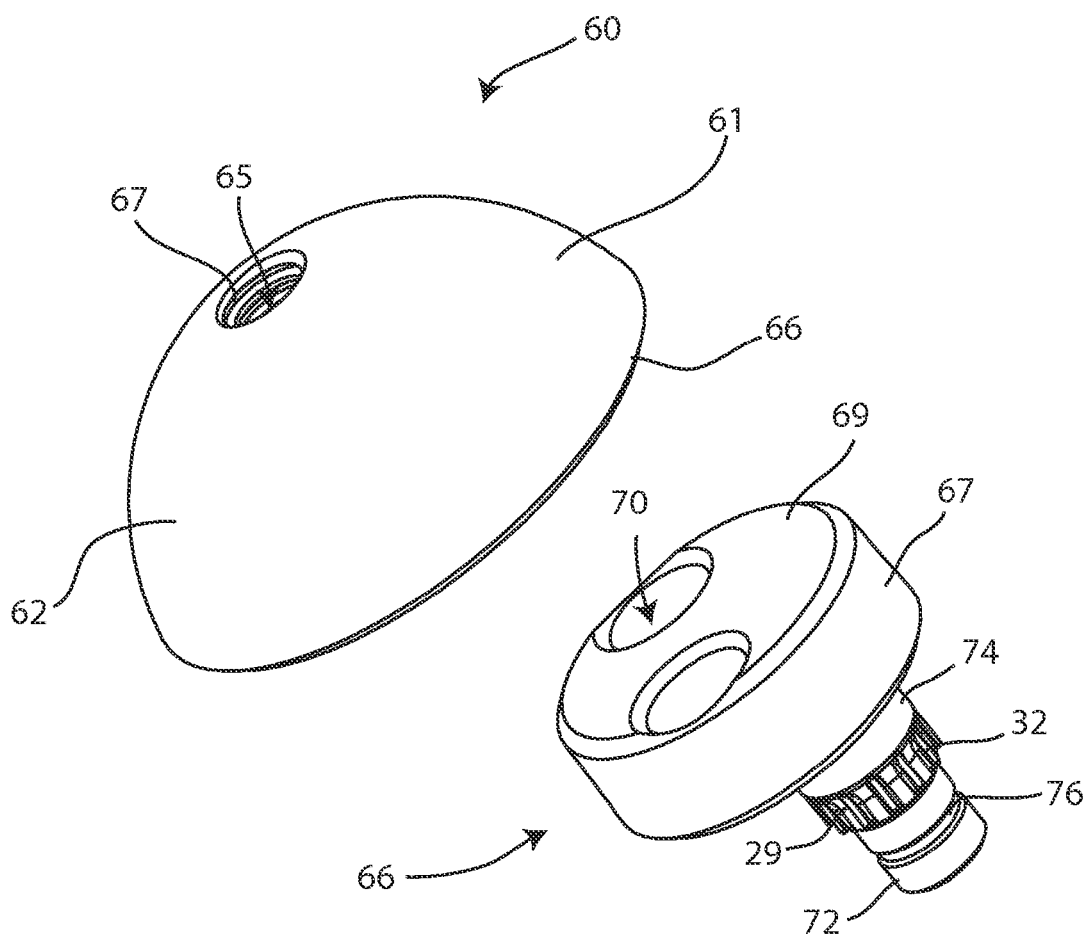
FIG. 13C is a top perspective exploded view of the glenosphere and a metaglene.

Referring to FIG. 13C, the aperture 65 may include a threaded portion 67 to engage a threaded instrument that may be used for insertion or removal of the glenosphere from an AP-SI complex that has been inserted into the bone as described above.

As illustrated in FIGS. 13B and 13C, the metaglene component 66 may be formed separately from the glenosphere 60, and may be substantially disc-shaped or stoutly cylindrical. Metaglene component may have similar or identical features to metaglene component 7170 described below.

Alternatively, the metaglene component 66 may be integrally formed with the body 61 of the glenosphere 66. The metaglene component 66 may otherwise by oval or polygonally shaped. Metaglene component 66 may include a body 67, a first, glenosphere-facing surface 69 and a distal surface 71.

The distal surface 71 of metaglene component 66 may include a post 72 that extends substantially perpendicularly away from the distal surface 71, which may include features similar to post 28 on the articulating component 20 described previously, such as a shoulder portion 29 with a plurality of notches 32, and a circumferential groove 76 shaped to lockably engage a complementary engagement ring 222 in the central hole of the AP-component. Additionally, the post 72 may include a step 74 that extends between the shoulder portion 29 and the distal surface 71. Alternatively as illustrated in FIG. 13D, the shoulder portion may be smooth, and include no engagement features such as notches, to allow the metaglene to rotate axially with respect to the central axis 205 of the central hole 206 of the AP-component 200.

The metaglene may also include at least one metaglene hole 70 that passes entirely through the body, and may be shaped to receive screws to fixate the metaglene to the bone. The metaglene holes 70 may also provide a place for securing an augment to the glenosphere.

Figure 13D:
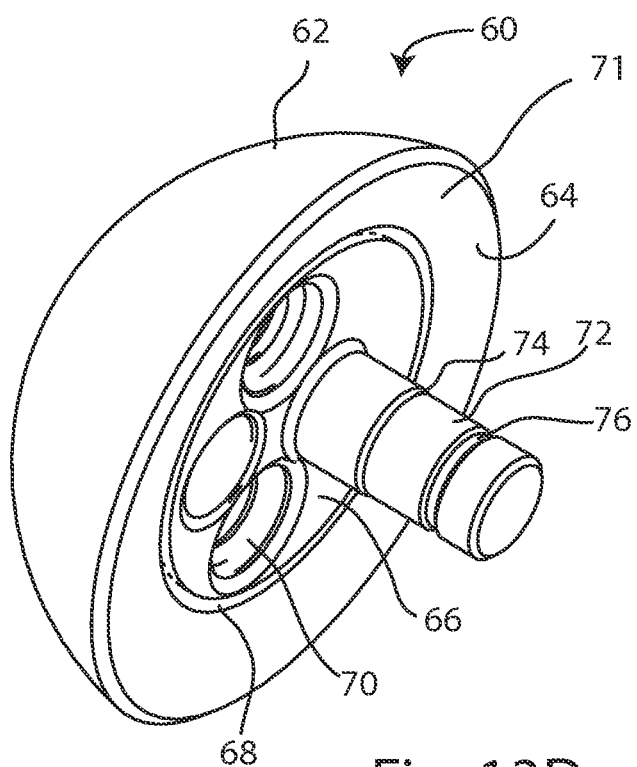
FIG. 13D is a bottom perspective, assembled view of the glenosphere of FIG. 13A.

As best seen in FIG. 13D, the metaglene 66 is shaped to be received by the recessed portion 68, and may engage the recessed portion 68 through a Morse-taper. The metaglene 66 may also be attached to the glenosphere via a press or snap fit. After the metaglene 66 is inserted into the recessed portion 68 of the glenosphere 60, the distal surface of the metaglene component 66 may sit flush with the bone facing surface 64 of the glenosphere 60.

Figure 14A:
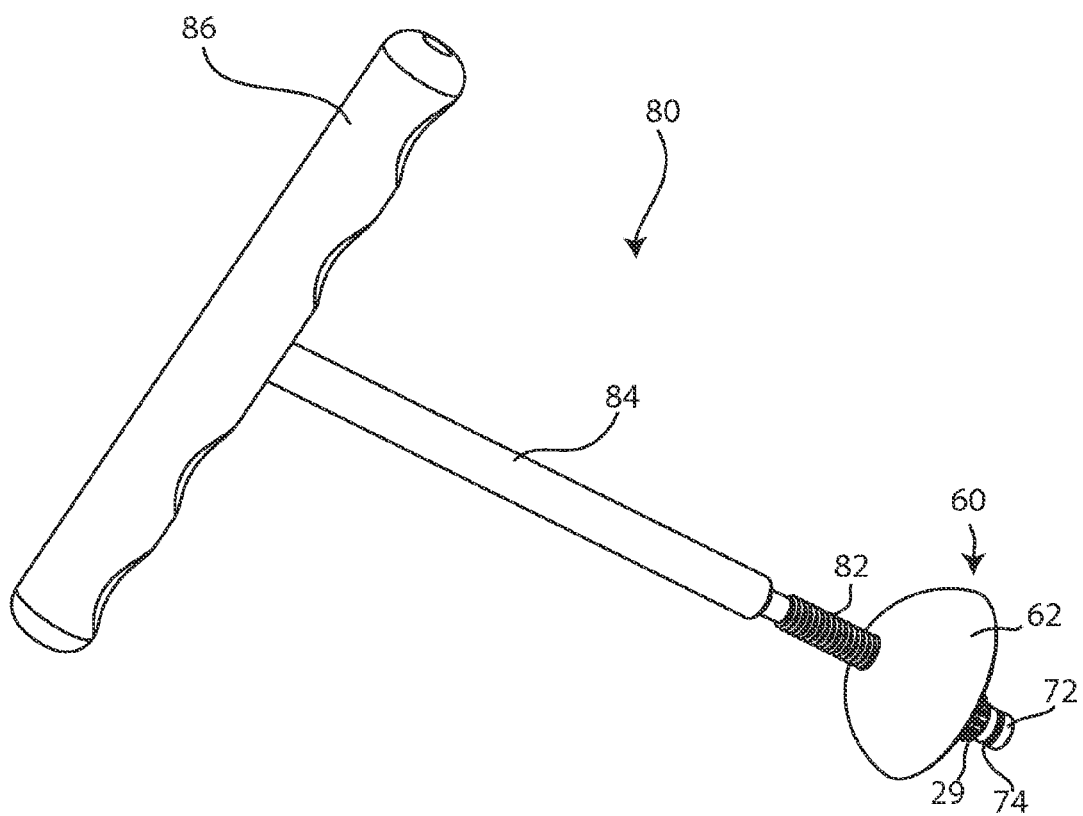
FIG. 14A is a perspective view of the glenosphere of FIG. 13D engaged with an actuating instrument with a handle, rod and threaded portion.
Figure 14B:
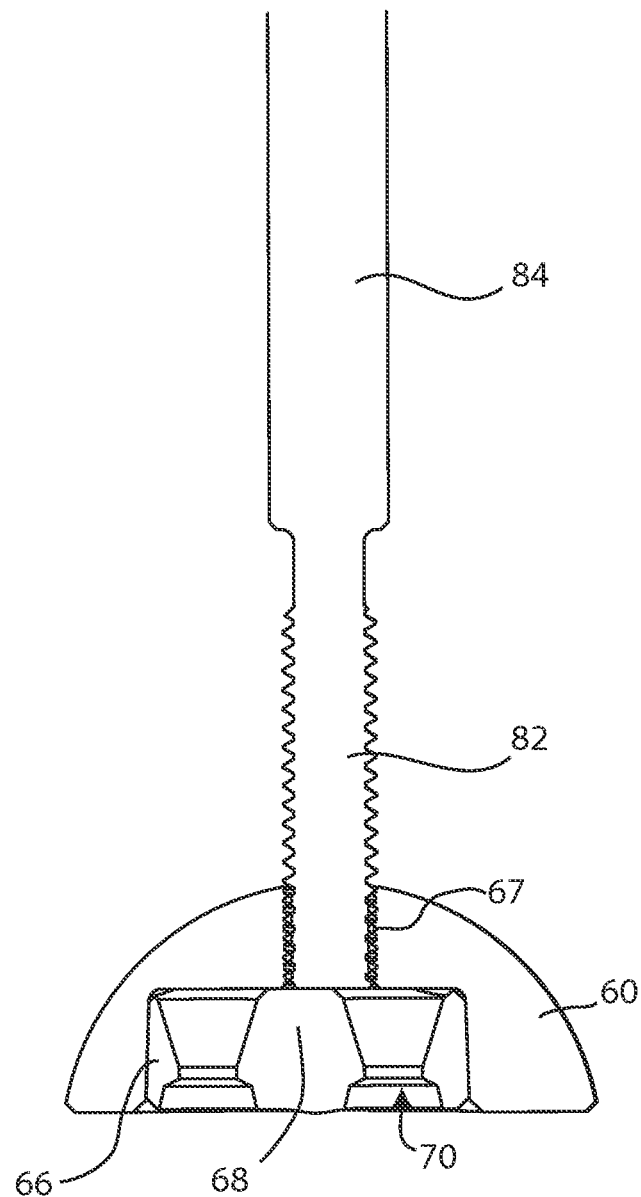
FIG. 14B is a cross section of the glenosphere of FIG. 13D engaged with the actuating instrument of FIG. 14A.

Referring to FIGS. 14A and 14B, the glenosphere 60 is shown engaged with an actuating instrument 80, which includes a threaded distal portion 82, and elongated intermediate portion 84, which may be rod-shaped and a proximal handle portion 86. The handle 86 may extend substantially perpendicular to the rod 84. The instrument 80 engages with the threads 67 of the aperture 65 located at the apex of the domed articulating surface 62.

To secure the glenosphere to the AP component, the post 72 may be partially inserted into the central hole 206 of the AP component. The instrument 80 may then be used to advance the glenosphere 60 and attached metaglene 66 component distally until the circumferential groove 30 engages the engagement ring 222 and a the glenosphere 60 becomes reversibly locked to the AP component 200. The instrument 80 may act to advance the glenosphere 60 and metaglene 66 construct by engaging the distal threaded portion 82 with the threaded portion 67 of the aperture 65 and turning the handle 86 in a first direction.

The instrument 80 may also be used to separate a glenosphere-metaglene construct that has been inserted into an AP-component 200, for example, to replace the glenosphere 60 with an articulating component 20. The threaded distal portion 82 of the instrument 80 may engage the threaded portion 67 of the aperture 65, and the handle 86 may be turned in a second direction that is opposite of the first direction. As the handle 86 is turned in the second direction, an upward force is applied against the threads 67 in the aperture, thus creating a separating force on the glenosphere-metaglene construct. The upward force may be great enough to overcome the snap fit lock of the engagement ring 222 with the circumferential groove 30 on the post 78, and the glenosphere may be gently removed from the AP component.

Alternatively, the actuating instrument 80 may be used to remove only the glenosphere component, leaving the metaglene component to be accessed by the surgeon for further removal. The threaded portion 82 of the actuating instrument 80 may engage the threaded portion 67 of the aperture such that as the handle 86 is turned in a first direction, the instrument 80 moves distally in the aperture 65 until it contacts the glenosphere-facing surface 69 of the metaglene 66. As the handle turns 86 in the first direction, a sufficient force is applied against the glenosphere-facing surface 69 of the metaglene to "pop off" the domed glenosphere component 60, overcoming the Morse-taper fit and releasing the glenosphere component, leaving only the metaglene 66 component attached to the AP component 200. The metaglene 66 can then also be removed by pulling upwards to release the engagement ring 222 from the circumferential groove 30, thus releasing the post 28 from the central hole 206.

It can be best seen in FIG. 14B that the recessed portion 68 and the attached metaglene 66 are offset from the center of the distal face 64. The offset may better allow a surgeon the ability to "dial" the metaglene 66 to the necessary anatomic position for the glenosphere 60. This is of particular importance in reverse total shoulder arthroplasty, where a glenoid may be inserted in a position that is not sufficiently anatomically inferior. Upon revision (removal of the glenoid and replacement with a glenosphere), scapular notching may occur, causing much pain and further shoulder degradation to the patient. By modularizing the metaglene component 66 and offsetting the placement of the metaglene 66 within the glenosphere 60, a surgeon may be able to "lateralize" the joint by moving the glenosphere further away from the original joint line.

The glenosphere 60 and the articulating component 20 may engage the AP component 200 without removal of either the AP component 200 or the SI component 100 of the glenoid vault system 10. Revision surgery is done with greater ease because the components can be snapped in and out of the SI and AP anchors 100, 200 without removal of any more bone.

Figure 15A:
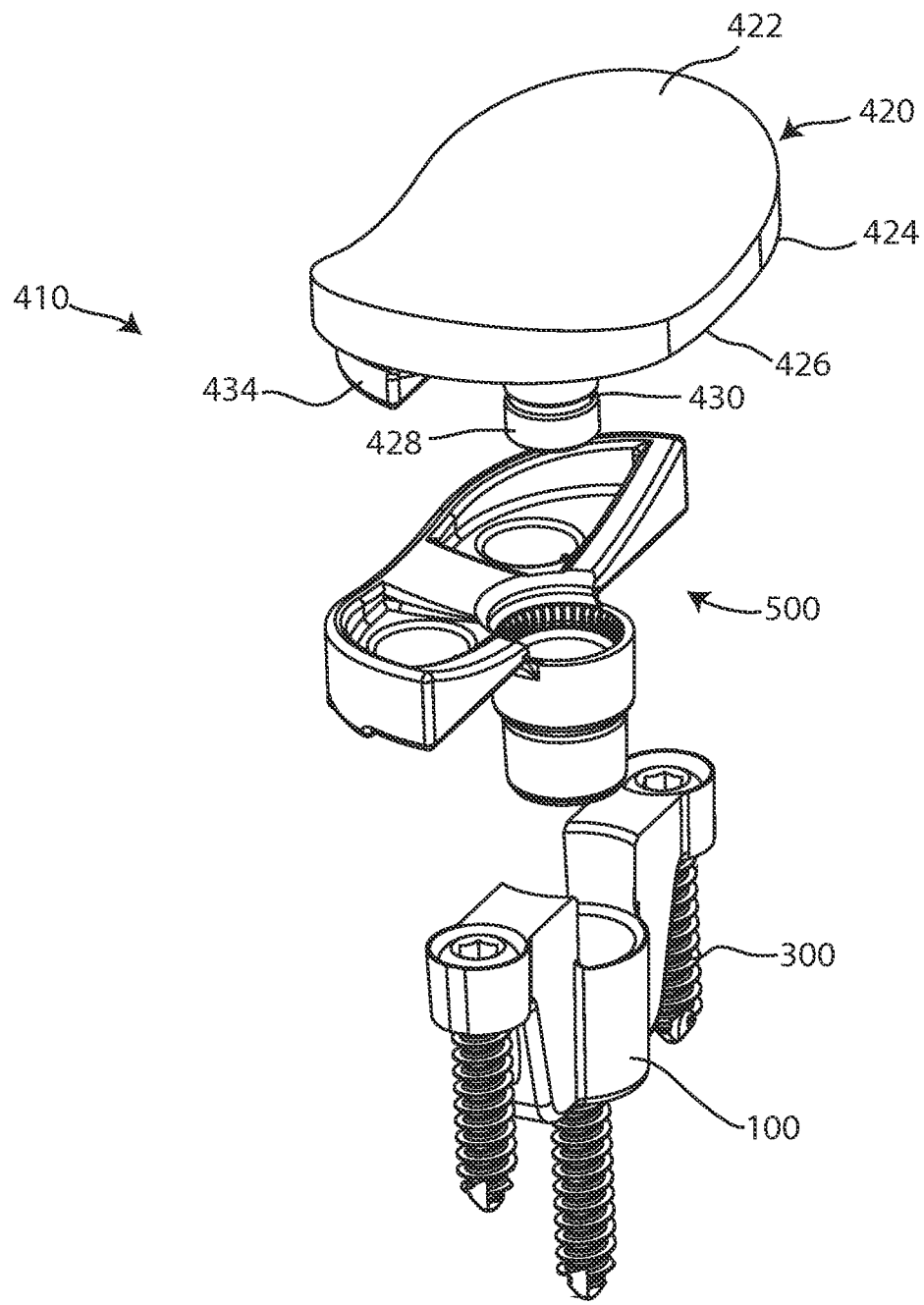
FIG. 15A is an exploded perspective view of a glenoid vault system with an SI component, an AP component with an augment, an articulating component and screws.
Figure 15B:
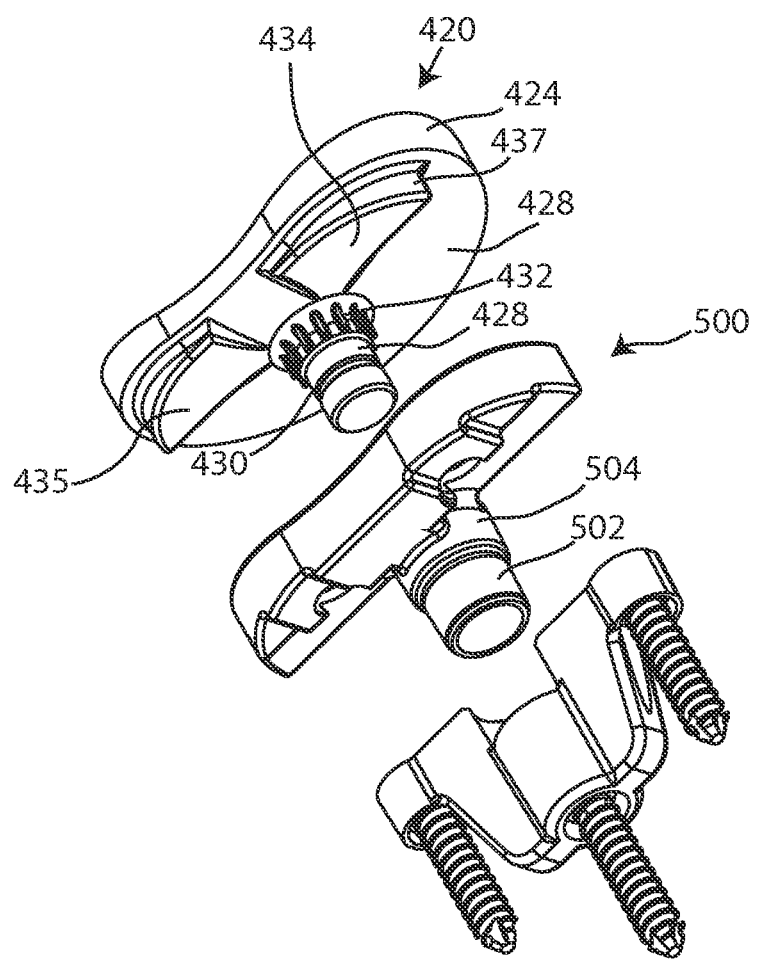
FIG. 15B is an exploded bottom view of a glenoid vault system with an SI component, and AP component with an augment, an articulating component and screws.
Figure 15C:
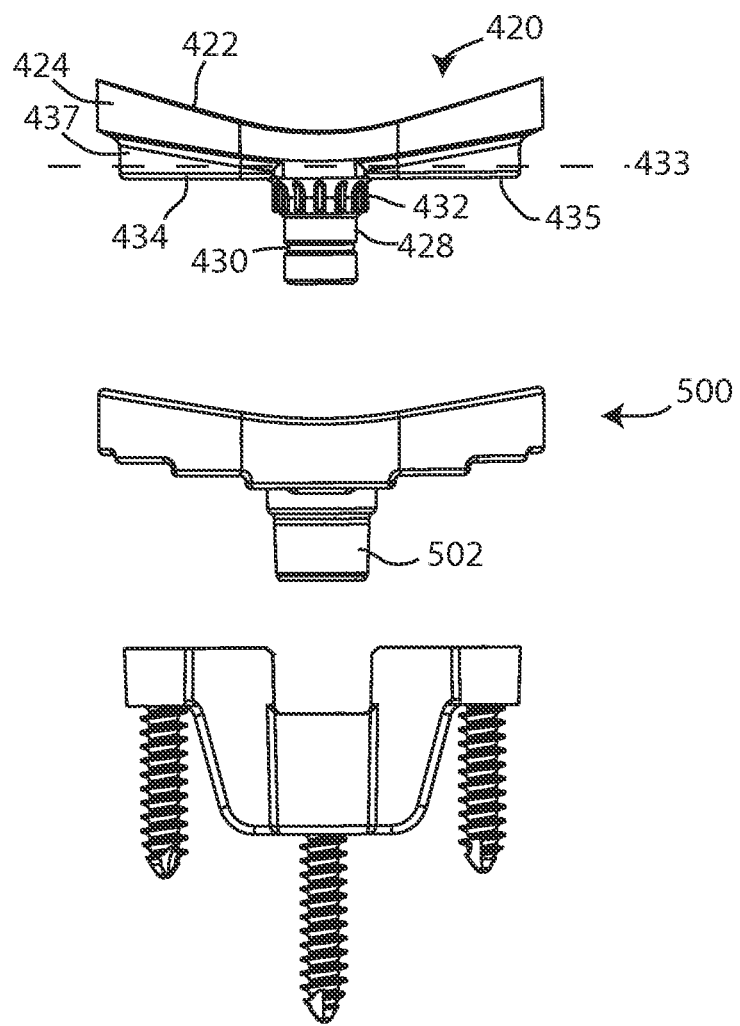
FIG. 15C is a side view of a glenoid vault system with an SI component, an AP component with an augment, an articulating component and screws.

Referring to FIGS. 15A-15C, an alternate embodiment of a glenoid vault system 410 includes an articulating member 420, an AP component 500 with an augment, the SI component 100 and the anchors or screws 300. The interaction between the different components is similar to the previous embodiment.

The articulating member 420 is substantially similar to the previously described embodiment of an articulating component 20. The articulating member 420 has a curvature shaped to mirror an anatomical shoulder with a semi-spherical or concave articulating surface 422 peripherally surrounded by a wall 424. The articulating component also includes a bone-facing surface 426 facing the opposite direction as the articulating surface 422 and a post 428 extending from the bone-facing surface 426 in a substantially central location of the bone-facing surface 426. The bone facing surface 426 may rest against the scapula. The post 428 may include a ring shaped cutout 430 toward the distal end of the post 428 and notches 432 toward the proximal end of the post 428. However, this embodiment of the articulating member 420 includes an augment 434 extending from the bone facing surface 426 separate from the post 428 and the augment 434 is not as long as the post 428. Augment 434 may be similar or identical to augment 5012 described below. It will be appreciated that in some instances or embodiments the augment 434 may extend or be longer than, or the same length as, the post 428.

Illustrated in FIG. 15B, the augment 434 may extend from only one side of the bone-facing surface 426. The augment 434 includes a surface portion 435 that extends along a transverse plane that is substantially parallel with a horizontal axis 433 that extends through the intersection of the distal post 428 with the bone-facing surface 426, as illustrated in FIG. 15C.

The surface portion 435 may be wing shaped and extend radially from the center of the bone-facing surface 426. The shape of the augment surface may vary. The augment may be peripherally defined by a perimeter wall 437 that extends perpendicular to the transverse plane 433. The height of the perimeter wall 437 may vary along the periphery of the augment to match the contoured bone facing surface 426 of the articulating member 420. The curvature of a portion of the peripheral wall may follow the peripheral curvature of the wall 424 of the articulating member 420. Another portion of the peripheral wall may extend straight across the length of the bone-facing surface 426.

Figure 16:
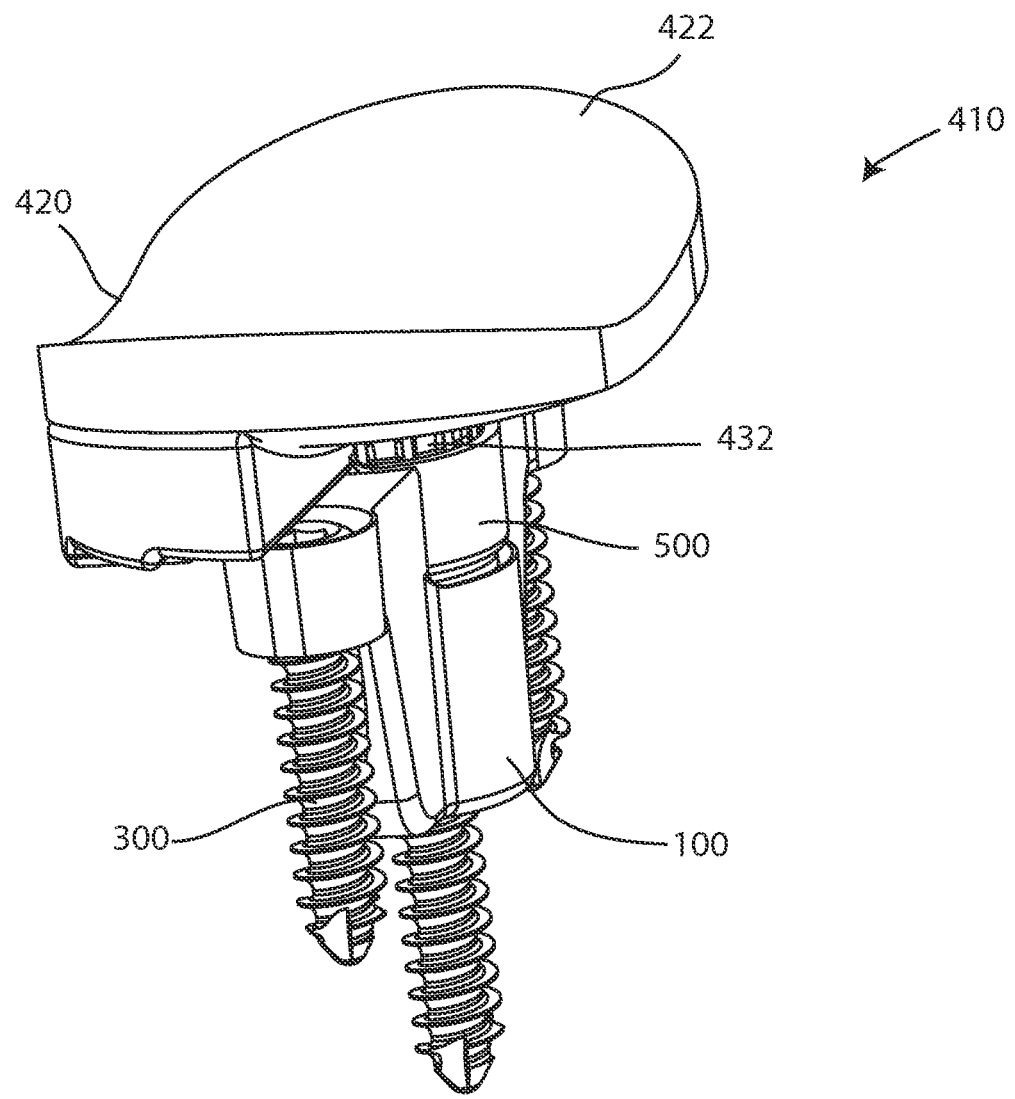
FIG. 16 is an assembled perspective view of the glenoid vault system of FIG. 15.

The surface area of the augment 434 may be less than half of the total surface area of the bone-facing surface 426. Referring to FIG. 16, the augmented articulating member 420 is shown engaged with an augmented AP member 500. The augment 434 interacts with a portion of the AP component 500 that will be discussed further herein. The augment 434 is provided to replace an area where much of the bone has been removed.

Figure 17:
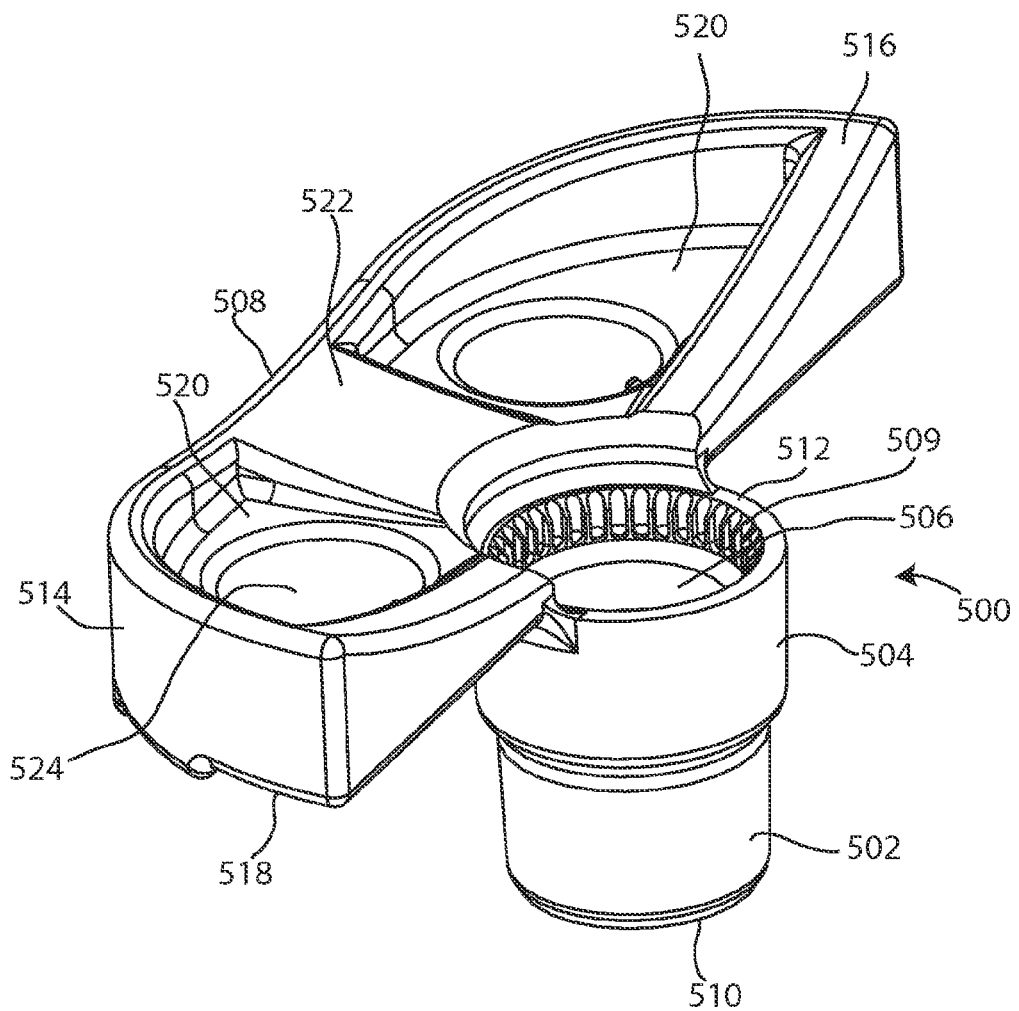
FIG. 17 is a perspective view of the AP component of FIG. 15.

Referring to FIG. 17, the AP component 500 may include the central cylindrical wall 504 defining central hole 506 extending entirely through the AP component with the central hole 506 passing into the tubular boss 502. The tube of the tubular boss 502 may be an extension of the central hole 506. The tubular boss 502 may be circumferentially smaller than the cylindrical wall 504 defining the central hole 506 while the circumference of the central hole 506 may remain constant through from the cylindrical wall 504 to a distal end 510 of the tubular boss 502. At a proximal end 512 the central hole 506 of the AP component 500 may reside notches or grooves 509 that may serve a complimentary fit with the notches 432 of the articulating component 420 to allow rotational orientation of the articulating component and prevent rotation of the articulating component 420 after engaging the AP component 500. The engagement of the post 428 with the central hole 506 may occur similar to the engagement of post 28 with central hole 206 as described previously.

An AP augment 508 extends away from the central hole 506 from the distal end 510 of the AP component 500 and may be shaped to receive the augment 434 of the articulating member 420. The AP augment 508 may extend 180° or more around the circumferential edge of the cylindrical wall 504. A peripheral wall 514 wraps around the AP augment 508 and may match the curvature of the articulating member 420. The AP augment 508 also include an articulating facing side 516 and a bone facing side 518. The articulating facing side 516 may include pockets 520 divided by a ridge 522. The pockets 520 receive and complimentary fit the augment 434 of the articulating member 420. The pockets 520 may match the curvature of the peripheral wall 514 of the AP augment 508. Each pocket 520 may include an augment hole 524 to allow for passage of a screw. The augment hole 524 may pass through the entire body of the AP augment 508 in substantially the same direction as the central hole 506. The screw may threadably or slidably pass through the augment hole 524 wherein the screw head may engage the augment hole 524 and secure the AP component 500 to the bone.

The AP component 500 may include the same or similar features as the previously described embodiment including the engagement ring 222 that engages the ring shaped cutout 430 of the articulating member 420. The AP component 500 also includes the grooves or notches 509 that interact with the notches 432 of the articulating member 420 in much the same manner as the previous embodiment to allow rotational orientation of the articulating component and prevent rotation of the articulating member 420 about the AP component 500.

A method of implanting this embodiment of the glenoid vault system 410 is similar to that previously described herein substituting the alternate embodiment AP component 500 for the previous AP component 200.

Figure 18:
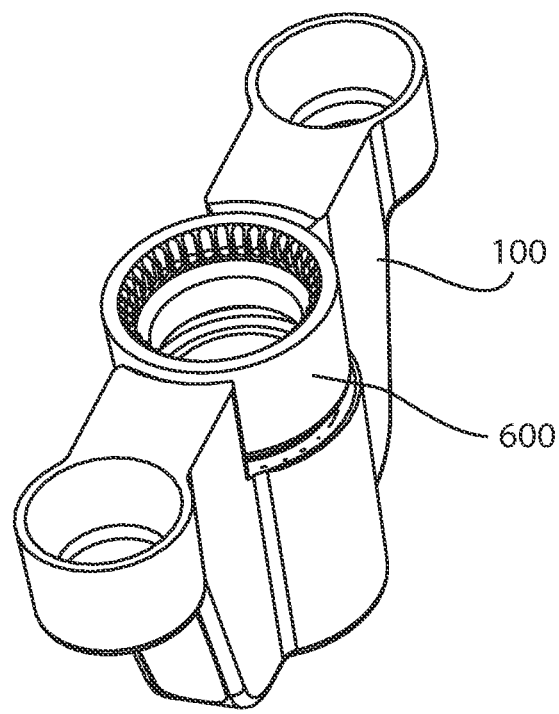
FIG. 18 is a perspective view of an assembled SI component of FIG. 1 or 15 and a cylindrical component.
Figure 19:
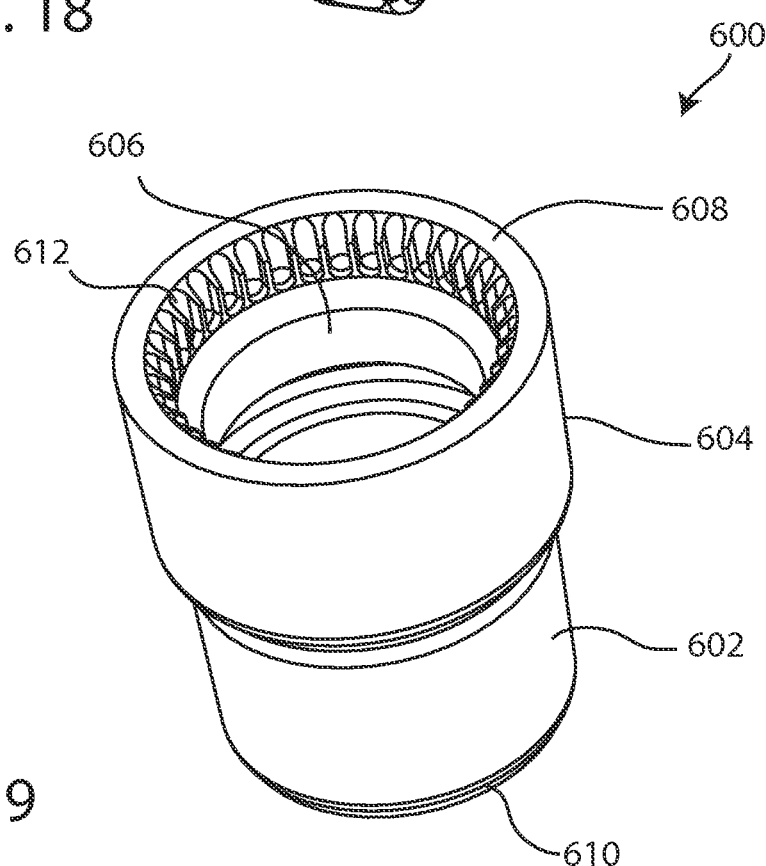
FIG. 19 is a perspective view of the cylindrical component of FIG. 18.

Referring to FIGS. 18 and 19, a cylindrical component 600 may include some of the similar features of the previous AP components 200, 500. The cylindrical component 600 includes the same or similar features as the previously disclosed AP components 200, 500 with the exclusion of arms and augments and simply includes the cylindrical portion itself. Cylindrical component 600 includes a tubular boss 602 extending from a cylindrical wall 604 defining a central hole 606. The tubular boss 602 may be circumferentially smaller than the cylindrical wall 604 defining the central hole 606 while the circumference of the central hole 506 may remain constant through from a proximal end 608 of the cylindrical wall 604 to a distal end 610 of the tubular boss 602. Similar to the previous embodiments, at the proximal end 608 of the cylindrical wall 604 reside notches or grooves 612 which may serve as a complimentary fit with the notches of the articulating members or components, or the glenosphere to allow rotational orientation of the articulating component and prevent rotation of the articulating member or component, or glenosphere after engaging the AP component 600.

The cylindrical component 600 may also include the engagement ring 222 as previously disclosed for securing an articulating component or member or glenosphere, particularly the post portion of the articulating component, to the cylindrical component 600. The security of the two parts may come from a seal or snap fit, or other locking means including a Morse taper (not shown) which may not require an engagement ring, as previously described herein.

The cylindrical component 600 may be advantageously suited for use with an augmented articulating component or augmented glenosphere in that no arms, like those found in the other AP components 200, 500, are in the way of the augments on the articulating component and glenosphere designs.

Figure 20:
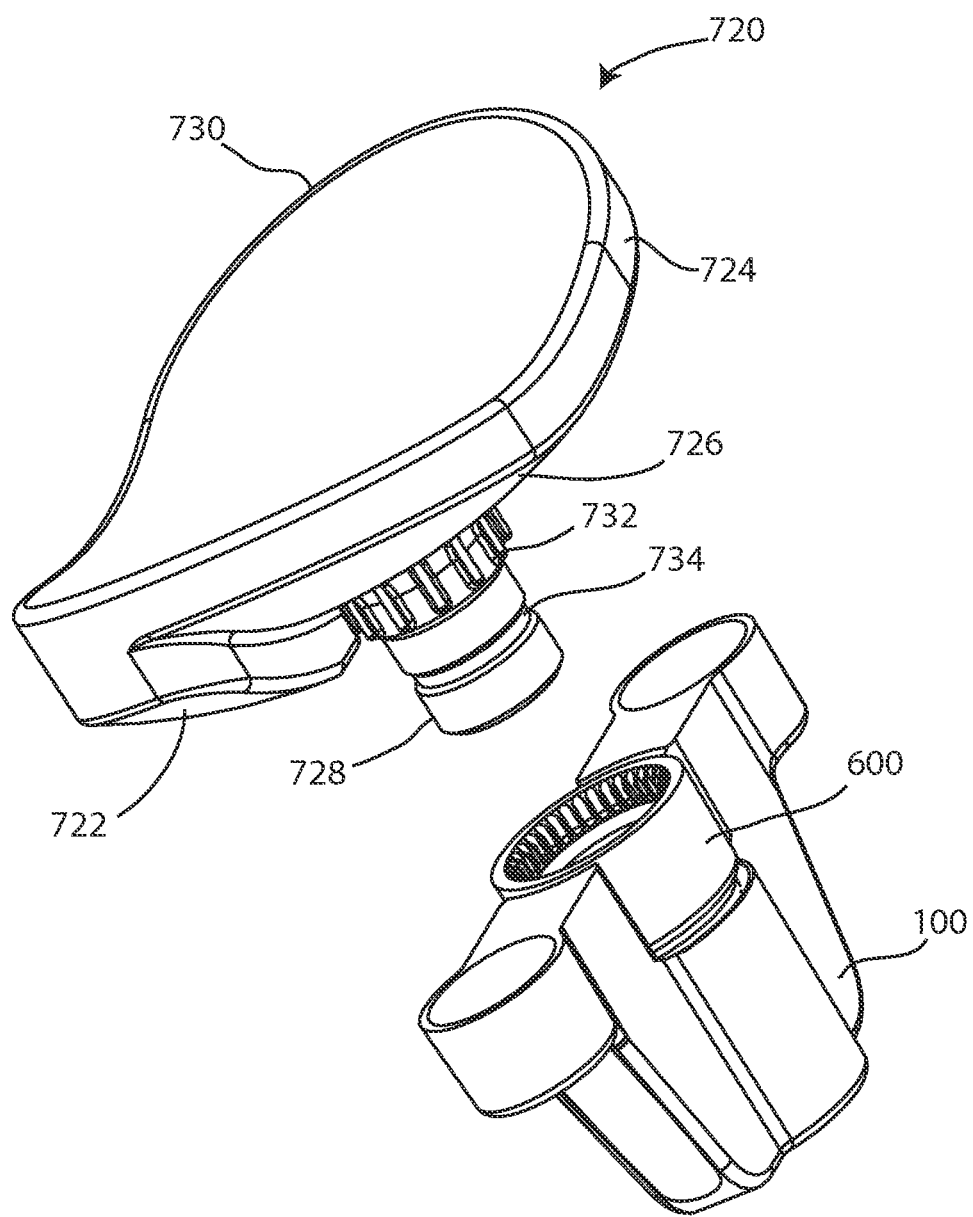
FIG. 20 is a partially exploded perspective view of the SI component of FIG. 1 or 15, the cylindrical component of FIG. 18 and an articulating component with augment.
Figure 21:
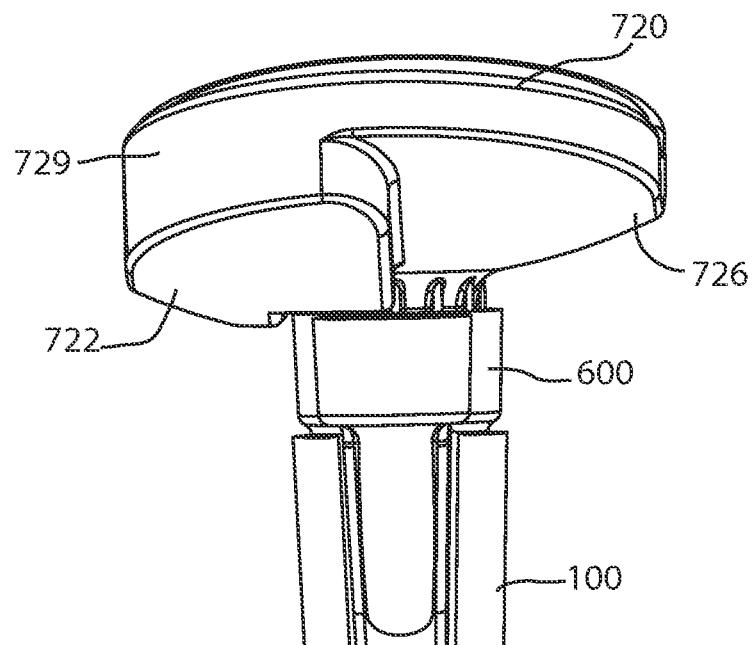
FIG. 21 is an assembled side view the SI component of FIG. 1 or 15, the cylindrical component of FIG. 18 and the articulating component with augment of FIG. 20.
Figure 22:
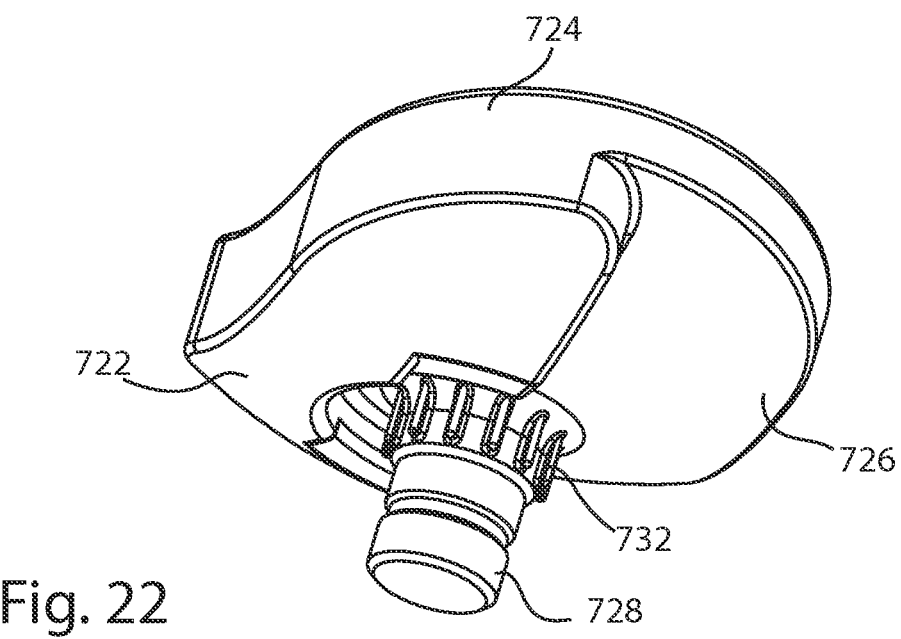
FIG. 22 is a bottom perspective view of the articulating component with augment of FIG. 20.

Referring to FIGS. 20-22, an articulating component 720 includes an augment 722 as part of the articulating component, essentially a one-piece articulating component with augment. A peripheral wall 724 extends from an articulating surface 730 to the bone-facing surface 726. The augment 722 may be separate from a post 728 and extend from a bone facing side 726 separate from where the post 728 extends from the bone facing side 726. The articulating component 720 further includes notches 732 that interact or engage the grooves or notches 612 of the cylindrical component in much the same manner as the previous embodiment forming a complimentary fit preventing rotation of the articulating component 720. The post 728 may further include the ring shaped cutout 734 for locking the articulating component 720 to the cylindrical component 600.

The augment 722 may also be rounded or smoothly tapered extending from the peripheral wall 724. The augment 722 may extend from the peripheral wall 724 toward a medial line or middle point of the articulating component 720 and wrap around the post 728 but not contacting the post 728. The post 728 may be greater in length than the augment 722. The augment 722 of the articulating component 720 is to replace that area of the shoulder where bone may be removed, as is the case with all the augment designs disclosed herein.

Figure 23:
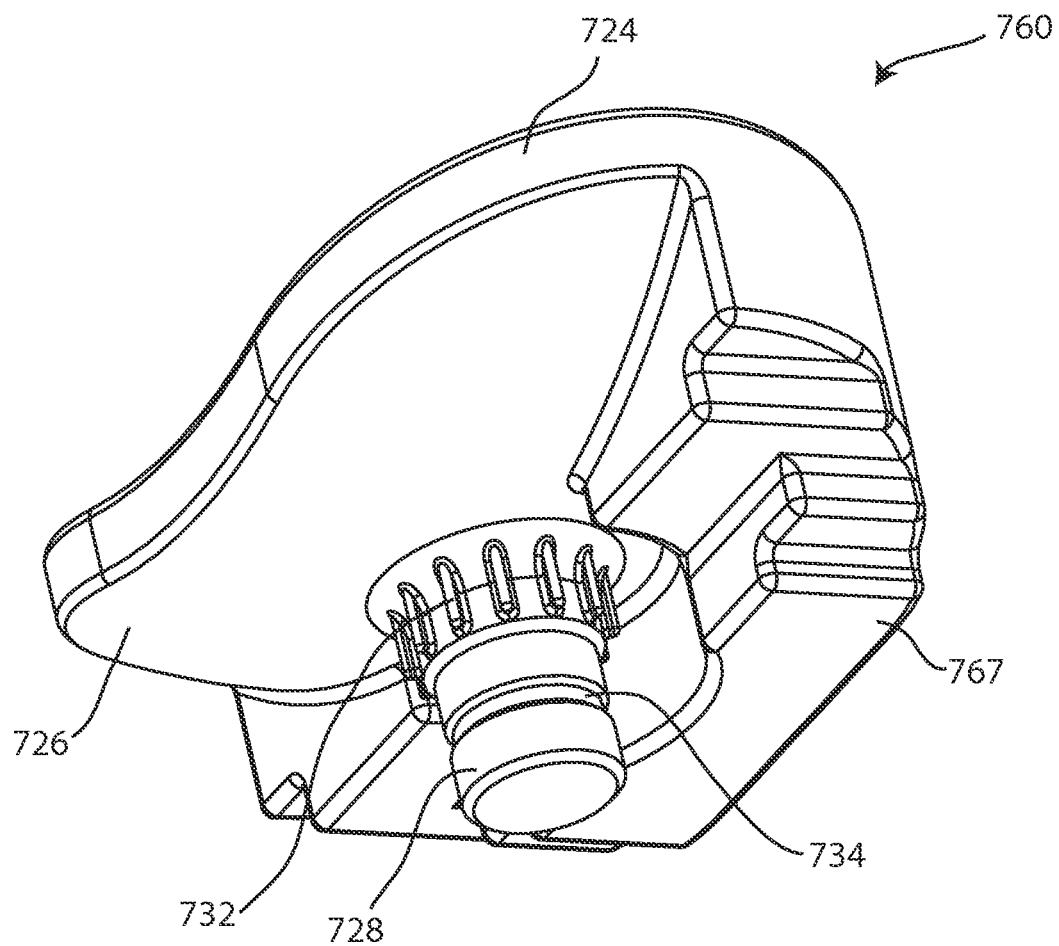
FIG. 23 is a bottom perspective view of an articulating component with stepped augment.

Referring to FIG. 23, an alternate embodiment of an articulating component 760 may include an augment 762 with a step-down taper. The step-downs may step down both peripherally and in a lateral direction from a middle point or medial line of the articulating component 760. The remainder of the alternate embodiment may be substantially similar as the previous articulating component 720 embodiment.

Figure 24:
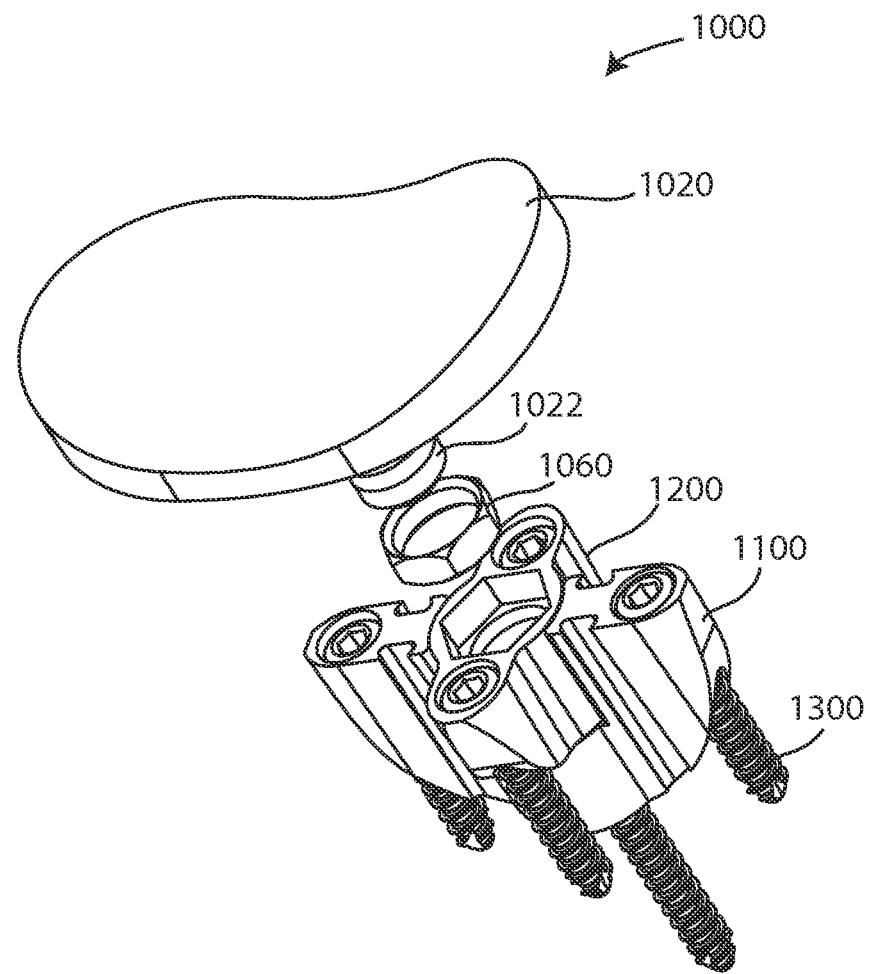
FIG. 24 is a partially exploded alternate embodiment of a glenoid vault system with a horizontal member, vertical member, screws, a hex component and an articulating component.
Figure 25:
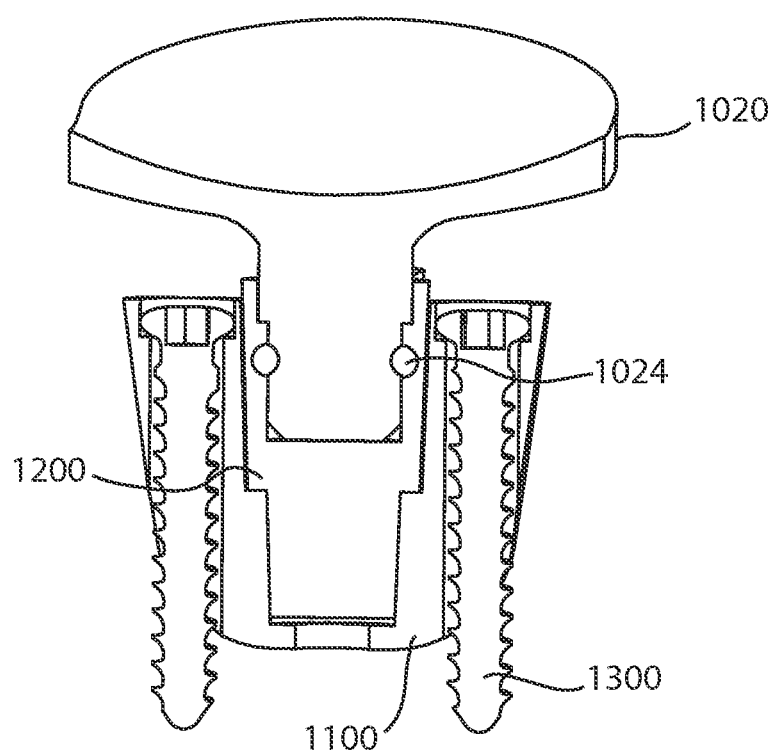
FIG. 25 is a cross sectional side view of the glenoid vault system of FIG. 24 with the horizontal member extending across the page.

Referring to FIGS. 24 and 25, there is depicted an alternate embodiment of a glenoid vault system 1000. The components in this embodiment are similar to the previous system 10. An articulating component 1020 is substantially similar to the previous articulating component 20; however the articulating component 1020 does not include notches to prevent rotation of the articulating component 1020. In this embodiment a polygon, or keyed, component 1060 that includes a cylindrical hole 1062, is inserted onto or wraps around a post 1022, which may be cylindrical in shape, of the articulating component 1020. The polygon component 1060 may be press fit onto the post. The polygon component 1060 may be hexagonal in shape. The polygon component 1060 engages a complimentary recess within an AP component 1200, preventing rotation of the articulating component 1020.

The post 1022 includes substantially the same feature of a cutout configured to interact with an engagement ring on the AP component 1200 to lock the post 1022 to the AP component 1200. The lock may be a snap fit, or seal 1024, or other locking means including a Morse taper (not shown) which may not require an engagement ring.

Figure 26:
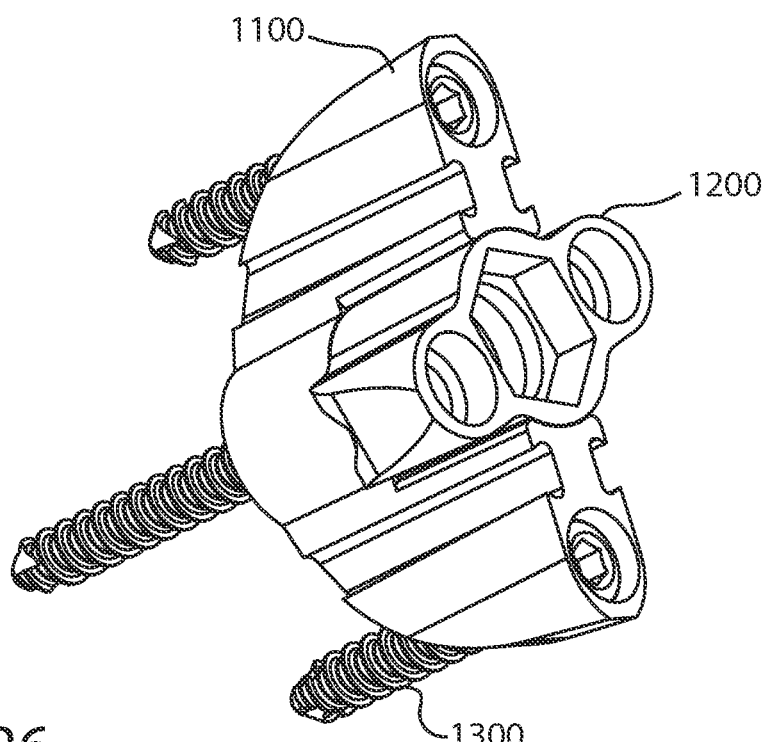
FIG. 26 is a perspective view of the vertical and horizontal members of FIG. 24.
Figure 27:
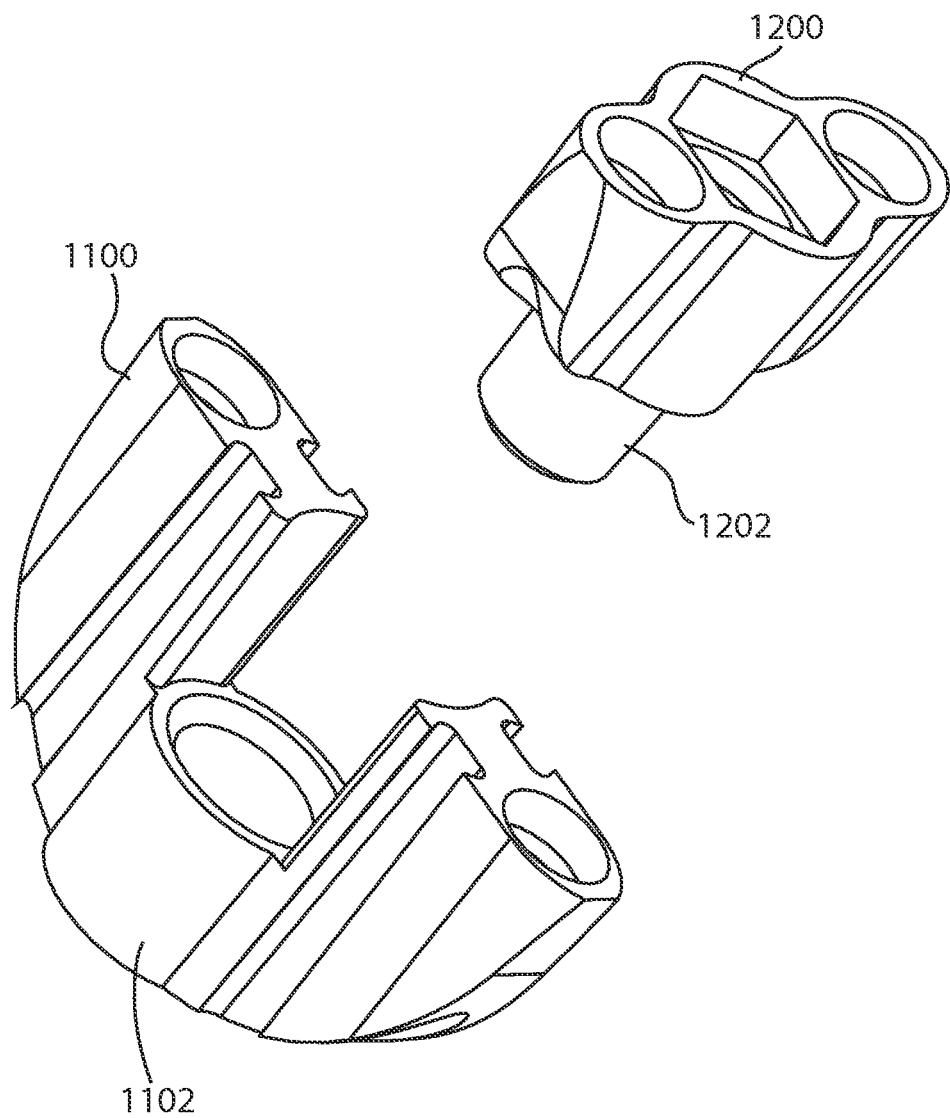
FIG. 27 is an exploded perspective view of the vertical and horizontal components of FIG. 24.

Referring to FIGS. 26 and 27, the glenoid vault system 1000 also includes an SI component 1100 and AP component 1200 and anchors or screws 1300 similar to the previous system 10. The features of these components differ slightly and will be described further herein. The interaction between the SI component 1100 and AP component 1200 is substantially the same as the previous system 10. A tubular boss 1202 of the AP component may slideably engage a central ring 1102 of the SI component, allowing the AP component to rotate within the central ring 1102.

Figure 28:
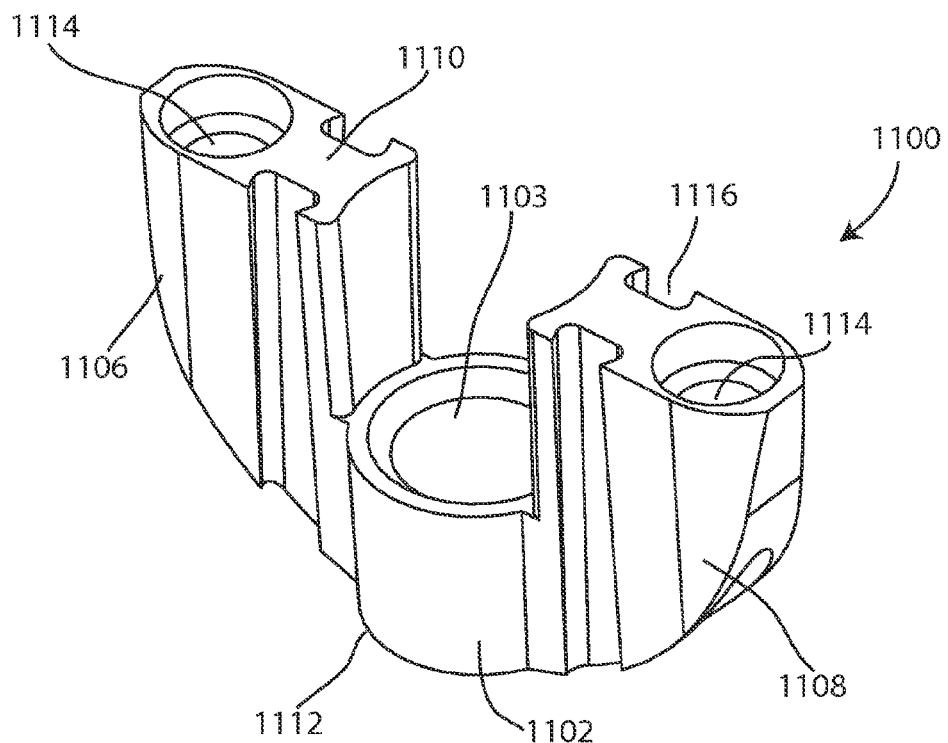
FIG. 28 is a perspective view of the vertical component of FIG. 24.
Figure 29:
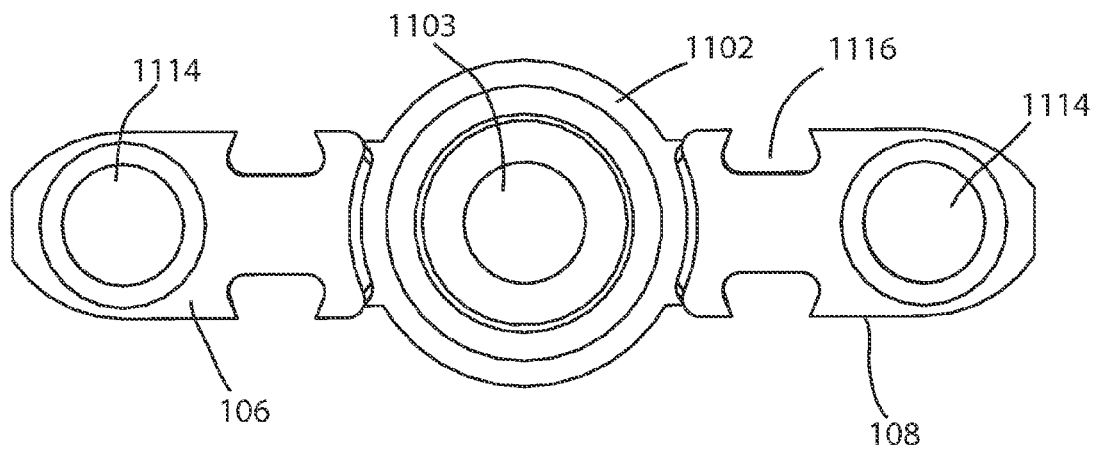
FIG. 29 is a top view of the vertical component of FIG. 24.

Referring to FIGS. 28 and 29, the SI component 1100 includes a central bore 1103 passing entirely through the central ring 1102 and arms 1106, 1108 extending from the central ring 1102. The arms 1106, 1108 extend in a wing-like manner from the central ring 1102 curvedly tapering from a proximal end 111 toward a distal end 1112. Instead of rings extending from the arms as in the previous embodiment, the arms include openings 1114 that may extend entirely through the arm to receive screws 1300 (not shown) in substantially the same manner as previously described in the previous embodiment. The arms 1106, 1108 may include tracks 1116 for receiving an augment (as depicted in FIGS. 34-38). The tracks 1116 may be dovetail shaped and may be on either side of the arms 1106, 1108, on one arm or both arms. The tracks 1116 may run partially or entirely from the proximal end 1110 to the distal end 1112. The SI component 1100, from a profile view, may be U-shaped.

Figure 30:
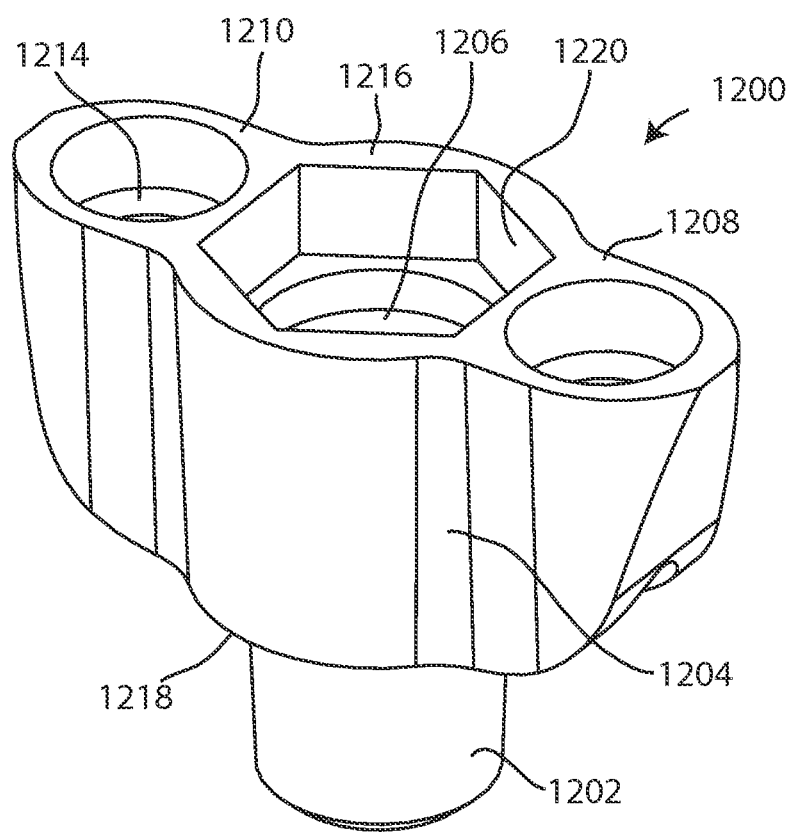
FIG. 30 is a perspective view of the horizontal component of FIG. 24.
Figure 31:
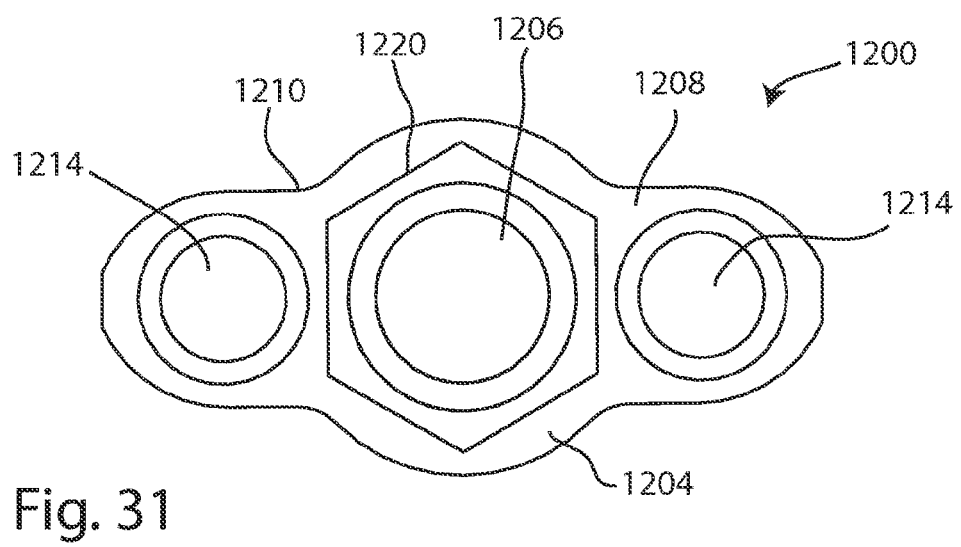
FIG. 31 is a top view of the horizontal component of FIG. 24.
Figure 32:
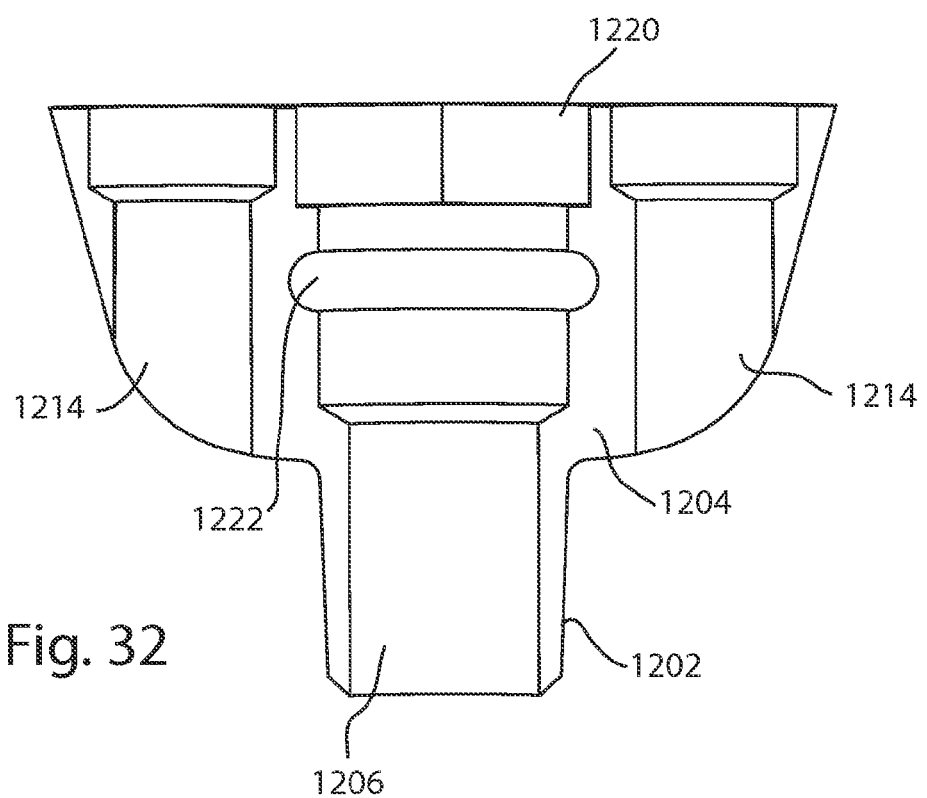
FIG. 32 is a cross sectional side view of the horizontal component of FIG. 24.

Referring to FIGS. 30-32, the AP component 1200 includes the tubular boss 1202 and a body 1204, with a central hole 1206 passing entirely through the center of the body 1204 and through the tubular boss 1202. The tubular boss 1202 may extend from the center of the body 1204 at a distal end 1218 of the AP component 1200. The AP component 1200 also includes AP arms 1208, 1210 extending similarly to the arms of the SI component 1100. The AP arms 1208, 12010 extend from the center of the body 1204 at the distal end 1218 toward a proximal end 1216 in a wing-like manner, curvedly tapering from the proximal end 1216 toward the distal end 1218. The arms include holes 1214 that may extend entirely through the arm to receive screws 1300 in substantially the same manner as the previously embodiment.

The AP component 1200 further includes a polygon recess or polygon key 1220 toward the proximal end 1216 within the body 1204 of the AP component 1200. The polygon recess 1220 provides complimentary fit for the polygon component 1060 wherein the polygon component 1060 may, but is not required to, sit flush with the proximal end 1216 within the polygon recess 1220. Within the central hole 1206 is an engagement ring 1222 that is substantially similar to the previous embodiment and interacts in substantially the same way to form a snap fit or seal or other similar locking mechanism including a Morse taper (not shown) which may not require an engagement ring.

Figure 33:
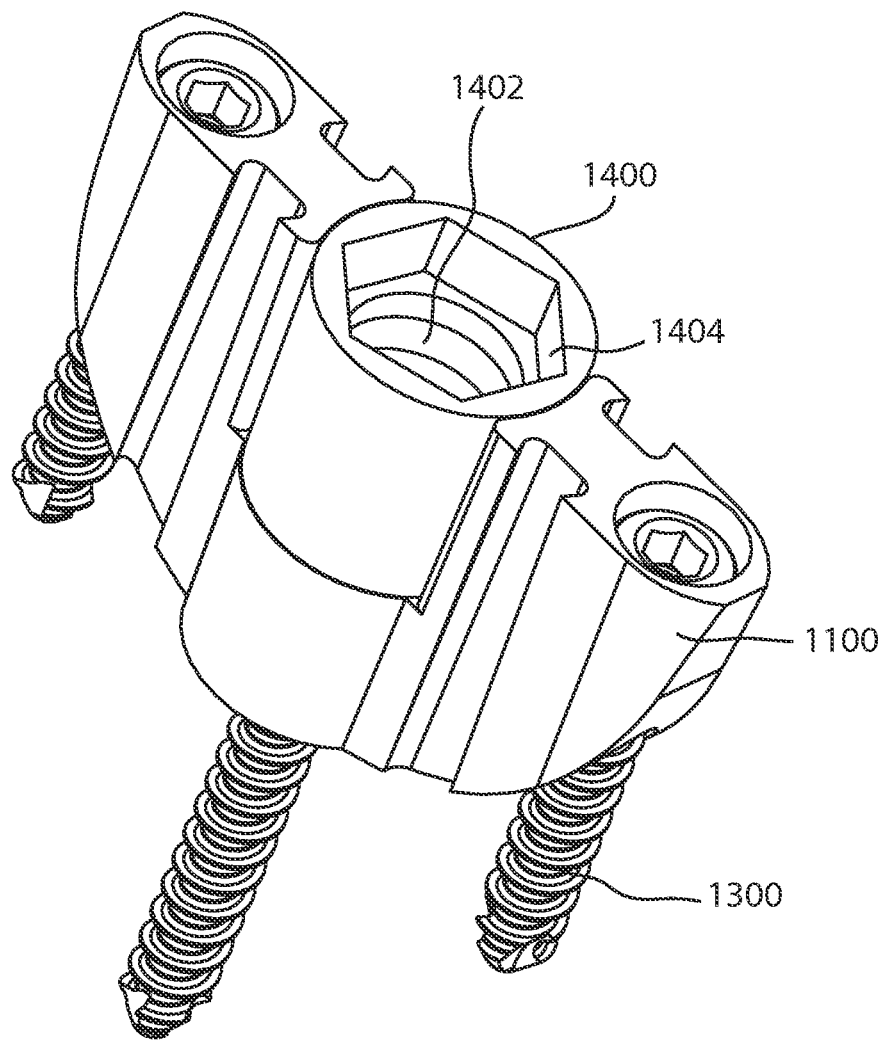
FIG. 33 is a perspective view of the vertical component of FIG. 24 and a cylindrical member.

Referring to FIG. 33, an alternate embodiment a cylindrical component 1400 with features of the AP component 1200 is shown, and is similar to the cylindrical component 600. The elements of the body of the AP component 1400 are substantially similar to component 600, having a tubular boss (not shown but within the central bore of the SI component 1100), a central hole 1402 and a polygon recess 1404. The cylindrical component may also include an engagement ring as previously described to lock the articulating component 1020 to the AP component 1400. This embodiment lacks arms and may be better suited to receive augments like those depicted in FIGS. 34-38.

Figure 34:
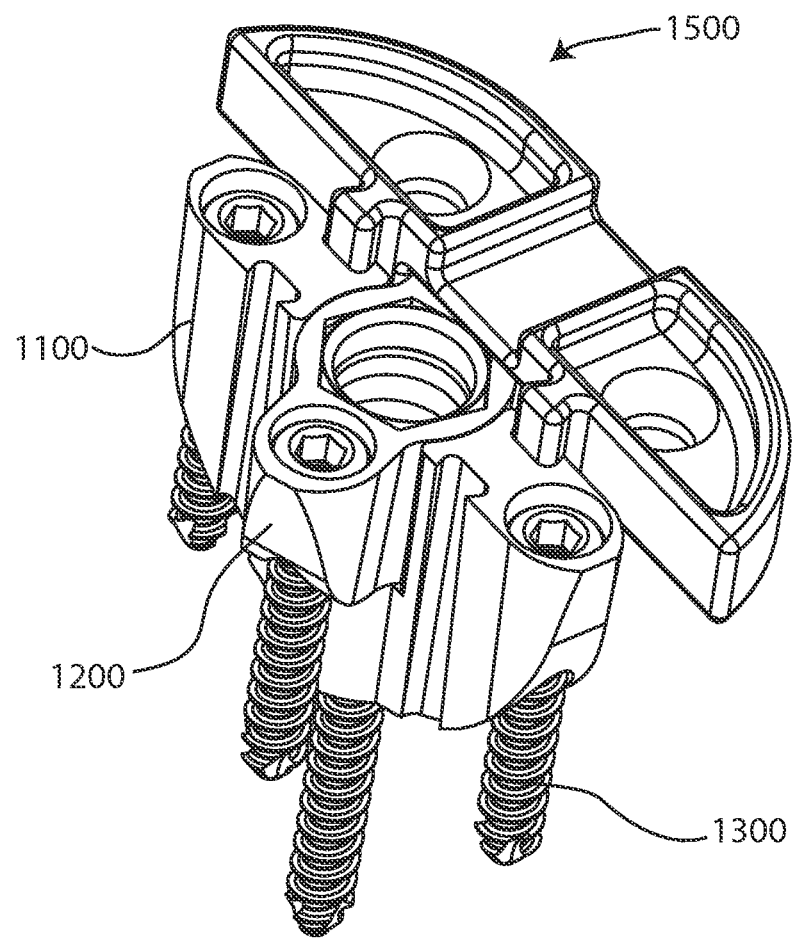
FIG. 34 is a perspective view of the vertical and horizontal component of FIG. 25 with an augment member.
Figure 35:
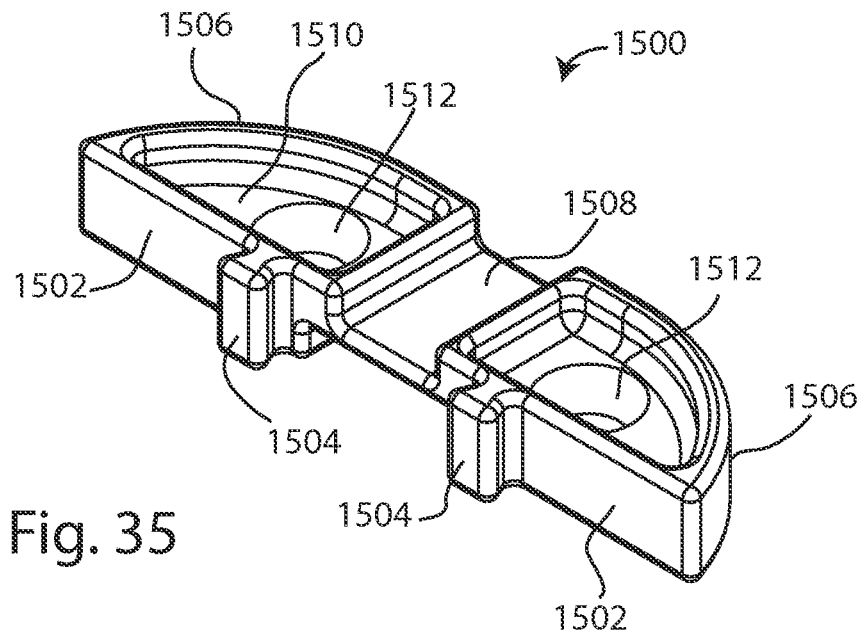
FIG. 35 is a perspective view of the augment member of FIG. 34.
Figure 36:
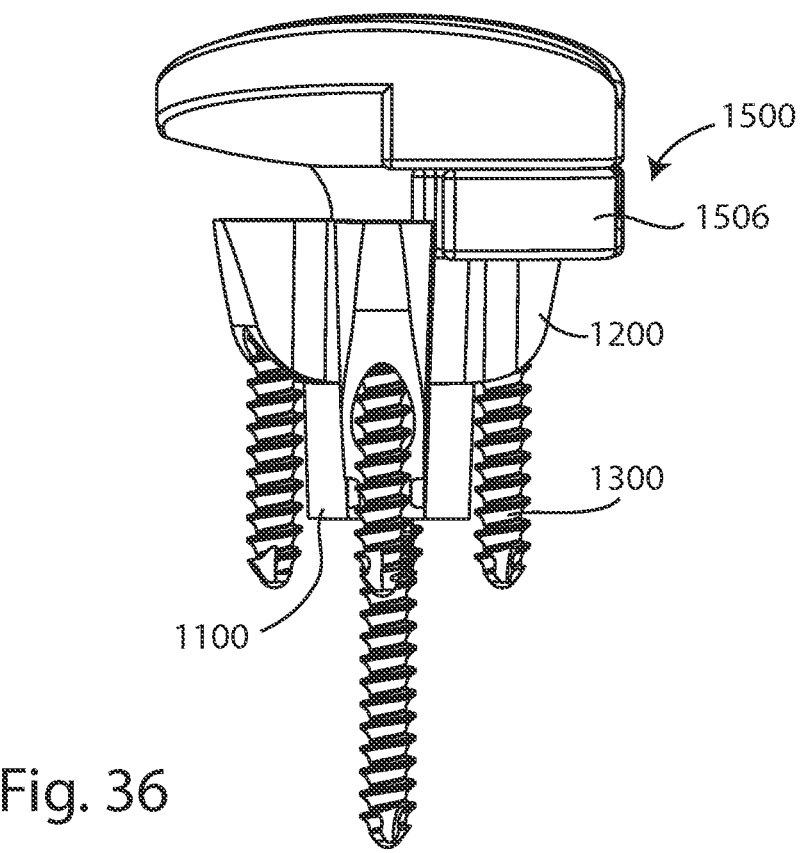
FIG. 36 is a side view of the glenoid vault system of FIG. 24 with the augment of FIG. 35.

Referring to FIGS. 34-36, an augment 1500 is shown with the SI component 1100 and the AP component 1200. The augment 1500 includes a straight edge 1502 with two dovetailed protrusions 1504 spaced apart from one another, perpendicular to the straight edge 1502, and configured to slide in the tracks 1116 of the SI component 1100. The straight edge 1502 terminates on each end of the augment where two curved edges 1506 arch back toward a midline of the augment 1500. A valley 1508 may divide the augment into two mirror image sides wherein each side of the augment includes a pocket 1510 which may receive a partial augment from the articulating component 1020 similar to the partial augment of articulating component 420 or the one-piece augment articulating components 720, 760. The pockets 1510 may include holes 1512 passing through the augment 1500 to allow for passage of screws 1300 to secure the augment 1500 to the bone.

Figure 37:
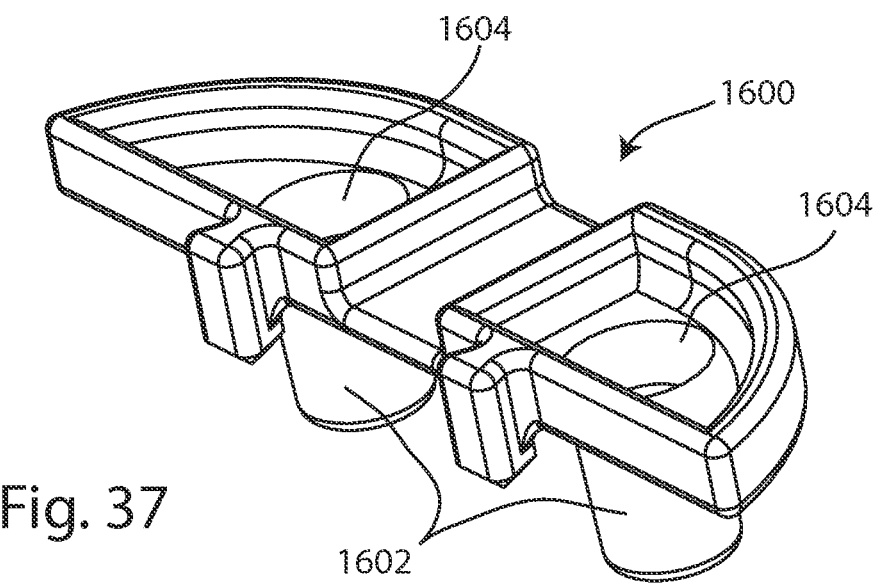
FIG. 37 is a perspective view of an alternate augment.
Figure 38:
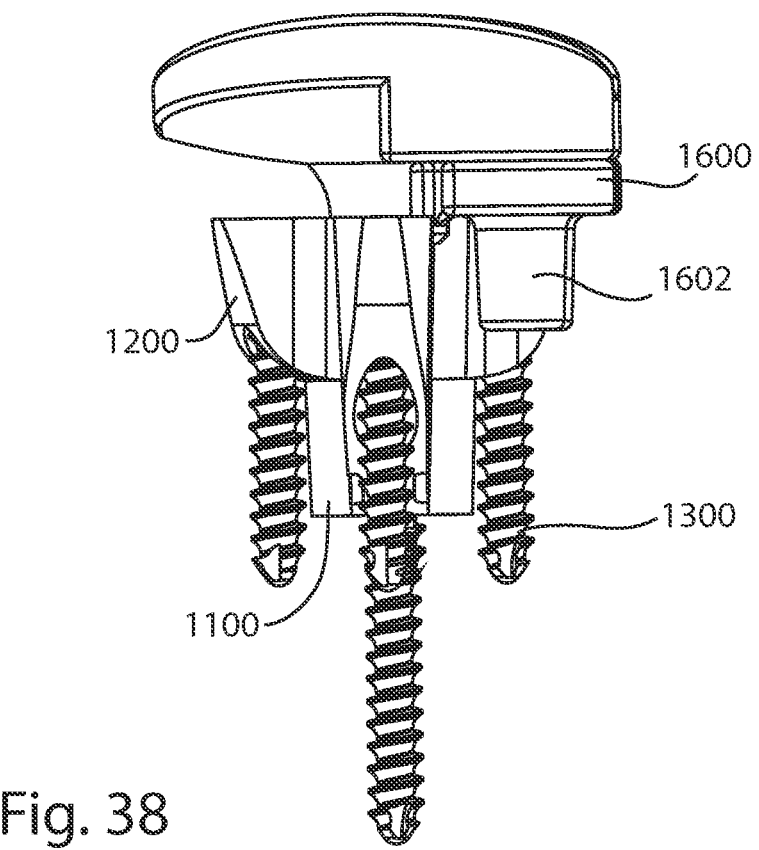
FIG. 38 is a side view of the glenoid vault system of FIG. 24 with the augment of FIG. 37.

Referring to FIGS. 37 and 38, an augment 1600 may include substantially the same features of the augment 1500; however, the augment 1600 may include tubular bosses 1602 extending in a direction away from the articulating component essentially extending the length of holes 1604 for receiving the screws 1300. The screws 1300 may secure the augment 1600 to the bone.

Figure 39:
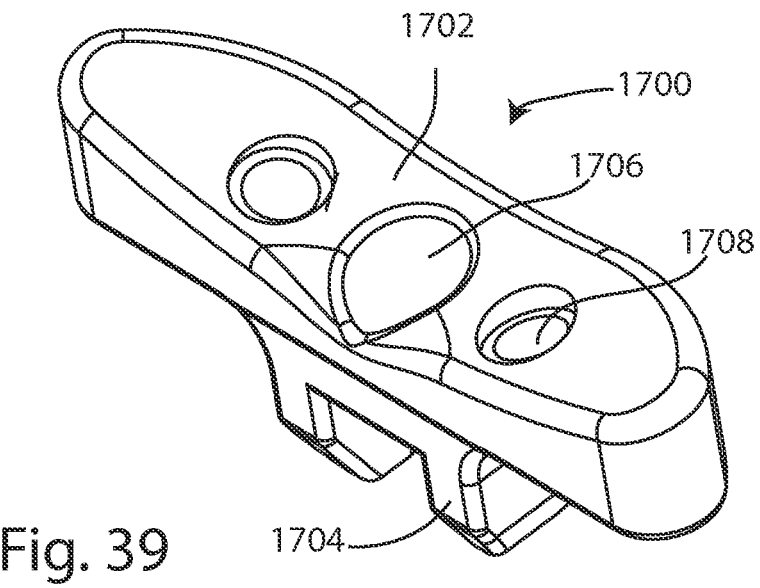
FIG. 39 is a perspective view of an alternate augment.
Figure 40:
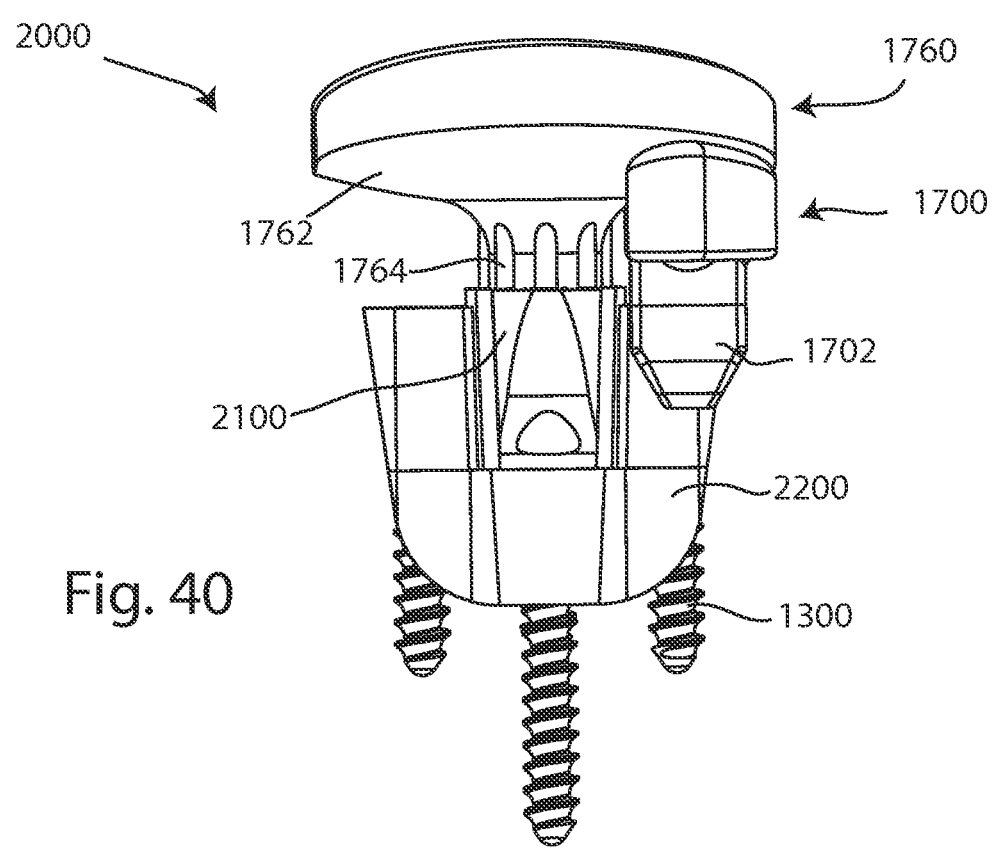
FIG. 40 is a side view of the glenoid vault system of FIG. 24 with the augment of FIG. 39.
Figure 41:
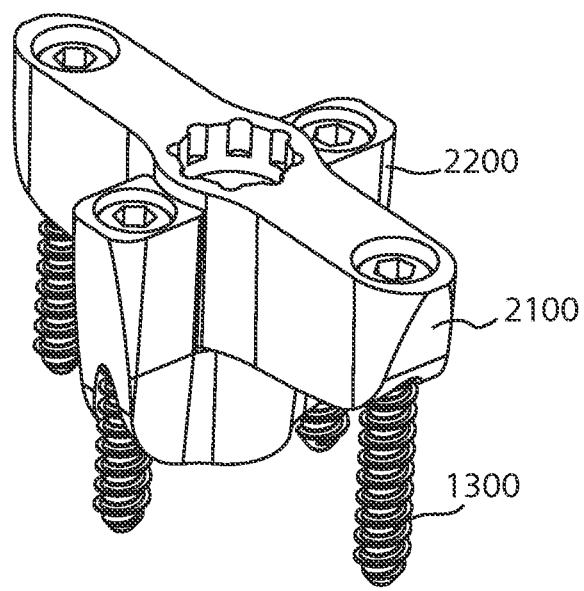
FIG. 41 is a perspective view of an alternate embodiment of an anchoring system for the glenoid vault with an alternate vertical member and horizontal member and screws.
Figure 42:
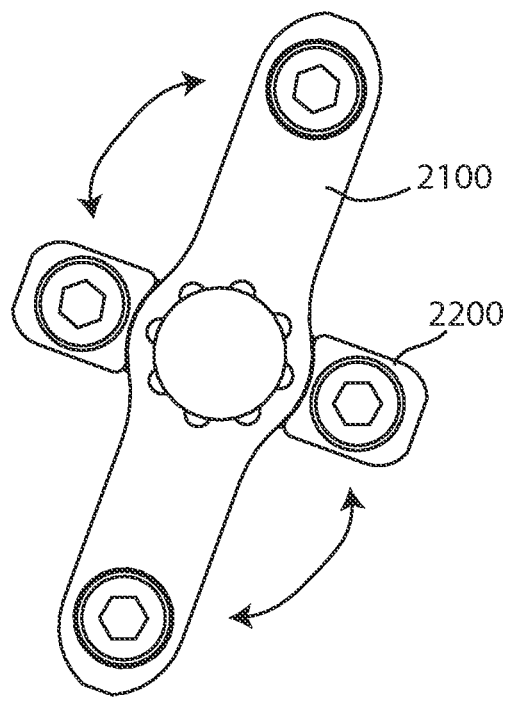
FIG. 42 is a top view of the alternate embodiment anchoring system of FIG. 41 with the vertical component rotated to show it is rotatable about the center of the horizontal component.
Figure 43:
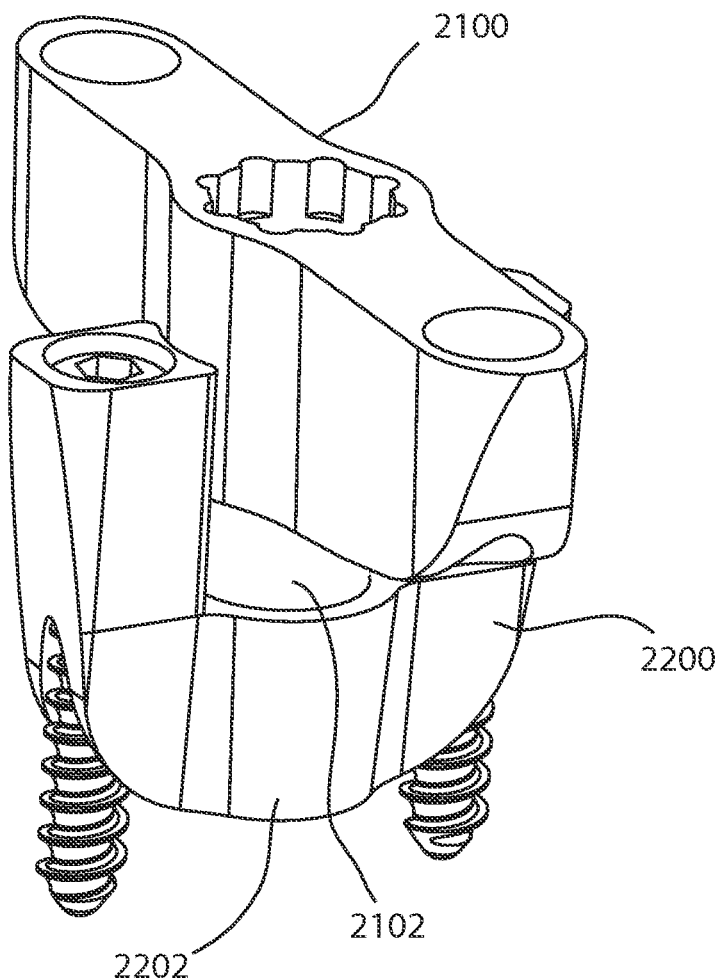
FIG. 43 is a perspective view of the anchoring system of FIG. 41 with the vertical member slightly exploded from the horizontal member.

Referring to FIGS. 39 and 40, an augment 1700 includes a curved surface 1702 shaped to lie against a bone facing surface 1762 of an articulating component 1760. The curvature of the curved surface 1702 may match the curvature of the bone facing surface 1762. Extending from the opposite side of the curved surface 1702 of the augment 1700 is a saddle 1704 that straddles a horizontal or AP component 2200. The augment 1700 may include a centralized hole 1706 passing through the body of the augment 1700 as well as additional holes 1708 passing through the body of the augment 1700 to allow for passage of screws to secure the augment 1700 to the bone.

Referring to FIGS. 40-43, an alternate embodiment of a glenoid vault system 2000 is depicted with a vertical or SI member 2100, a horizontal or AP member 2200, screws 2300 and an articulating component 1750. The augment 1700 may or may not be present in this embodiment. This system 2000 is similar to the previously disclosed systems 10, 1000 with the exception that a portion of the vertical member 2100 fits in the horizontal member 2200 instead of vice versa. In this instance the horizontal member 2200 is embedded into the bone and then a portion of the vertical member 2100 slides into a portion of the horizontal member 2200.

The horizontal member 2200 includes all of the same elements as previously described for a previously described AP component 200 with the exception that the features of the central rings 102, 1102 of the previous embodiments are now found in the horizontal member 2200 instead of the vertical member 2100. The horizontal member 2200 is embedded in the bone in an anterior posterior direction first and then the vertical member 2100 is embedded in the bone in a generally superior inferior direction. The horizontal member 2200 includes a central ring 2202 that is large enough to receive a tubular boss 2102 extending from the vertical member 2100.

Figure 44:
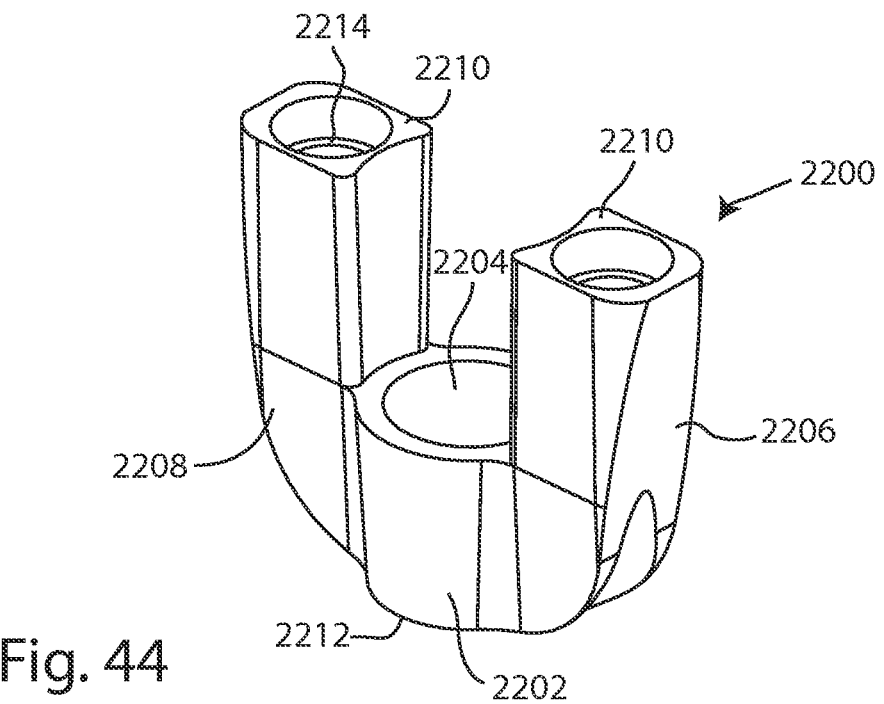
FIG. 44 is a perspective view of the horizontal member of FIG. 41.

Referring to FIG. 44, the horizontal member 2200 includes the central ring 2202 that defines a central bore 2204 that may pass partially or entirely through the central ring 2202. A screw 1300 may pass through the central bore 2204 to aid in securing the horizontal member 2200 to bone. Arms 2206, 2208 extend from the central ring 2202 rather abruptly in a proximal direction terminating at a proximal end 2210. The arms 2206, 2208 may be somewhat longer from the proximal end to a distal end 2212 than previous embodiments of the SI components 100, 1100. The arms 2206, 2208 may each include a bore 2214 which extend the entire length of the arm from the proximal end 2210 to the distal end 2212 and are configured to receive screws 1300. The bores 2214 may surround a larger portion of the screws 1300 because of the greater length of the arms 2206, 2208 in a proximal/distal direction. Toward the distal end 2212 of the arms 2206, 2208 a portion of the arms 2208, 2008 on the lateral side may be cut away to expose the threads of the screw 1300 to allow for greater security and fixation of the screws 1300 to the bone. Many features of the horizontal member 2200 are similar to those of the previously disclosed SI components 100, 1100 including the curvature of the arms toward the central ring 2204 matching the curvature of the central ring 2204 to allow the vertical member 2100 to rotate.

Figure 45:
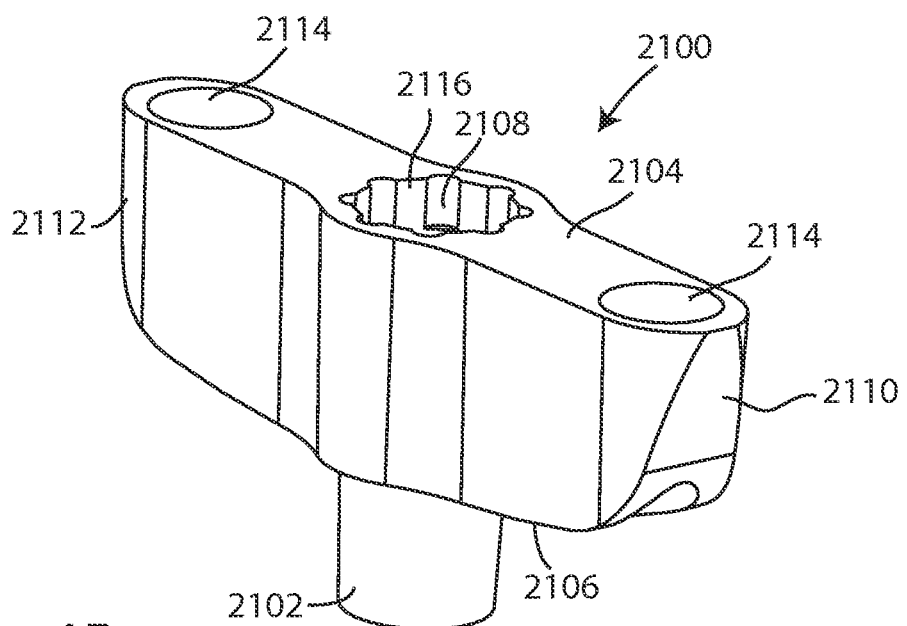
FIG. 45 is a perspective view of the vertical member of FIG. 41.

Referring to FIG. 45, the vertical member 2100 is short, narrow and elongated. The vertical member 2100 is stout from a proximal end 2104 to a distal end 2106. The tubular boss 2102 extends from the distal end and includes a portion of a central hole 2108 that may extend entirely from the proximal end 2104 to the distal end 2106 and through the entire length of the tubular boss 2102. The vertical member 2100 is elongated because of vertical member arms 2110, 2112 extending outwardly in opposite directions from the central hole 2108. The vertical member arms 2110, 2112 each include a hole 2114 to receive screws to secure the vertical member 2100 to the bone. The holes 2114 are separate from the central hole 2108. The walls within the central hole 2108 toward the proximal end 2104 may include grooves or notches 2116 that may form a keyed fit or complimentary interaction with articulating component notches 1764 seen in FIG. 40. These notches or grooves 2116 allow rotational orientation of the articulating component and prevent rotation of the articulating member 1760 after it engages the vertical member 2100. These notches or grooves 2166 may be rounded or squared or any shape that may prevent rotation and have the complimentary fit on the articulating component 1760.

The vertical member 2100 may also include an engagement ring (not shown) that is similar to the previous embodiment engagement ring 222. The engagement ring provides a reversible locking of the articulating component 1760 to the vertical member 2100 through a snap fit or seal, or other locking means including a Morse taper (not shown) which may not require an engagement ring, in substantially the same manner as previously disclosed.

The method for inserting the vertical and horizontal members into the bone is substantially similar as previously described except with the bone may require anterior-posterior preparation first instead of superior-inferior preparation. The order of implantation and interaction between the components can be changed and is not meant to be restrictive.

Referring to FIGS. 46-51, an alternate embodiment of a glenoid vault system 3000 with a horizontal member 3200 and vertical member 3100 is depicted. The system 3000 is substantially similar to the previous system 2000 with a few notable exceptions. Horizontal member tracks 3202 are in place of the bores 2214 in the arms 2206, 2208 of the horizontal member 2200. Likewise vertical member tracks 3102 are in place of the holes 2114 of the arms 2110, 2112 of the vertical member 2100. The tracks 3102, 3202 may be dovetailed to receive anchors 3300, which may be blade anchors similar to those found in U.S. published patent application no. 2010/0204739, which is herein incorporated by reference, and are further depicted in FIG. 50. Another type of anchor is that depicted in FIG. 51 and which provides an alternate embodiment of the anchor 3300. The anchor 3300 may be a bone-augmenting anchor 3302 that may provide for alternate fixation by adding greater size to the blade portion 3304. The blade portion 3304 of the bone-augmenting anchor may be rectangular or trapezoidal in cross sectional shape. The blade anchors 3300 may be embedded or inserted into the bone in the manner as described in the incorporated patent application.

The method for implantation using blade anchors 3300 may be slightly different simply because the blade anchors may require little to no bone preparation for securing those anchors to the bone and is outlined in the published patent application referenced herein.

Figure 46:
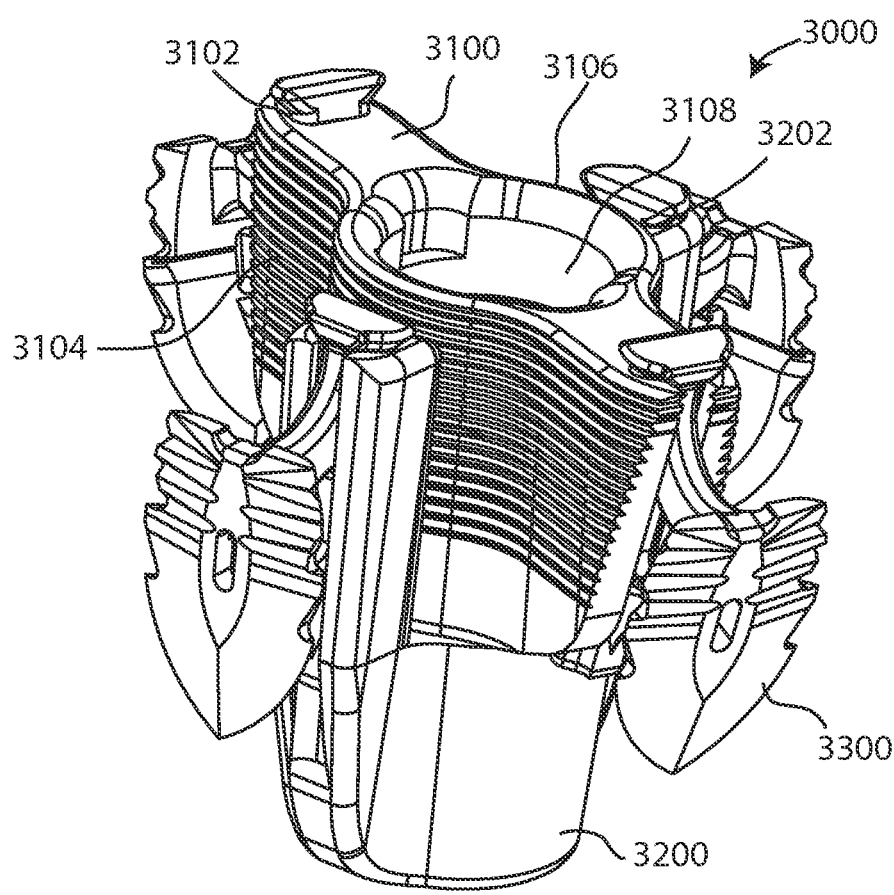
FIG. 46 is a perspective view of an alternate embodiment of an anchoring system for the glenoid vault with blade anchors.
Figure 47:
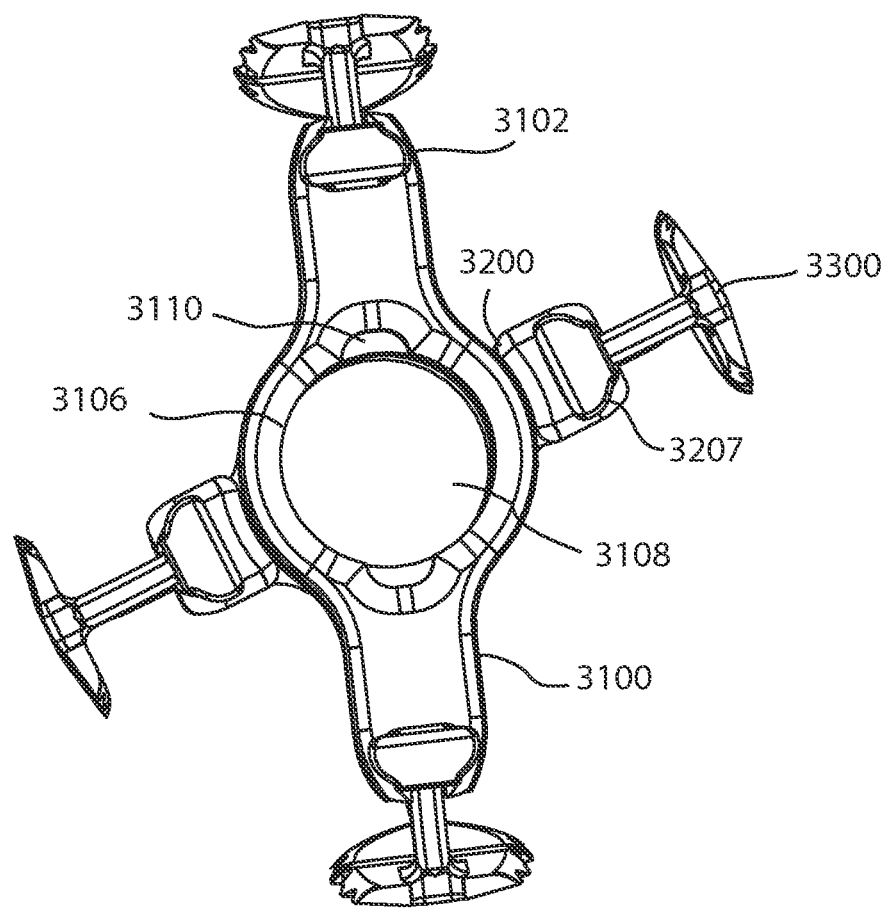
FIG. 47 is a top view of the anchoring system of FIG. 46.
Figure 48:
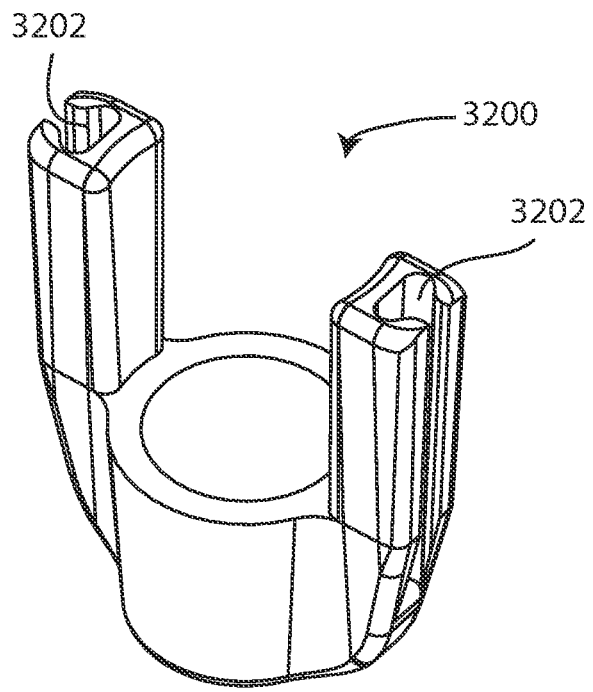
FIG. 48 is a perspective view of the horizontal member of FIG. 46.
Figure 49:
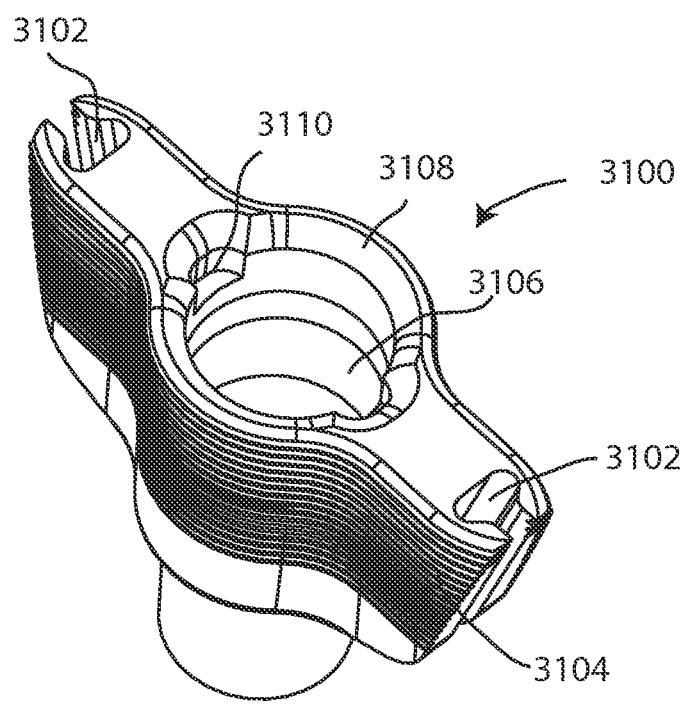
FIG. 49 is a perspective view of the vertical member of FIG. 46.
Figure 50:
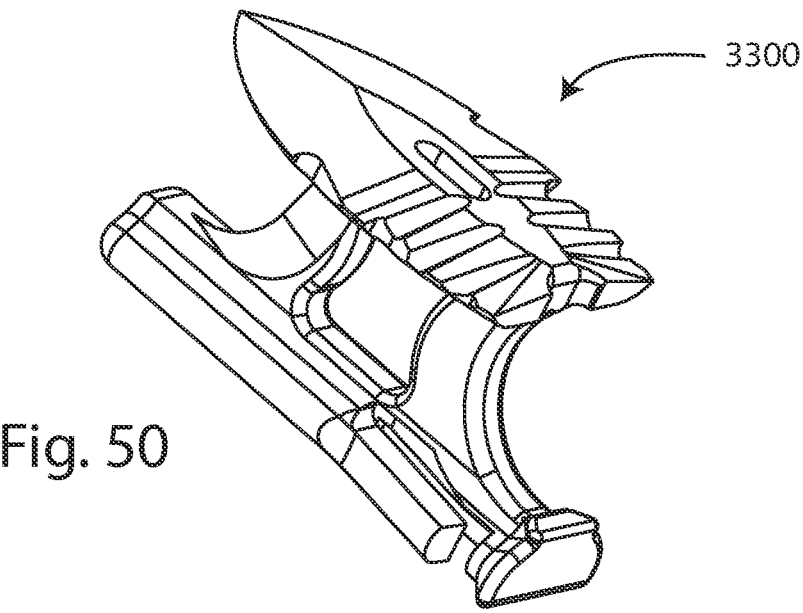
FIG. 50 is a perspective view of a sample blade anchor for use in the systems of FIGS. 46, 52 and 54.
Figure 51:
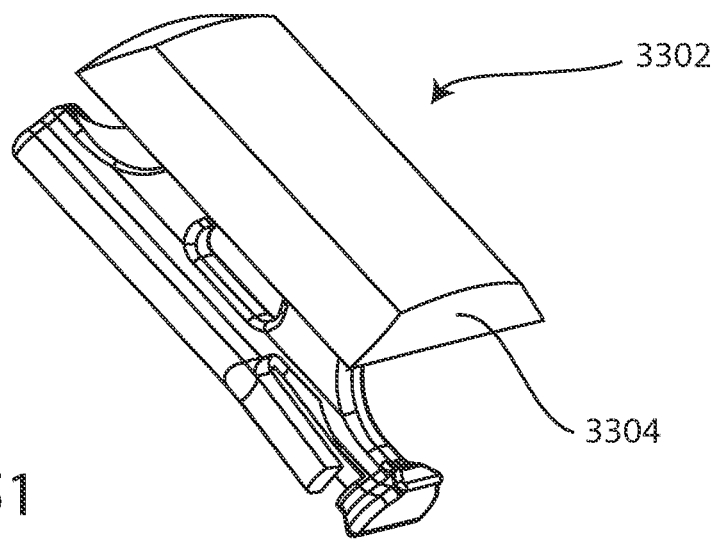
FIG. 51 is a perspective view of an alternate embodiment of an anchor with bone wall filler.

Referring to FIGS. 46 and 49, the vertical member 3100 also includes new features such as roughened or interrupted surface geometry that may be circumferential ridges 3104 that may aid in preventing pull out of the vertical member 3000. Ridges 3104 may be used in all the previous embodiments as well. The vertical member 3100 also includes a wall 3106 cylindrically surrounding a central hole 3108. The wall 3106 includes to at least two cutouts 3110 on opposing sides of the wall 3106 toward a proximal end. The cutouts 3110 provide a keyed or complimentary fit with an articulating component (not shown) to allow rotational orientation of the articulating component and prevent rotation of the articulating component after engaging the vertical member 3100. The shape, size and number of the cutouts may vary and may be similar to those previous described as notches or grooves herein.

Figure 52:
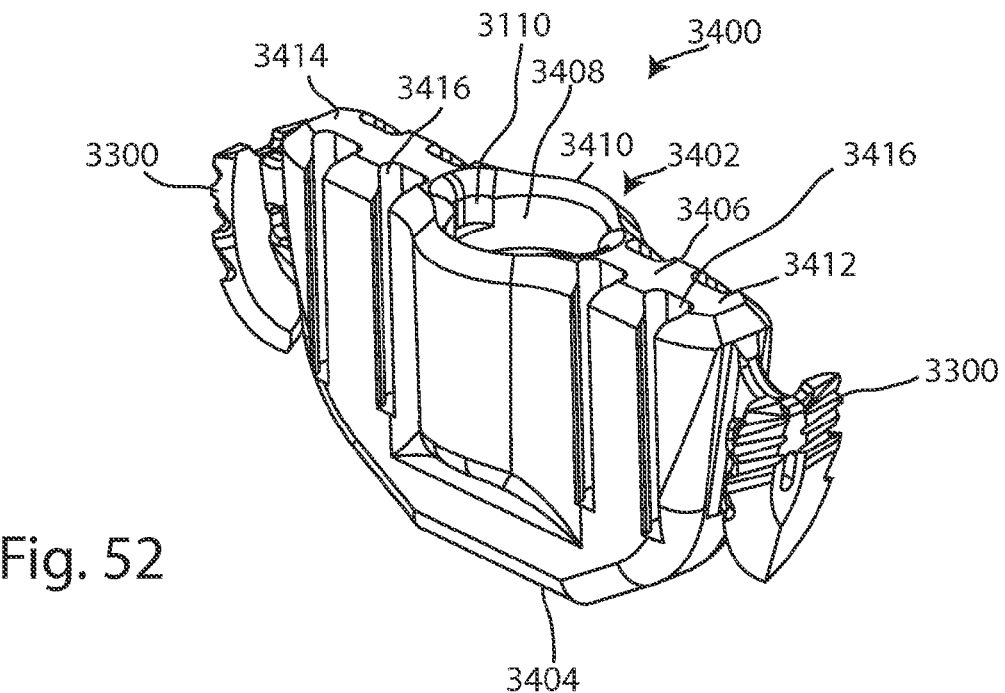
FIG. 52 is a perspective view of a one piece vertical member with built in anchors and slots to receive more anchors.
Figure 53:
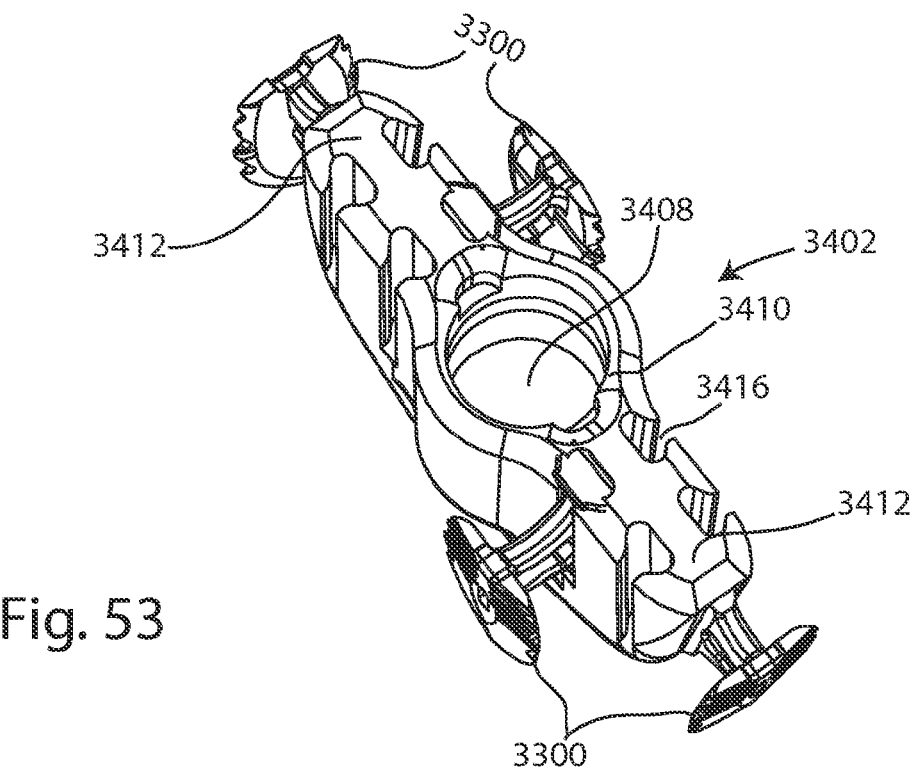
FIG. 53 is a top perspective view of the one piece vertical member of FIG. 50 with horizontal anchors in the slots.

Referring to FIGS. 52 and 53, a single anchoring system 3400 includes only a vertical member 3402 that is implantable in a shoulder in superior-inferior direction. The vertical member includes features substantially similar to the previous embodiment vertical member 3100; however the present embodiment does not interact with a horizontal member. This vertical member 3402 includes a distal end 3404, a proximal end 3406, and a central hole 3408 defined by a cylindrical wall 3410 substantially the same as the previous embodiment vertical member 3100 with the same cutouts 3110 as previously described. The central hole 3408 terminates just prior to a distal end 3404 and does not pass through the entire body of the vertical member 3402. Arms 3412, 3414 extend from the cylindrical wall 3406 in opposite directions away from the central hole 3408. The arms 3410, 3412 terminate with blade anchors 3300 integrally formed with the body of the vertical member 3400.

One or more tracks 3416 may be integrally formed within the body of the vertical member 3402 and extend from the proximal end 3406 toward the distal end 3404 terminating just prior to the distal end. The tracks 3416 may be dovetailed and are configured to receive anchors 3300. The number of tracks 3416 may vary and may extend from only one side of the arms 3412, 3414 or both sides. An articulating member may interact and engage the vertical member 3402 in much the same manner as any of the previous embodiment herein described.

Figure 54:
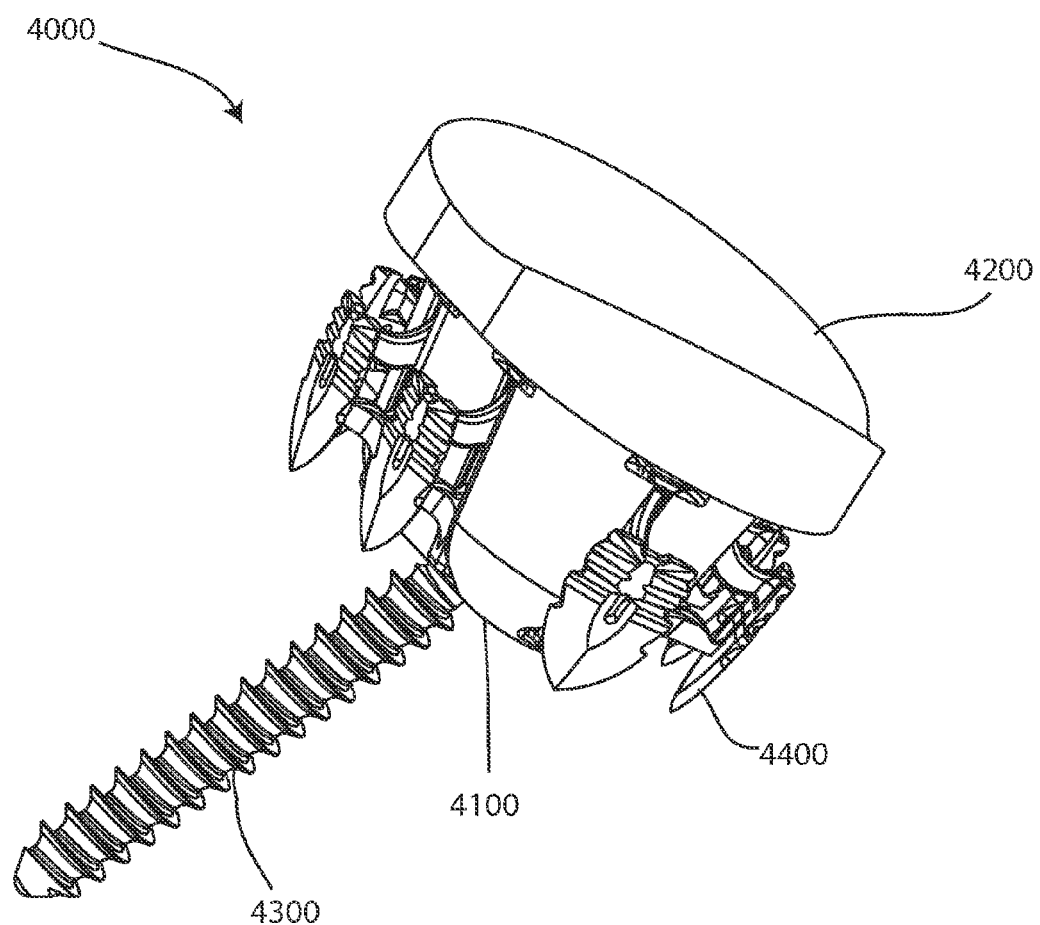
FIG. 54 is a perspective view of an alternate embodiment glenoid vault system with a vault, screw, anchors and glenoid.
Figure 55:
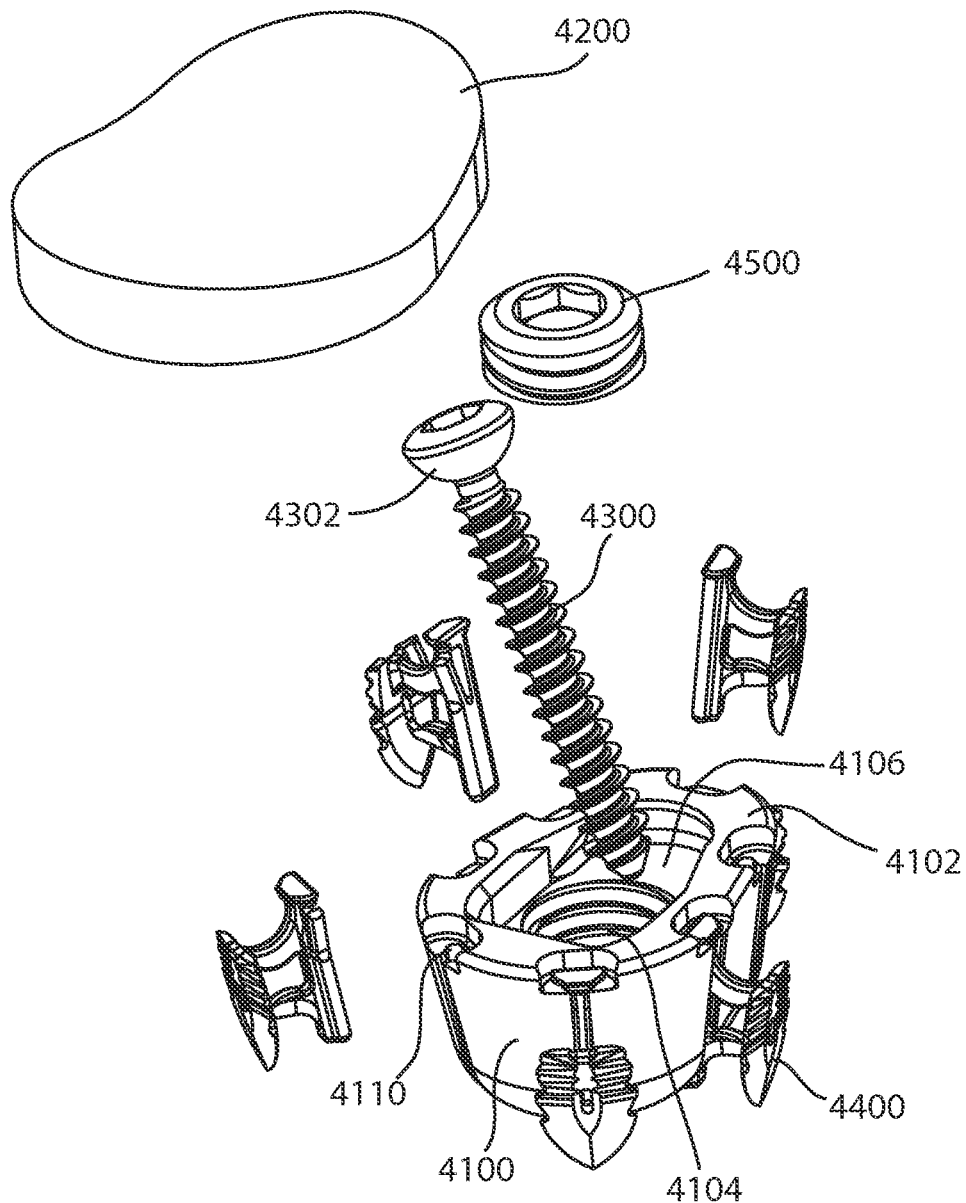
FIG. 55 is an exploded perspective view of the system of FIG. 54.
Figure 56:
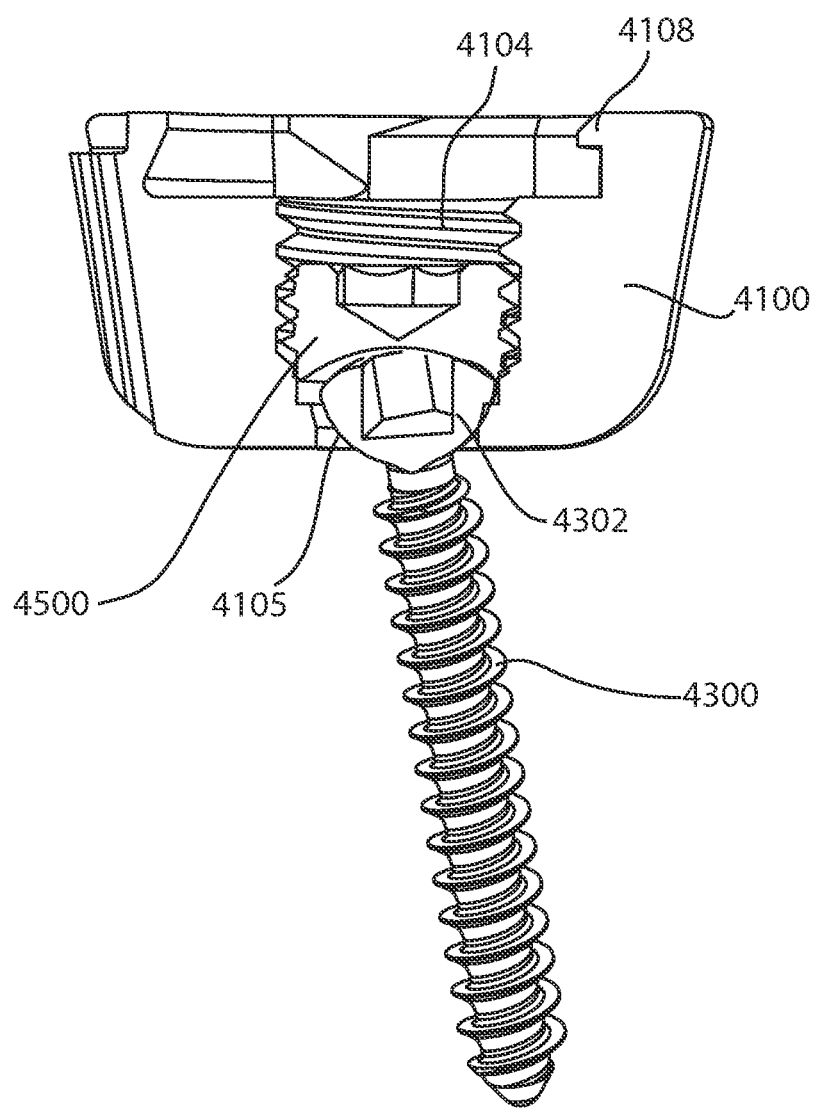
FIG. 56 is a cross sectional view of the vault and screw of FIG. 54.

Referring to FIGS. 54-56, an alternate embodiment of a glenoid vault system 4000 is depicted. The system 4000 includes a vault 4100 that may be pear-shaped, but may also be ovoid, spherical, cylindrical or many other shapes. The shape of the vault 4100 may depend on the bone preparation and the patient anatomy. The system also includes an articulating component 4200, a screw 4300, which may be a scapular spine screw, blade anchors 4400 as previously described herein, and a locking nut 4500.

The vault 4100 may comprise a circumferential wall 4102 defining the shape of the vault and encircling a central hole 4104 and an articulating void 4106 adjacent to and proximal the central hole 4104. The central hole 4104 may be cylindrical and may threadably or slidably receive the screw 4300. A screw seat 4105 (refer to FIG. 56) sits toward a distal end of the central hole 4104 and engages a head of the screw 4302 and allows the screw 4300 to pivot to secure the vault 4100 to the best bone. The locking nut 4500 is threaded and short and threadably engages the central hole 4104 locking the screw 4300 in place and preventing back-out. The locking nut 4500 fits at least partially, if not entirely, within the central hole 4104.

The articulating void 4106 provides a space for the articulating member 4200 to engage and lock to the vault 4100. The articulating void 4106 defined by the wall 4102 may have the same shape as the vault 4100. The void 4106 may taper, providing an overhang 4108 of the wall 4102 to provide a snap fit for engaging the articulating component 4200. The wall 4102 may also include an engagement ring similar to those embodiments previously described that protrudes toward the central hole 4104 into the void 4106.

Multiple tracks 4110 may be embedded in the outside of the wall 4102. The tracks may be substantially similar as the tracks 3416, 3102 previously described herein and interact with the blade anchors 4400 in substantially the same manner as previously described herein.

Figure 57:
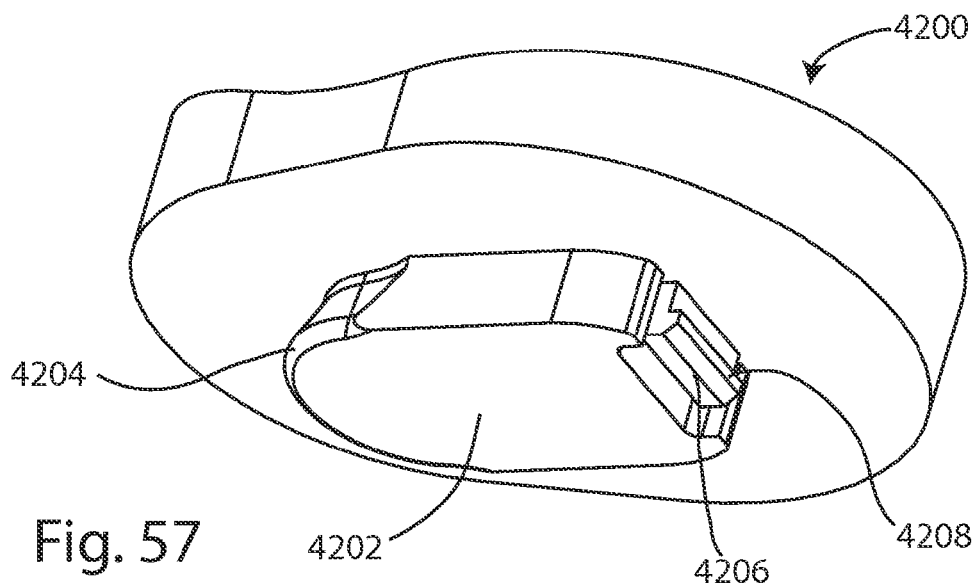
FIG. 57 is a bottom perspective view of the glenoid of the system of FIG. 54.

Referring to FIG. 57, the articulating component 4200 may be similar to those embodiments previously described with the exception of the post. A post 4202 extends from the bone facing side of the articulating component 4200 but may form a larger footprint from those posts previously disclosed. The post 4202 may include a first locking mechanism 4204 and a second locking mechanism 4206. The first locking mechanism 4204 is a reverse taper that extends out from where the post initially protrudes from the bone facing side of the articulating component 4200. On the opposite side of the post 4202 is the second locking mechanism 4206 that comprises a shoulder 4208 to snap into the void 4106 below the overhang 4108 of the wall 4102.

Figure 58:
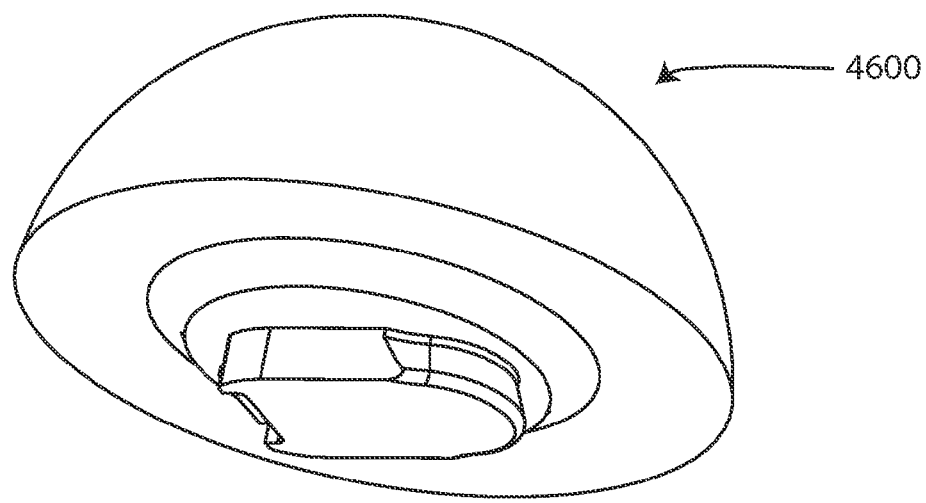
FIG. 58 is a bottom perspective view of a glenosphere that may be attached to the vault system of FIG. 54 in place of the glenoid.

Referring to FIG. 58, the articulating glenosphere 4600 shows a similar engagement feature as the articulating component 4200 and engages the vault 4100 in substantially the same manner as the articulating component 4200. The articulating component 4200 and glenosphere 4600 are reversibly locked to the vault so revision surgeries are easily accomplished without having to remove the vault 4100.

One method for implanting the vault system 4000 is to prepare the bone for the vault 4100 and securing the vault to the bone with the screw 4300. After securing the vault 4300 the locking nut 4500 locks the screw into place. The blade anchors 4400 may insert into the bone before, during or after the screw 4300 is inserted or fixed. The articulating component 4200 or glenosphere 4600 is then locked to the vault. The order in which the different components are secured is meant to be illustrative and not restrictive and the order may change within the scope of the system 4000.

In all embodiments described within this specification it will be appreciated that any articulating component or glenosphere will interact with the vaults in such a manner to allow for easy attachment while maintaining a robust design. The engagement allows for interchangeability from an articulating component to a glenosphere for easy revision. The engagement described previously with a snap fit or seal, or other locking means including a Morse taper (not shown) which may not require an engagement ring, of either the articulating component post or the glenosphere post engaging the appropriate AP/horizontal or SI/vertical component with the groove and or ring.

The features of all of the different systems described above may include the following: the vertical member width may be less than 6 mm; the horizontal member width may be less than or equal to 5 mm; overall vault depth may be less than 20 mm; the central portion or central ring diameter may be less than 9 mm; the central hole or central bore may be used for a scapular spine screw; and the cross members/components length or anchor sizing can be varied.

Figure 59A:
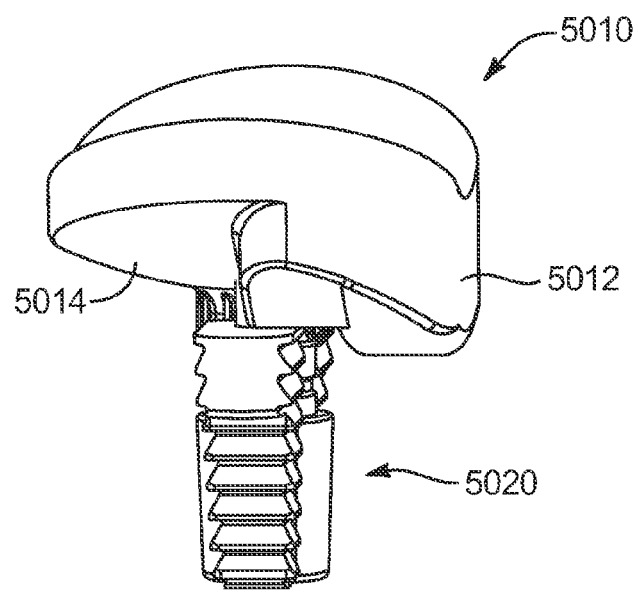
FIG. 59A is an oblique view of a glenoid component with a superior-inferior component.

Referring to FIG. 59A, an example of a glenoid component 5010, with an attached Superior-Inferior (SI) implant component 5020 is illustrated. Glenoid component 5010 may be similar or identical to articulating component 20. The attached SI implant component 5020 may share some or all of the features of SI component 100. The SI implant component 5020 may also be referred to as an SI component, and may otherwise be a broach, or other component for anchoring a device to a bone, such as a trial.

The glenoid 5010 illustrated in FIG. 59A 5010 includes an augment component 5012 that may protrude outward from a distal, bone facing surface 5014 of the glenoid component 5010. The augment 5012 may be similar to augment 434 described above. The augment component 5012 may otherwise be formed separately from glenoid component 5010, and may be reversibly attachable to both the SI component 5020 and the glenoid component 5010. In FIG. 59A, the augment component 5012 is operationally assembled between the SI-component 5020 and the glenoid component 5010. The distal surface 5014 of the augment component 5012 may include a connection feature, such as an aperture, designed to engage a complementary portion of the SI component 5020.

Figure 59B:
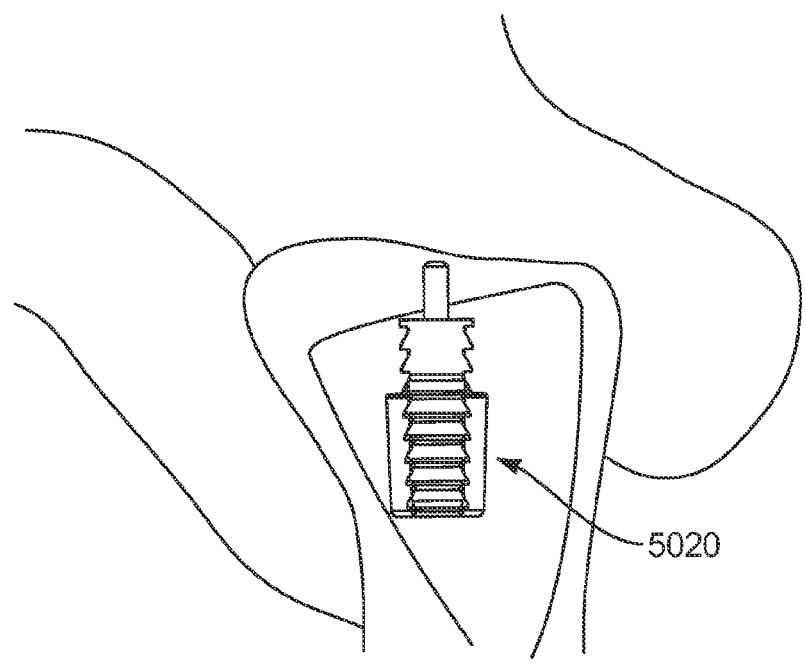
FIG. 59B is a side view of the glenoid component and superior-inferior component of FIG. 59A installed in a bone.
Figure 60:
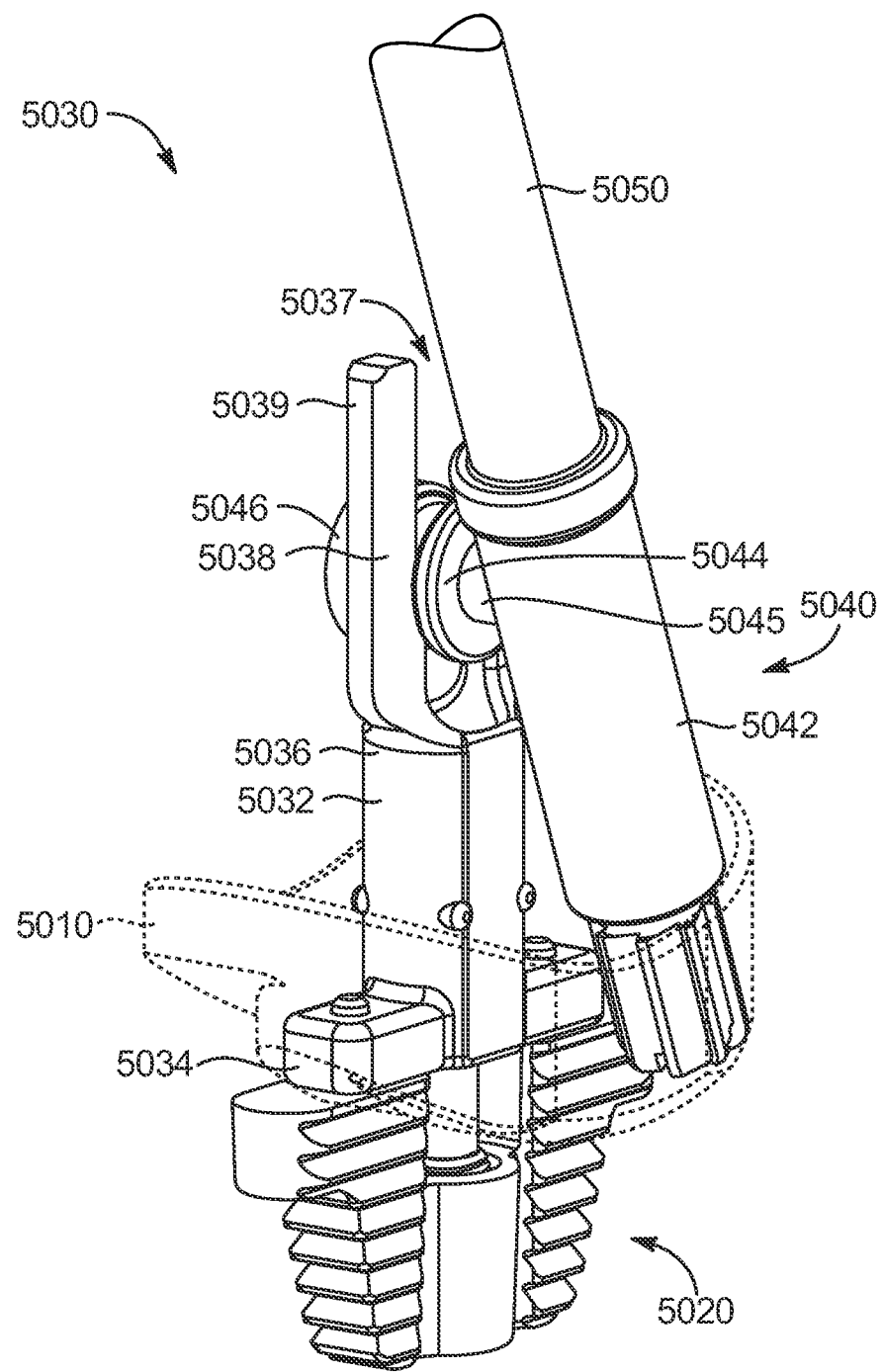
FIG. 60 is an oblique view of an augment preparing instrument with the superior-inferior component of FIG. 59A.
Figure 61:
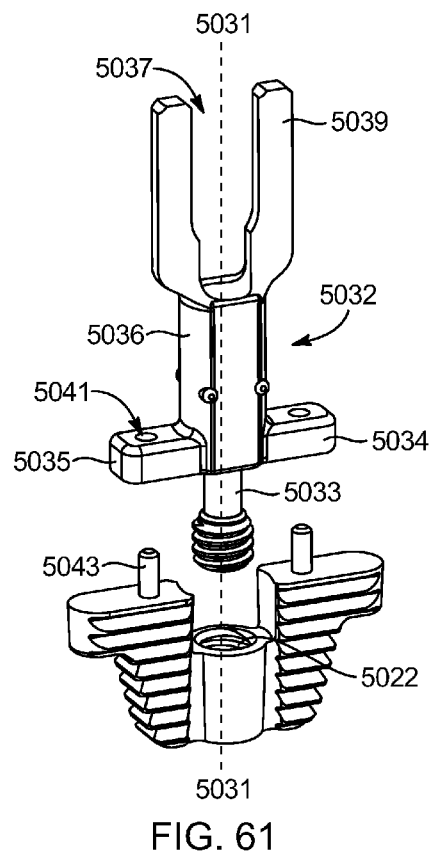
FIG. 61 is an oblique exploded view of a connecting feature of the augment preparing instrument of FIG. 60 with the superior-inferior component of FIG. 59A.
Figure 62:
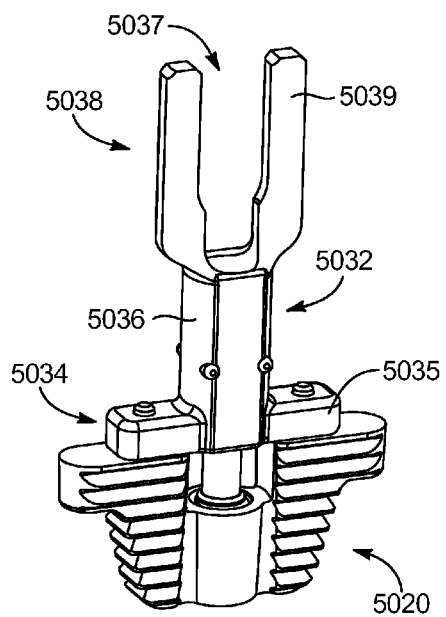
FIG. 62 is an oblique assembled view of the connecting feature and the superior-inferior component of FIG. 61.

Referring to FIG. 59B, the SI component 5020 is shown embedded into the bone of the shoulder joint, which may be a glenoid process. Referring to FIG. 60, an augment preparation instrument 5030, which may also be referred to as an instrument, is shown assembled with the SI component 5020, and in relation to a prospective augmented glenoid component 5010. Augment preparing instrument 5030 may include an SI component connecting feature 5032, which may also be referred to as a connection feature. Connection feature 5032 may be integral to the instrument 5030, or may be formed separately and be reversibly attachable to the instrument 5030. In operation, the connection feature 5032 may be secured to the SI broach 5020 to operationally couple the instrument 5030 to the SI broach 5020. Referring also to FIGS. 61 and 62, the connecting feature 5032, which may also be referred to as a connection unit, may include a distal broach-contacting portion 5034, a medial portion 5036 and a proximal forked portion 5038. The proximal forked portion 5038 may include at least one arm 5039, or prong that extend proximally from the medial portion 5036. In the example shown, the connection unit 5032 includes two arms 5039 that define a central channel 5037 that is located between the arms 5039.

The medial portion 5036 may extend distally from the proximal forked portion 5038, and may be substantially cylindrical. The medial portion 36 may also be square, triangular or otherwise irregularly shaped. The medial portion 5036 may intersect the broach-contacting portion 5034. As illustrated in FIG. 61, the broach-contacting portion 5034 may include at least one lateral arm 5035 that extends substantially perpendicularly to a central axis 5031 that extends through the central channel 5037 and further through the medial portion 5036. The central axis 5031 may also be referred to as a vertical axis. In FIGS. 61 and 62, it can be seen that broach-contacting portion 5034 includes two lateral arms 5035, and each arm 5035 may include an anti-rotation feature 5028 that comprises an aperture 5041 shaped to receive a complementary protruding feature 5043, such as a peg, post, or rail, on the SI component 5020. In an alternate embodiment, the anti-rotation feature 5028 of the lateral arms 5035 may include a male mating feature, such as a peg, and the SI component may include a complementary female mating feature, such as a groove or aperture. When the connection feature 5032 is operationally engaged with the SI component, as seen best in FIG. 63, at least a portion of the protruding feature 5043 on the SI component 5020 may be contained within the aperture 5041 on the lateral arm 5035. The anti-rotation feature 5028 is configured to substantially prevent rotation of the SI-connecting feature 5032 about the central axis 5031 that extends through the center of the medial portion 5036.

Figure 63:
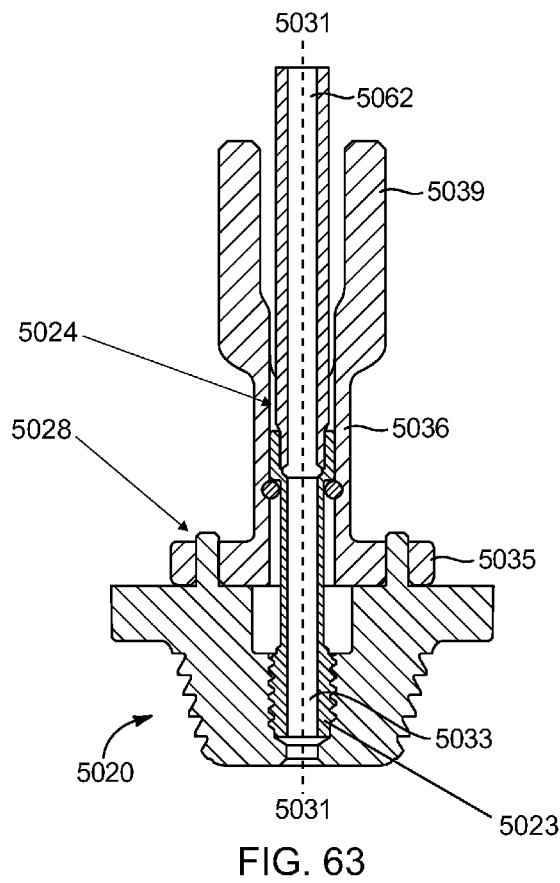
FIG. 63 is a longitudinal cross sectional view of the connecting feature and the superior-inferior component of FIG. 61.
Figure 64:
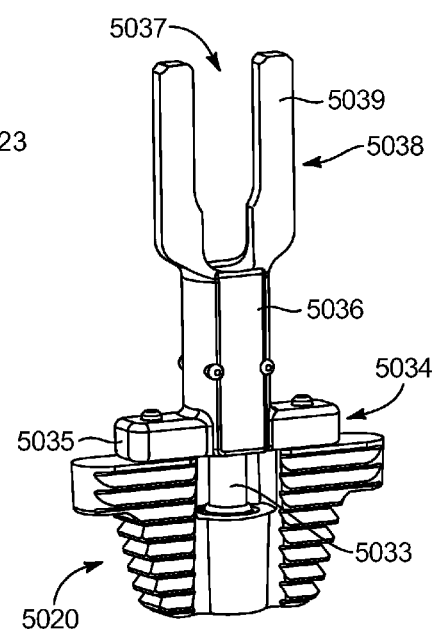
FIG. 64 is another oblique assembled view of the connecting feature and the superior-inferior component of FIG. 61.

The connecting feature 5032 may also include an SI component-fastener 5033, as illustrated in FIG. 61. The SI component fastener 5033 may also be referred to as a fastener. The fastener 5033 may extend distally from a substantially central location between the lateral arms 5035 of the broach-contacting portion 5034, and the fastener 5033 may be at least partially threaded with threads 5023. The fastener 5033 may be shaped to be received within the central ring of the SI component 5020. Referring to FIGS. 63 and 64, the connecting feature 5030 is shown operationally complied to the SI component 5020.

Figure 65:
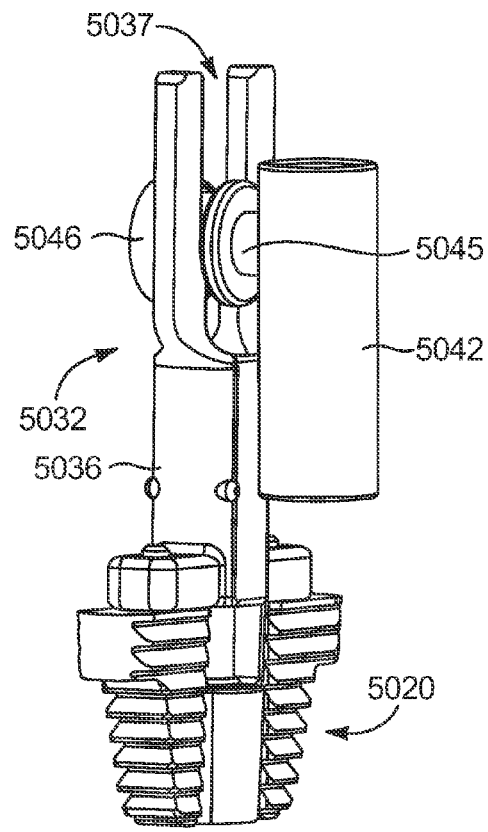
FIG. 65 is an oblique view of a guide component of the augment preparing instrument of FIG. 60 with the connecting feature and the superior-inferior component of FIG. 61.
Figure 66:
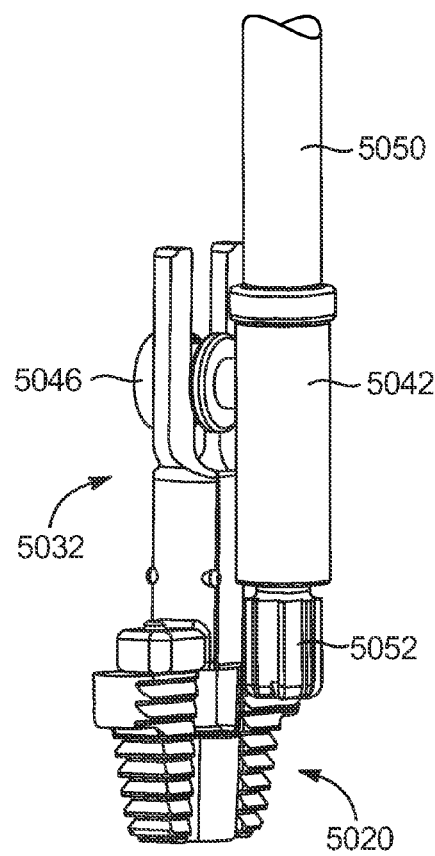
FIG. 66 is an oblique view of a bone preparing instrument with the guide component, the connecting feature, and the superior-inferior component of FIG. 65.

The augment preparing instrument 5030 may also include a guide component 5040, or guide portion that is shaped to engage a portion of a bone preparing instrument 5050, such as a drill, burr or mill. The guide component 5040 may be integrally formed with the connection feature 5032, or may be formed separately. The guide component 5040 may be reversibly attachable to the connection feature 5032. Referring also to FIGS. 65 and 66, the guide portion 5040 may include a sleeve 5042 and an arm 5044. At least a portion of the sleeve 5042 may be hollow to receive the bone preparing instrument 5050, and the sleeve 5042 may be substantially tubular. In another embodiment, the sleeve 5042 may be rectangle, square or otherwise irregularly shaped.

The arm 5044 may extend outward from the sleeve 5042, and may include a neck portion 5045 and an engagement feature 5046. The neck portion 5045 may extend between the sleeve 5042 and the engagement feature 5046. The engagement feature 5046 may be substantially cylindrical and may include a circumferential groove 5047 or channel that extends at least partially around the engagement feature 5046. The groove 5047 may be shaped to engage the at least one arm 5039 of the proximal forked portion 5038 of the connection feature 5032. When the at least one arm 5039 of the proximal forked portion 5038 is engaged with the groove 5047 of the engagement feature 5046, the guide component 5040 may be lockably coupled to the connection feature 5032. When the guide component 5040 is coupled to the connection feature 5032, the guide component 5040 may be rotatable about an axis that extends through the engagement feature 5046.

Referring to FIGS. 61-66, a method for assembling the instrument 5030 to the SI component 5020 and to a bone-removal instrument is illustrated. The bone-removal instrument may be a burr or a mill. The SI component connecting feature 5032, may embedded into the bone of the shoulder joint, and may be oriented such that the fastener 5033 is aligned with a central ring 5022 of the SI component 5020, and such that the apertures 5041 in the lateral arms 5035 of the broach contacting portion 5034 engage the complimentary post features 5043 located on the SI component 5020. The SI component connecting feature 5032 may then be positioned such that at least a portion of the fastener 5033 is contained within the central ring 5022, and such that the post features 5043 are at least partially contained in the apertures 5041 of the lateral arms 5035.

An actuating instrument 5062 may be a cavity 5024 of the connection feature 5032 and used to further secure the fastener 5033 by rotating the fastener 5033 about the vertical axis 5031 to engage the threads 5023 and move the fastener 5033 distally into the SI component 5020. The SI component connecting feature 5032 is shown assembled to the SI component 5020 in FIG. 64.

Referring to FIGS. 65 and 66, the guide component 5040 may be attached to the SI component connecting feature 5032 by sliding the at least one arm 5044 of the engagement feature 5046 into the channel 5037, such that the sleeve 5042 is oriented substantially parallel to the SI component connecting feature 5032. A bone preparing instrument 5050 may then be inserted into the sleeve 5042 such that a bone contacting portion 5052 extends distally from the sleeve 5042.

Figure 67:
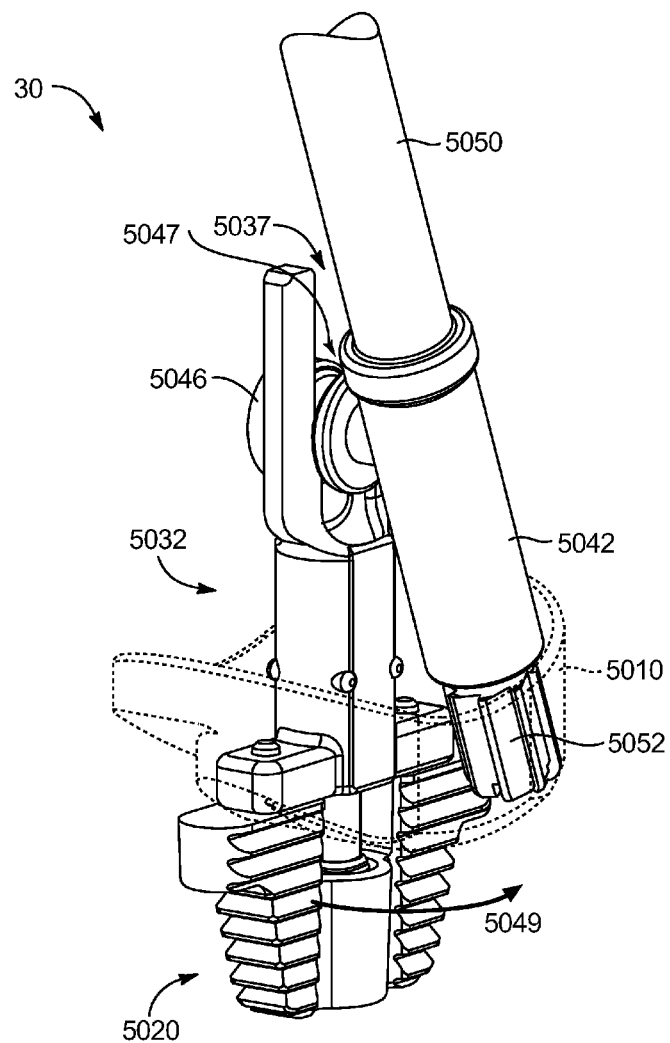
FIG. 67 is an oblique view of the bone preparing instrument, the guide component, the connecting feature, and the superior-inferior component of FIG. 65, with an augmented glenoid component shown in dashed lines.

Referring to FIG. 67, when the at least one arm 5044 of the engagement feature 5046 is contained in the channel 5037, the guide component 5040 may be rotatable relative to the SI connecting feature 5032. When the bone preparing instrument 5050 is placed into the sleeve 5042, the bone preparing instrument 5050 may be rotated with the sleeve 5042 as illustrated by motion arrow 5049. As the bone preparing instrument 5050 is moved along the bone surface, a desired portion of bone may be shaped or removed. Additionally, the bone preparing instrument 5050 may be rotated within the sleeve or otherwise actuated, and the bone-contacting portion 5052 of the bone removal instrument 5050 may act to remove a portion of bone that to match the shape of the augment 5012 of an augmented glenoid component 5010.

Figure 68:
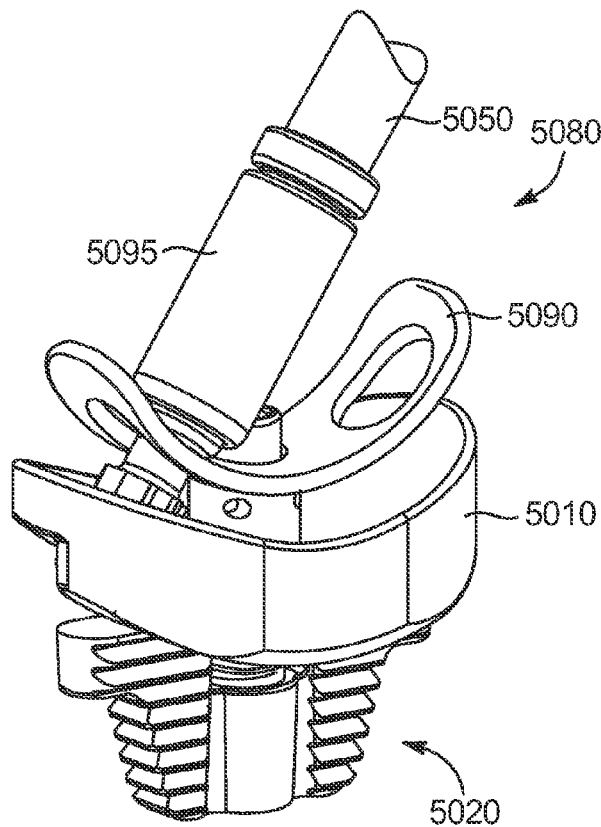
FIG. 68 is an oblique view of another augment preparing instrument with the superior-inferior component of FIG. 59A, with an augmented glenoid component.

Referring to FIGS. 68-71, an alternative system for preparing a bone, such as a glenoid process, to receive an augmented glenoid is depicted. System 5080 may be used for preparing the bone portion corresponding to the central area of the augmented glenoid component 5010, which is illustrated in FIG. 68.

FIG. 68 illustrates system 5080 assembled with the SI component 5020, and relative to the desired placement of an augmented glenoid component 5010. System 5080 may include an SI component connecting feature 5082 and a guide component 5090. Also illustrated in FIG. 68 is a bone-pre-paring instrument 5050, which may be a burr, mill or drill, coupled to a drill sleeve 5095.

Figure 69:
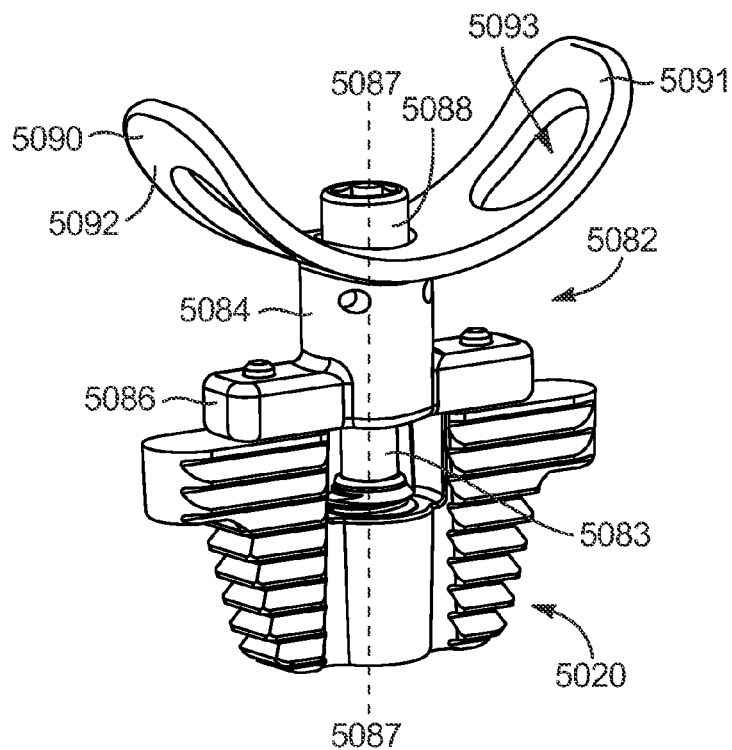
FIG. 69 is an oblique view of a connecting feature and a guide component of the augment preparing instrument and the superior-inferior component of FIG. 68, without the augmented glenoid component.

Referring to FIG. 69, the SI component connecting feature 5082 may include a body, or medial portion, 5084, which may be substantially cylindrical. The body, or medial portion, 5084 may otherwise be square, triangular or irregularly shaped. At least one lateral arm 5086 may extend from a distal portion of the body 5084. Illustrated in FIG. 69, two lateral arms 5086 extend outward from the body 5084 opposite to one another. Each arm 5084 may include at least one aperture, groove, or other female mating feature to engage a complementary male mating feature on the proximal surface of the SI component 5020. In an alternate embodiment, the SI component 5020 may include a female mating feature, and the lateral arm 5086 may include a complementary male mating feature. When the connecting feature 5082 engages the SI component 5020, at least a portion of the male mating feature of the SI component may be contained within the female mating feature of the lateral arm 5086, thus substantially preventing rotation of the body 5084 about a central axis 5087.

The body, or medial portion, 5084 may include a fastener 5083, which may be similar or identical to fastener 5033 described previously in this application. The body, or medial portion, 5084 may also include a proximal neck 5088, which may also be substantially cylindrical, and extend proximally from the body 5084. The diameter of the proximal neck 5088 may be less than the diameter of the body 5084, and may be shaped to engage with a guide component 5090.

The guide component 5090 may include a first surface 5091 and a second surface 5092 opposite the first surface 5091. The guide component 5090 may be substantially flat and U-shaped, and may include at least one opening 5093 that extends from the first surface 5091 to the second surface 5092, and shaped to engage a bone-preparing instrument 50, as illustrated in FIG. 70A.

The openings 5093 may have an oblong shape, or may otherwise be circular or polygonal. As illustrated in FIG. 69, the body 5084 may be coupled to the SI component 5020 by inserting the fastener 5083 into a central portion of the SI component. The apertures on the arms 5084 may engage a rod or other complimentary feature on the SI component to further secure the SI connecting feature 5082 to the SI component 5020 and to substantially prevent rotation of the SI-connecting feature 5082 about the central axis 5087 that extends through the center of the body 5084.

Figure 70A:
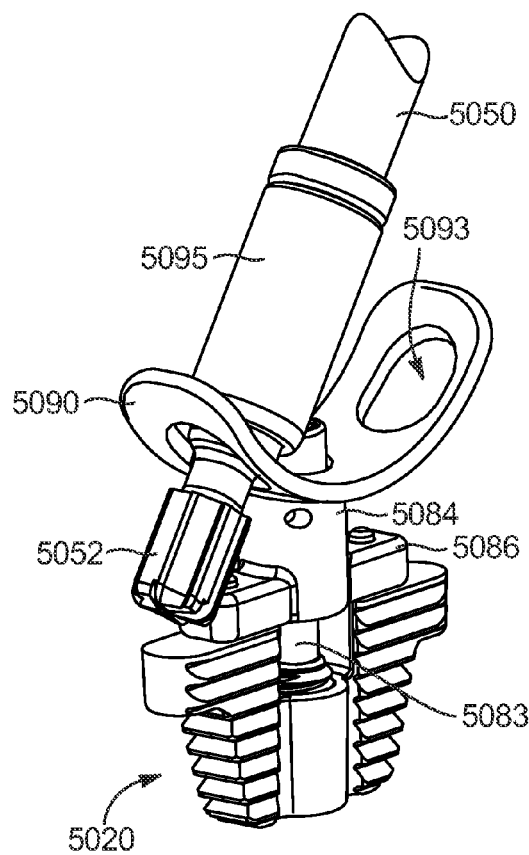
FIG. 70A is an oblique view of the augment preparing instrument and the superior-inferior component of FIG. 68, without the augmented glenoid component.
Figure 70B:
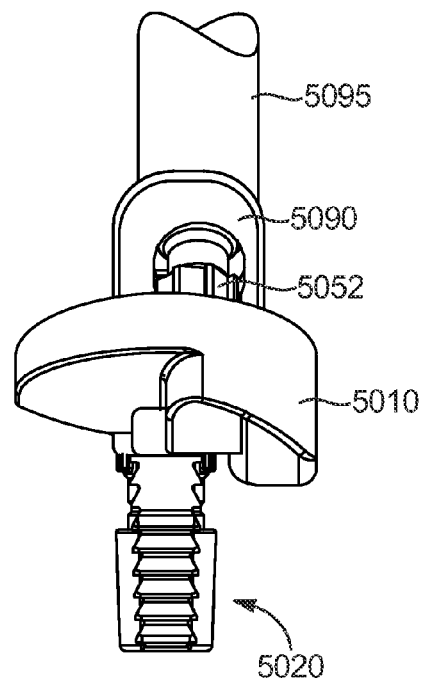
FIG. 70B is a side view of the augment preparing instrument and the superior-inferior component of FIG. 70A, with the augmented glenoid component of FIG. 68.

As illustrated in FIG. 70A, a sleeve 5095 may be placed such that a distal portion of the sleeve 5095 may contact a portion of the first surface 5091 defining the opening 5093. A bone-preparing instrument 5050, such as a burr or drill, may be inserted into the sleeve 5095 such that the bone-contacting portion 5052 extends from the distal portion of the sleeve 5095 and further extends through the opening 5093 of the guide component 5090 to a predetermined drill depth. The predetermined drill depth may define the desired central area of the augmented glenoid. The bone-preparing instrument 5050 may then be actuated to remove a portion of bone complementary to the augmented glenoid component 5010, as illustrated in FIG. 70B.

Figure 71:
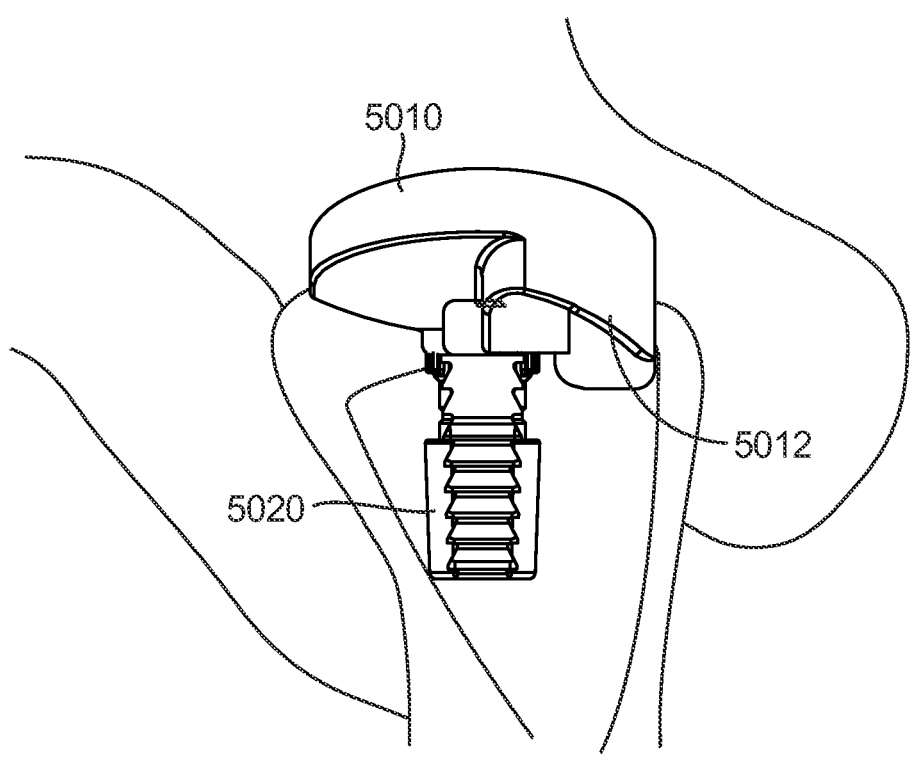
FIG. 71 is a side view of a glenoid component and superior-inferior component installed in a bone.
Figures 72A, 72B:
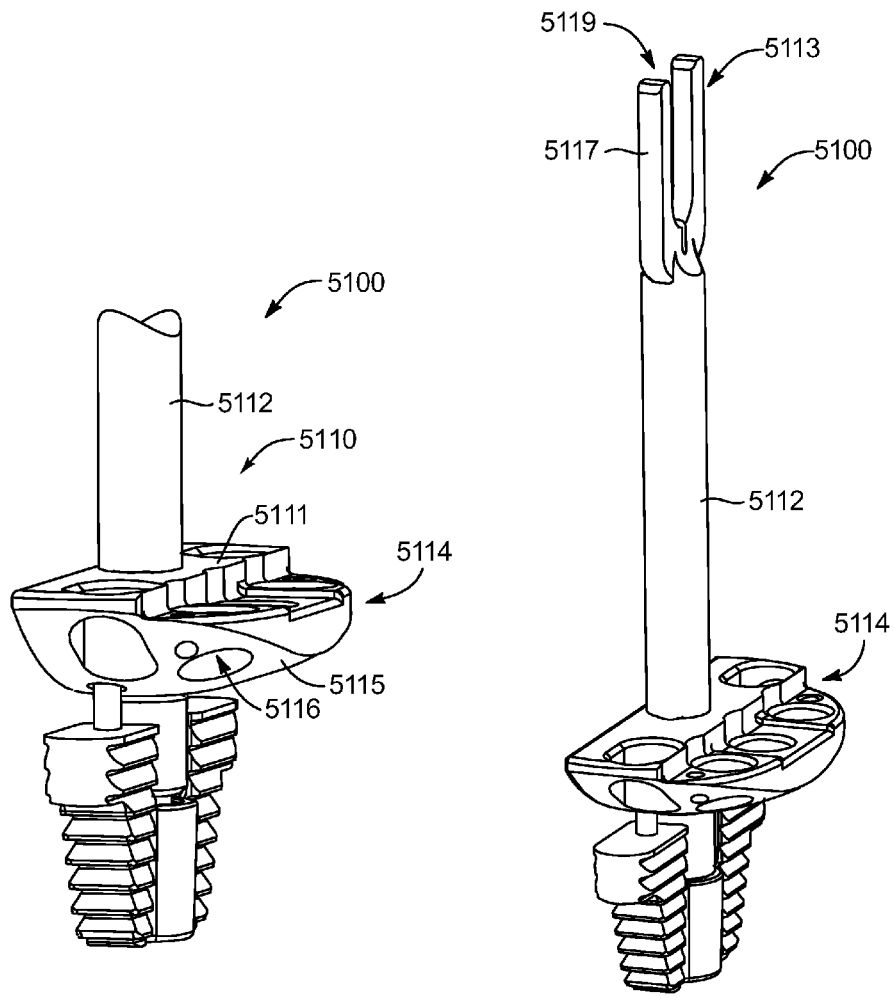
FIG. 72A is an oblique view of a portion of yet another augment preparing instrument with the superior-inferior component of FIG. 59A.
FIG. 72B is an oblique view of the augment preparing instrument and the superior-inferior component of FIG. 72A.

Referring to FIG. 71, an augmented glenoid component 5010 is shown in the bone, wherein the proximal bone surface has been shaped to complement the augment 5012 of the glenoid component 5010.

Referring to FIGS. 72A-74D, an alternative system for preparing a section of bone to receive a glenoid component 10 with an augment 12 is illustrated. System 5100 includes an augment guide 5110 that may couple to the SI component 5020. The augment guide 5110 may include an elongated rod, or medial portion, 5112 and a body 5114. The elongated rod, or medial portion, 5112 may include a proximal forked-portion 5113. The proximal forked portion 5113 may have a similar structure to proximal fork portion 5038 described previously in this application, and may include two arms 5117 that define a channel 5119.

The body 5114 may include a proximal surface 5111 and a distal surface 5115, and may be coupled to the rod 5112. As seen best in FIGS. 72A and 72B, the proximal surface 5111 may be substantially flat, and may include a plurality of surface features including steps and grooves. The proximal surface 5111 may alternatively be smooth and include no surface texture features. The distal surface 5115 may be curved. The curvature of the distal surface 5115 may be similar to or identical to the curvature of the augment 5012 of the glenoid to be inserted.

The body 5114 may also include a guide surface 5120 that intersects the proximal surface 5111 and the distal surface 5115. The body may include a plurality of apertures 5116. The apertures 5116 may be shaped to receive a bone-preparing instrument 5050, which may be an end mill.

Figure 73A:
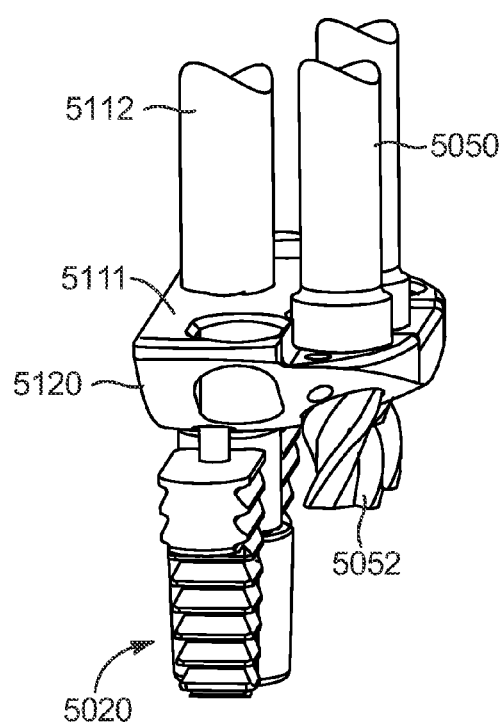
FIG. 73A is an oblique view of a bone preparation instrument with a portion of the augment preparing instrument and the superior-inferior component of FIG. 72A.

Referring to FIG. 73A, system 100 may be coupled to the SI component 5020. When the system 100 is coupled to the SI component 5020, a distal portion of the elongated rod 5112 may engage a central portion of the SI component 5020, and the guide surface 120 may lie coplanar with a portion of the SI component 5020.

When the distal portion of the elongated rod 5112 is engaged with the SI component, the distal surface 5115 of the body 5114 may contact a proximal portion of the SI component 5020. The distal surface 5115 may include at least one opening to engage a complimentary peg feature on the proximal surface of the SI component 5020 to further secure the body 5114 to the component 5020.

Figure 73B:
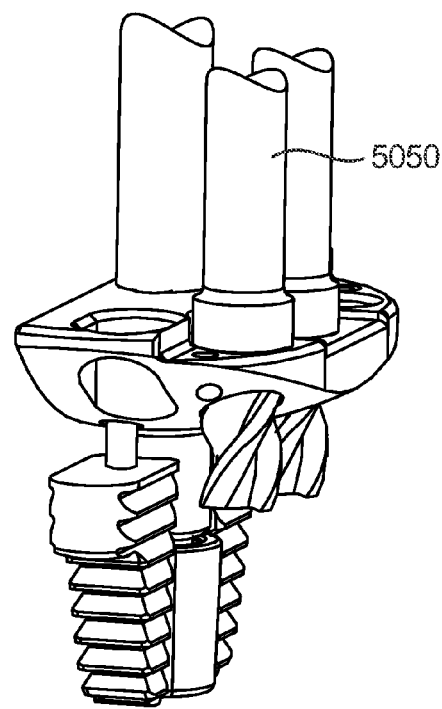
FIG. 73B is an oblique view of a second bone preparation instrument with the bone preparation instrument, the portion of the augment preparing instrument, and the superior-inferior component of FIG. 73A.

An end mill 5050 may be placed such that bone-contacting surface 5052 extends through at least one of the apertures 5116. When the end mill 5050 is inserted into the aperture 5116, the end mill 5050 may be substantially parallel to the elongated rod 5112. The end mill 5050 may be used to drill guide holes into the bone to a predetermined depth. As illustrated in FIG. 73B, the predetermined depth is shown with respect to the prospective augment 5012 of the glenoid component 5010.

Referring to FIGS. 74A-74D, a ronguer, or other bone removal instrument may be coupled to the augment guide 5110 after drilling the guide holes. The augmented guide may be rotated 180 degrees to allow access of the attached rounger to the guide holes.

Figure 74A:
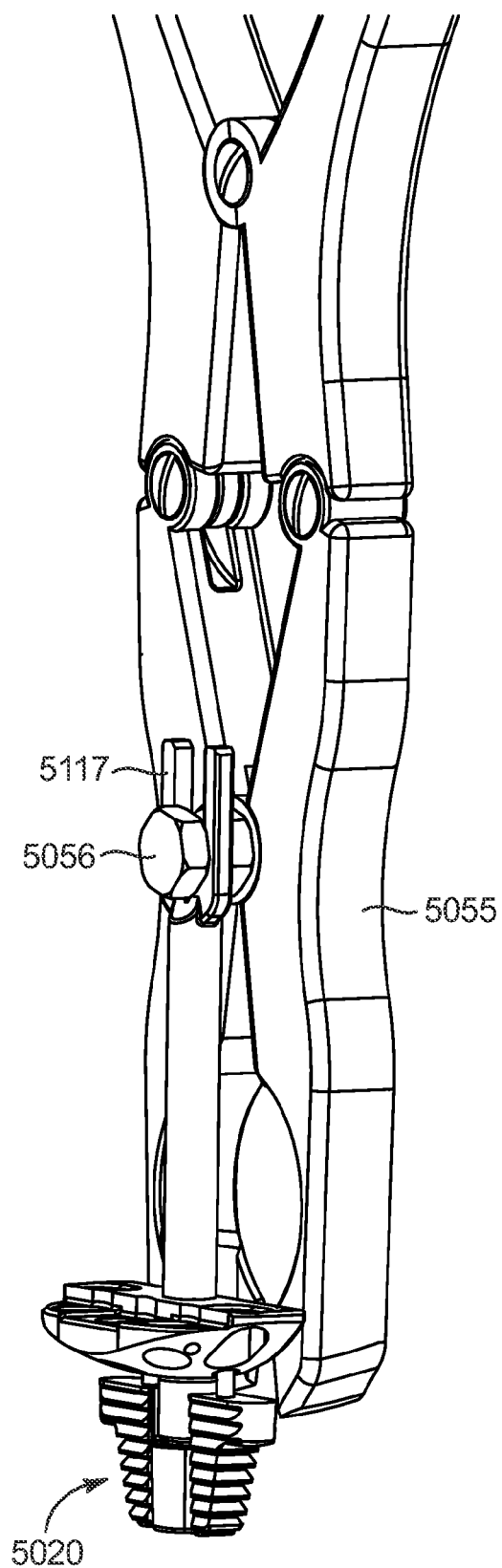
FIG. 74A is an oblique view of a rongeur coupled to the portion of the augment preparing instrument and the superior-inferior component of FIG. 73A.
Figures 74B, 74C:
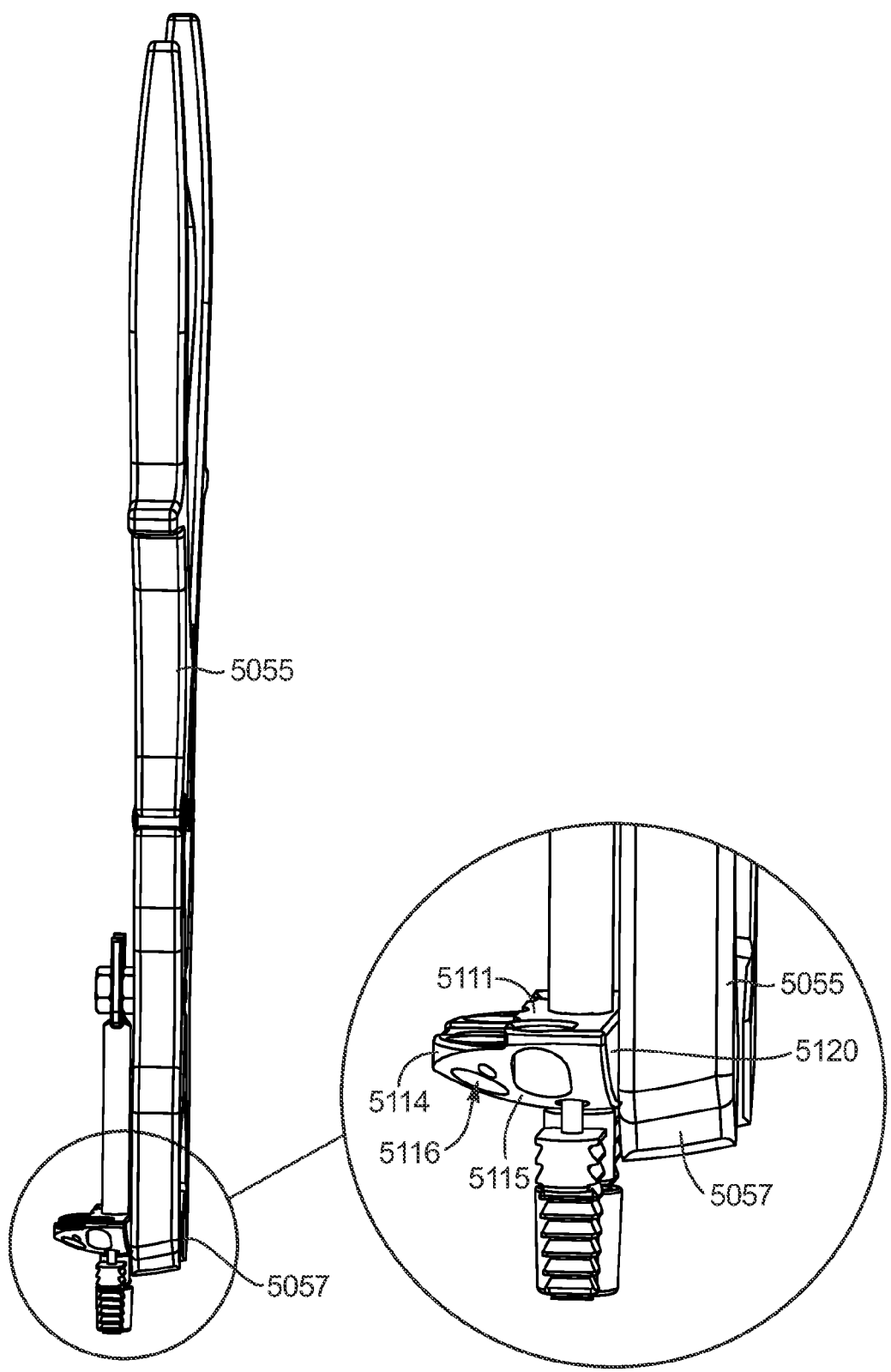
FIG. 74B is a side view of the rongeur, the portion of the augment preparing instrument, and the superior-inferior component of FIG. 74A.
FIG. 74C is an enlarged detail view of a portion of FIG. 74B.
Figure 74D:
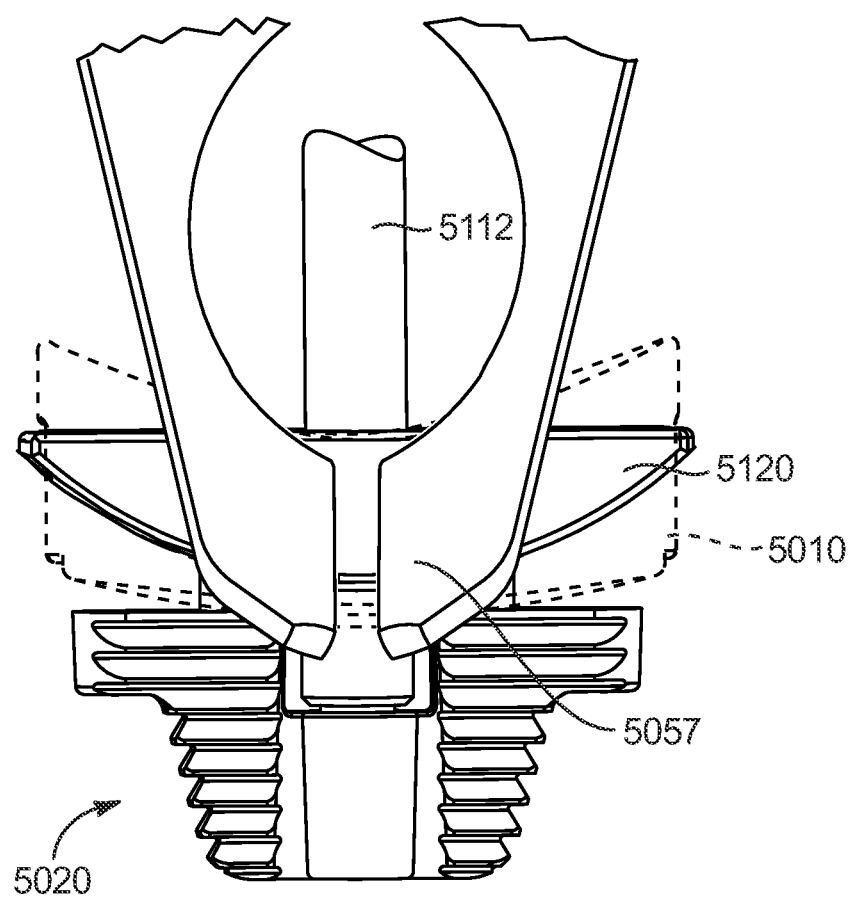
FIG. 74D is another enlarged detail view of a portion of the rongeur, the portion of the augment preparing instrument, and the superior-inferior component of FIG. 74A from a different angle.

The ronguer 5055 may include a coupling feature 5056 that engages the proximal forked portion 5113 of the elongated rod 5112. The coupling feature 5056 may be similar or identical to engagement feature 5046 described earlier in this application. When the ronguer 5055 is coupled to the augment guide 5110, a distal working end 5057 of the ronguer may lie parallel to the guide surface 5120, as illustrated in FIG. 74C. The working end 5057 may be actuated such that the action of the working end 5057 removes a portion of bone that matches the medial contour of the augment, as illustrated in FIG. 74D.

Referring to FIGS. 75A-81B, examples of a modular articular surface attachment system are illustrated. Specifically, the modular articular surface attachment system may be designed for use with a glenoid-articulating component, such as articulating component 20 or glenosphere 60 to replace a worn or otherwise non-functional bearing surface with minimal disturbance to a secure scapula platform.

Figure 75A:
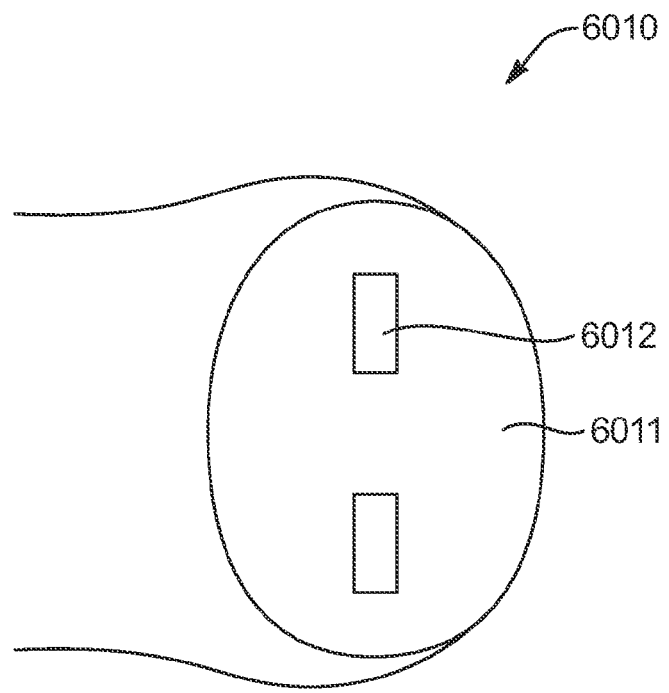
FIG. 75A is a side view of a glenoid component with rectangular channels.

Referring to FIG. 75A, an articular glenoid component system is illustrated including screw-in posts, which may provide an articular surface attachment feature. The system includes an articulating component, which may be referred to as a poly unit 6010. The articulating component may also have similar features to articulating component 20 described above. The poly unit 6010 may be attached to, or may be integral with an articulating surface. The articulating surface may be a glenoid articulating surface, such as articulating surface 22.

Poly unit 6010 may be have a substantially circular or oval profile, and may be disk-like. In alternate examples, poly unit 6010 may have a square or otherwise polygonal profile. The poly unit 6010 and may include a first proximal surface 6011. The first surface 6011 may include at least one channel 6012, groove, or aperture that is shaped to receive a complementary anchor feature, such as a screw, rod, pin, peg or other anchor feature that may be inserted into bone. The anchor feature may also be similar or identical to SI component 100 or AP component 200, or a combination of both.

Figure 75B:
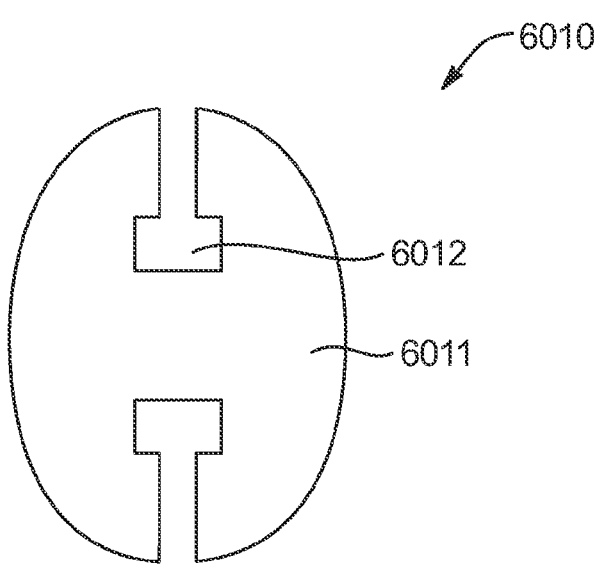
FIG. 75B is a side view of another glenoid component with T-shaped channels.

In the example shown in FIG. 75A, the poly unit may include two channels 6012. The channels 6012, which may also be referred to as grooves or slots may be rectangular, or may otherwise be rounded or T-shaped, as illustrated in FIG. 75B. It is contemplated that the channels 6012 have alternative sub-surface geometry, such as T-shaped or U-shaped geometries.

Figure 75C:
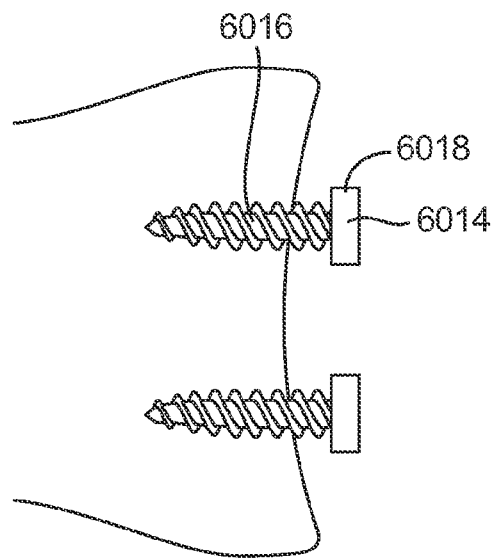
FIG. 75C is a top view of two anchors installed in a glenoid bone.

FIG. 75C illustrates a glenoid bone surface with two anchors 6014, which may also be referred to as anti-rotation features, inserted into a glenoid. The anchors 6014 may be pegs, screws or other protruding features shaped to engage the channels 6012 of the poly unit 6010. The anchors 6014 may include a first portion 6016 which is embedded in the bone and a second portion 6018 that protrudes outward from the surface of the bone. The first portion 6016 may be at least partially threaded, or may include other bone-engaging features such as roughening or circumferential teeth to enhance fixation of the anchors 6014 into the bone. The second portion 6018 of anchor 6014 may have a larger diameter than the first portion 6016.

After the anchors 6014 have been fixed within a bone, the poly unit 6010 may be attached to the anchors 6014. When the poly unit 6010 is attached to the anchors 6014, at least some of the second portion 6018 of the anchors 6014 may be contained within the channels 6012 of the poly unit 6010 to lockably connect the poly unit 6010 to the anchors 6014. In alternative embodiments, the anchors 6014 may be connected to the poly unit 6010 via a snap fit, press fit, or threading. When the poly unit 6010 has been attached to the anchors 6014, rotation and back out of the poly unit 6010 may be substantially restricted.

Figure 76A:
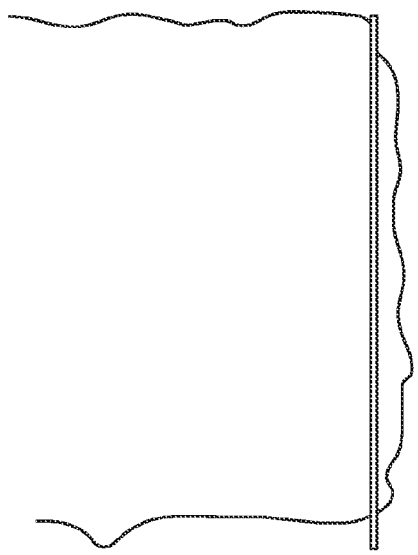
FIG. 76A is a top view of a glenoid bone with a resection line indicated.
Figure 76B:
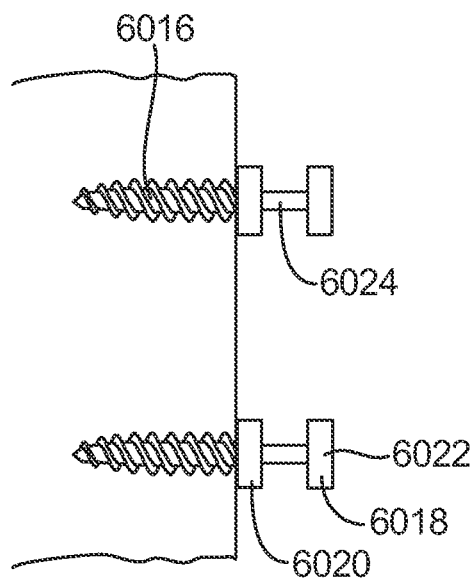
FIG. 76B is a top view of two anchors installed in the glenoid bone after resection along the resection line.

Referring to FIGS. 76A-76D, a method for preparing the anchors 6014 and attaching the poly unit 6010 is described. The glenoid vault surface may be resurfaced to provide controllable geometry. Referring to FIG. 76A, a resurface level 6009 of the glenoid vault is illustrated. A template or placement guide may be used to indicate the desired placement of the anchors 6014 into the bone. The first portion 6016 of at least one anchor may be inserted into the resurfaced bone, such that the second portion 6018 protrudes outward from the glenoid surface. The second portion 6018 of each anchor 6014 may include a seat portion 6020, which may also be referred to as a shoulder that contacts the bone when the anchor is fixed to the bone. The second portion 6018 may also include a head portion 6022 and an intermediate portion 6024 that extends between the seat portion 6020 and the head portion 6022. The head portion 6022 may have a circular profile, or may otherwise be oval or polygonal. The head portion 6022 may extend substantially perpendicular to the middle portion 6024. The diameter of the middle portion 6024 may be smaller than the diameter of the head portion 6022.

Figure 76C:
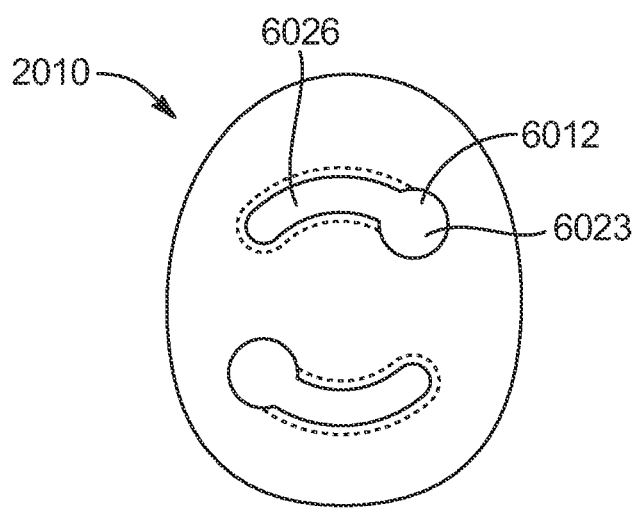
FIG. 76C is a side view of yet another glenoid component with arcuate undercut channels.
Figure 76D:
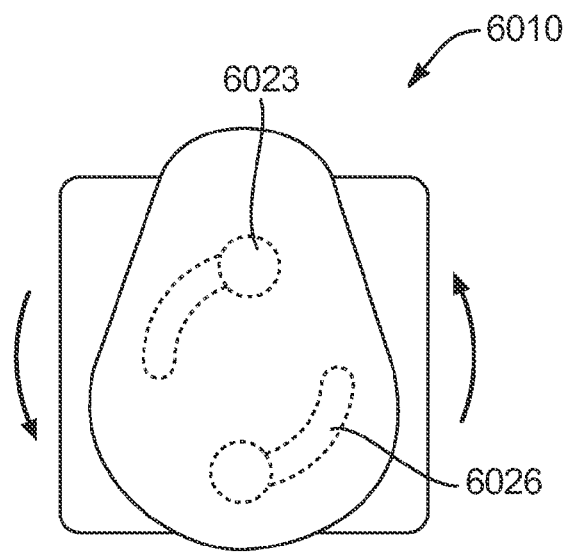
FIG. 76D is a side view of yet another glenoid component arcuate tapered channels.

Referring to FIGS. 76C and 76D, poly unit 6010 is illustrated with alternative channel geometry. In this example, channel 6012 may include a tapered portion, and may be designed to engage and lockably attach the poly unit 6010 to the anchors 6012 that have been inserted into the bone. The tapered channels 6012 may include an insertion portion 6023 and a tail portion 6026. The insertion portion 6023 may have a diameter that is greater than the tail portion 6026, and may be have a substantially circular perimeter. The geometry of the insertion portion 6023 may be complementary to the profile of the head portion 6022 of the anchors 6014. The tail portion 6026 may extend from the insertion portion 6023, and may be curved, as illustrated in FIG. 76C. In an alternative example, the tail portion 6026 may be straight. The tail portion 6026 may have a diameter that varies along the length of the opening, such that the diameter is greatest where the tail portion 6026 intersects the insertion portion 6023, and smallest at the point farthest from the insertion portion 6023. In an alternative example, the diameter of the tail portion 6026 may remain constant along the entirety of its length.

To attach the poly unit 6010 to the prepared glenoid surface containing a plurality of anchors 6014, the poly unit 6010 may be positioned such that the head portion 6022 of the anchors 6014 are aligned with the insertion portion 6023 of the tapered channels 6012. The head portion 6022 of the anchor 6014 may then be at least partially inserted into the insertion portion 6023. Once the head portion 6022 is contained within the insertion portion 6023, the poly unit 6010 may be rotated, as indicated by motion arrows 6025. Rotation may be counter-clockwise, such that as the poly unit 6010 is rotated, the intermediate portion 6024 of the anchor 6014 slides within the tail portion 6026. As the poly unit 6010 is further rotated, the intermediate portion 6024 may be pressed upon by the sides of the tail portion 6026 of the channel 6012 to lockably connect the anchor 6014 to the poly unit 6010. As the intermediate portions 6024 are pressed upon by the sides of the tail portions 6026 of the channels 6012, rotation in the opposite direction becomes restricted and more difficult.

In an alternative example, rotation may be clock-wise. In yet another example, the poly unit 6010 may be moved laterally, rather than rotated to secure the intermediate portion 6024 within the tail portion 6026.

Figure 77A:
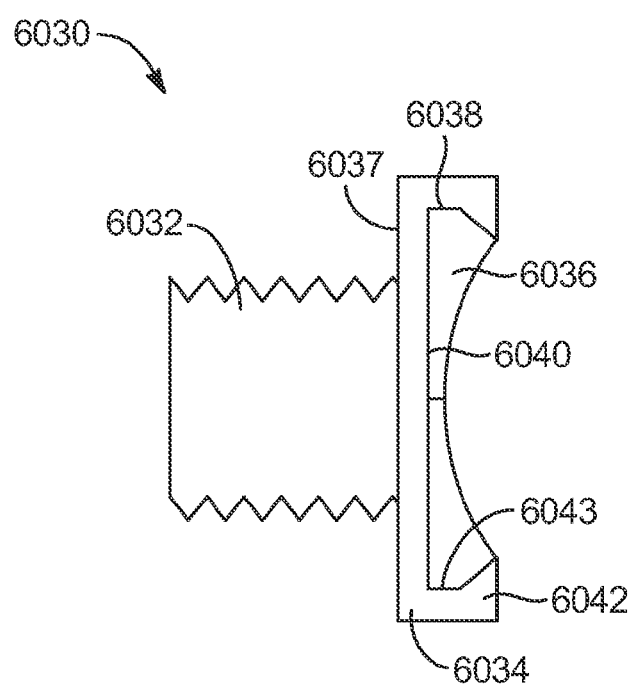
FIG. 77A is a top view of a glenoid insert.
Figure 77B:
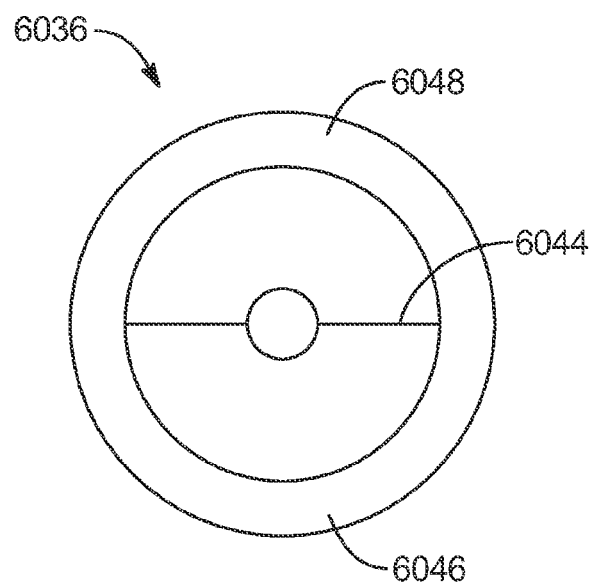
FIG. 77B is a side view of yet another glenoid component.
Figure 77C:
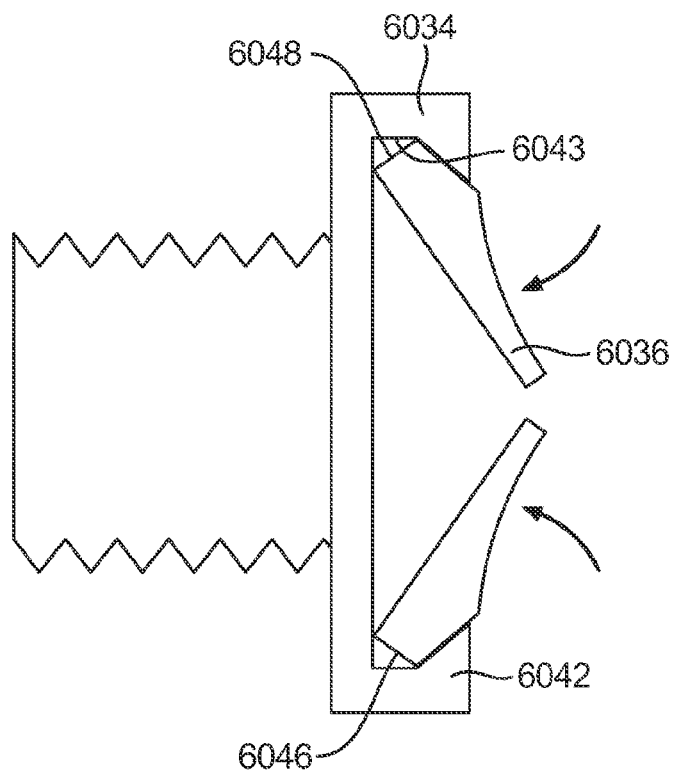
FIG. 77C is a top view of the glenoid component of FIG. 77B installed in the glenoid insert of FIG. 77A.

Referring to FIGS. 77A-77C, an alternative glenoid articulating surface system is shown. The system includes a two-piece articular surface. The two pieces are fixed in place through compression to one another. Glenoid insert feature 6030 may include a shaft portion 6032, an insertion platform 6034 and a poly unit 6036 that may be snapped or otherwise reversibly locked to the platform 6034. The insertion platform 6034 may include a first surface 6037 and a second surface 6038. The shaft portion 6032 may also be referred to as a fixation component, and may be at least partially threaded. The shaft portion may otherwise contain other bone-fixation features such as surface roughening or teeth. The shaft portion 6032 may be cylindrical, and oriented substantially perpendicular to the insertion platform 6034 and may extend from the first surface 6037 of the insertion platform 6034.

The second surface 6038 may include a recessed portion 6040 that is defined by a rim, which may also be called a prong or a circumferential ledge 6042. The ledge 6042 may extend outward from the recessed portion 6040, and may include a cutout portion 6043 shaped to receive an edge of the poly unit 6036.

Referring to FIG. 77B, poly unit 6036 may be substantially cylindrical, and may be deformable about a defined diameter 6044. The threaded shaft 6032 may be inserted into a bone, for example, the glenoid process. The poly unit 6036 may then be attached to the platform 6034, as illustrated in FIG. 77C.

The poly unit 6036 may include a first edge 6046 and a second edge 6048 that is oriented on the opposite side of circular profile of the poly unit to the first edge 6046. The poly unit 6036 may have a first configuration, as illustrated in FIG. 77B, in which the first edge 6046 and second edge 6048 lie substantially in a first plane. The poly unit 6036 may also have a second configuration, as illustrated in FIG. 77C, in which the poly unit 6036 is bent such that a central diametrical portion 6044 is out of the first plane and the first edge 6046 and second edge 6048 are brought closer to one another.

To attach the poly unit 6036 to the platform, the poly unit 6036 may be transitioned from the first configuration to the second configuration. The first edge 6046 and second edge 6048 may then engage the cutout portion 6043 of the platform 6034 as illustrated in FIG. 77C. The poly unit 6036 may then be transitioned into its neutral, non-deformed state such that the edges 6046, 6048 are lockably snapped into the cutout portion 6043 and edges 6046 and 6048 lie at least partially under the ledge 6042. When the edges 6048, 6046 are snapped into place, the poly unit 6036 is substantially secured to the platform 6034.

Figure 78:
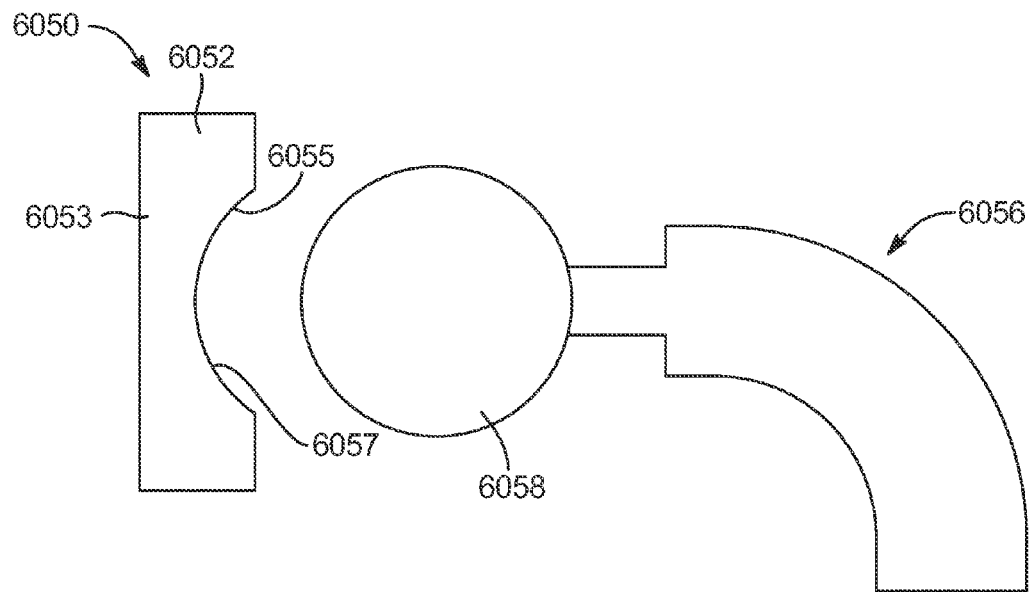
FIG. 78 is a side view of a shoulder arthroplasty system with a glenoid socket and a humeral stem.

Referring to FIG. 78, a system for inversion of the sacrificial surface for ease of articulating component replacement is shown. Glenoid system 6050 may include a socket component 6052 that may be attached to the bone. A poly head component 6054 may include a spherical head 6058 portion that may be reversibly attached to a metal stem component 6056, via a taper-fit or thread mechanism. The socket component 6052 may include a first, bone-facing surface 6053 and a second surface 6055 opposite to the bone-facing surface 6053. The second surface 6055 may include a contoured portion 6057. The contoured portion 6057 may be shaped to contact a portion of the spherical head 6058.

Figure 79A:
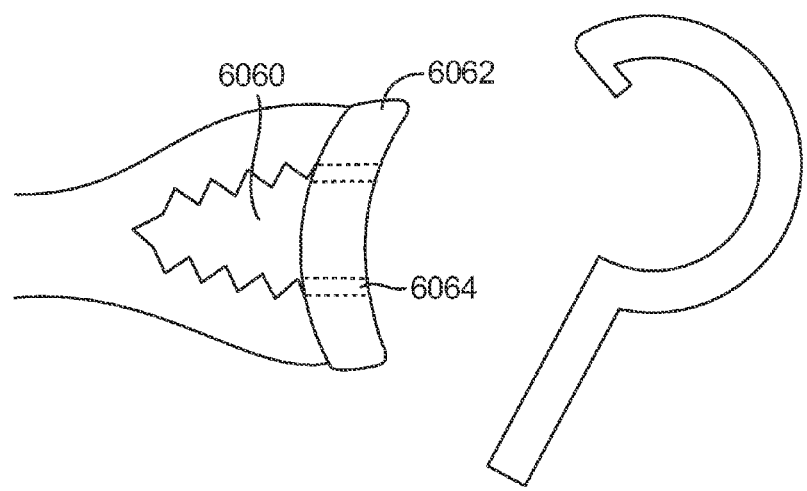
FIG. 79A is a top view of a modular glenoid component with a spanner wrench.
Figure 79B:
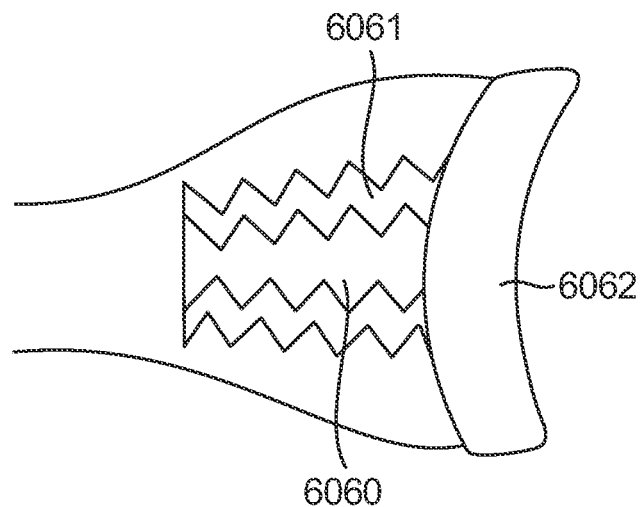
FIG. 79B is a top view of the glenoid component of FIG. 79A with a casing.

Referring to FIGS. 79A-79D, another system for inversion of the sacrificial surface for ease of articulating component replacement is illustrated. The system may include an insert portion 6060, which may include a threaded, or ribbed portion. Referring to FIG. 79A, the insert is shown embedded in a bone. The system may also include a glenoid surface component 6062, which is shaped to engage the insert portion 6060. The surface component 6062 may be integrally formed with the insert 6060, or may be separately formed and lockably attachable to the insert 6060 via a snap fit or threaded fit. The surface component 6062 may include a plurality of grooves 6064. The grooves 6064 may be shaped to receive an insert tool such as a spanner wrench, as illustrated in FIG. 79A. Referring to FIG. 79B, the insert 6060 may be a permanent metal insert, and may be encapsulated by an additional insert casing 6061 to prevent back-out.

Figure 79C:
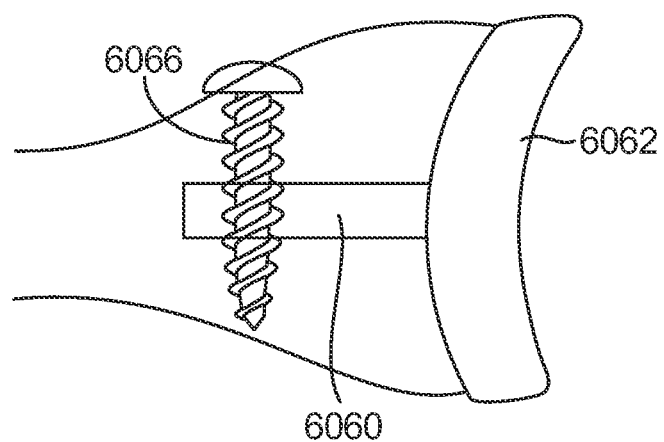
FIG. 79C is a top view of the glenoid component of FIG. 79B transfixed by a screw.

Referring to FIG. 79C, after the insert 6060 has been inserted into the bone, and the surface component 6062 has been attached to the insert, a cross-pin 6066 may be used to further secure the insert 6060 in the bone and to substantially prevent slippage of the insert 6060 within the bone. A drill guide may be used to position and prepare a hole in the correct anatomical position for the insertion of the cross-pin 6066. Alternatively, a screw may be used to secure the insert 6060 within the bone.

Figure 79D:
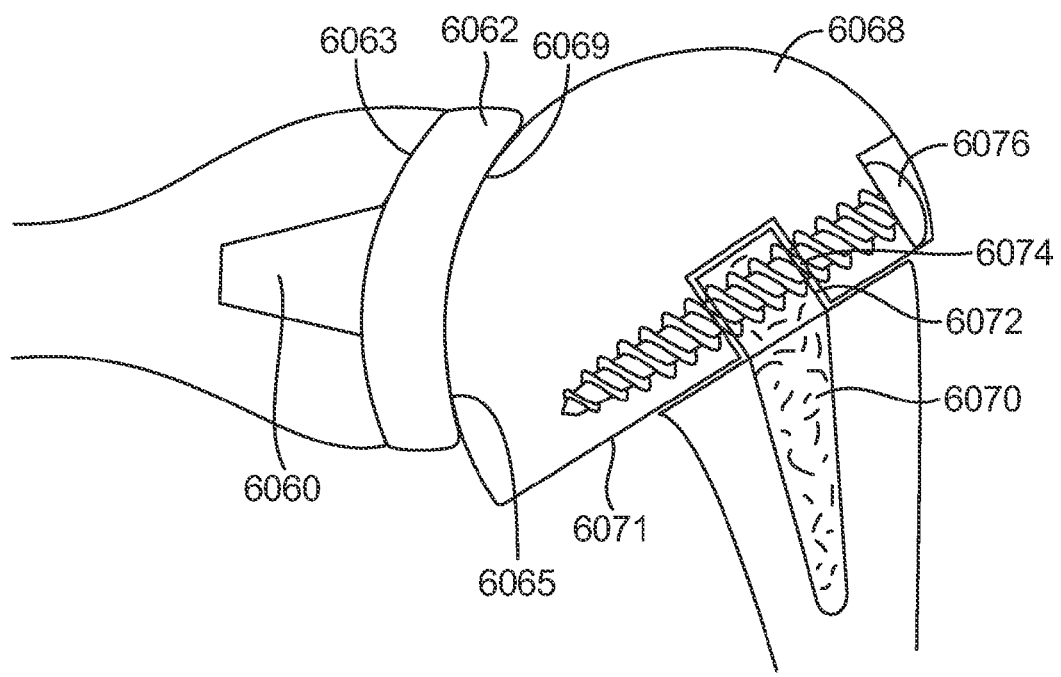
FIG. 79D is a side view of the glenoid component of FIG. 79A with a modular humeral component.

The screw may be similar to a sheet metal screw, and may not require a pre-drilled hole. As illustrated in FIG. 79D, the insert 6060 may be embedded within the bone with the surface component 6062 attached. The surface component 6062 may include a bone-contacting surface 6063 and a second surface 6065 opposite the bone facing surface 6063.

The second surface 6065 may have a curvature that is complementary to a poly ball 6068. Poly ball 6068 may include an articulating surface 6069 and a substantially flat bone-facing surface 606071. The poly ball 6068 may be positioned such that a portion of the articulating surface 6069 contacts the second surface 6065 of the surface component 6062. The poly ball 6068 may be secured to a bone using a stem component 6070. The stem component 6070 may be lockably attached to the poly ball 6068 at the bone-facing surface 6071. When the stem component 6070 is attached to the poly ball 6068, a proximal portion 6072 of stem 6070 may be contained within a recess 6074 that is located on the bone-facing surface 6071 of the poly ball 6068. The stem component 6070 may be metal, or may be composed of an alternative biocompatible material. A cross-pin 6076 may be used to further secure the stem component 6070 to the poly ball 6068. A distal portion of the stem 6070 may be inserted into a bone opposite to the articulating surface 6069 surface component 6062 interface.

Figure 80A:
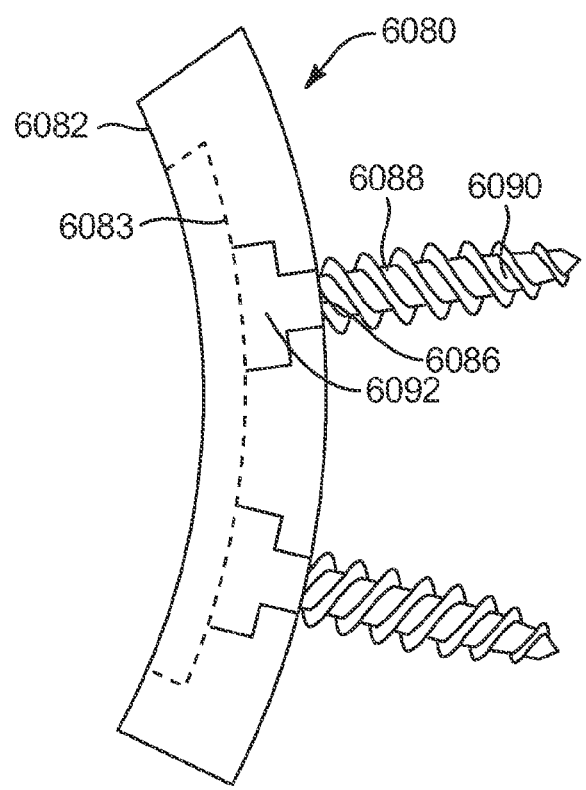
FIG. 80A is a top view of yet another glenoid component.
Figure 80B:
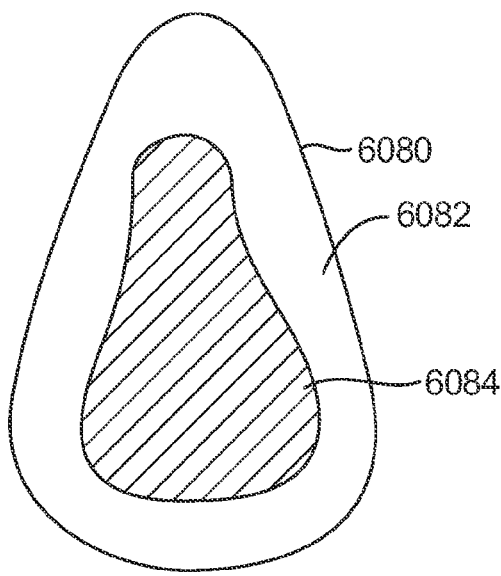
FIG. 80B is a side view of the glenoid component of FIG. 80A.

Referring to FIGS. 80A and 80B, another alternative modular glenoid articulating surface system is shown. The system includes a dual material surface for increased wear resistance and may include a rim component 6080. The rim component 6080 may include a first surface 6082. The first surface 6082 may have a recessed portion 6083 shaped to receive a poly unit 6084. The recessed portion 6083 may include at least one aperture 6086, shaped to receive a screw 6088. In FIG. 6B, recessed portion 6083 includes two apertures 6086, each aperture containing a screw 6088. The screws 6088 may include a distal threaded portion 6090 and a head portion 6092. The head portion 6092 may be seated against the recessed portion 6083 that defines the aperture 6086.

A poly component 6084 is shown engaged with the rim component 6080 in FIG. 80B. The poly unit 6084 may be reversibly attached to the recessed portion 6083 of the rim component 6080 via a snap or lock fit. After the screws 6088 have been placed through the apertures 6086, the poly unit 6084 may be fitted into the recessed portion such that when the poly unit 6084 is attached to the recessed portion, the poly unit 6084 may contact the screw heads 6092 to secure the screws 6088 in a locked position relative to the rim component 6080.

Figure 81A:
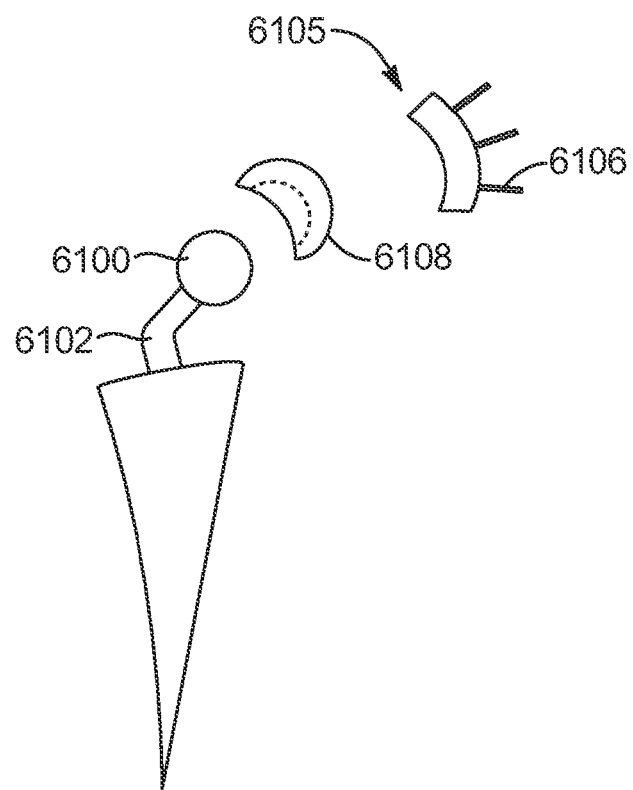
FIG. 81A is a side view of another shoulder arthroplasty system.
Figure 81B:
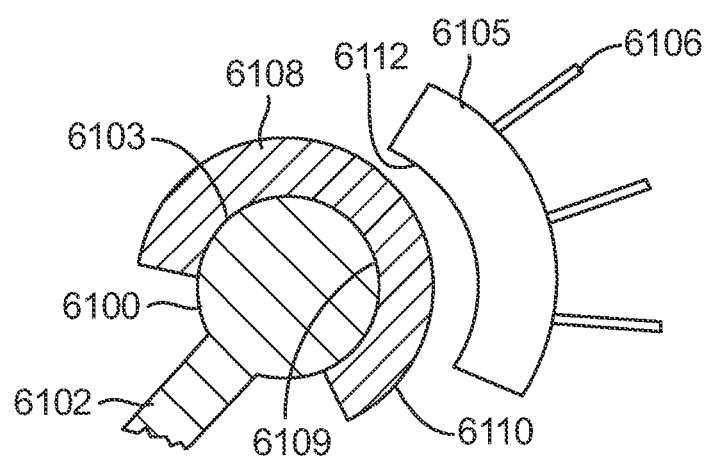
FIG. 81B is an enlarged detail cross section view of a portion of the shoulder arthroplasty system of FIG. 81A.

Referring to FIGS. 81A-81D, a system that includes a removable articular shell over a ball surface to give two effective bearing surfaces is described. Referring to FIGS. 81A and 81B, a spherical head 6100 and attached metal stem portion 6102 is illustrated. The system also includes an articulating platform 6105 attached to a plurality of anchors 6106. The system may also include a poly unit 6108 that may at least partially encompass a portion of the spherical head 6100. As shown in FIG. 81A, the spherical head 6100 may be integrally formed with the stem portion 6102, and the stem portion 6102 may be inserted into a bone. The spherical head 6100 may include an exterior, first articulating surface 6103.

The poly unit 6108 may be substantially C-shaped and may include a first, interior surface 6109 and a second, exterior surface 6110. The poly unit 6108 may be positioned such that the interior surface 6109 contacts at least a portion of the first articulating surface 6103 of the spherical head 6100, as illustrated in FIG. 81B.

The articulating platform 6105 may include a second articulating surface 6112 and a bone-facing surface 6114. A plurality of anchors 6106 may extend from the bone-facing surface 6114. The second articulating surface 6112 may have a curvature complementary to the curvature of the exterior surface 6110 of the poly unit 6108.

Figure 81C:
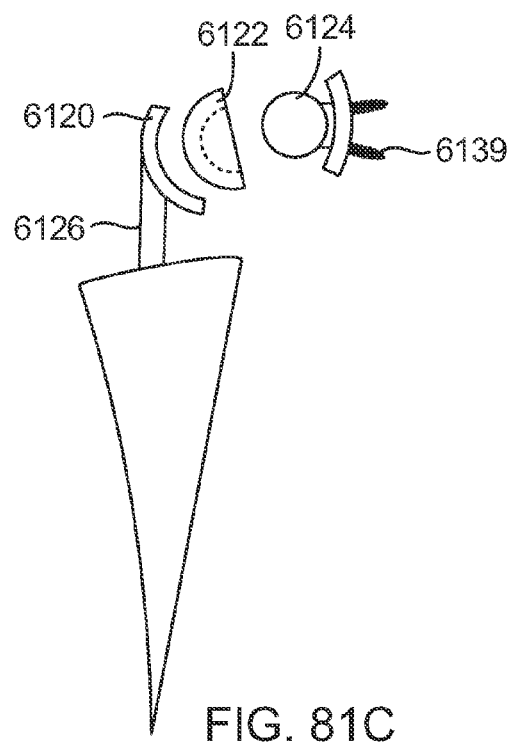
FIG. 81C is a side view of yet another shoulder arthroplasty system.
Figure 81D:
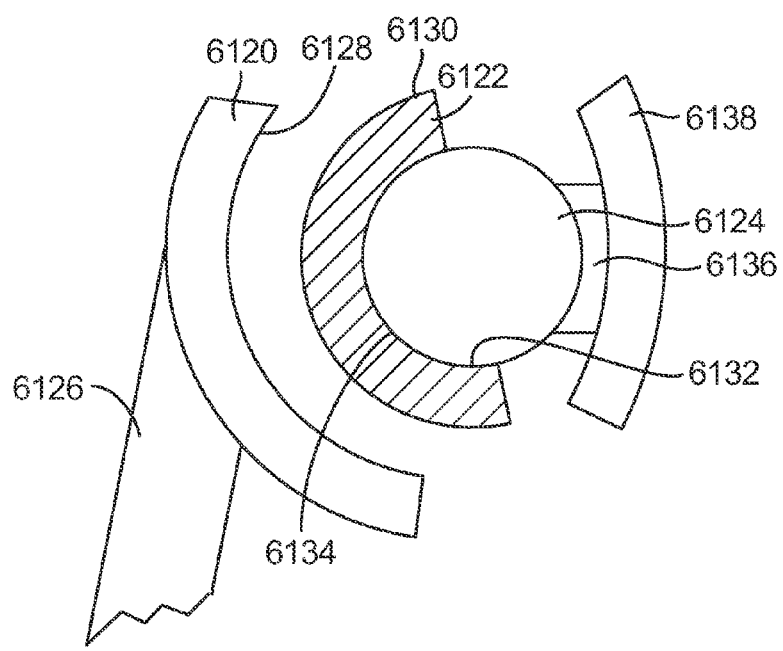
FIG. 81D is an enlarged detail cross section view of a portion of the shoulder arthroplasty system of FIG. 81C.

Referring to FIGS. 81C and 81D, an alternative configuration for the modular glenoid articular surface system described in FIGS. 81A and 81B is presented. The system may include an articulating platform 6120, a poly unit 6122 and a spherical head component 124. The articulating platform 6120, which may be have similar characteristics to articulating platform 6105, may be connected to a distal stem component 6126. Distal stem component 6126 may be insertable into a first bone. The articulating platform 6120 may include a contoured surface 6128. The poly unit 6122 may be substantially C-shaped, and include an exterior surface 6130 and an interior surface 6132.

The spherical head component 6124 may include an exterior articulating surface 6134. The spherical head component 6124 may also be attached to a neck 6136. The neck 6136 may extend between the spherical head 6124 and a connecting feature 6138. The neck 6136 may include an elbow, or may extend substantially linearly with no bending. The connecting feature 6138 may include a plurality of anchors 6139, such as screws, pins, nails, or hooks that may be used to anchor the spherical head 6124 to a second bone.

When the system is assembled, the interior surface 6132 of the poly unit 6122 may contact a portion of the articulating surface 134 of the spherical head 6124. The exterior surface 6130 of the poly unit 6122 may contact the contoured surface 6128 of the articulating platform 6120.

It will be appreciated that any of the examples described in FIGS. 75A-81D may be mixed and matched into alternate embodiments as well.

Referring to FIGS. 82-118, additional examples of a shoulder prosthetic system and more precisely to a glenoid or glenosphere vault system for repairing or revising a shoulder, is described. Further FIGS. 82-118 also relate to a method for preparing the glenoid for prosthetic insertion. The examples shown in FIGS. 82-118 may be adapted or designed to interface with the system of modular SI 7100 and AP components 7200 previously described. Further, it is to be understood that the concepts illustrated in FIGS. 82-118 may be readily adapted to other systems. It is also contemplated that the systems and methods set forth herein, or any adaptations, may be useful outside of and beyond shoulder repair and humerus repair.

Figure 82:
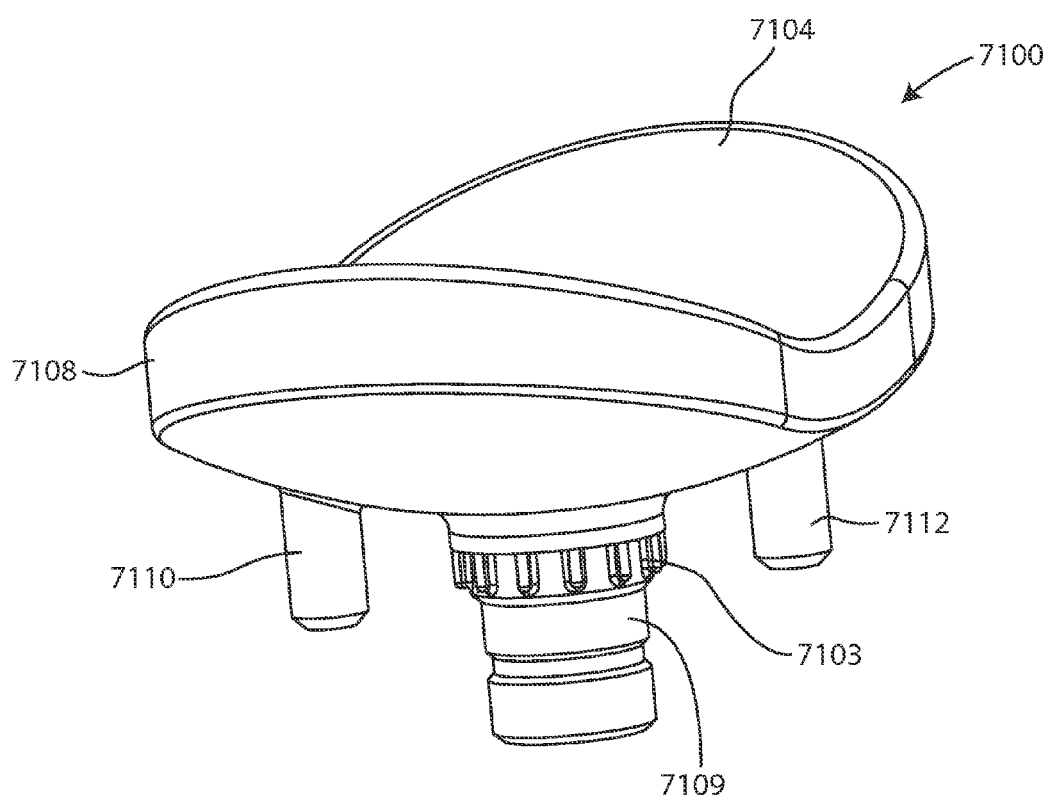
FIG. 82 is a perspective view of an anatomical articulating component including two posts.
Figure 83:
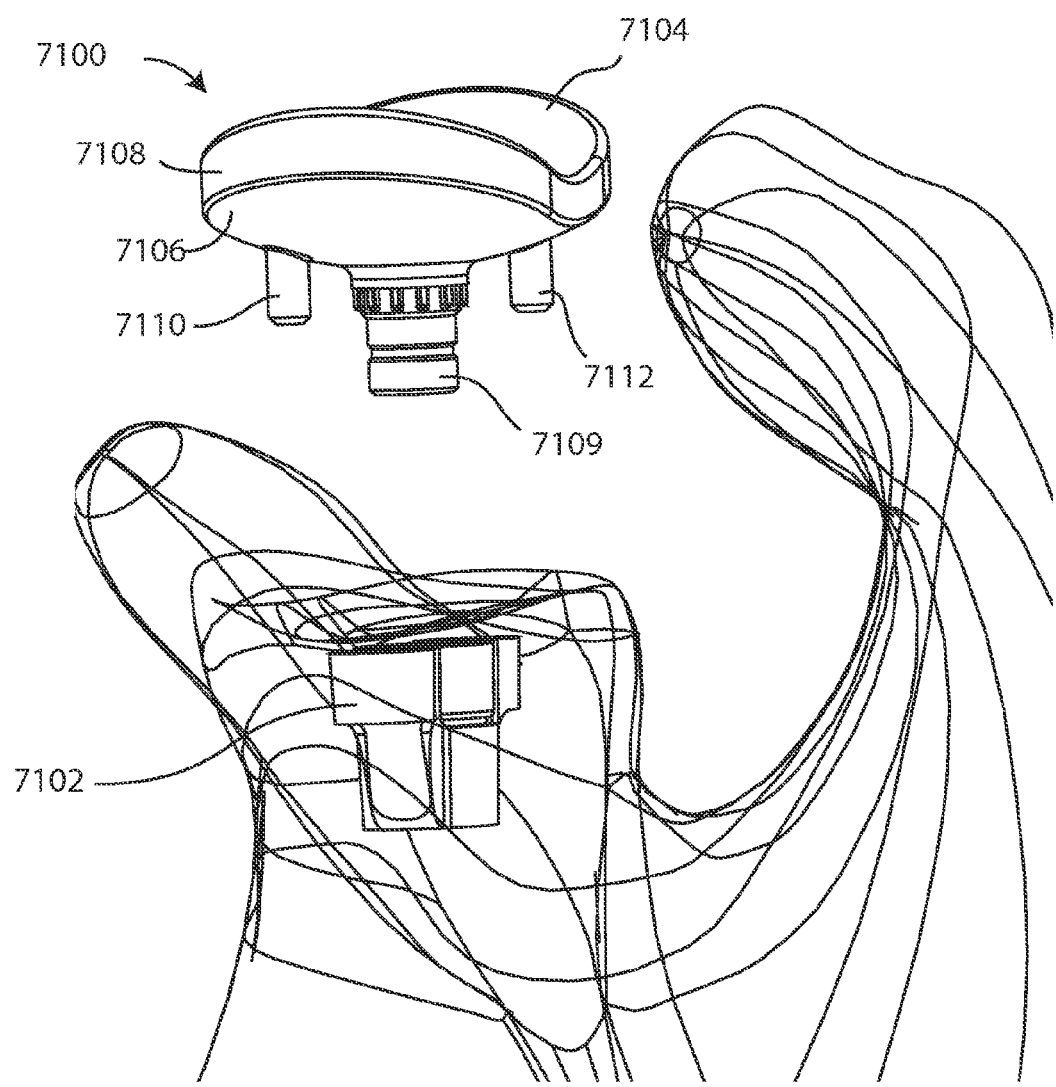
FIG. 83 is an exploded view of the anatomical articulating component of FIG. 82 engaging a bone anchor assembly in subchondral bone.

Referring to FIGS. 82-82, an anatomical articulating component, which may be referred to as a glenoid component 7100 with anti-rotation features is illustrated. The glenoid component 7100 may be shaped to interact with an anterior-posterior (AP) component 7101 and/or a superior-inferior (SI) component 7102 of a shoulder arthroplasty system, such as the systems described previously in this application, as illustrated in FIG. 83. The glenoid component 7100 may alternatively be shaped to interact with another type of glenoid or bone anchor component.

The glenoid component 7100 may include share similar characteristics with articulating component 20, and may be shaped to mirror an anatomical shoulder. Glenoid component 7100 may a first articulating surface 7104 and a second bone facing surface 7106 that is opposite to the first articulating surface 7104. The bone facing surface 7106 may also be referred to as a medial surface. The glenoid component 7100 may also include a first side portion 7108 or perimeter that extends between and intersects the articulating surface 7104 and the bone facing surface 7106. The glenoid component may have a cylindrical shaft 7109 that extends from the bone facing side 7106 of the glenoid component 7100 and is shaped to engage a central aperture, or tubular boss of the AP component 7101. Shaft 7109 may also be referred to as a post, and may be similar or identical to post 28 described above.

The shaft 7109 may include one or more protrusions 7103 which extend radially from the shaft. FIG. 82 illustrates a shaft with a plurality of protrusions 7103 arranged evenly around the shaft. The SI component 7102 and the AP component 7101 may have similar or identical features AP component 7200.

Additionally, the glenoid component 7100 may include at least one anti-rotation feature, such as a post, groove, rail, hole, pin or other surface roughening that acts to provide rotational stability to the glenoid component 7100 within the shoulder arthroplasty system. For example, the glenoid component 7100 illustrated in FIGS. 82 and 83 may include at least one post that protrudes from the bone facing surface 7106. In this example, the glenoid component 7100 may include two posts 7110, 7112 that extend from the bone facing surface 7106 on opposing sides of the shaft 7109. The number and orientation of posts may vary.

In an example of use, the SI component 7102 and the AP component 7101 may be placed into subchondral bone as an AP-SI complex, which may also be referred to as an anchor assembly. When the AP-SI complex is formed, at least a portion of the AP component 7101 may be received by a central bore or body in the SI-component, similar to the system above. The glenoid component 7100 may then be attached to the AP component 7101 in a desired orientation with respect to the subchondral bone. When the glenoid component 7100 is attached to the AP component 7101, at least a portion of shaft 7109 may be lockably received within the central aperture of the AP component 7101. Under other circumstances, the glenoid component 7100 may mate with a different anchor assembly or unitary anchor or base.

As the shaft 7109 is inserted into the central aperture of the AP component 7101, the protrusions 7103 may mesh with complementary slots or grooves in the central aperture of the AP component, and the posts 7110, 7112 may be simultaneously driven into a prepared section of the surrounding bone, specifically, into the subchondral bone around the anchor assembly. When the posts 7110, 7112 engage the surrounding bone, rotation about the shaft 7109 is substantially prevented, providing rotational stability to the glenoid component 7100 within the SI-AP complex. Further rotational stability may be provided by the protrusions 7103 in the complementary slots.

Figure 84:
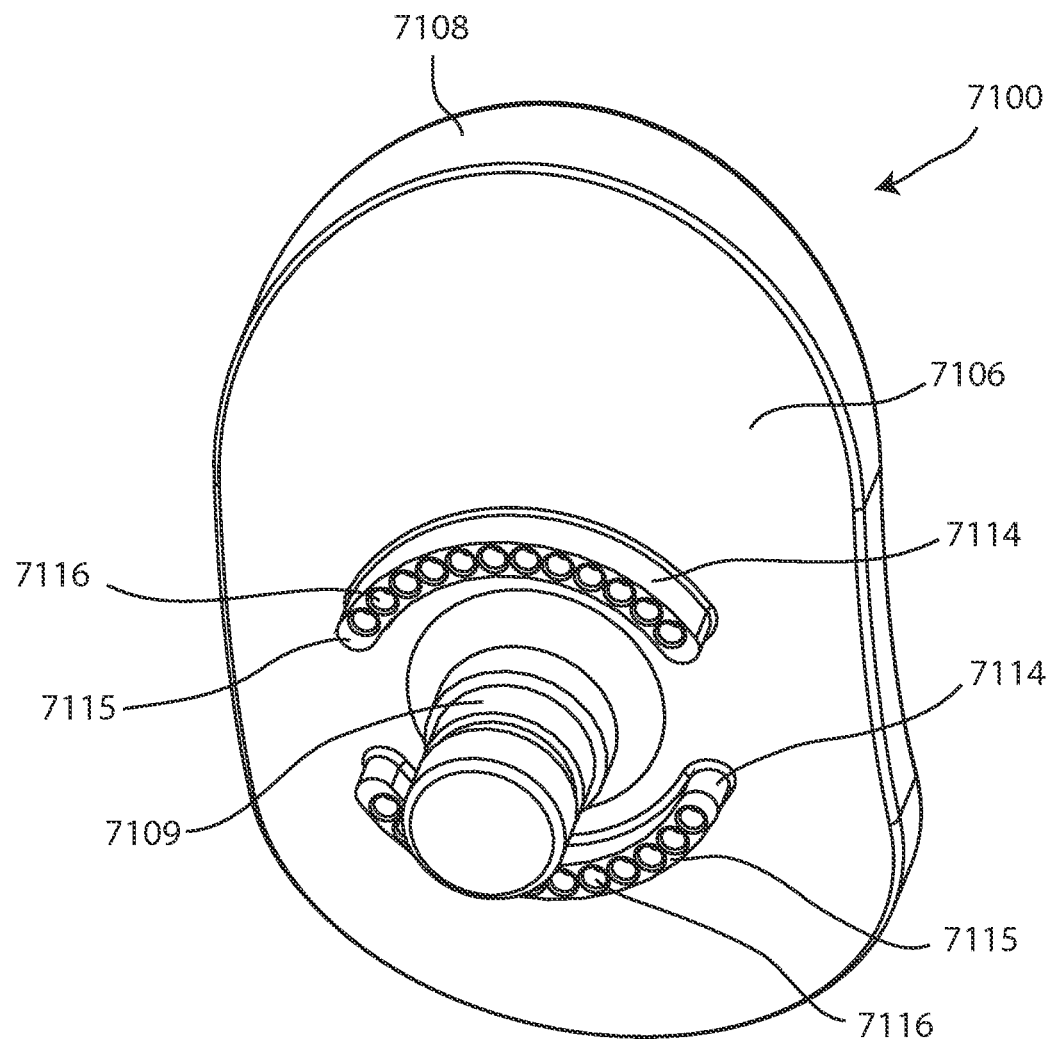
FIG. 84 is bottom perspective view of another anatomical articulating component with two elongated anti rotation features.
Figure 85:
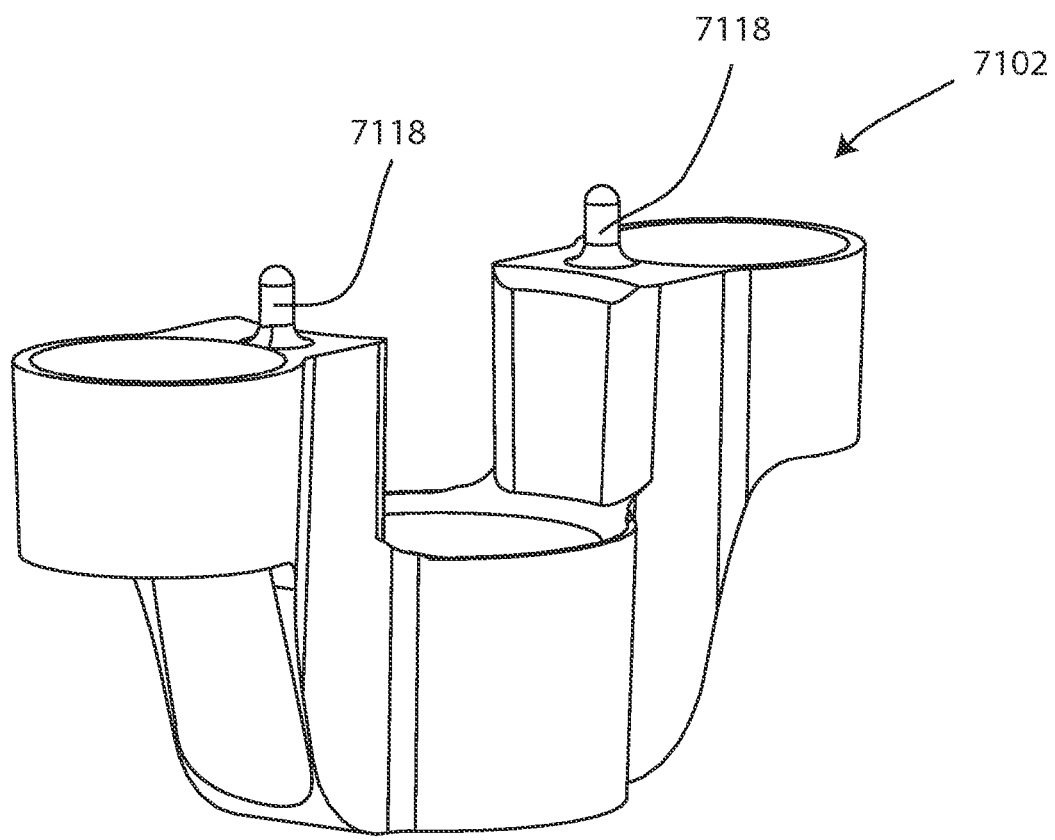
FIG. 85 is a perspective view of a bone anchor assembly with shaped to engage the anti-rotation figures of the anatomical articulating component of FIG. 84.

Referring to FIGS. 84-87, in another example, glenoid component 7100 may include at least one extruded portion 7114 with a plurality of holes 7116 or slots that may be shaped to accept posts or other complementary features that protrude from the SI component 7102. As illustrated in FIG. 84, the glenoid component 7100 includes two extruded portions 7114 that lie symmetrically in a semicircular path around the central shaft 7109 on the bone facing surface 7106. The extruded portions 7114 may include a raised surface portion 7115. As best seen in FIG. 84, the extruded portions 7114 include a plurality of circular holes 7116, or other female mating features, that lie adjacent to one another along the length of the extruded portions. The holes 7116 may otherwise be elliptical or polygonally shaped. The holes 7116 may be shaped to receive a post 7118 or other male mating feature that protrudes from a top portion of the SI component, as illustrated in FIG. 85.

In another example, the extruded portions 7114 may include male mating features, such as posts or pins, and the top portion of the SI component 7102 may include female mating features. In yet another example, the extruded portions 7114 may include general protruding female mating features, such as posts. The posts may include additional mating features, such as teeth, ridges, notches or holes that interact with complementary mating features on an interior surface of male mating features, such as holes, on the SI component 7102.

Figure 86:
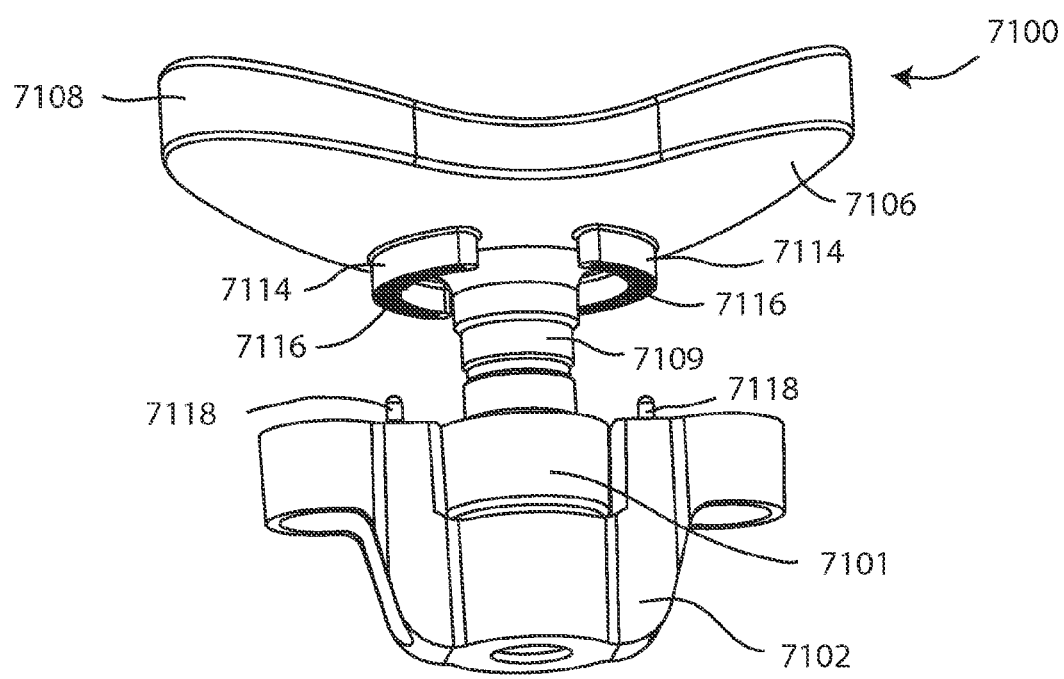
FIG. 86 is an exploded view of the anatomical articulating component of FIG. 84 engaging the bone anchor assembly of FIG. 85.
Figure 87:
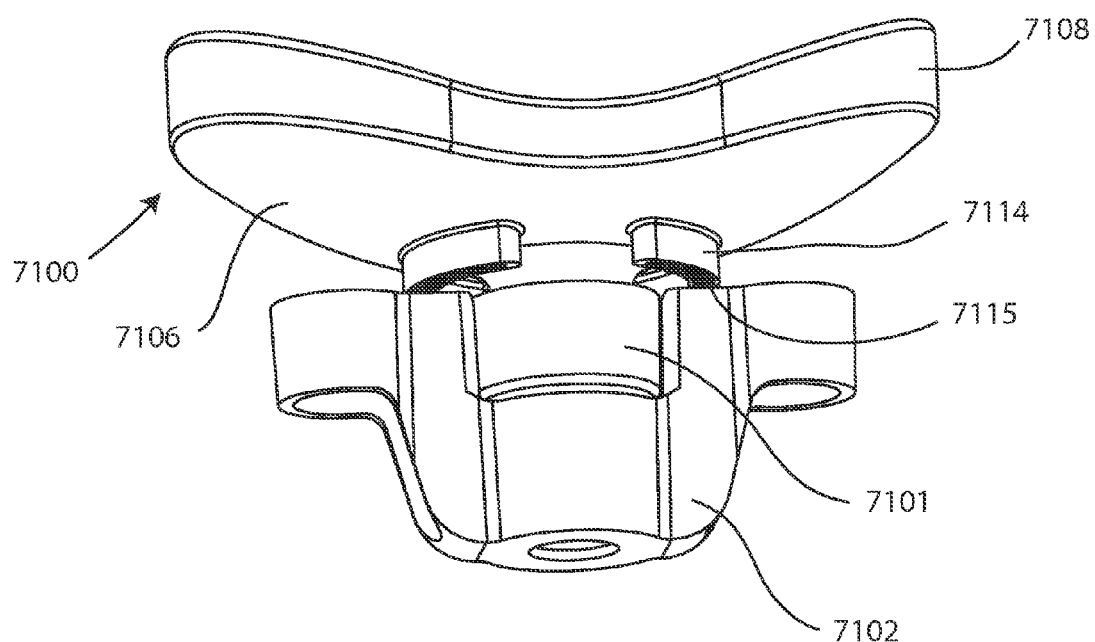
FIG. 87 is a perspective view of the anatomical articulating component of FIG. 84 operatively assembled with the bone anchor assembly of FIG. 85.

In operation, a user may connect the glenoid component 7100 to the anchor system by sliding a first portion of the shaft 7109 into the central aperture of the AP component 7101, which may be connected to the SI component 7102, as illustrated in FIGS. 86 and 87. When connecting the glenoid component 7100 to the anchor system, the user may select a desired rotational orientation of the glenoid component 7100 with respect to the anchor system by rotating the glenoid component about the shaft 7109. The user may then further slide or ratchet the shaft 7109 into the central bore of the AP component such that the posts 7118 of the SI component engage the corresponding holes 7116 of the glenoid component 7100, and such that the raised surfaces 7115 of the extruded portions 7114 approach or contact the SI component. Referring to FIG. 87, the glenoid component 7100 with extruded portions 7114 is shown fully engaged with the SI-AP complex. When the posts 7118 are at least partially received within the holes 7116, rotation of the glenoid component 7100 about the shaft 7109 is substantially restricted.

Figure 88:
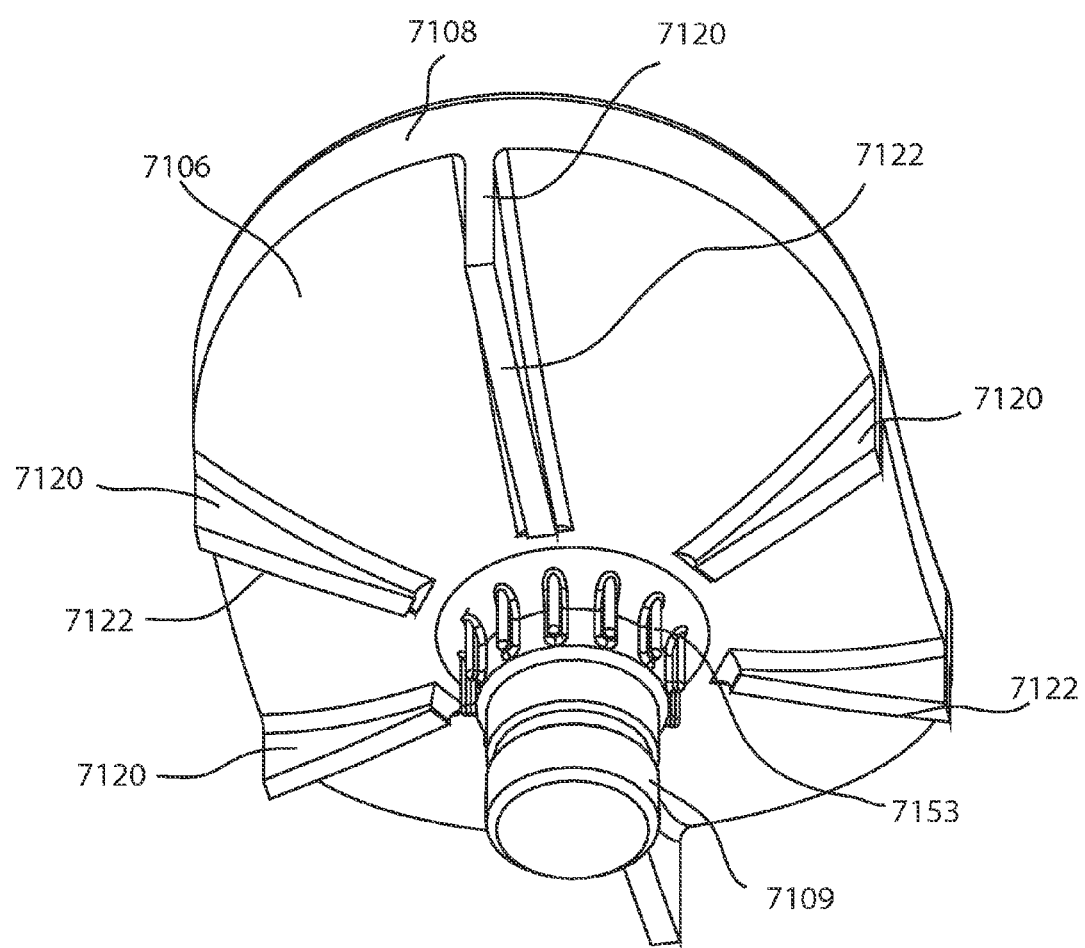
FIG. 88 is a bottom perspective view of another anatomical articulating component with a plurality of ridges.
Figure 89:
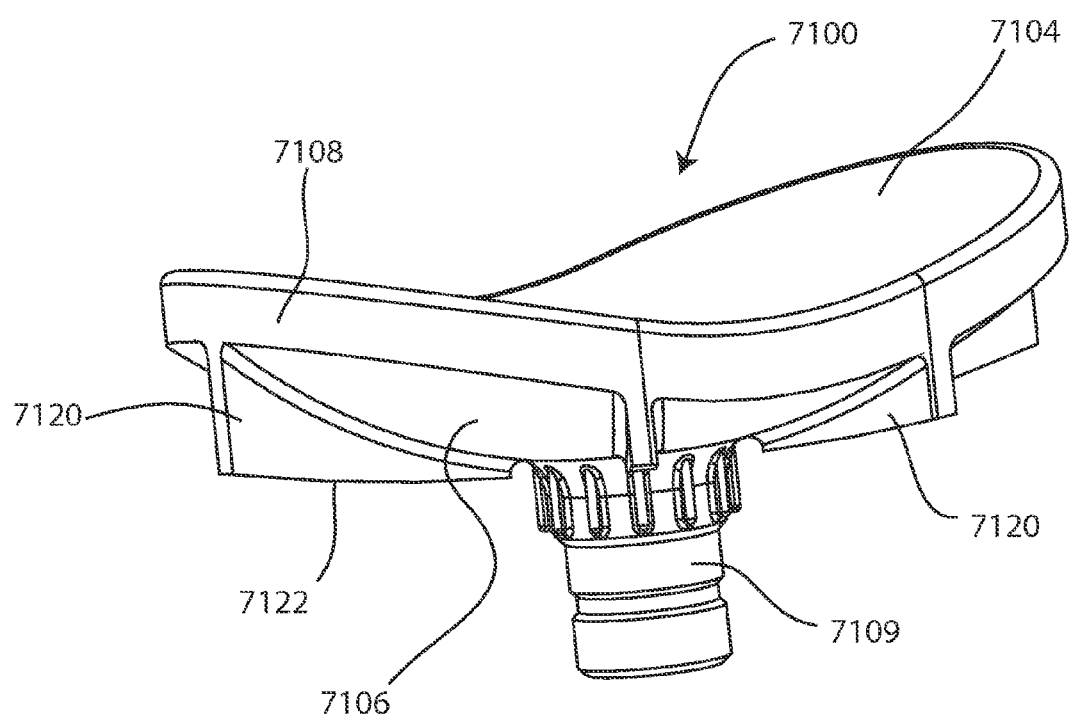
FIG. 89 is a side perspective view of the anatomical articulating component of FIG. 88.
Figure 90:
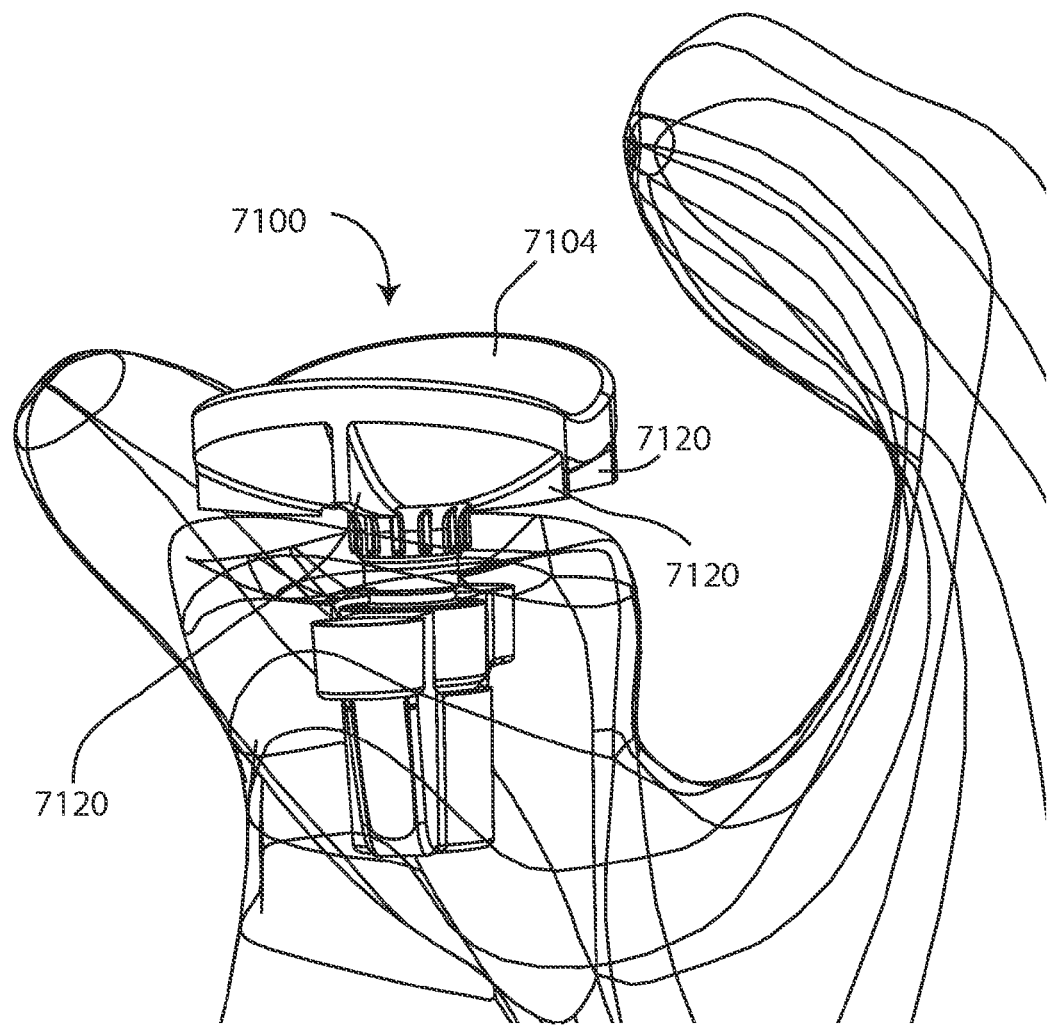
FIG. 90 is a side view of the anatomical articulating component of FIG. 88 operatively engaged with a bone anchor assembly in subchondlar bone.

Referring to FIG. 88-90, another example of glenoid component 7100 with an anti-rotation feature is illustrated. Glenoid component 7100 may include a plurality of ridges, keels or rails 7120 that extend across the bone facing surface 7106. FIG. 88 illustrates ridges 7120 that extend radially outward from the center of the bone-facing surface 7106. Each of the ridges 7120 may include a sharpened bone engaging edge 122. The edge 122 may otherwise be rounded or blunt. The edges 122 may all lie in the same plane along their entire length, or may otherwise be curved to bend out of a plane. In alternative examples, the ridges 7120 may be oriented parallel to one another along a length of the glenoid component 7100.

In operation, ridges 7120 may provide resistance to glenoid 7100 rotation by engaging the subchondral bone that has been prepared to accept the ridges 7120 when the glenoid 7100 is connected to the AP-SI complex, as illustrated in FIG. 90.

Referring to FIGS. 91-101, various examples of connection mechanisms for securing the glenoid component 7100 to the anchor assembly of a shoulder arthroplasty system are illustrated. These various connection mechanisms allow for interchangeability for the glenoid component 7100, or other articulating components, such as a glenosphere for a reverse shoulder. Often, a total shoulder arthroplasty will require a revision due to, for example, wear of the articulating component. Current systems require removal of the glenoid vault attachment means, which may injure the scapula, decrease available bone stock, and reduce the likelihood for success of the revision. In the present system, various connection mechanisms may provide for a quick-connect means for easily removing the articulating component without disturbing the glenoid vault fixation.

Figure 91:
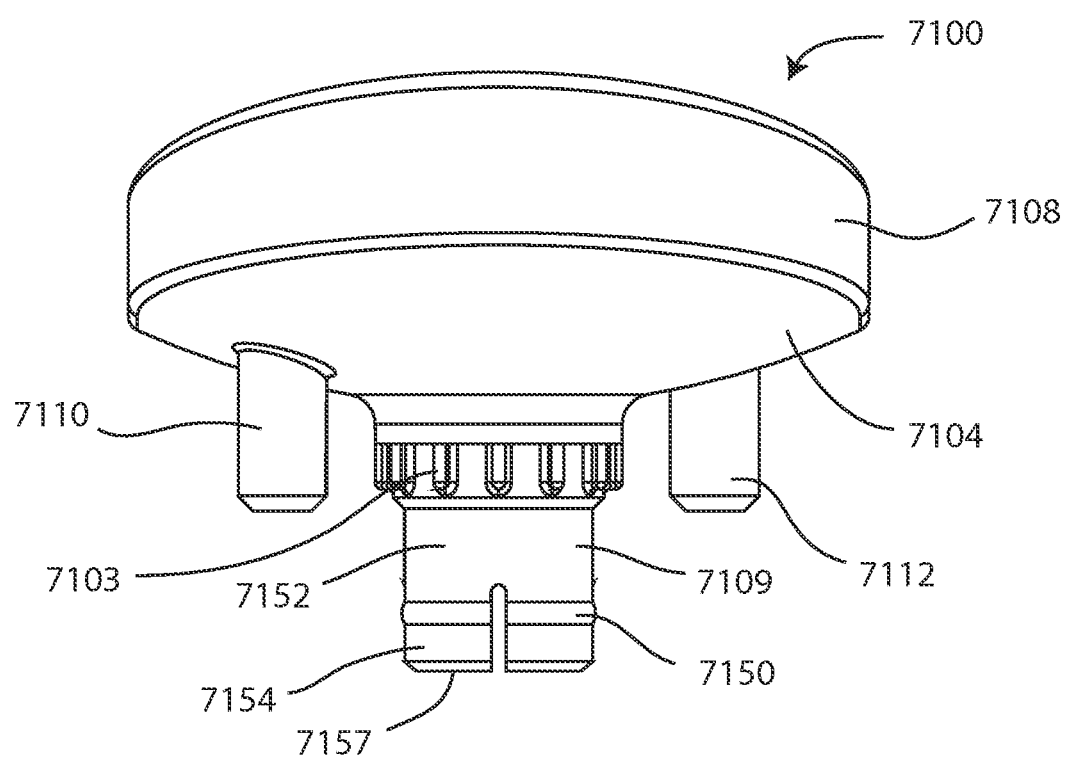
FIG. 91 is a side view of an anatomical articulating component including a shaft and a snap feature.
Figure 92:
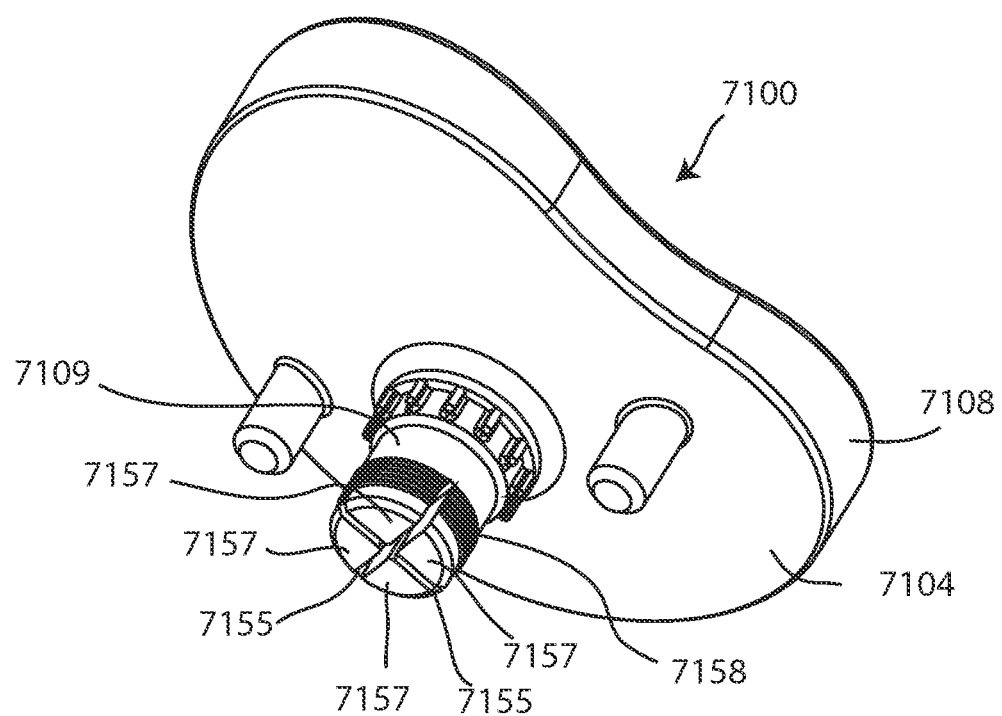
FIG. 92 is a bottom perspective view of the anatomical articulating component of FIG. 91.
Figure 93:
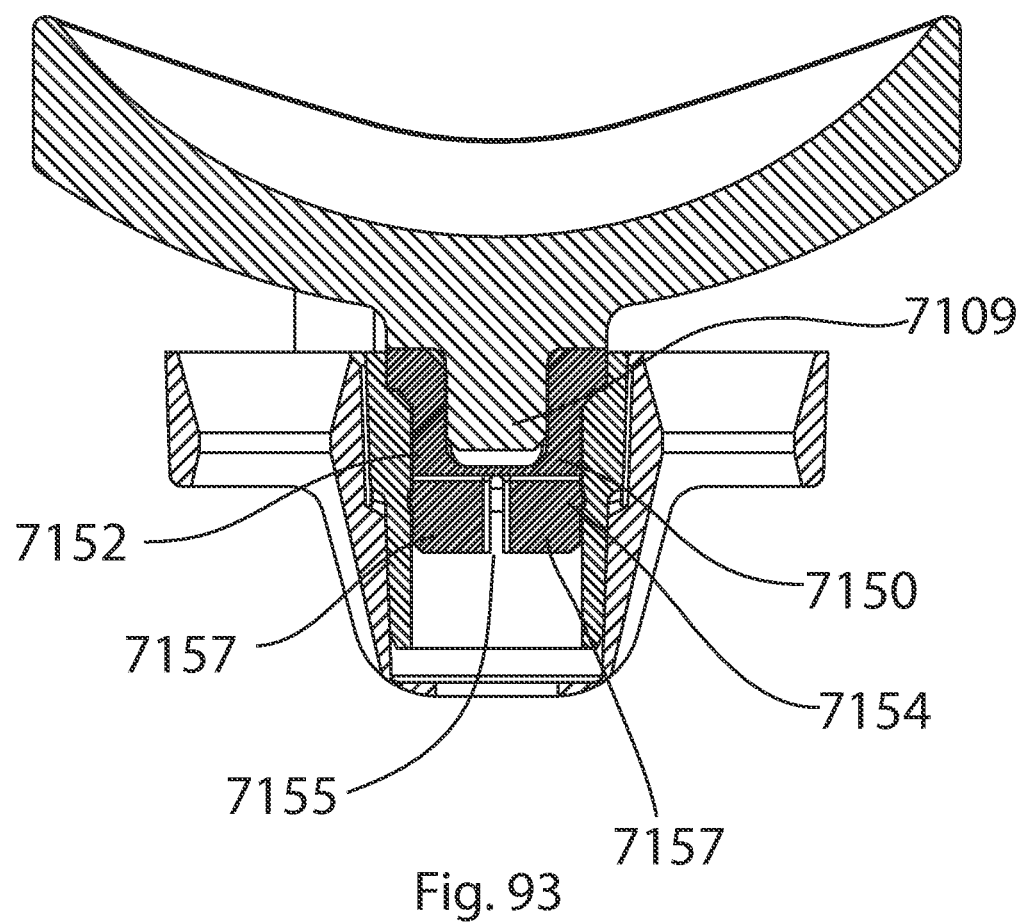
FIG. 93 is a cross section view of the anatomical articulating component of FIG. 91 operatively engaged with a bone anchor assembly.

As illustrated in FIGS. 91-93, the glenoid component 7100 may include a snap feature 7150 that is attached to a distal portion of shaft 7109 of glenoid component 7100. As illustrated in FIG. 91, the glenoid component 7100 may include additional anti-rotation features, such as the posts 7110, 7112, or ridges described previously.

The snap feature 7150 may be integral to the shaft 7109, or may be formed separately and lockably secured to the shaft 7109 by sliding a portion of the snap feature 7150 onto a portion of the shaft 7109. The snap feature 7150 may sit distal to the notches 7103 on the distal shaft 7109. The snap feature 7150 may include a proximal cylindrical body portion 7152 and a distal engagement portion 7154. The body portion 7152 may otherwise be square or irregularly shaped.

The engagement portion 7154 may also be cylindrical, and by radially toothed. The snap feature 7150 may include at least one flexible member 7157, which may also be referred to as a prongs or flange. In the example illustrated, the flexible members are four prongs that are separated 7157 via two intersecting grooves 7155, 7156 that cut across the diameter of the cylinder, as illustrated in FIG. 92. The grooves 7155 may allow the flanges 7157 to be compressed slightly inward towards one another with applied force.

The flanges 7157 may be biased towards a neutral, non-compressed configuration, as illustrated in FIG. 92. When the flanges 7157 are in the non-compressed configuration, the engagement portion 7154 may have a first diameter. The first diameter may be greater than or equal to the diameter of the central aperture of the AP component 7101. The bias may be overcome by compressing the flanges 7157 inwards towards the center, transitioning the engagement portion 7154 into an insertion configuration. When the flanges 7157 are in the insertion configuration, the engagement portion 7154 may have a second diameter, wherein the second diameter is less than or equal to the diameter of the central aperture of the AP component 7101.

To attach the glenoid component 7100 to the assembled SI-AP complex, the flanges 7157 may be compressed radially inward into the insertion configuration, such that the engagement portion 7154 may be passed into the central aperture of the AP component 7101. The inward compression of the flanges 7157 may be performed manually by an operator or a tool, or may be caused by the contact of the outer perimeter of the central aperture of the AP component with the flanges 7157 as the glenoid component 7100 is pressed towards the SI-AP complex. As the engagement portion is moved along the central aperture of the AP component 7100, the flanges 7157 may be released back into the neutral configuration to engage the inner wall of the aperture, substantially preventing back-out of the glenoid component 7100 from the AP-SI complex. The engagement portion 7154 may also include additional anti-backout features, such as threads, slanted grooves or teeth 7158 that frictionally engage the inner wall of the central aperture of the AP component, as best seen in FIG. 92. Additional rotational stability may be provided by the interaction of the proximal notches 7103 with an interior surface of the central aperture of the AP component 7101.

A snap feature, similar or identical to snap feature 7150, may also be included in a variety of alternative articulating components, such as a metaglene component 7170 that engages a glenosphere, similar or identical to metaglene component 66 that engages glenosphere 60 as described above. Metaglene component 7170 may be formed separately from the glenosphere 7175, or may otherwise be integral to the glenosphere.

Figure 94:
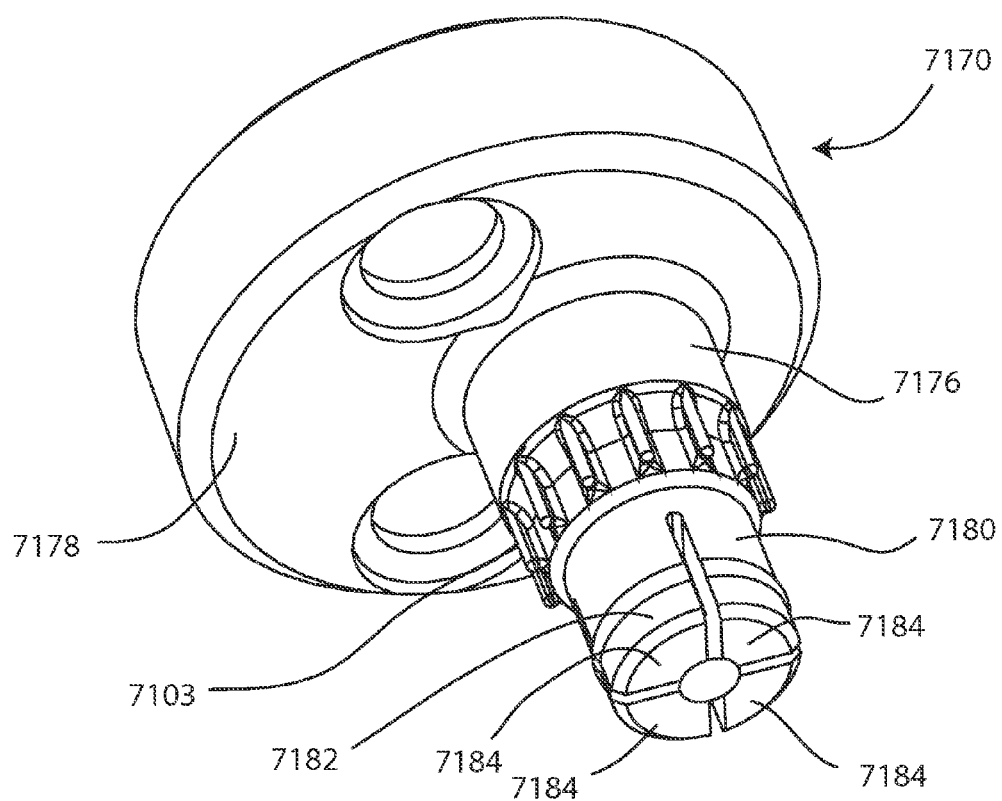
FIG. 94 is a bottom perspective view of a metaglene component with a shaft and snap feature.
Figure 95:
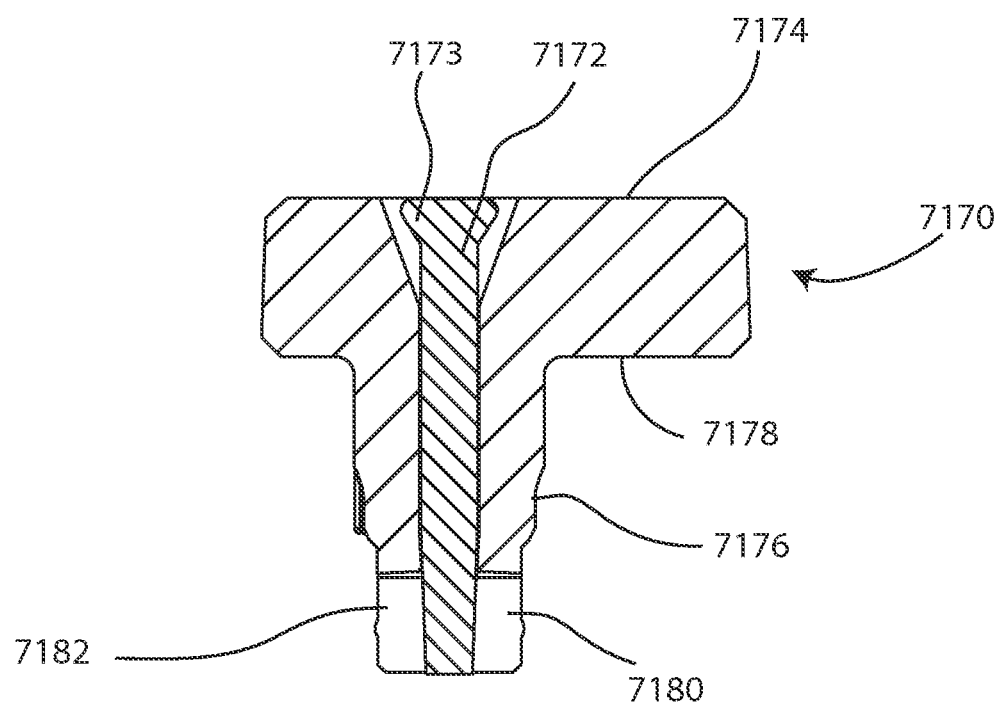
FIG. 95 is a cross section view of the metaglene component of FIG. 94 with a tapered screw.
Figure 96:
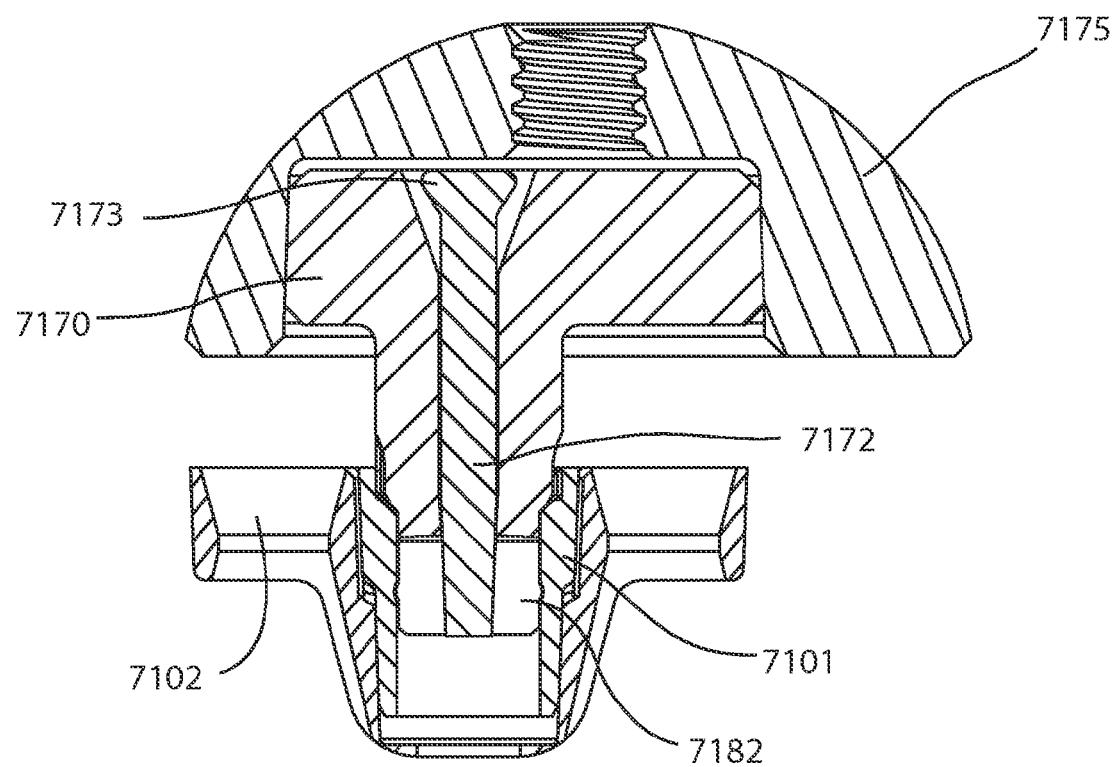
FIG. 96 is a cross section view of the metaglene component of FIG. 94 operatively assembled with a bone anchor assembly and a glenosphere.
Figure 97:
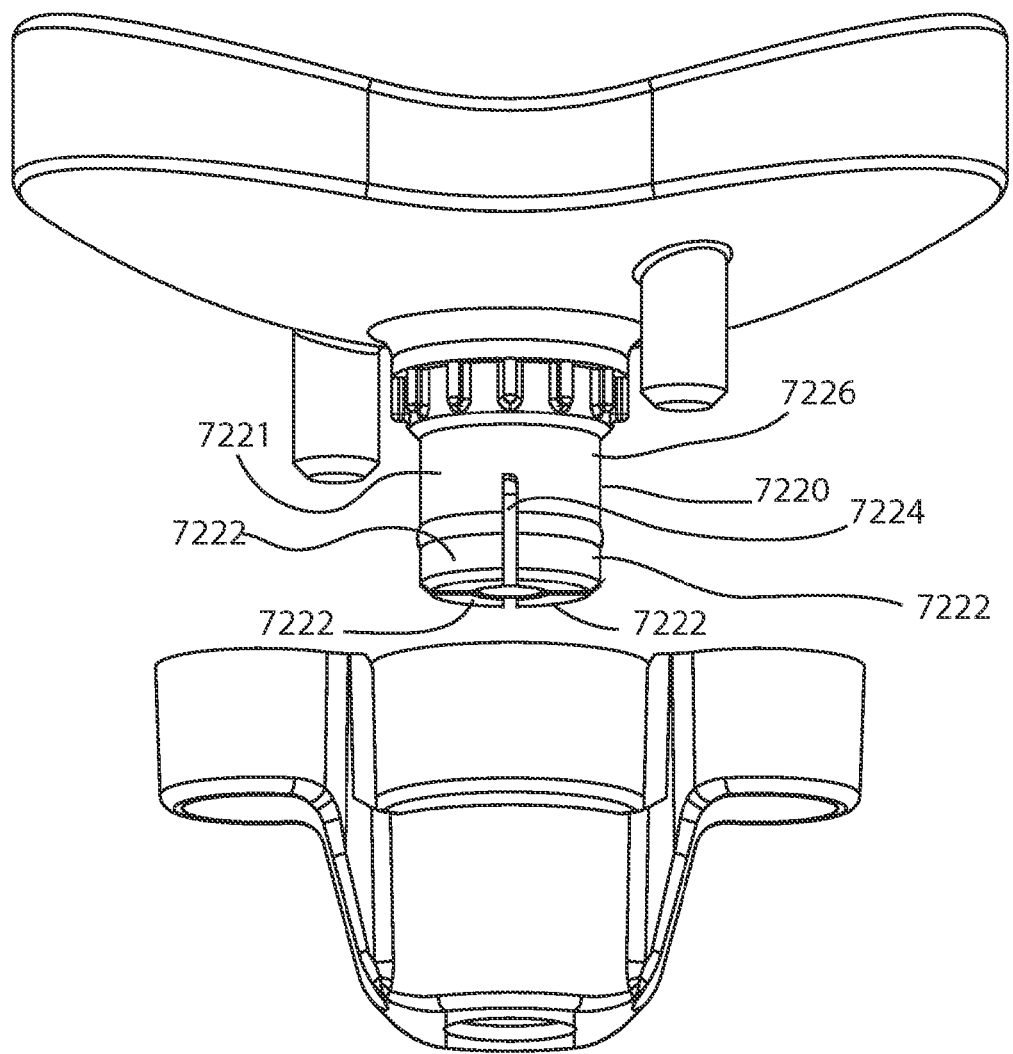
FIG. 97 is an exploded view of an anatomical articulating component with a snap feature and a central post engaging a bone anchor assembly.

As illustrated in FIGS. 94-96, the metaglene component 7170 may includes an internal screw 7172, which may be at least partially tapered. The screw 7172 may extend through the body of the metaglene component 7170 from a first proximal surface 7174 through a shaft or internal channel 7176 that extends from a second distal surface 7178. Screw 7172 may be partially threaded, totally threaded or non-threaded. Screw 7172 may also include a head portion 7173. When the screw 7172 is contained within the metaglene component 7170, the head of the screw 7178 may lay flush with the proximal surface 7174 of the metaglene component as illustrated in FIG. 95. Alternatively, the screw 7178 may protrude from the proximal surface 7174. The head of the screw 7173 may include a feature to engage a driver tool, such as a screw driver.

Shaft 7176 may be similar or identical to shaft 7109, and may also have similar or identical features as post 28 described previously. The shaft 7176 may include a snap feature 7180 that has similar characteristics to snap feature 7150, including a distal engagement portion 7182 with a plurality prongs or flanges 7184. The flanges 7184 may be biased toward a neutral position in which the engagement portion has a first diameter less than or equal to the diameter of the central aperture of the AP component 7101, and such that the engagement portion can be easily inserted into the central aperture of the AP component 7101.

In this example, the shaft 7176 may be inserted into the central aperture of the AP component 7101. When the engagement portion 7182 is contained within the central aperture, the tapered screw 7172 may be turned to actuate the transition of engagement portion 7182 into a locking configuration. When tapered screw 7172 is turned, the screw may be advanced within the shaft 7176 to press the flanges 7184 outwards to engage the inner wall of the central aperture and to lockably secure the metaglene component 7170 to the SI-AP complex.

The tapered screw may also be used in conjunction with a glenoid component.

In an alternative example, the flanges 7184 may be biased toward a neutral position in which the engagement portion has a first diameter greater than or equal to the diameter of the central aperture of the AP component 7101, and turning the tapered screw 7172 may stabilize the flanges 7184 to prevent deflection, but may not actively urge the flanges outward. After the metaglene component 7170 has been secured within the SI-AP complex, a glenosphere component or other articulating component may be attached to the metaglene 7170. Referring to FIG. 96, the metaglene component 7170 is shown operatively assembled with a glenosphere 7175 and the SI-AP complex.

Referring to FIGS. 97-100, another example of a glenoid component 7100 with an alternative snap feature 7220 is illustrated. Snap feature 7220 may allow for easy removal of the glenoid component 7100 in the case of shoulder revision surgery. The snap feature 7220 may share some characteristics with snap feature 7150. For example, snap feature 7220 may be integral to a shaft 221 that extends from the bone-facing surface 7106, and includes four flanges 7222 that are separated by two intersecting grooves 7224 that extend along an engagement portion 7226 of snap feature 7220. Snap feature 7220 may otherwise have a different number of flanges that are separated by grooves. The thickness and length of the flanges may be variable.

Figure 98:
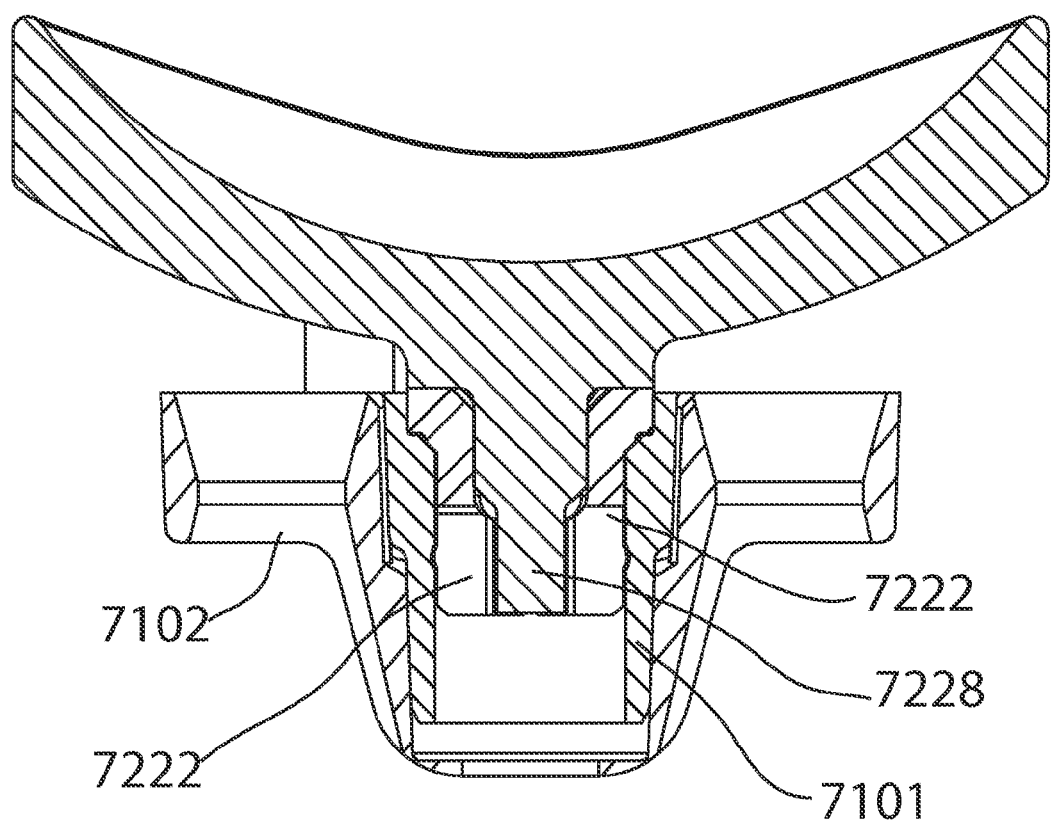
FIG. 98 is a cross section view of the anatomical articulating component of FIG. 97 operatively assembled with a bone anchor assembly.

In this example, the flanges 7222 may be biased towards a collapsed position. The bias may be overcome by a central post 7228 that is placed in a substantially central location of the snap feature 7220, where the intersecting grooves meet. The placement of the central post 7228 may urge the flanges 7222 apart from one another into an expanded position, as best seen in FIG. 98. The central post 7228 may also be referred to as a boss, or stem. The central post 7228, which may also be referred to as a rod, wedge or expanding device may be fabricated from a polymer, such as polyethylene.

In operation, as the glenoid component 7100 is passed into a central aperture of the SI-AP complex that has been anchored into a bone, the grooves 7224 may allow partial collapse of the flanges 7222 towards one another to pass into the central aperture of the AP component, similar to the example described in FIG. 94-96. Referring to FIG. 98, a cross section view of the glenoid 7100 operatively assembled with the SI-AP complex is illustrated.

Figure 99:
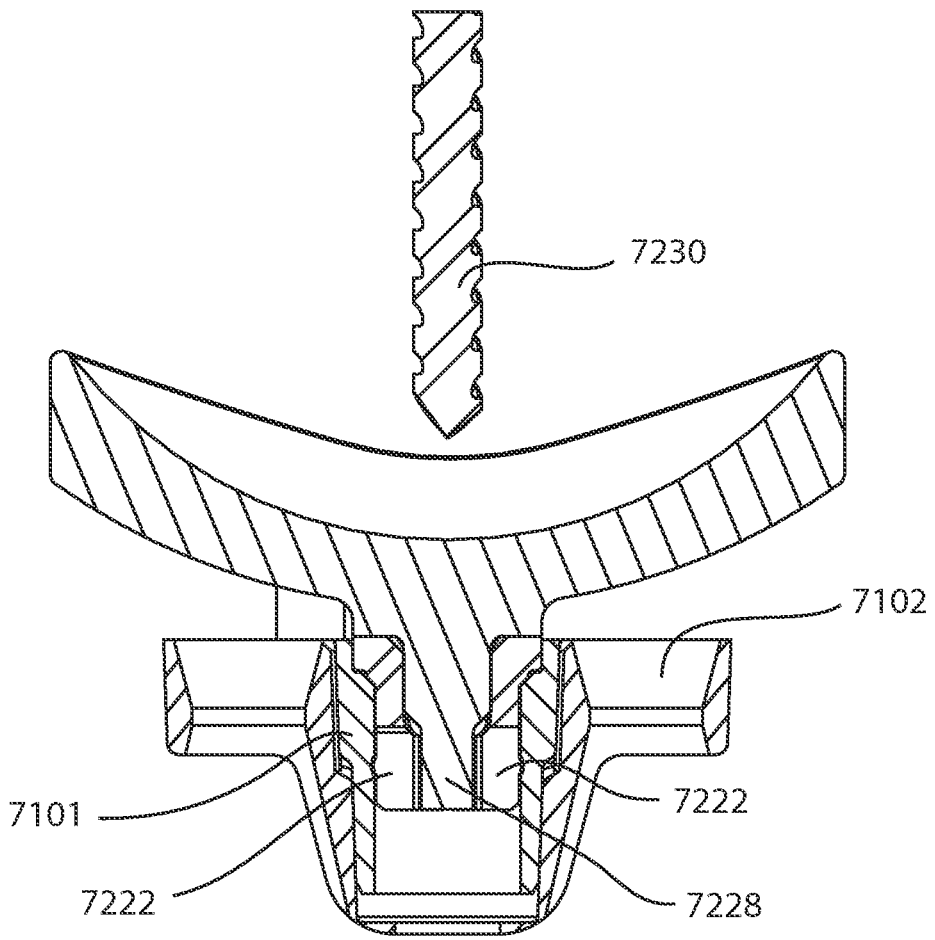
FIG. 99 is a cross section view of a system with the anatomical articulating component of FIG. 97 operatively assembled with a bone anchor assembly and a drill component.
Figure 100:
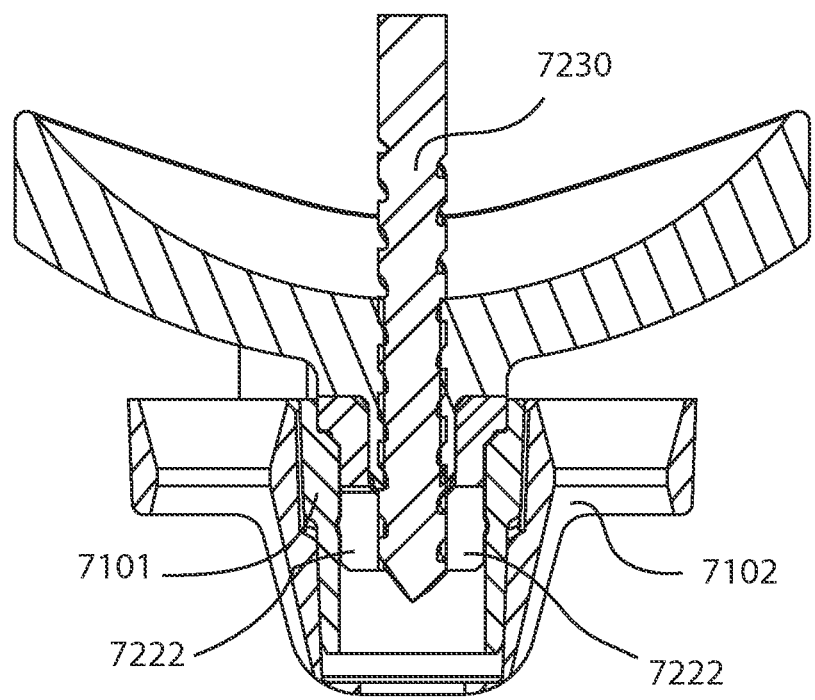
FIG. 100 is a cross section view of the system of FIG. 99 with the drill component.
Figure 101:
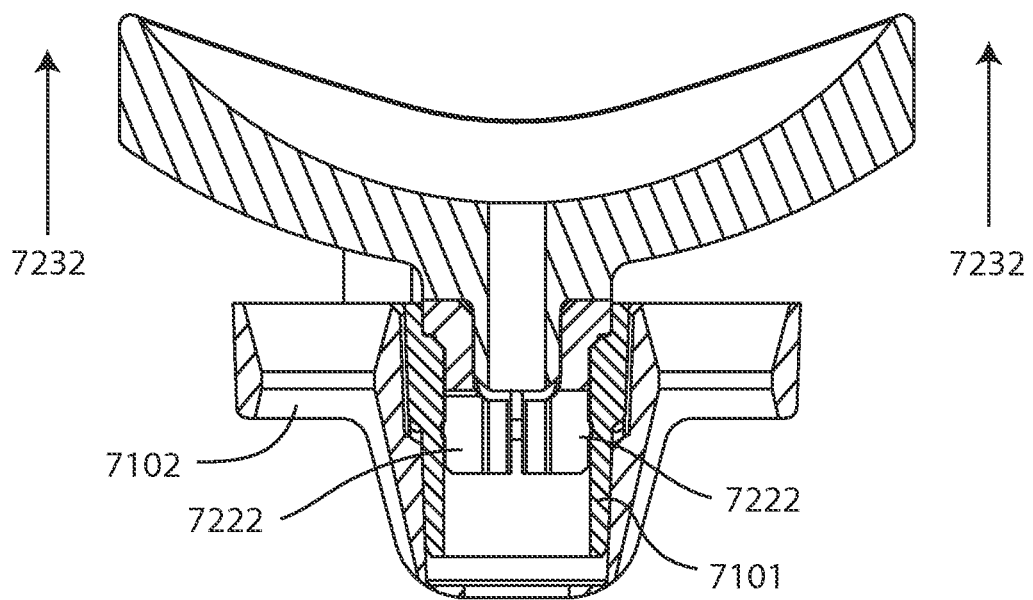
FIG. 101 is a cross section view of the system of FIG. 99 after removal of the central post.

For removal of the glenoid component 7100 from the anchor construct, as in the case of a shoulder revision surgery, a drill 7230 may be inserted through the center of the glenoid component 7100, as illustrated in FIGS. 99 and 100. As the drill 7230 is advanced into the glenoid component, the extruded poly stem 7228 is removed or destroyed. The drill 7230 may then be removed. As the drill 7230 is removed, the flanges 7222 may collapse inwards, as illustrated in FIG. 101, causing the engagement portion 7226 to disengage from the interior surface of the aperture of the AP component 7101. The glenoid component 7100 may then be easily lifted away from the anchor construct, as indicated by motion arrows 7232

In yet another example of a snap feature with a flexible member, the flexible member may remain in a compressed state inwardly towards a centerline of the engagement portion. The snap feature may include a high amount of radial grooves or threading. The high amount of radial groves allows the position required to seat the articulating component against bone as the engagement feature is driven into the bone anchor has more resolution. The constant compression of the flanges may ensure a ridged fit axially between the engagement feature and the bone anchor, for example, the SI-AP complex. The grooves may be radial rings, or a tightly wound cut helix within the perimeter of the engagement feature. This may result in reduced axial play once the system is implanted.

Referring to FIGS. 102-106, a device is illustrated that may be used in a shoulder arthroplasty system to address severe asymmetric bone loss in the glenoid. For example, a surgeon may desire to use a bone graft, rather than a poly augment in a younger patient with severe asymmetric bone loss.

Figure 102:
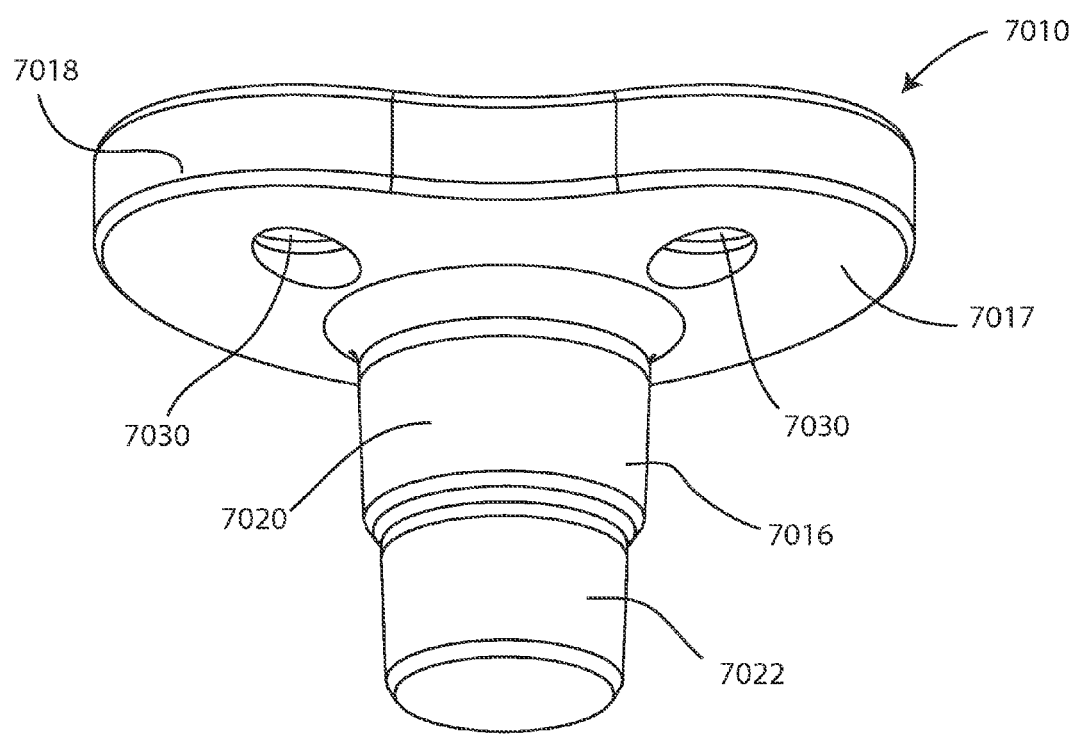
FIG. 102 is a bottom perspective view of an intermediate component.

As illustrated in FIG. 102, the device includes an intermediate component 7010 that may be securable to the SI component 7102 or other bone anchor, such as a trial, and may include a feature to accommodate an articulating component, such as glenoid component 7100 or articulating component 20. The intermediate component 7010 may include a distal shaft 7016 and a proximal tray 7018. The distal shaft 7016 may be generally cylindrical and may share some or all of the characteristics of post 28, shaft 7109, or shaft 7176 described previously. The shaft may include a snap feature similar to snap features 7150 or 7180, or may include additional fixation features such as notches, teeth, threading, circumferential grooves or other surface features.

The distal shaft 7016 extend from a distal surface 7017 of tray component 7018. The stem 7016 may include a neck portion 7020 that extends between the distal surface of the tray 7018 and an engagement portion 7022. The neck 7020 may have a greater diameter than the engagement portion 7022. The neck may include a plurality of circumferential notches or grooves or teeth that help provide rotational stabilization when the tray 7018 interacts with the SI-AP complex. The engagement portion 7022 may be shaped to engage a central bore of the SI component 7102 or the AP component 7101 or a different bone anchor.

Figure 103:
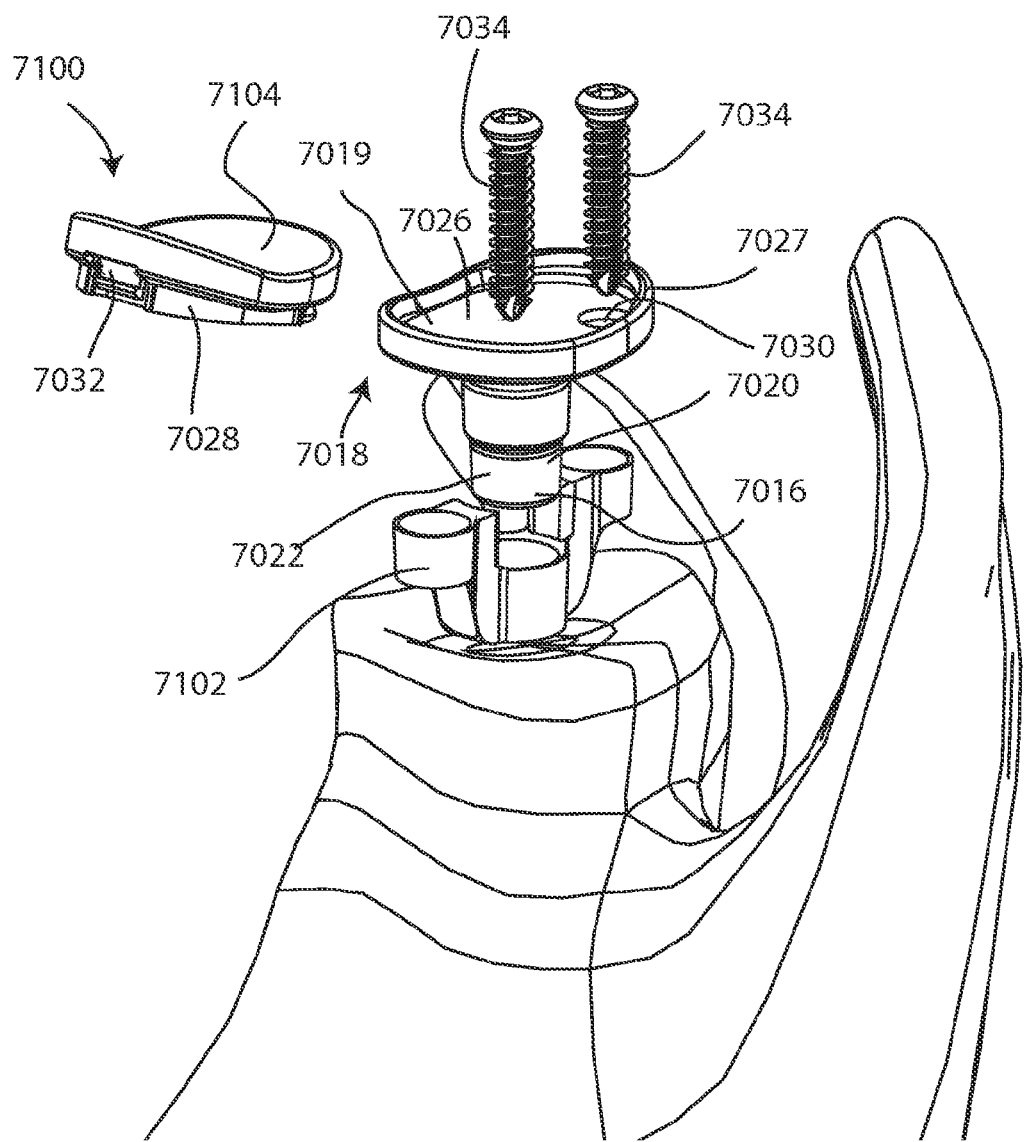
FIG. 103 is a top exploded view of the a system with the intermediate component of FIG. 102 with a distal bone anchor assembly and a proximal anatomical articulating component.

As seen best in FIG. 103, the proximal tray 7018 may include a top surface 7019 that is opposite the distal surface 7017. Top surface 7019 may include a recessed portion 7026 that is shaped to receive a complementary extended portion 7028 on an articulating component, such as glenoid component 7100. The recessed portion 7026 may be at least partially bounded by a raised perimeter 27. The recessed portion 26 may also include a plurality of holes 30 to accommodate screws in order to enhance fixation of the system into the bone.

In an alternative example (not shown), the top surface 7019 may include a protruded portion that is shaped to engage a complementary recessed portion on an articulating component. In yet another example (not shown), top surface 7019 may include a protruded portion with a first surface area, and a recessed portion with a second surface area. The second surface area may be contained within the first surface area, or may be separate on the articulating surface. The protruded portion and recessed portions may be shaped to interact with corresponding, complementary recessed and protruding portions on an articulating component.

Figure 104:
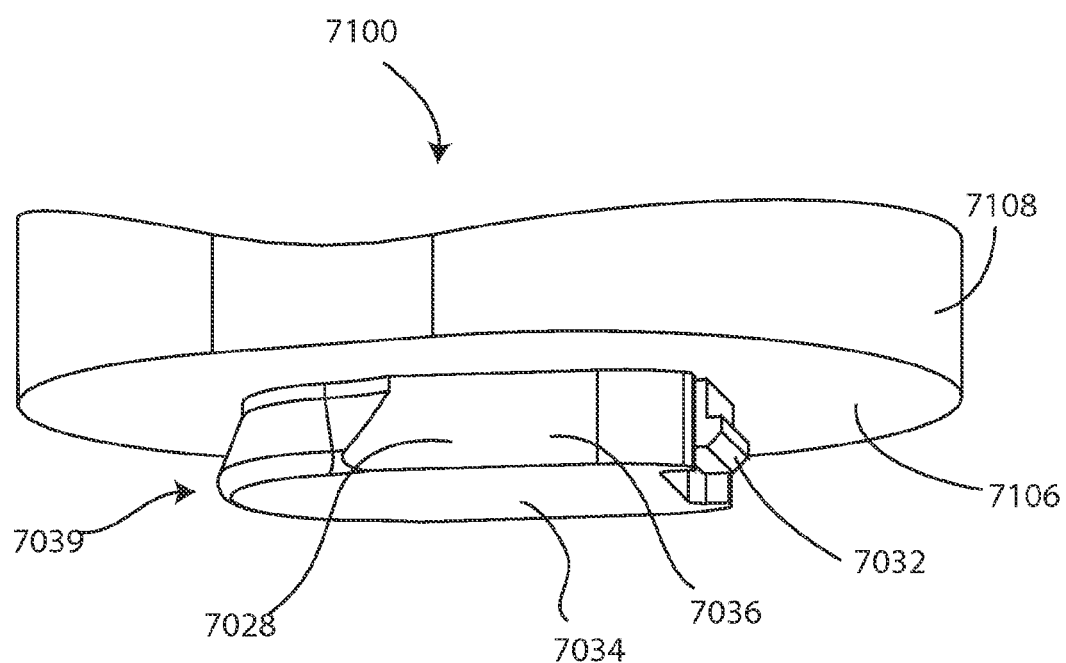
FIG. 104 is a bottom perspective view of an anatomical articulating component with an engagement tab.
Figure 105:
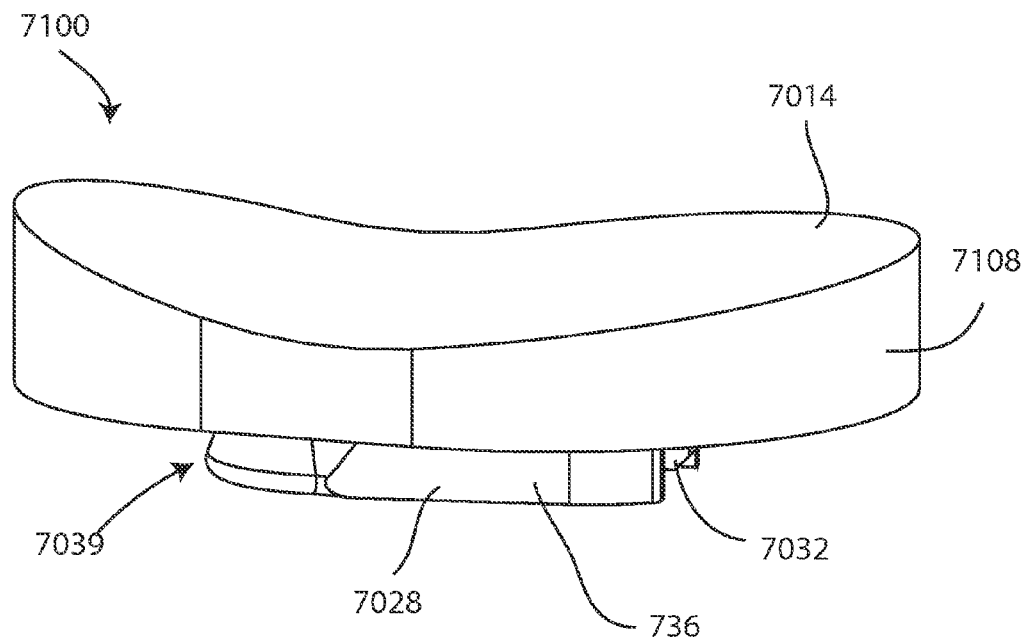
FIG. 105 is a top perspective view of the anatomical articulating component of FIG. 104.

In the example illustrated in FIG. 103, glenoid 7100 may include an extended portion 7028, which may have a complementary shape to the recessed portion of intermediate component 7010. Referring to FIGS. 104 and 105, the extended portion 7028 may extend from the bone facing surface 7106. Extended portion 7028 may include a second side portion 7036 that extends from the bone facing surface of glenoid 7100 and a distal face portion 7034. The length of the second side portion 7036 may be less than the length of side portion 7108 of the glenoid component 7100. Extended portion 7028 may protrude from a substantially central location on the bone facing surface 7106 of glenoid 7100, or may otherwise be off center. Extended portion 7028 may include at least one connection feature, such as tab 7032 that extends from a portion of the second side portion 7036. Extended portion 7028 may also include a projection 7039 opposite the tab 7032.

In this example, when glenoid 7100 is coupled to the intermediate component 7010, at least a portion of extended portion 7028 is contained within the recessed portion 7026. The glenoid 7100 may be lockably secured to the intermediate component 7010 when the distal face 7034 contacts the intermediate component 7010 and the connection feature 7032 mates with a locking feature on the intermediate component (not shown), such as a lip or ledge that captures tab 7032.

Figure 106:
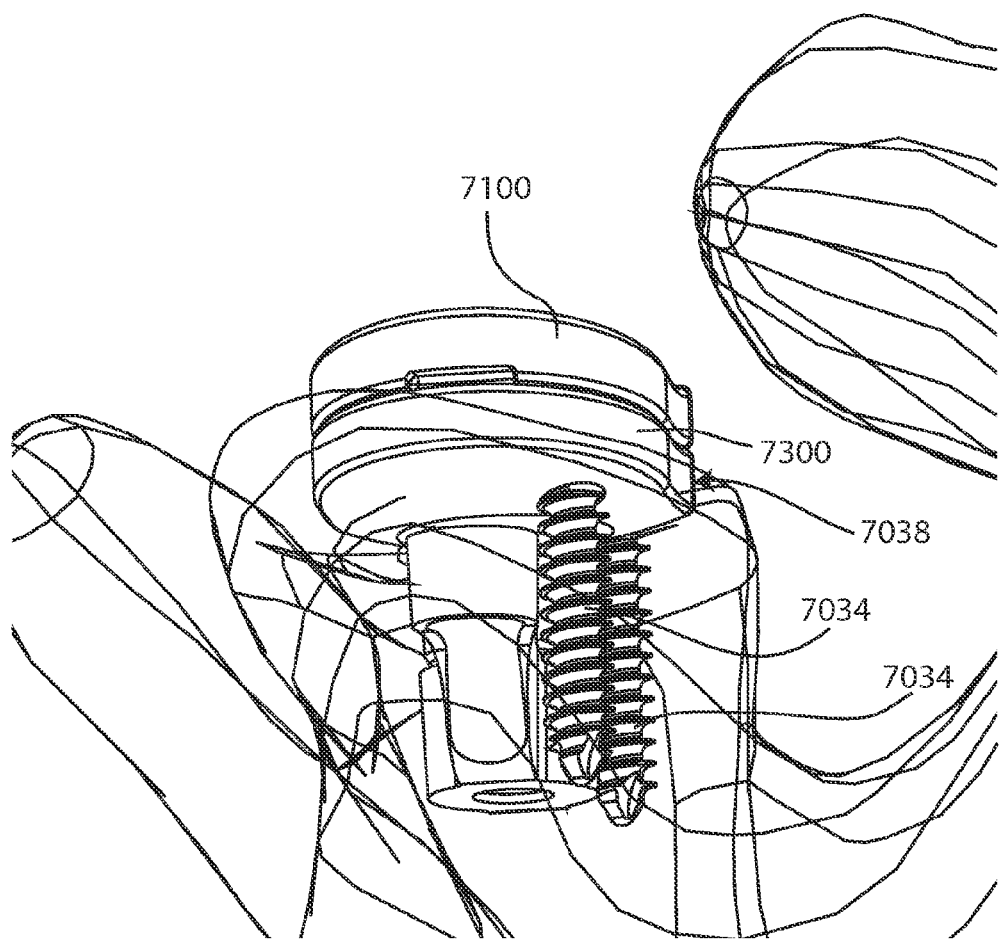
FIG. 106 is a bottom perspective view of the system of FIG. 103 operatively assembled in subchondral bone.

In an example of use, the intermediate component 7010 may be coupled to the SI-component 7102 by lockably sliding the engagement portion 7022 of the stem 7016 at least partially into the central bore of the SI component 7102, as illustrated in FIG. 103. The SI component 7102 may be inserted within the subchondral bone. Once the intermediate component 7100 has been secured to the SI-component 7102 to form an SI component-intermediate component complex, the complex may be further secured within the scapula by inserting at least one screw 7034 into at least one of the plurality of holes 7030 and further into the subchondral bone, as illustrated in FIG. 106. The screw 7034 may extend through a block of bone graft or other bone augmentation material (not shown). The articulating component 7100 may then be attached to the tray 7018 by inserting the extended portion 7028 of the articulating component 7100 into the complementary recessed portion 7026.

As illustrated in FIG. 106, the intermediate component 7010 essentially replaces the AP component 7101 to provide a boundary between the portion of subchondral bone that has experienced bone loss and the articulating component 7100. This boundary defines a space 7038 that may be filled with a bone graft or other stabilizing material. It is also contemplated that intermediate component 7010 may be secured to the AP component 7101, rather than the SI component 7102, or may be secured to the SI-AP complex. Alternatively, intermediate component 7010 is contemplated for use independently of the anchor system described above, and may be used with other anchor assemblies or unitary anchors or bases of other shoulder repair or revision systems.

Figure 107:
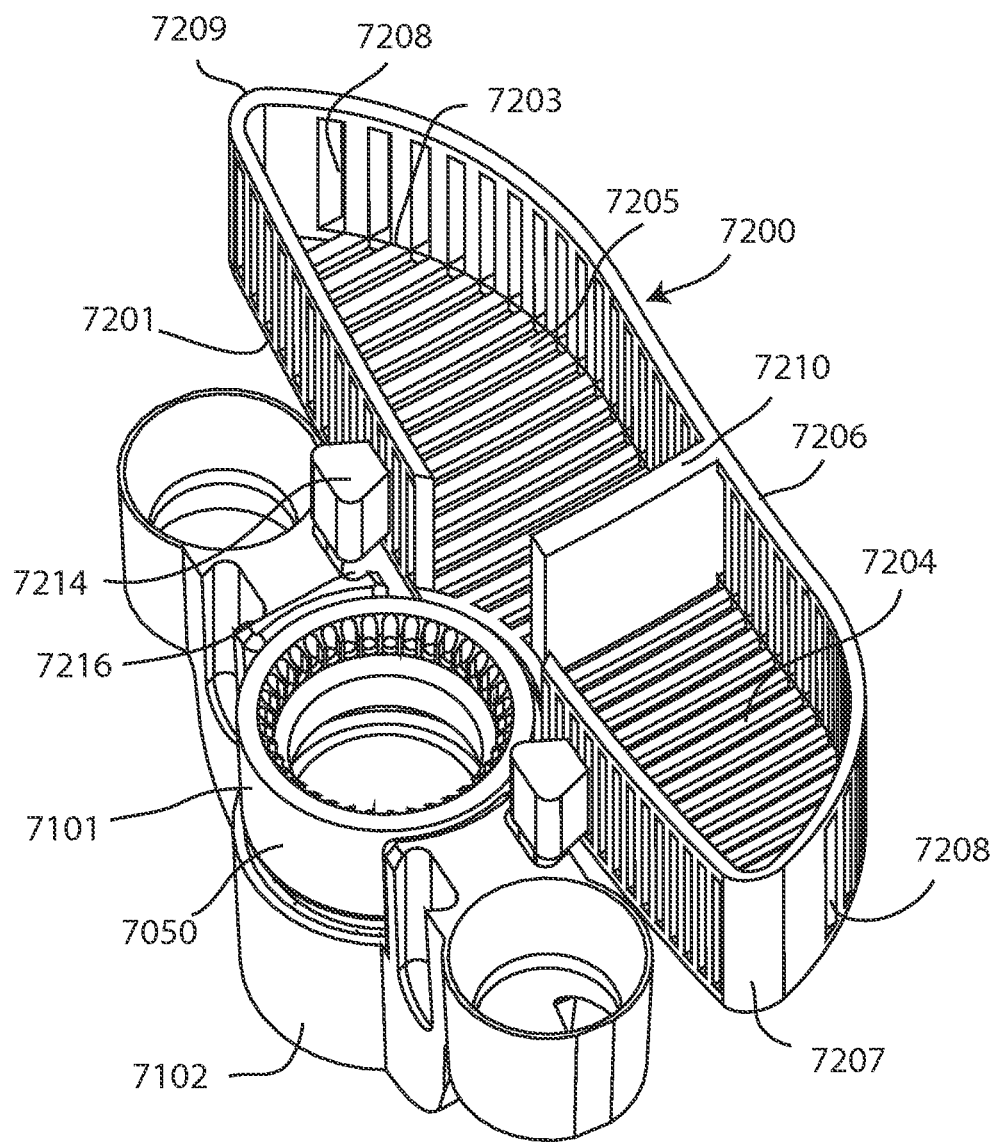
FIG. 107 is a top perspective view of a bone anchor assembly aligned with a bone cage.

Referring to FIGS. 107-110, a device that is attachable to a shoulder arthroplasty system to address bone loss in a glenoid is illustrated. The device includes a cage 7200, which may also be referred to as a frame, a shell, or a scaffold. The cage 7200 may be designed to be secured to and SI component 7102, such as SI component 100, or it may be used in an alternative shoulder arthroplasty system. The cage 7200 includes features to accept bone graft or another bone substitute. Referring to FIGS. 106 and 107, the cage 7200 may include a pocket 7204. The pocket 7204 may be at least partially encircled by a primary wall 7206. The primary wall 7206 may extend along the perimeter of the pocket 7204 and may be substantially normal to the plane of a base surface, which may also be referred to as a floor surface 7205 of the pocket 7204. The primary wall may otherwise encircle only a portion of the pocket.T The base surface 7205 may extend between a first edge 7201 of cage 7200 and a second edge 7203. The first edge 7201 may be complementary to the outer profile of the SI-AP complex or other anchor. FIG. 107 shows a first edge 7201 which is substantially linear, with a semicircular indentation 211 that complements the cylindrical wall 7050 of the central aperture of the AP component 7101. The second edge 7203 may be contoured to match the curvature of the first side portion 7108 of articulating component 7100. The first edge 7201 and second edge 7203 may intersect or merge at a first end 7207 and a second end 7209.

Figure 109:
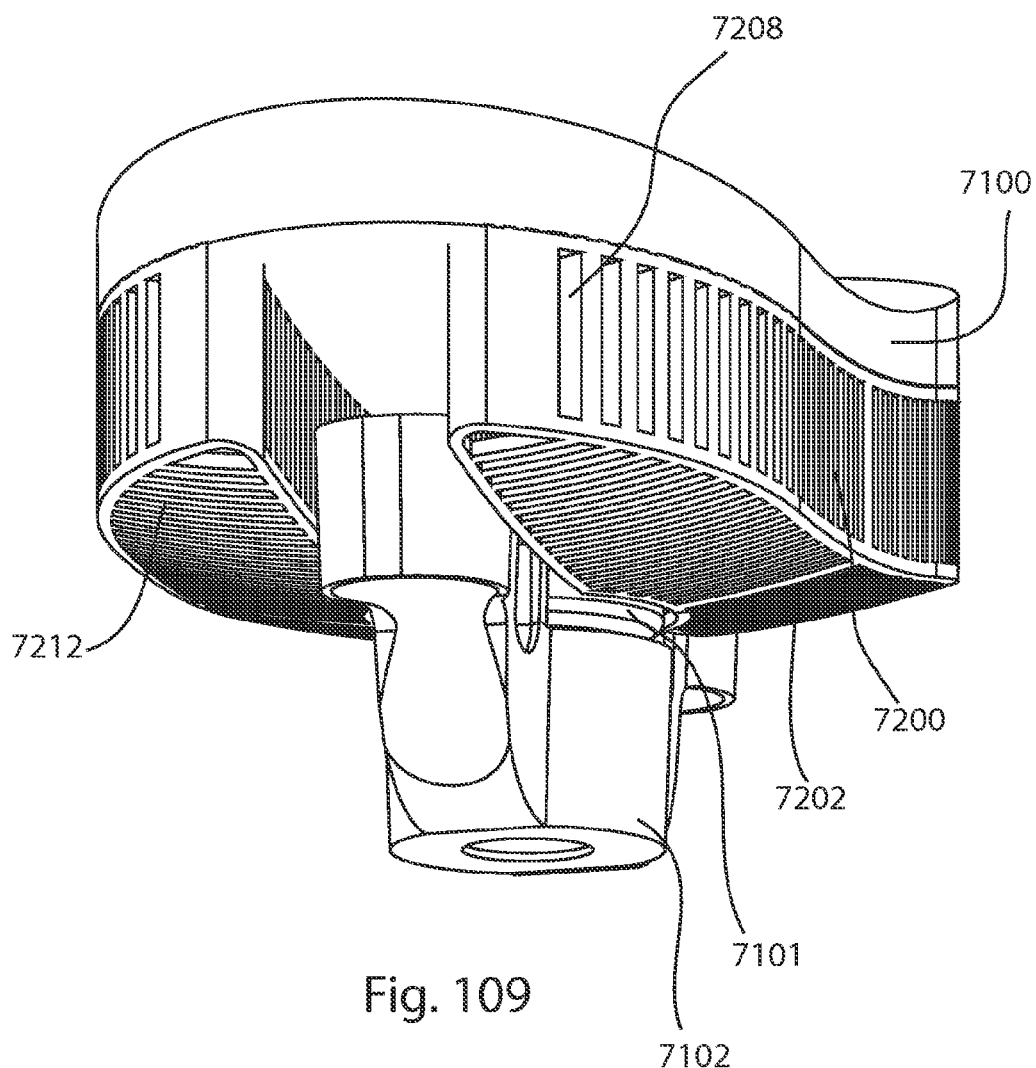
FIG. 109 is a bottom perspective view of the system of FIG. 108 operatively assembled.

The cage 7200 may also include a first lateral face 7202, seen best in FIG. 109, which may be bone facing, and may contact the medial surface of the glenoid when the system is installed. The first lateral face 7202 may be opposite the base surface 7205 of the pocket 7204.

The primary wall 7206 may include a plurality of elongated apertures 7208. The apertures 7208 may be substantially rectangular, and may permit the passage of bone graft or other bone biological material into or out of the pocket 7204. The apertures may otherwise be rounded and irregularly spaced along the primary wall 7206. The apertures 7208 may be distributed along the entire primary wall 7206, or along a portion of the primary wall 7206. The pocket 7204 may be partitioned into smaller pockets by at least one secondary wall 210 that extends from the primary wall 7206 into the interior of the pocket 7204 and also extends in a plane that is normal to the plane of the pocket base 7205. The pocket base 7205 may also include a plurality of elongated, substantially rectangular apertures 7212. The apertures 7212 may otherwise be elliptical or irregularly shaped.

The cage 7200 may also include at least one male connection feature, such as a rail 7214, that extends outward from a portion of the primary wall 7206 extending along the first edge 7201. The connection feature 7214 may be shaped to mate with a complementary female recessed connection feature, such as groove 7216 on the SI component 7102 to secure the cage 7200 to the SI component 7102 during assembly. In other examples, the male and female connection features may be reversed, or each of the primary wall 7206 and the SI component may have a combination of corresponding, complementary male and female mating features.

Figure 108:
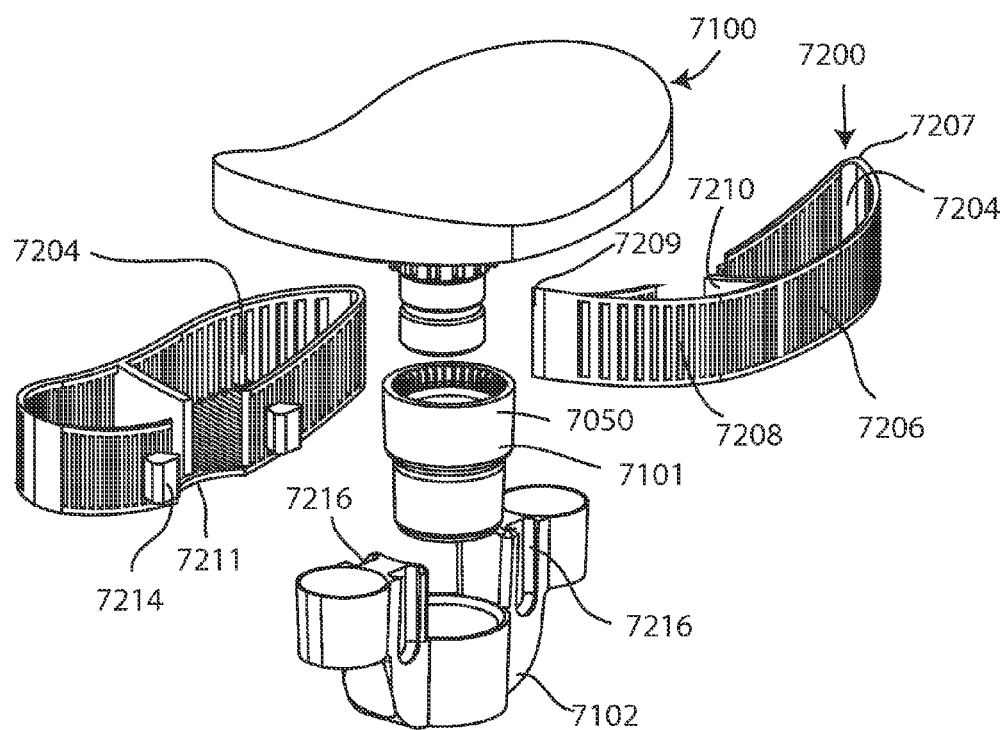
FIG. 108 is an exploded view of a system with an anatomical articulating component, a bone anchor assembly and the bone cage of FIG. 107.
Figure 110:
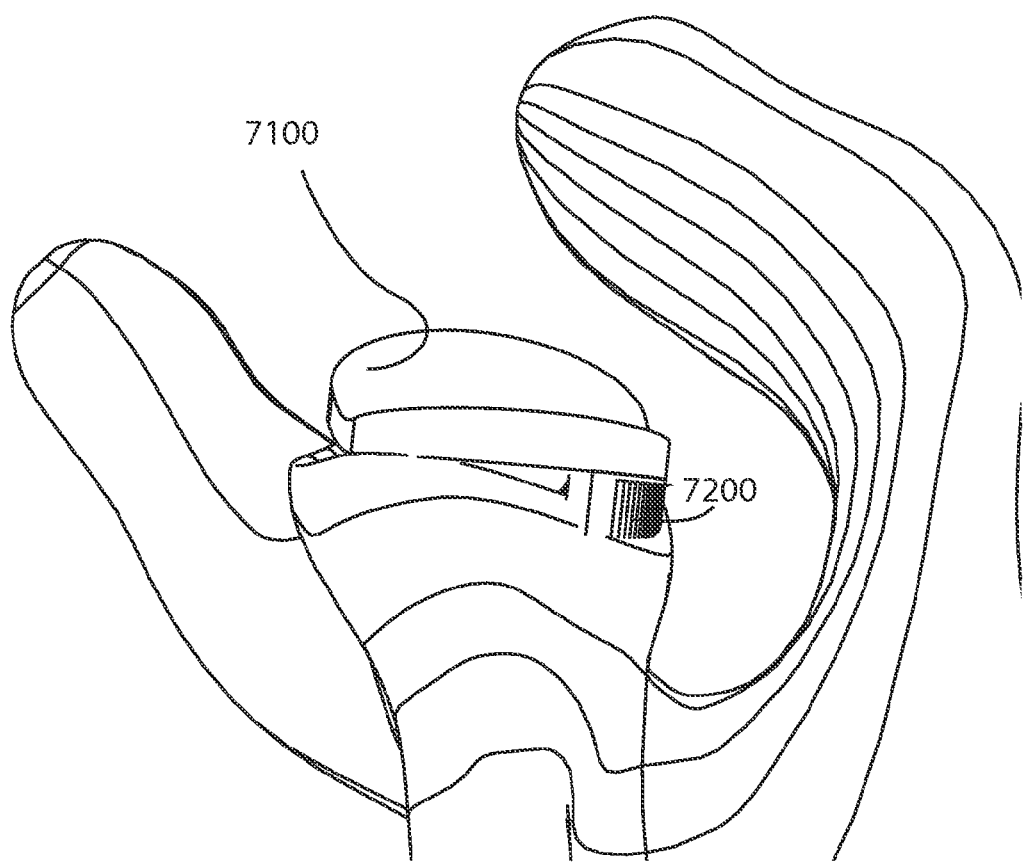
FIG. 110 is a side view of the system of FIG. 108 operatively assembled in subchondral bone.
Figure 111:
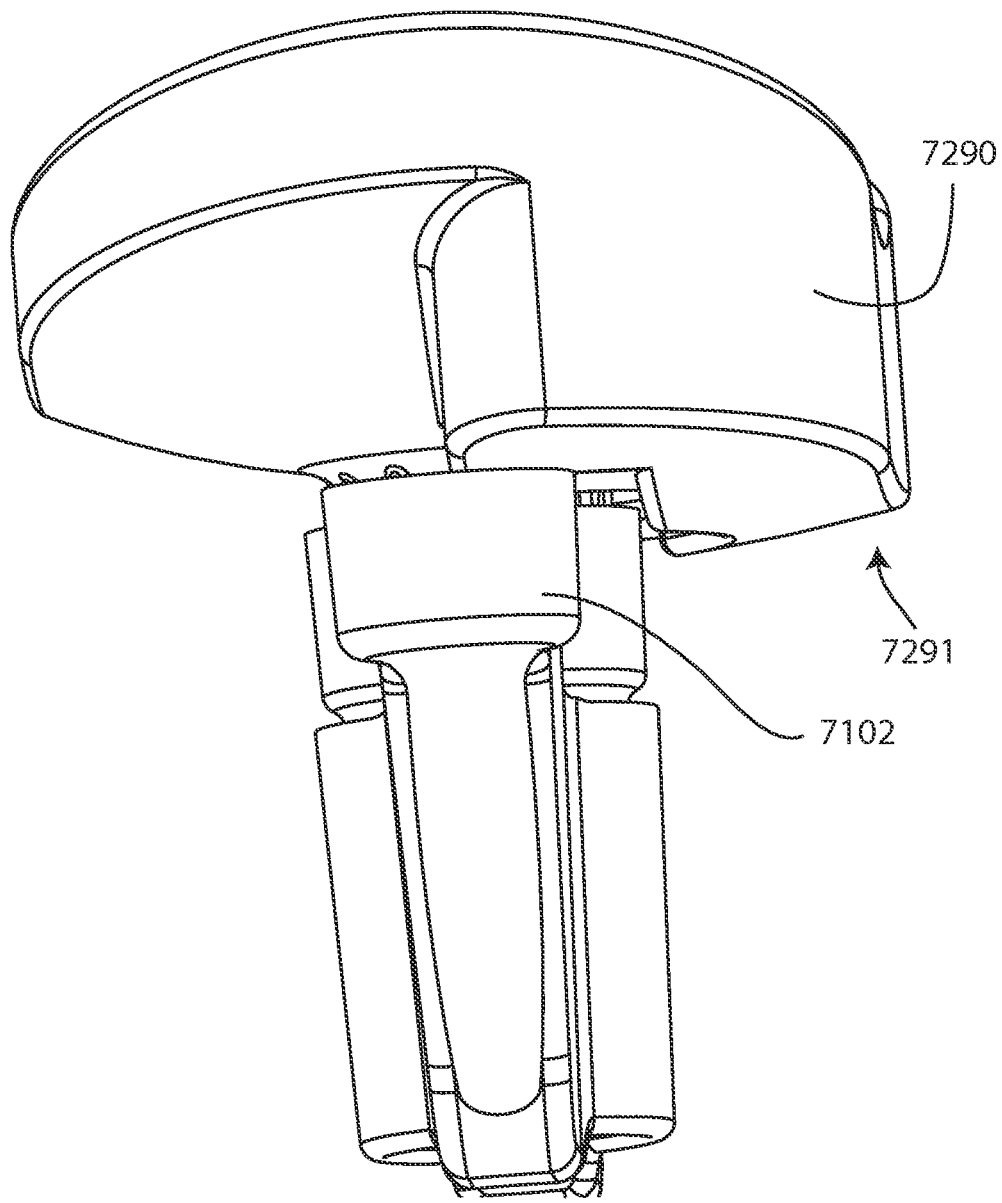
FIG. 111 is a perspective view of an augmented glenoid component.

Referring to FIG. 107, the cage 7200 is shown aligned with the SI-AP complex, as well as with glenoid component 7100. To operatively assemble the cage 7200 to the SI-AP complex, the cage 7200 may be attached to the SI-AP complex by sliding the connection feature 214 of the cage 7200 at least partially into the recessed feature 216 on the SI component 7102. The semicircular indentation 7211 may contact the wall 7050 of the central aperture of the AP component 7101. The assembled system may be inserted into the subchondral bone. A bone graft may be inserted into the pocket 7206. The glenoid component 7100 may then be attached by inserting the shaft 7109 into the aperture of the AP component 7101. FIG. 110 illustrates system assembled with cage 7200 inserted into the subchondral bone. FIGS. 108 and 109 illustrate an arrangement with two cages 7200. In another example (not shown), the cage 7200 may be used in combination with the intermediate component 7010; the cage 7200 may be positioned in space 7038 to at least partially fill the void.

FIG. 30 illustrates an implant construct with an augmented glenoid component 7290. The augment 7291 extends from a bone-facing surface to fill a bone void, in some ways similar to the function of the cage 7200.

Referring to FIGS. 112-118, instruments and methods for preparing a glenoid vault for placement of an augmented glenoid are described. To prepare the glenoid vault to receive a glenoid component with an augment, for example augment 434 of augment 5012, instrument 7300, which may also be referred to as an augment preparation guide, may be attached to the SI component 7102. Instrument 7300 may be used to guide a cutting tool, such as a mill, along a defined pathway to resect a desired portion of bone. Preparation guide 7300 may be shaped similarly to glenoid component 7100, or another articulating component of choice, and may include a proximal platform 7301 that includes a plurality of interconnected guide slots 7302. Platform 7301 may include a first proximal surface 7310 and a second bone-facing surface 7312. The first proximal surface 7310 may be semispherical, or concave, and may be peripherally surrounded by a wall 7314, which may also be referred to as a side portion. The wall 7314 may extend between the first surface 7310 and the bone facing surface 7312, where the bone facing surface 7312 is opposite the first surface 7310. The bone facing surface 7312, which may also be referred to as a second surface, may include a distal shaft 7304 that extends from a substantially central location on the bone facing surface 7312. Distal shaft 7304 may be similar to shaft 7109, and is shaped to reversibly engage a central bore in the SI component 7102 or the AP component 7101.

The platform 7301 may further include a plurality of guide slots 7302. The slots 7302 may intersect the first surface 7310 and the bone facing surface 7312. The slots 7302 may be interconnected, meaning that they share at least a portion of their outer boundaries with one another, to form a guide path for a burr or mill. Referring FIGS. 112-118, various examples of arrangements of guide slots 7302 are illustrated.

Figure 112:
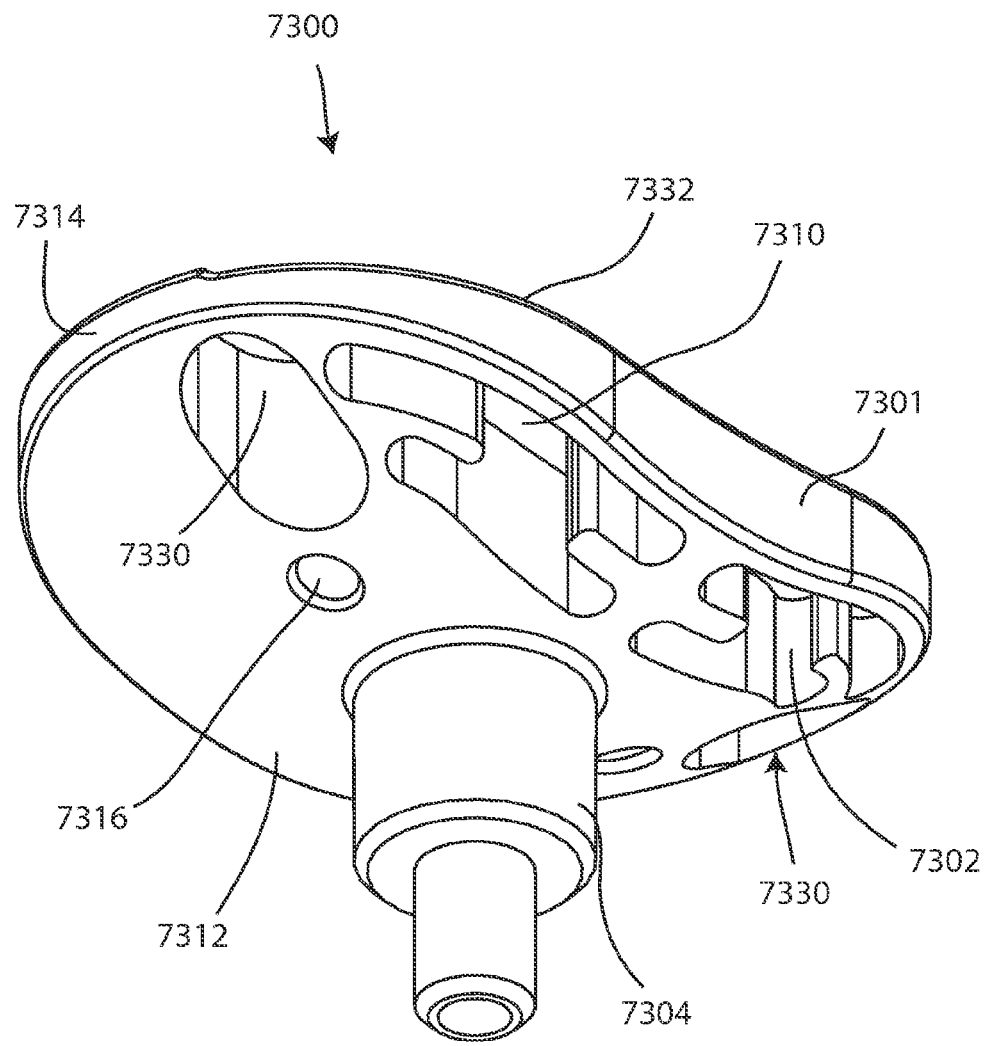
Figure 113:
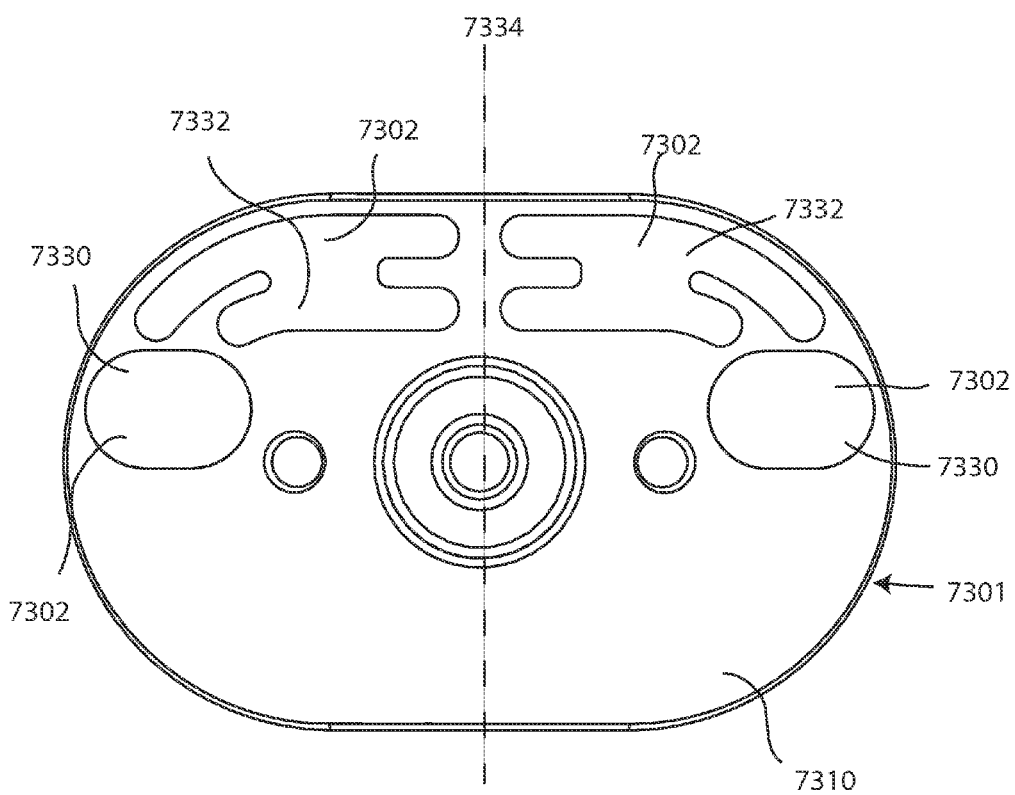
Figure 116:
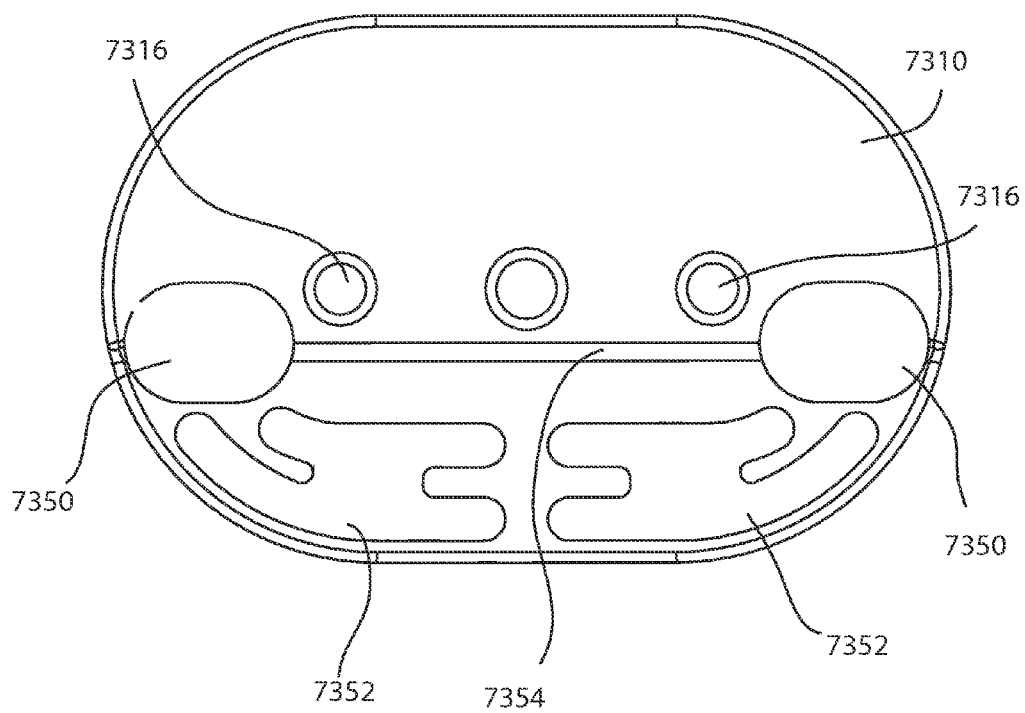

In the example illustrated in FIGS. 112, 113 and 116, a first arrangement of guide slots is illustrated. The first arrangement of guide slots may include two elliptical slots 7330 and two irregularly shaped slots 7332. The elliptical slots 7330 and irregularly shaped slots 7332 may be distributed symmetrically about an axis 7334.

Figure 114:
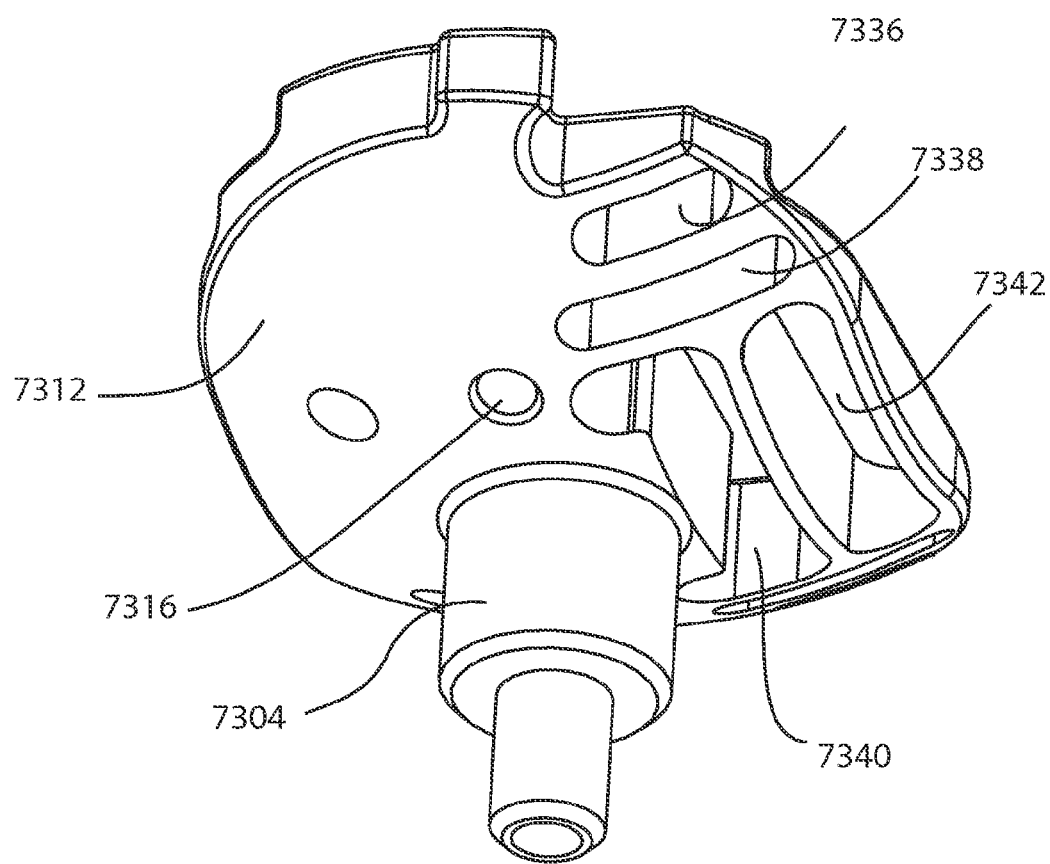
Figure 115:
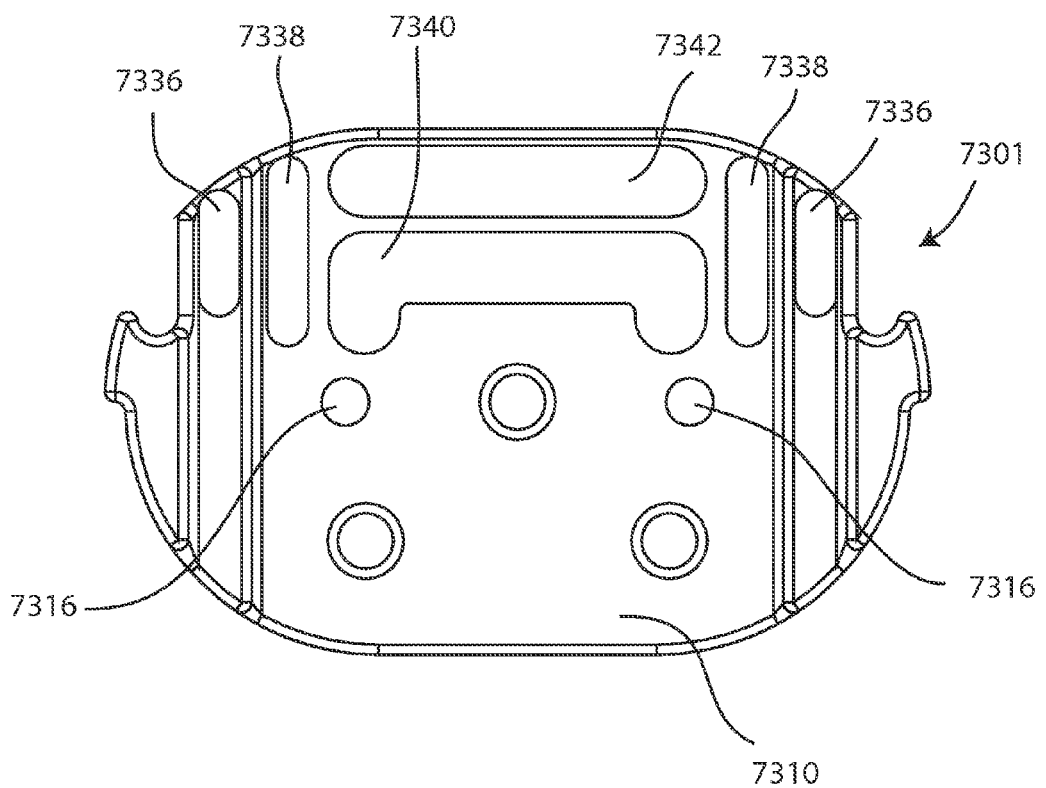

Referring to FIGS. 114 and 115, a second example of an arrangement of guide slots 7302 is illustrated. The second arrangement of guide slots may include two small oval slots 7336 and two larger oval slots 7338 that are disposed symmetrically about a central elongated U-shaped slot 7340 and a large elliptical slot 7342 that extends parallel to the central portion of the elongated U-shaped slot.

Figure 117:
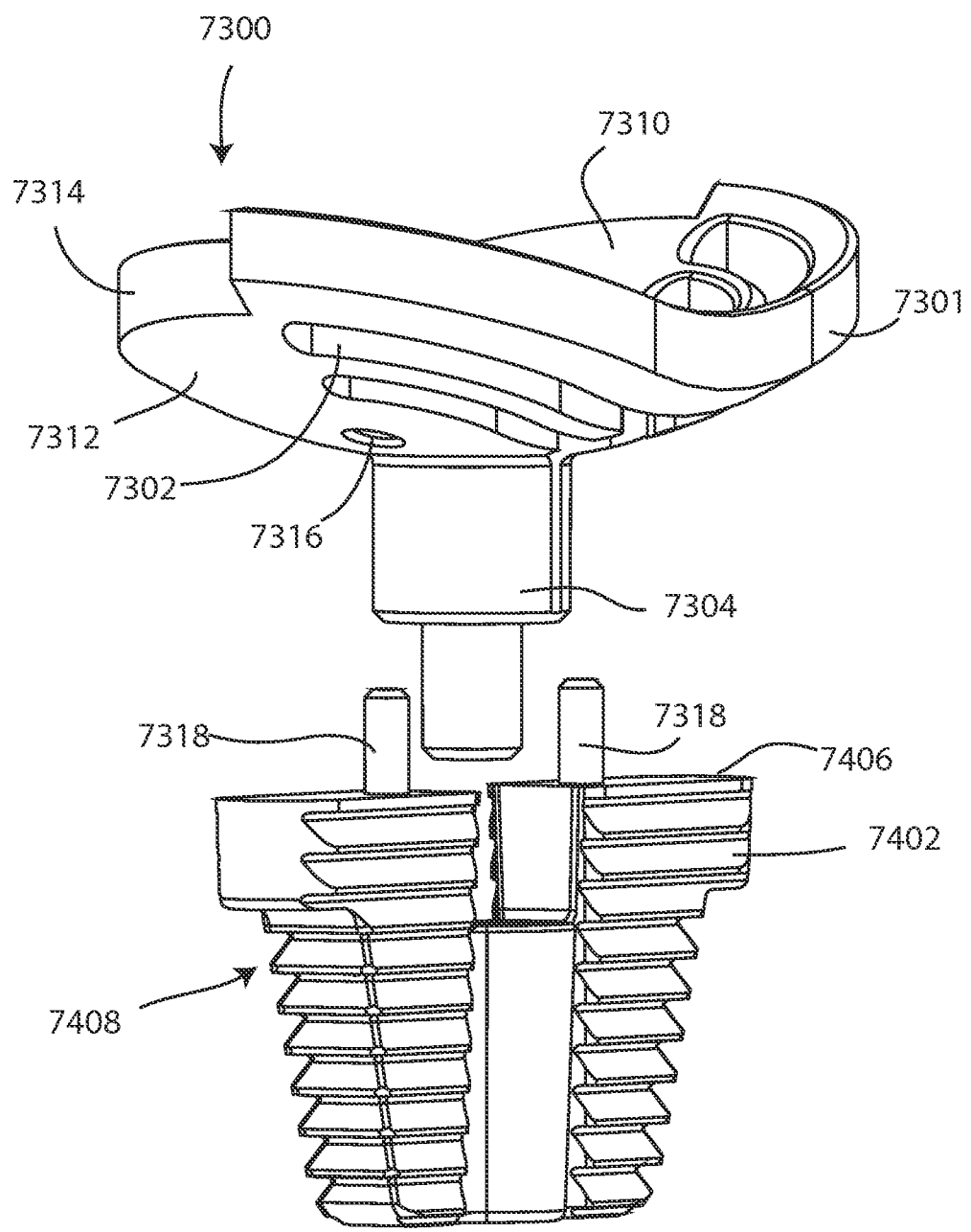
Figure 118:
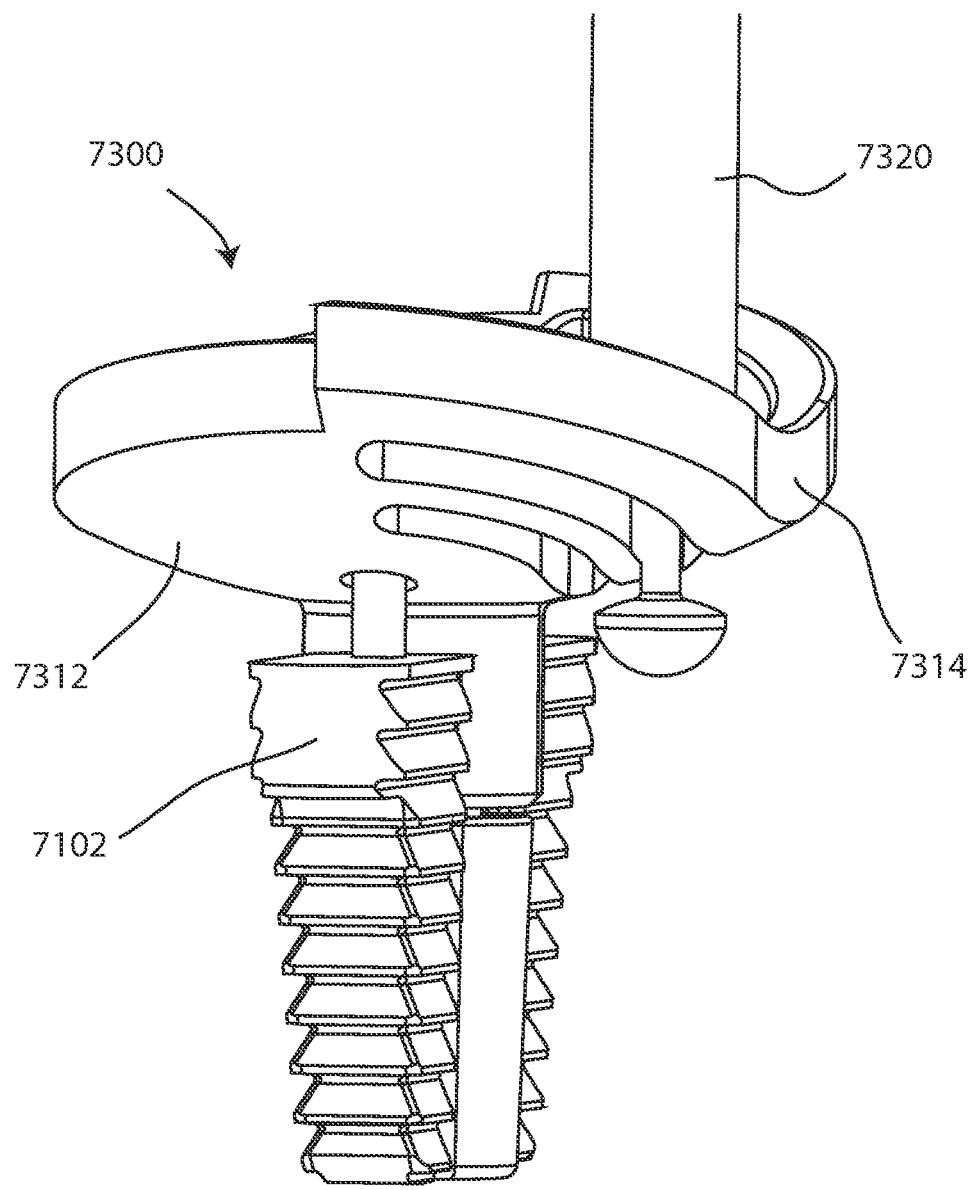

Referring to FIGS. 117 and 118, a third example of an arrangement of guide slots 7302 is illustrated. The third arrangement may include two arcuate slots, one longer than the other, which generally follow the outer profile of the platform.

FIGS. 117 and 118 illustrate a broach/trial component 7402 which may be used to form a pocket or recess in a bone, the pocket shaped to receive an appropriately sized SI component. The broach/trial component 7402 includes posts 7318 which protrude from a top or lateral surface 7406 of the broach/trial component. The broach/trial may have an outer shape which is similar to or identical to the outer shape of the corresponding SI component. However, in order to form the pocket, the broach/trial may include one or more cutting features 7408. FIG. 117 illustrates a broach/trial which is essentially covered in cutting features.

In an example of use, the SI broach/trial 7102 may be inserted into the subchondral bone. Instrument 7300 may then be attached to the SI broach/trial 7102 by inserting at least a portion of the shaft 7304 into the central aperture of the SI broach/trial 7102, as illustrated in FIGS. 117 and 118. To provide for rotational stability, body 7308 may include anti rotation features, similar to those described above. In this example, the body 7308 includes two female mating features 7316, such as circular holes to receive complementary male mating features, such as cylindrical posts 7318, on the SI broach/trial 7102. In an alternative example, the SI broach/trial may include female mating features shaped to engage complementary male mating features on the body 7308. These anti-rotation features may be similar or identical to the anti-rotational features described previously. Once the instrument 7300 has engaged the SI broach/trial, a mill 7320 may be placed into the guided slots 7302, and may be moved along the prepared pathway that is defined by the interconnected slots 7302 to resect bone along the path, as illustrated in FIG. 118.

The present embodiments may be embodied in other specific forms without departing from its spirit or essential characteristics. It is appreciated that various features of the above described examples and embodiments may be mixed and matched to form a variety of other combinations and alternatives. It is also appreciated that this system should not be limited simply to shoulder replacement, revision or repair and may easily be adapted to other joint replacement technology, including, but not limited to hip repair. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system configured to receive a bone-preparing instrument to prepare a bone to receive a component comprising at least one augment portion, the system comprising:
   a connection feature that includes:
      a central vertical axis;
      a medial portion;
      at least one lateral arm extending laterally away from the central vertical axis and extending laterally away from the medial portion;
      an anti-rotation feature disposed on the at least one lateral arm;
      at least one fastener extending distally away from the medial portion along the central vertical axis; and
      a forked portion extending proximally away from the medial portion, the forked portion including at least two arms spaced apart to form a central channel;
   a superior-inferior component configured to be embedded into the bone, the superior-inferior component including a central ring configured to receive and to couple removably with the at least one fastener of the connection feature and to receive and to couple with the component subsequent to the at least one fastener of the connection feature being removed, the superior-inferior component including a complementary feature configured to interact with the anti-rotation feature to substantially prevent the connection feature from rotating about the central vertical axis with respect to the superior-inferior component; and,
   a guide portion configured to couple with the connection feature, the guide portion being configured to receive the bone-preparing instrument.

2. The system of claim 1, wherein the anti-rotation feature further comprises at least one of a protruding feature and an aperture and the complementary feature on the superior-inferior component includes the other of the protruding feature and the aperture.

3. The system of claim 1, wherein the guide portion comprises a sleeve configured to receive the bone-preparing instrument, the sleeve being configured to be rotated about an axis which is perpendicular to the central vertical axis of the connection feature.

4. The system of claim 3, wherein the guide portion comprises at least one aperture configured to receive the bone-preparing instrument.

5. The system of claim 3, wherein the sleeve has a shape selected from the group consisting of tubular, rectangular, square, oblong, circular and polygonal.

6. The system of claim 3, wherein a longitudinal axis of the sleeve and the central vertical axis of the connection feature are spaced apart and are substantially parallel to each other.

7. The system of claim 3, wherein the sleeve removably receives the bone-preparing instrument.

8. The system of claim 1, wherein the at least one fastener is configured to be rotated to couple with the superior-inferior component.

9. The system of claim 1, wherein the connection feature further comprises a cavity configured to receive an actuating instrument configured to rotate the at least one fastener so as to couple the at least one fastener to the superior-inferior component.

10. The system of claim 1, wherein the guide portion comprises a sleeve and an arm extending away from the sleeve, the arm including an engagement feature and a circumferential groove, and wherein the central channel of the forked portion is configured to receive the circumferential groove.

11. The system of claim 1, wherein the superior-inferior component is configured to decouple with the at least one fastener.

12. A system configured to receive a bone-preparing instrument to prepare a bone to receive an anterior-posterior component comprising at least one augment portion and at least one post, the system comprising:
   a connection feature that includes:
      a central vertical axis;
      a medial portion;
      at least one fastener extending distally away from the medial portion along the central vertical axis;
      an anti-rotation feature; and
      a forked portion extending proximally away from the medial portion, the forked portion including at least two arms spaced apart to form a central channel;
   a superior-inferior component configured to be embedded into the bone, the superior-inferior component including:
      a central ring configured to receive and to couple removably with the at least one fastener of the connection feature and to receive and to couple with the at least one post of the component subsequent to the at least one fastener of the connection feature being removed; and a complementary feature configured to interact with the anti-rotation feature to substantially prevent the connection feature from rotating about the central vertical axis with respect to the superior-inferior component; and, a guide portion configured to couple with the connection feature, the guide portion including:

a sleeve configured to receive the bone-preparing instrument; and, an arm extending away from the sleeve, the arm being configured to couple with the connection feature, wherein the central channel of the forked portion is configured to receive the arm of the guide portion.

13. The system of claim 12, wherein the arm of the guide portion comprises an engagement feature and a circumferential groove, wherein the central channel of the forked portion is configured to receive the circumferential groove.

14. The system of claim 12, wherein the sleeve is configured to be rotated about an axis which is perpendicular to the central vertical axis of the connection feature.

15. The system of claim 12, wherein the at least one fastener is configured to be rotated to couple with the superior-inferior component.

16. The system of claim 15, wherein the connection feature further comprises a cavity configured to receive an actuating instrument configured to rotate the at least one fastener so as to couple the at least one fastener to the superior-inferior component.

17. The system of claim 12, wherein the anti-rotation feature further comprises at least one of a protruding feature and an aperture and the complementary feature on the superior-inferior component includes the other of the protruding feature and the aperture.

18. The system of claim 17, wherein the connection feature further comprises at least one arm extending laterally away from the medial portion and the central vertical axis, wherein the anti-rotation feature is disposed on the at least one arm.

* * * * *